(12) United States Patent
Lee et al.

(10) Patent No.: US 8,222,634 B2
(45) Date of Patent: Jul. 17, 2012

(54) ANTHRACENE DERIVATIVES AND ORGANIC ELECTRONIC DEVICE USING THE SAME

(75) Inventors: Dong-Hoon Lee, Daejeon (KR); Jae-Chol Lee, Daejeon (KR); Jae-Soon Bae, Daejeon (KR); Jun-Gi Jang, Daejeon (KR); Kong-Kyeom Kim, Daejeon (KR); Dae-Woong Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 5 days.

(21) Appl. No.: 12/450,842

(22) PCT Filed: May 16, 2008

(86) PCT No.: PCT/KR2008/002755
§ 371 (c)(1),
(2), (4) Date: Oct. 15, 2009

(87) PCT Pub. No.: WO2008/143440
PCT Pub. Date: Nov. 27, 2008

(65) Prior Publication Data
US 2011/0024725 A1 Feb. 3, 2011

(30) Foreign Application Priority Data

May 17, 2007 (KR) .................. 10-2007-0048158

(51) Int. Cl.
*H01L 51/30* (2006.01)
*C07D 213/74* (2006.01)
*C07D 401/12* (2006.01)
*C07D 401/14* (2006.01)
*C07D 409/12* (2006.01)
*C07F 7/08* (2006.01)

(52) U.S. Cl. .................... 257/40; 257/E51.025; 546/14; 546/140; 546/160; 546/264; 546/276.7; 546/281.4; 546/304

(58) Field of Classification Search ................ None
See application file for complete search history.

(56) References Cited

U.S. PATENT DOCUMENTS
2006/0046097 A1    3/2006    Kim et al.

FOREIGN PATENT DOCUMENTS
| | | |
|---|---|---|
| CN | 1898355 | 1/2007 |
| JP | 2004-095850 | 3/2004 |
| JP | 2005-089674 | 4/2005 |
| JP | 2006-041103 | 2/2006 |

OTHER PUBLICATIONS

F. Zaragoza Dorwald, Side Reactions in Organic Synthesis; A Guide to Successful Synthesis Design, Wiley-VCH, Weinheim, Preface, p. IX (2005).*

* cited by examiner

*Primary Examiner* — Janet Andres
*Assistant Examiner* — Timothy R Rozof
(74) *Attorney, Agent, or Firm* — McKenna Long & Aldridge LLP

(57) ABSTRACT

The present invention relates to a novel anthracene derivative and an organic electronic device using the same. The organic electronic device according to the present invention shows excellent characteristics in efficiency, driving voltage, and life time.

10 Claims, 1 Drawing Sheet

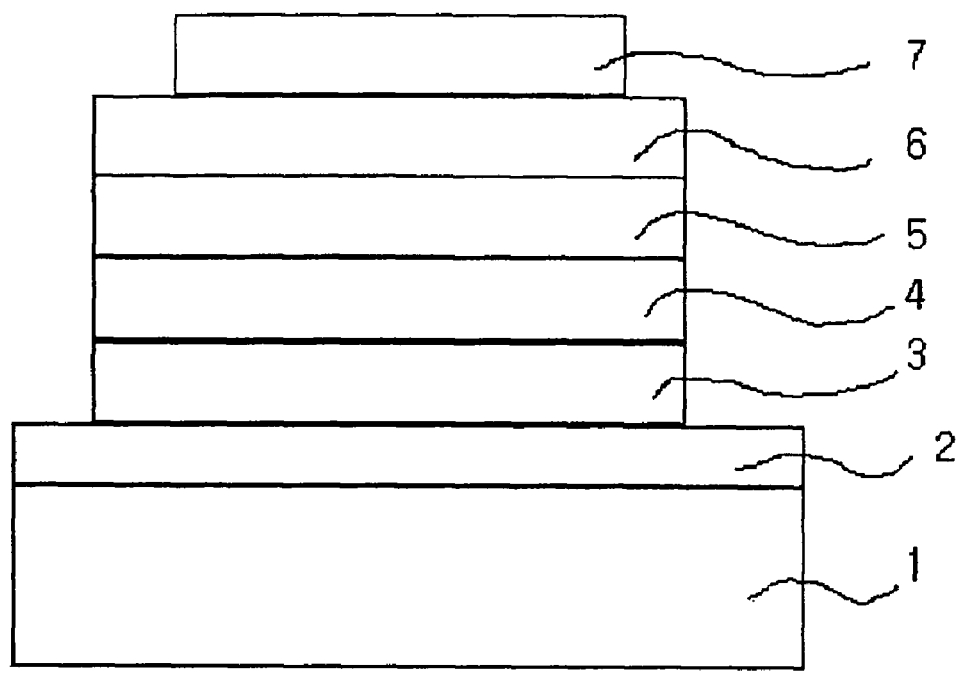

ANTHRACENE DERIVATIVES AND ORGANIC ELECTRONIC DEVICE USING THE SAME

This application claims the benefit of PCT/KR2008/002755 filed on May 16, 2008 along with Korean Patent Application No. 10-2007-0048158 filed on May 17, 2007, both of which are hereby incorporated herein by reference for all purposes in their entirety.

TECHNICAL FIELD

The present invention relates to a novel anthracene derivative having a pyridyl group bonded to anthracene, and to an organic electronic device using the same.

This application claims priority from Korean Patent Application No. 10-2007-48158 filed on May 17, 2007 in the KIPO, the disclosure of which is incorporated herein by reference in its entirety.

BACKGROUND ART

The term, organic electronic device, as used in the present specification refers to a device using an organic semiconductor material, which requires hole and/or electron exchange between an electrode and an organic semiconductor material. The organic electronic device can be largely classified into two types according to its operational principle as follows. One type is an electronic device having a configuration in which an exciton is formed in an organic material layer by photons flown from an external light source into the device and the exciton is separated into an electron and a hole, the electron and the hole formed are transported to a different electrode, respectively and used as a current source (voltage source), and the other type is an electronic device having a configuration in which holes and/or electrons are injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC) drum and an organic transistor, which all require an electron/hole injecting material, an electron/hole extracting material, an electron/hole transporting material, or a light emitting material for driving the device. Hereinafter, the organic light emitting device will be mainly and specifically described, but in the above-mentioned organic electronic devices, the electron/hole injecting material, the electron/hole extracting material, the electron/hole transporting material or the light emitting material injection functions according to a similar principle.

In general, the term "organic light emitting phenomenon" refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast and high-speed response.

The materials used for the organic material layer of the organic light emitting device can be classified into a light emitting material and a charge-transporting material, for example, a hole injecting material, a hole transporting material, an electron transporting material and an electron injecting material, according to their functions. The light emitting materials can be divided into a blue, green or red light emitting material and a yellow or orange light emitting material required for giving more natural color, according to a light emitting color. Further, a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material and an electron injecting material should be essentially composed of a stable and efficient material. However, the development of a stable and efficient organic material layer material for the organic light emitting device has not yet been fully realized. Accordingly, the development of new materials is continuously desired.

DISCLOSURE

Technical Problem

The present inventors have synthesized an anthracene derivative having a novel structure, and then have found that the novel anthracene derivative having a pyridyl group bonded to anthracene can exhibit effects of increased efficiency, lower voltage and higher stability of a device when it is used to form an organic material layer of the organic electronic device. In addition, the present inventors have found that in the case both an amino group and a pyridyl group are present like the anthracene derivative, an electron injecting ability is increased as compared to the case that both the groups are not present, thus significantly reducing driving voltage and increasing efficiency.

Therefore, it is an object of the present invention to provide a novel anthracene derivative having a pyridyl group bonded to anthracene and an organic electronic device using the same.

Technical Solution

The present invention provides an anthracene derivative that is represented by the following formula 1:

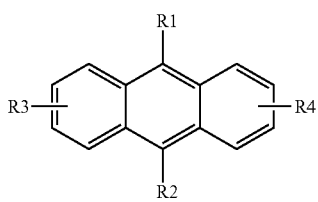

[Formula 1]

wherein R1 and R2 may be the same as or different from each other, and are independently selected from the group consisting of a $C_6$ to $C_{40}$ aryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, a $C_3$ to $C_{40}$ heteroaryl group and an arylamine group; a $C_3$ to $C_{40}$ heteroaryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; and a $C_6$ to $C_{40}$ amino group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group, at least one of R3 and R4 is represented by the following formula 2:

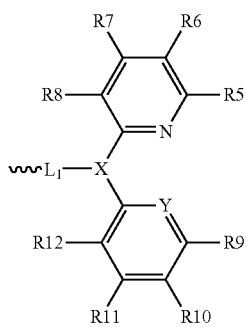

[Formula 2]

wherein X is selected from the group consisting of N, P and P=O,

Y is selected from the group consisting of C—H and N, $L_1$ is a direct bond; or is selected from the group consisting of a $C_2$ to $C_{40}$ alkenylene group which is unsubstituted or substituted with at least one selected from the group consisting of a $C_1$ to $C_{40}$ alkyl group, a $C_2$ to $C_{40}$ alkenyl group, a $C_2$ to $C_{40}$ alkynyl group, a $C_1$ to $C_{40}$ alkoxy group, a $C_6$ to $C_{40}$ aryl group, and a $C_3$ to $C_{40}$ heteroaryl group; a $C_6$ to $C_{40}$ arylene group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; $C_5$ to $C_{40}$ heteroarylene group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; and a $C_6$ to $C_{40}$ arylamine group which is unsubstituted or substituted with at least one selected from the group consisting of a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group, R5, R6, R7, R8, R9, R10, R11, and R12 may be the same as or different from each other, and are selected from the group consisting of hydrogen; a silicon group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; a $C_1$ to $C_{40}$ alkyl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; a $C_3$ to $C_{40}$ cycloalkyl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; a $C_2$ to $C_{40}$ alkenyl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; a $C_1$ to $C_{40}$ alkoxy group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; an amino group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; a $C_6$ to $C_{40}$ aryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; and a $C_3$ to $C_{40}$ heteroaryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group, or are bonded with an adjacent group to form an aliphatic, aromatic, heteroaliphatic, or heteroaromatic condensed ring, or to form a spiro bond, and when any one of R3 and R4 is represented by formula 2, the other is selected from the group consisting of hydrogen; a $C_6$ to $C_{40}$ aryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_3$ to $C_{40}$ aryl group, a $C_3$ to $C_{40}$ heteroaryl group and an arylamine group; a $C_3$ to $C_{40}$ heteroaryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; and a $C_6$ to $C_{40}$ amino group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group.

In an embodiment of the present invention, R1 and R2 of formula 1 may be the same aryl groups. It is preferable that the aryl groups be the substituted or unsubstituted phenyl group, biphenyl group or naphthyl group.

In another embodiment of the present invention, R1 and R2 of formula 1 may be the same heteroaryl groups. It is preferable that the heteroaryl groups be the substituted or unsubstituted pyridyl group, bipyridyl group, quinolyl group or isoquinolyl group.

In still another embodiment of the present invention, R1 and R2 of formula 1 may be the amino groups substituted with the same $C_6$~$C_{40}$ aryl groups or the same $C_3$~$C_{40}$ heteroaryl groups.

In a further embodiment of the present invention, R1 and R2 of formula 1 may be specifically selected from the group consisting of the following structural formulas:

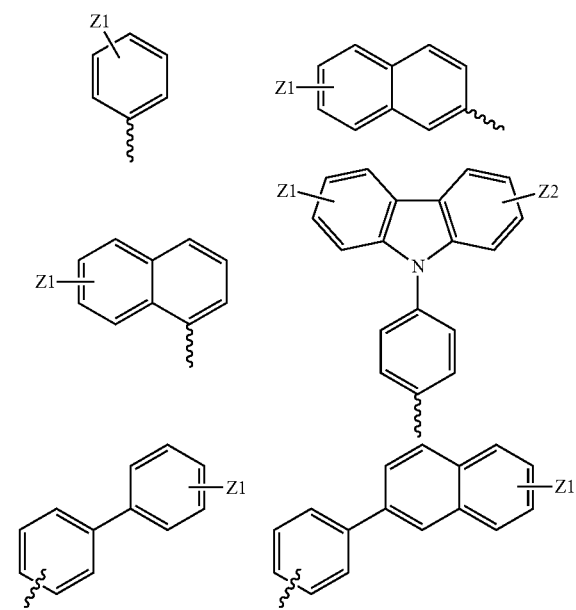

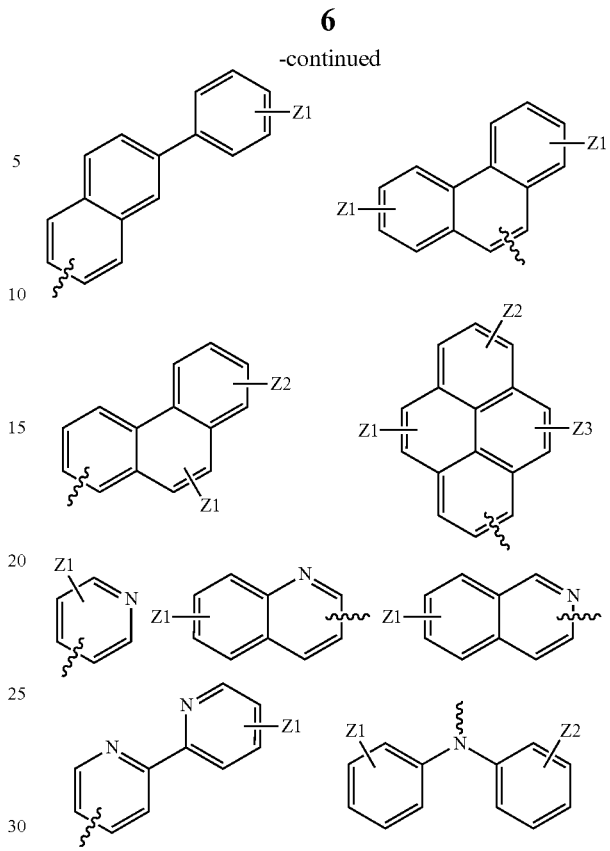

wherein Z1 to Z3 are the same as or different from each other, and may be independently hydrogen or selected from the groups defined in respects to R1 and R2 of formula 1.

In a yet another embodiment of the present invention, in formula 2, it is preferable that $L_1$ be a direct bond, an unsubstituted $C_6$~$C_{40}$ arylene group, or an unsubstituted $C_5$~$C_{40}$ heteroarylene group.

Advantageous Effects

The novel anthracene compound according to the present invention can be used as a material for an organic material layer of an organic electronic device including an organic light emitting device by the introduction of a pyridyl derivative to the anthracene compound. The organic electronic device including an organic light emitting device, which uses the anthracene compound according to the present invention as a material for an organic material layer, shows significantly reduced driving voltage and excellent characteristics in efficiency, life time, or the like.

DESCRIPTION OF DRAWINGS

FIG. 1 illustrates an example of an organic light emitting device according to the present invention.

NUMERAL REFERENCES 1. substrate
2. anode
3. hole injecting layer
4. hole transporting layer
5. organic light emitting layer
6. electron transporting layer
7. cathode

BEST MODE

Substituent groups will be described in detail.

The alkyl group is preferably one having 1 to 40 carbon atoms, which does not give steric hindrance. Specific examples thereof include, but not limited thereto, a methyl group, an ethyl group, a propyl group, an isopropyl group, a butyl group, a t-butyl group, a pentyl group, a hexyl group and a heptyl group.

The cycloalkyl group is preferably a cycloalkyl group having 3 to 40 carbon atoms, which does not give steric hindrance. More preferable specific examples thereof include a cyclopentyl group and a cyclohexyl group.

The alkenyl group is preferably an alkenyl group having 2 to 40 carbon atoms, and specifically it is one substituted with an aryl group such as a stilbenzyl group and a styrenyl group.

The alkoxy group is preferably an alkoxy group having 1 to 40 carbon atoms.

Examples of the aryl group include a phenyl group, a naphthyl group, an anthracenyl group, a biphenyl group, a pyrenyl group, a perylenyl group, and a derivative thereof, but are not limited thereto.

Examples of the arylamine group include a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a ditolylamine group, a phenyltolylamine group, a carbazole group and a triphenylamine group, but are not limited thereto.

Examples of the heterocyclic group include a pyridyl group, a bipyridyl group, a triazine group, an acridyl group, a thiophene group, a puran group, an imidazole group, an oxazole group, a thiazole group, a triazole group, a quinolinyl group, and an isoquinoline group, but are not limited thereto.

Examples of halogen include fluorine, chlorine, bromine, and iodine.

In the present specification, the term "adjacent group" means a substituent group that is adjacent to the corresponding substituent group, and the adjacent substituent group includes a hydrogen atom that is not represented by Formula.

If the $C_2$ to $C_{40}$ alkenylene group is substituted, the substituent is at least one selected from the group consisting of a substituted or unsubstituted $C_1$ to $C_{40}$ alkyl group, a substituted or unsubstituted $C_2$ to $C_{40}$ alkenyl group, a substituted or unsubstituted $C_2$ to $C_{40}$ alkynyl group, a substituted or unsubstituted $C_1$ to $C_{40}$ alkoxy group, a substituted or unsubstituted $C_6$ to $C_{40}$ aryl group, and a substituted or unsubstituted $C_3$ to $C_{40}$ heteroaryl group.

Preferable specific examples of the compound of formula 1 include the followings, but not limited thereto.

TABLE 1

| Formula | R1 | R2 | L₁ | Ar₁ |
|---|---|---|---|---|
| 1-1 | naphthyl | naphthyl | direct bond | phenyl |
| 1-2 | phenyl | phenyl | direct bond | phenyl |
| 1-3 | naphthyl | naphthyl | direct bond | phenyl |
| 1-4 | biphenyl | biphenyl | direct bond | phenyl |
| 1-5 | N-phenylcarbazolyl | N-phenylcarbazolyl | direct bond | phenyl |

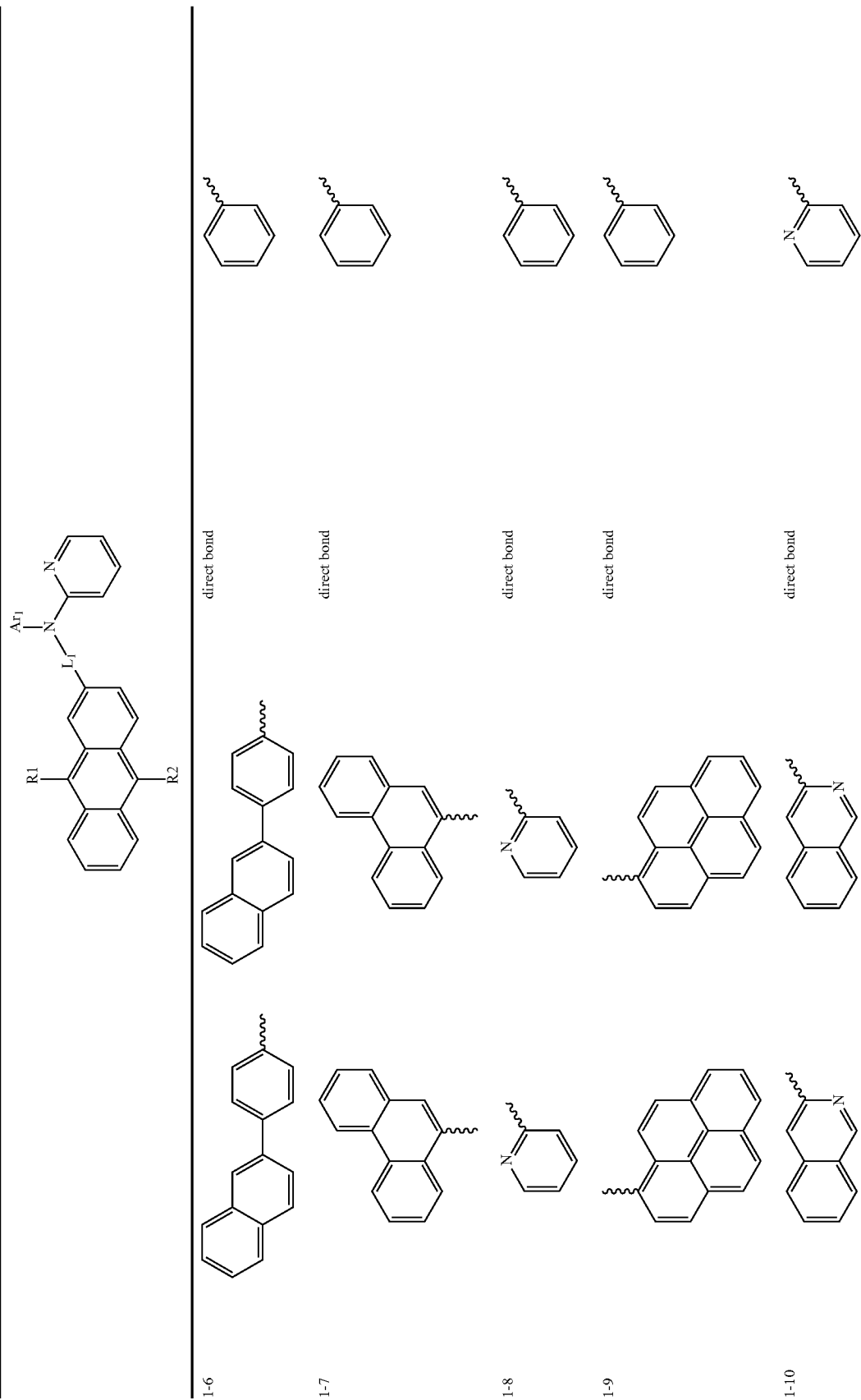

TABLE 1-continued

| | R1 | R2 | L1 | Ar1 |
|---|---|---|---|---|
| 1-11 | 2-naphthyl | 2-naphthyl | direct bond | 2-pyridyl |
| 1-12 | phenyl | phenyl | direct bond | 2-pyridyl |
| 1-13 | 1-naphthyl | 1-naphthyl | direct bond | 2-pyridyl |
| 1-14 | biphenyl | biphenyl | direct bond | 2-pyridyl |
| 1-15 | N-carbazolylphenyl | N-carbazolylphenyl | direct bond | 2-pyridyl |
| 1-16 | 2-naphthylphenyl | 2-naphthylphenyl | direct bond | 2-pyridyl |

TABLE 1-continued
| | | | | |
|---|---|---|---|---|
| 1-17 | 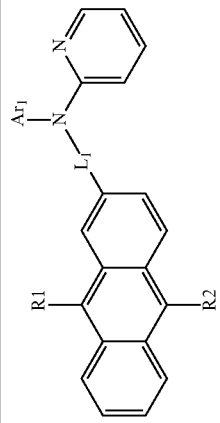 | direct bond | 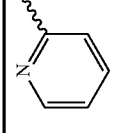 | 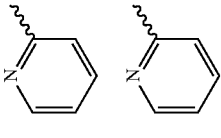 |
| 1-18 | | direct bond | 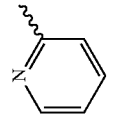 | 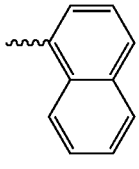 |
| 1-19 | | direct bond | 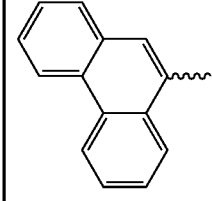 | 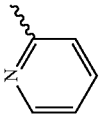 |
| 1-20 | | direct bond | 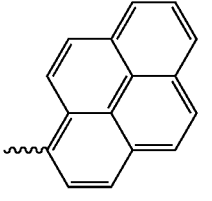 |  |
| 1-21 | | direct bond | 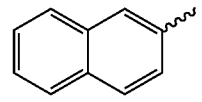 | |

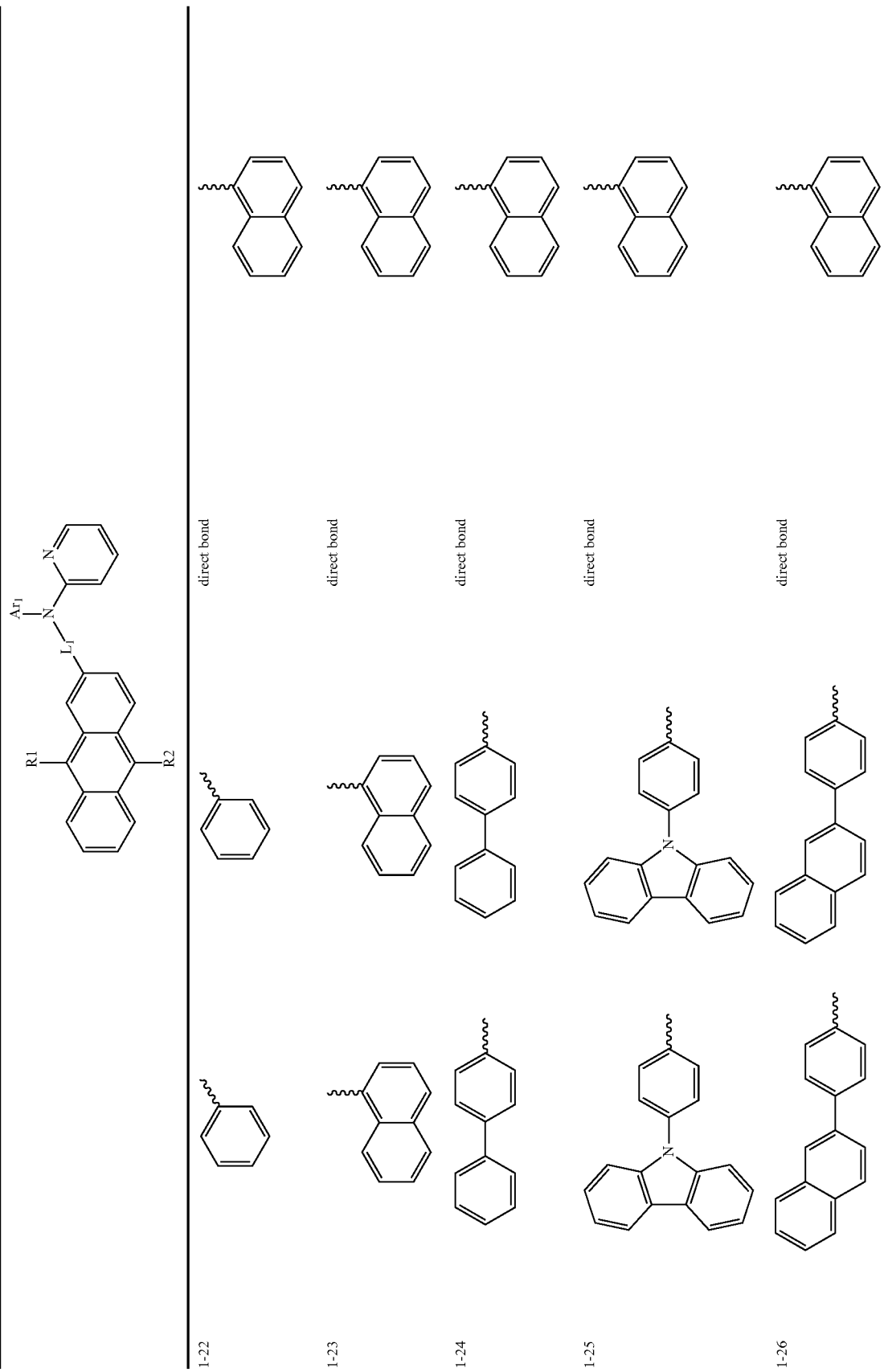

TABLE 1-continued
| | | | | |
|---|---|---|---|---|
| 1-27 | 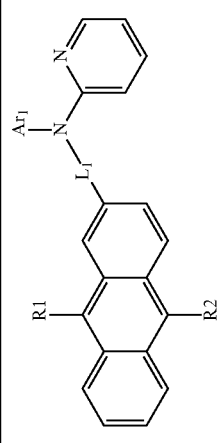 | 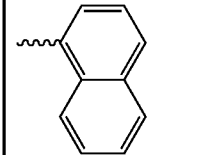 | direct bond | 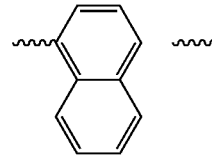 |
| 1-28 | | 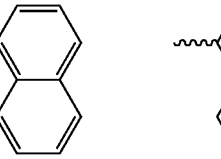 | direct bond | 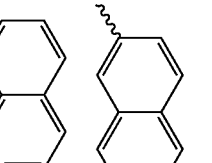 |
| 1-29 | | 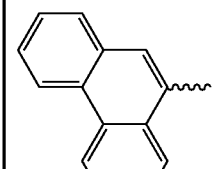 | direct bond | 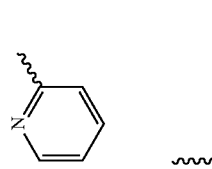 |
| 1-30 | | 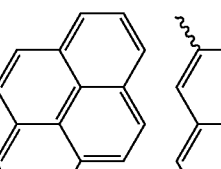 | direct bond | 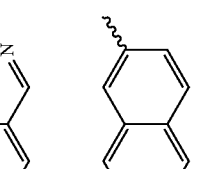 |
| 1-31 | | 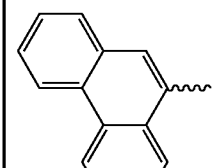 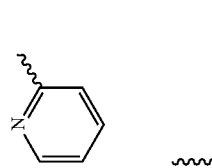 | direct bond | 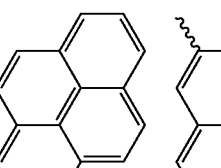 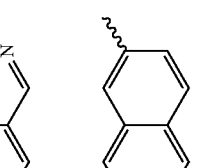 |

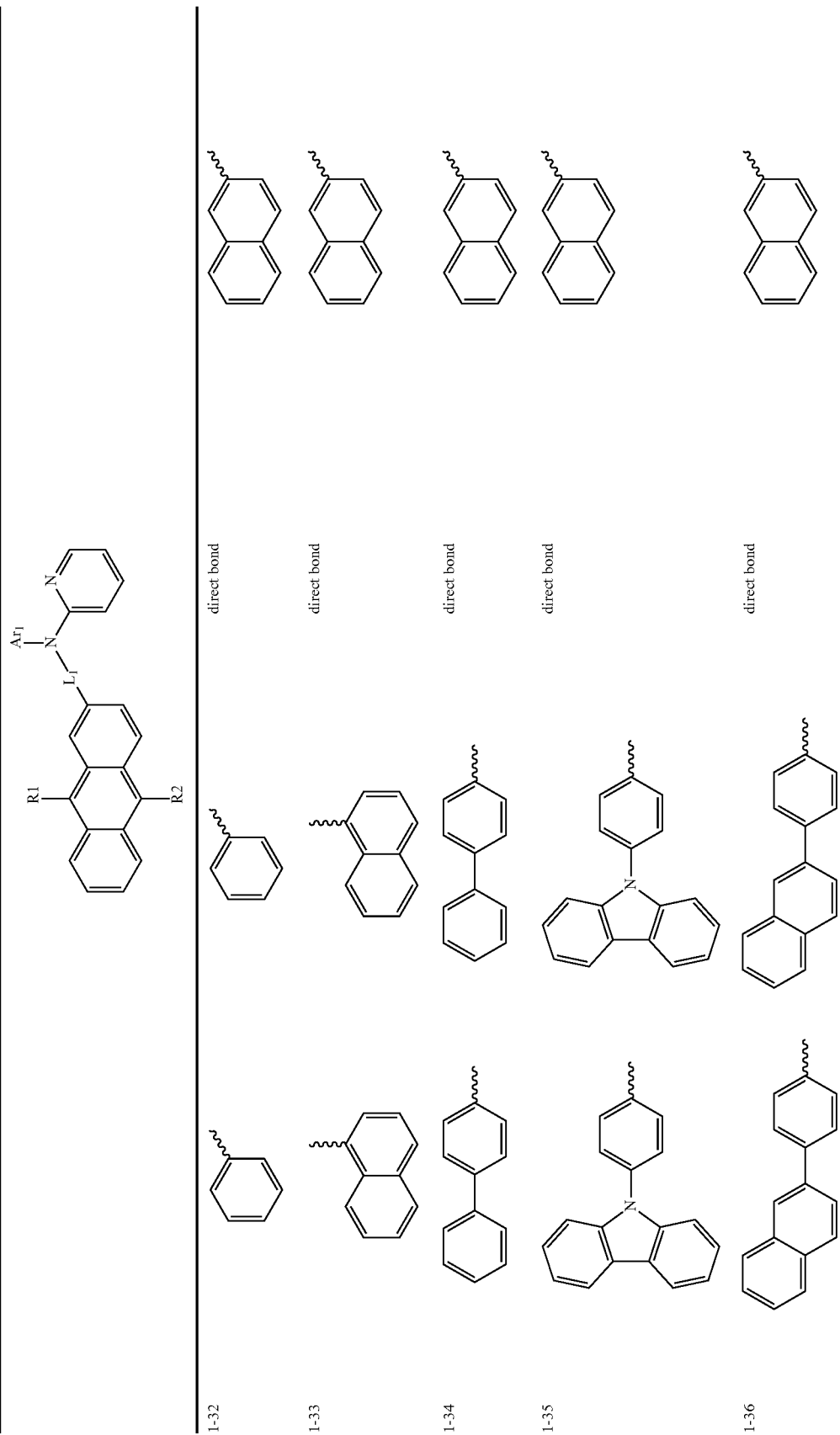

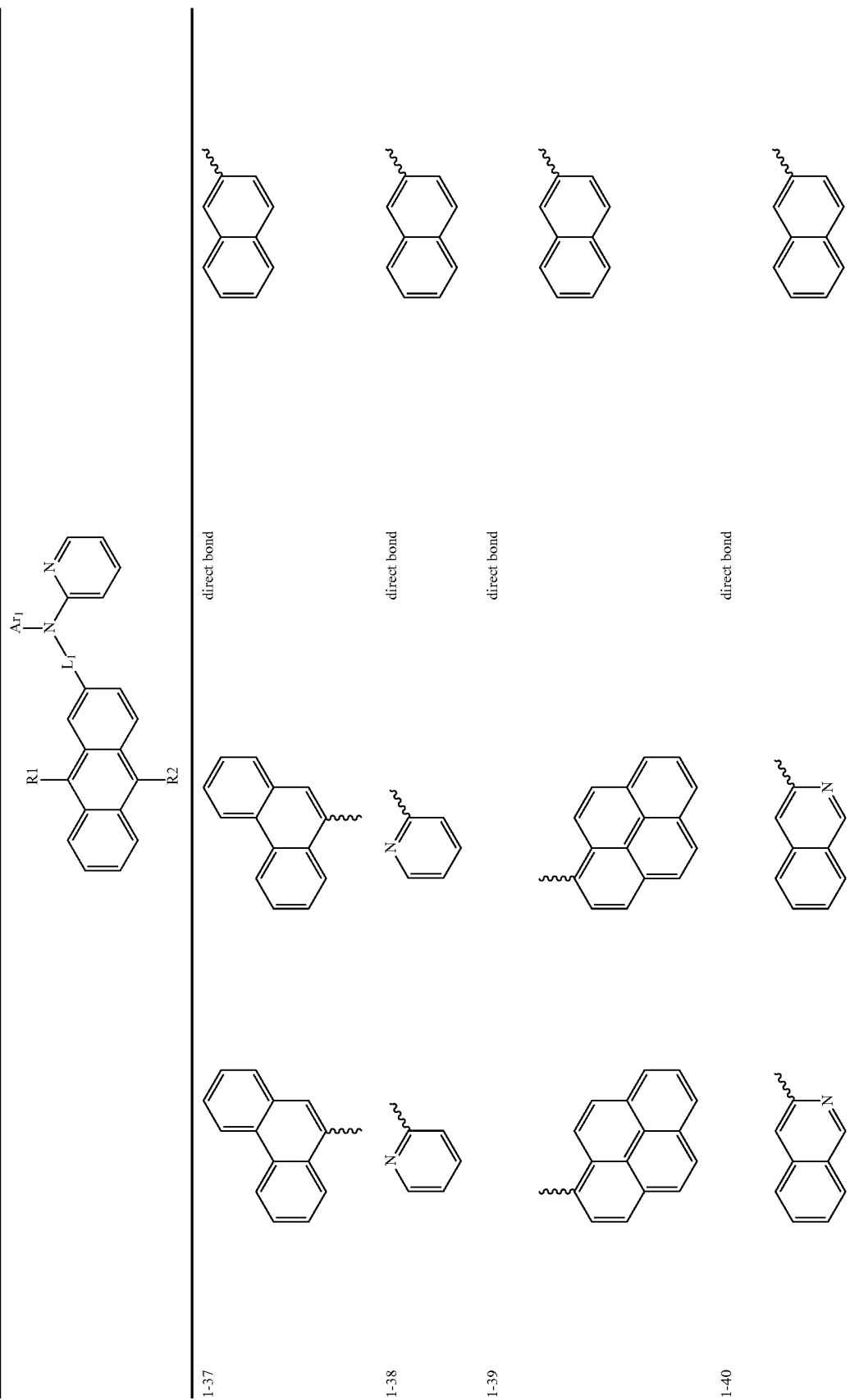

TABLE 1-continued
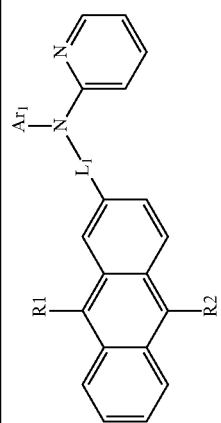
| | | | |
|---|---|---|---|
| 1-41 |  |  | direct bond |
| 1-42 |  | 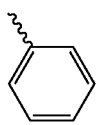 | direct bond |
| 1-43 | 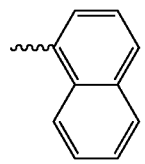 | 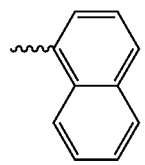 | direct bond |
| 1-44 | 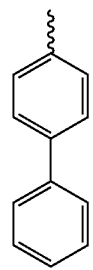 | 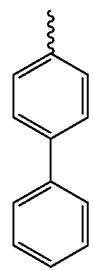 | direct bond |

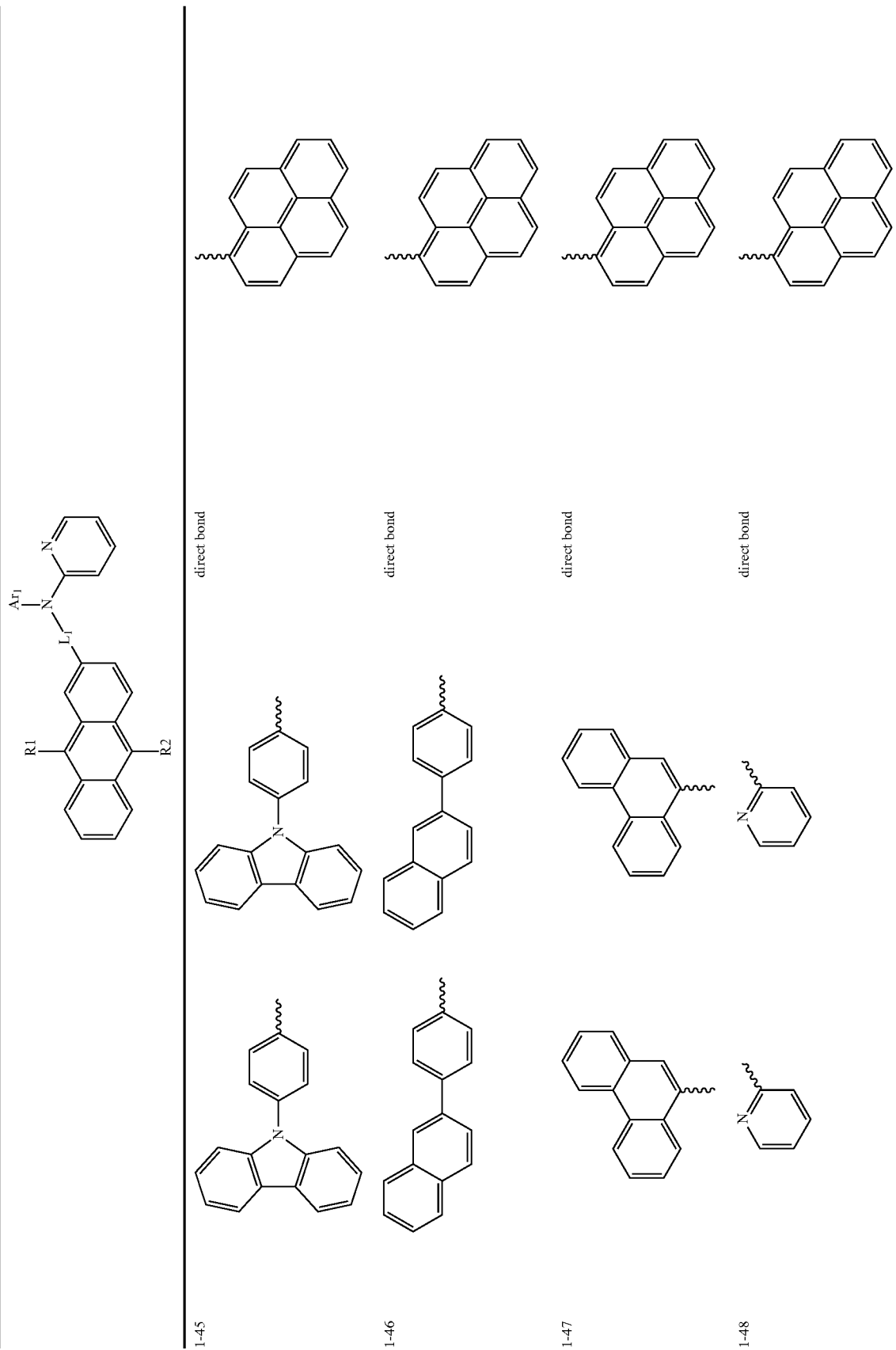

TABLE 1-continued
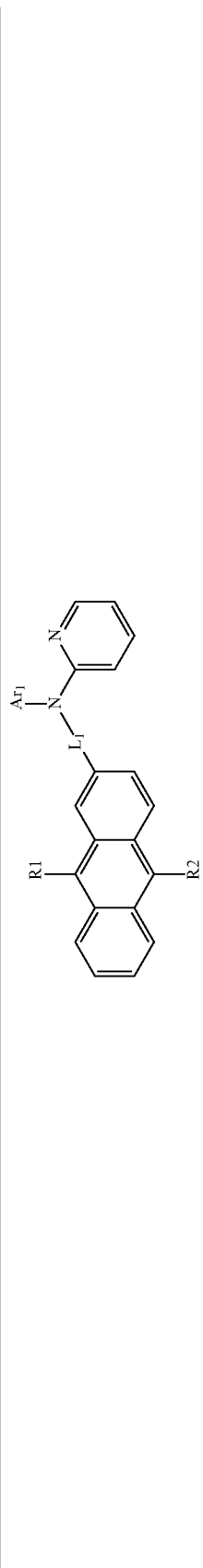
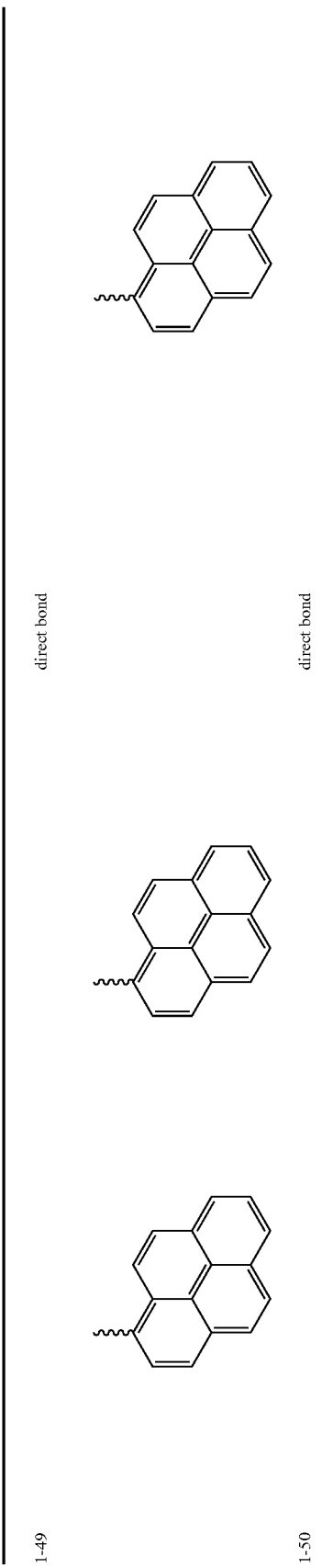
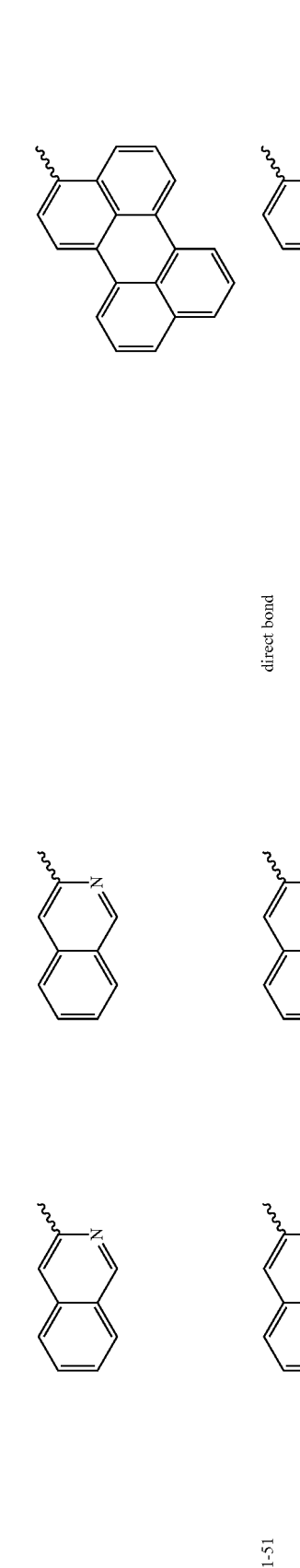

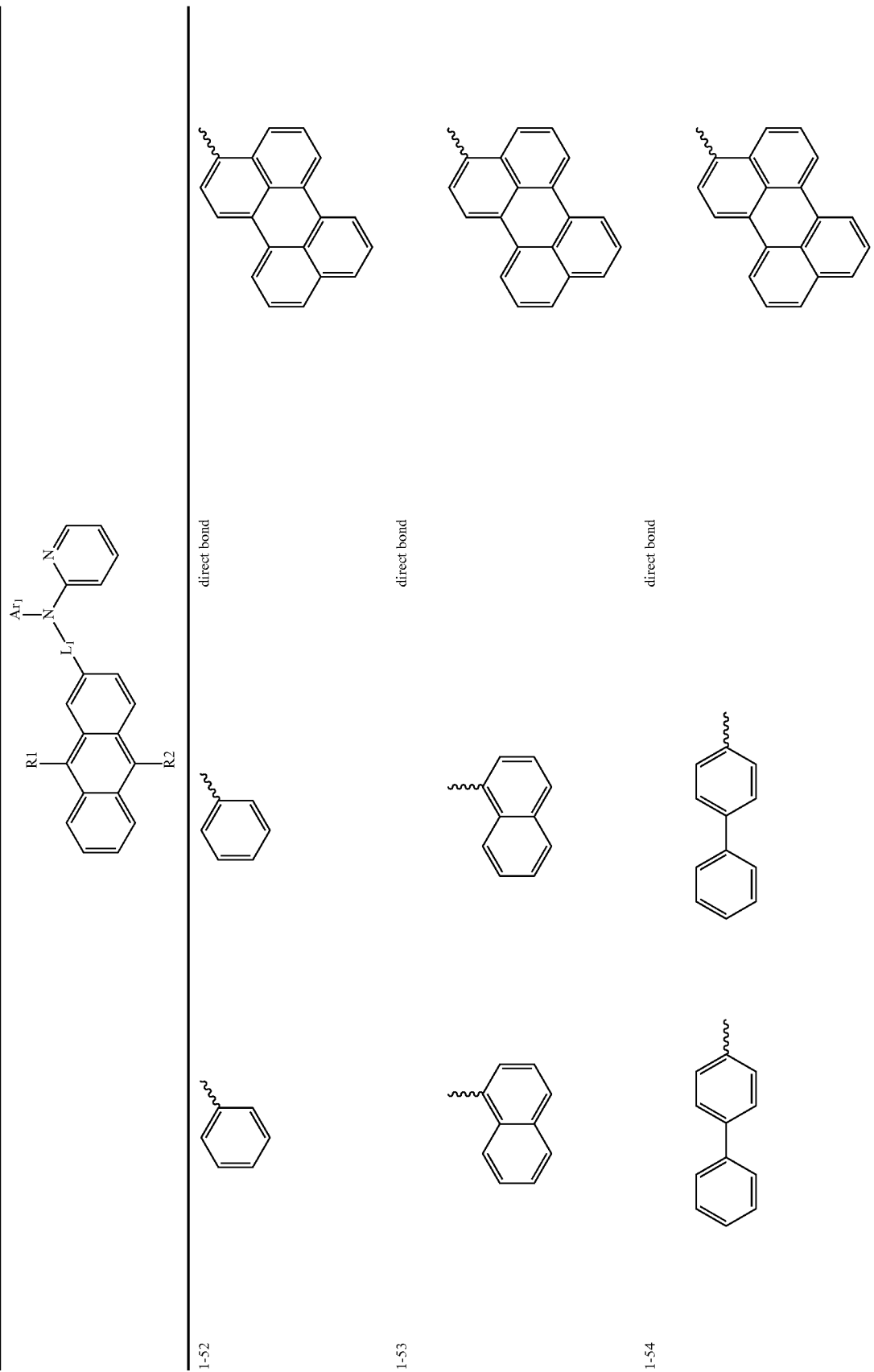

TABLE 1-continued
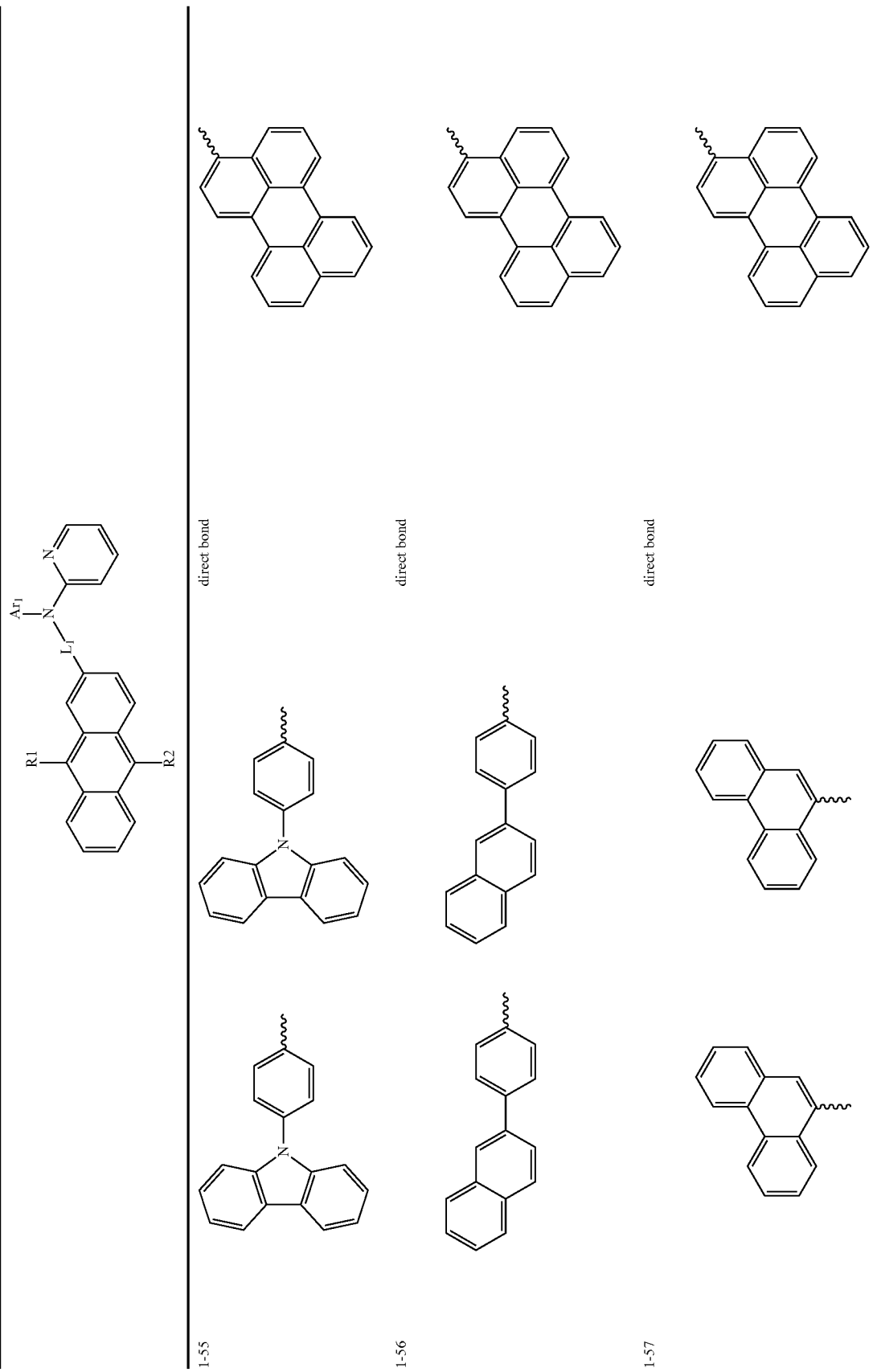

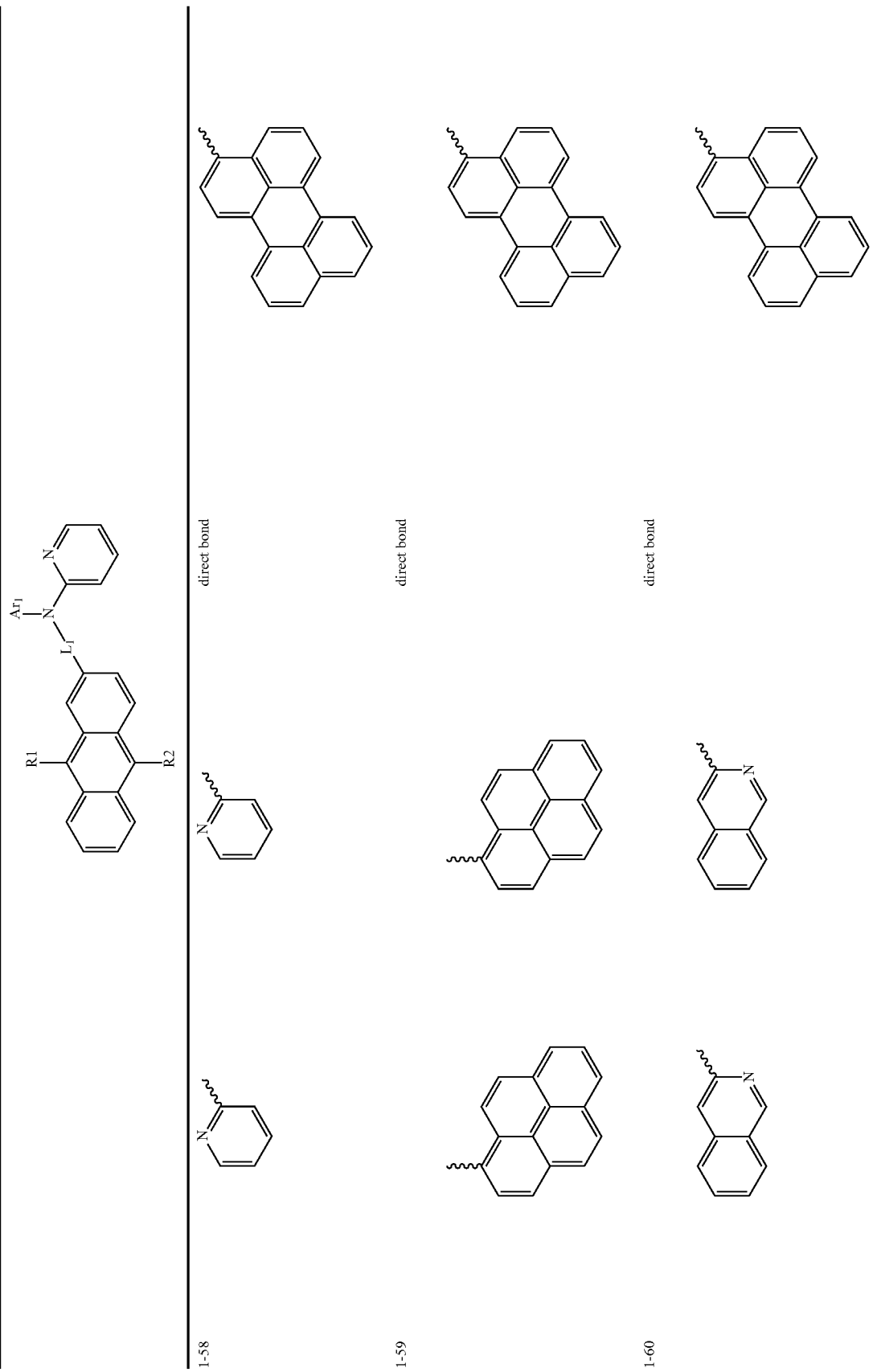

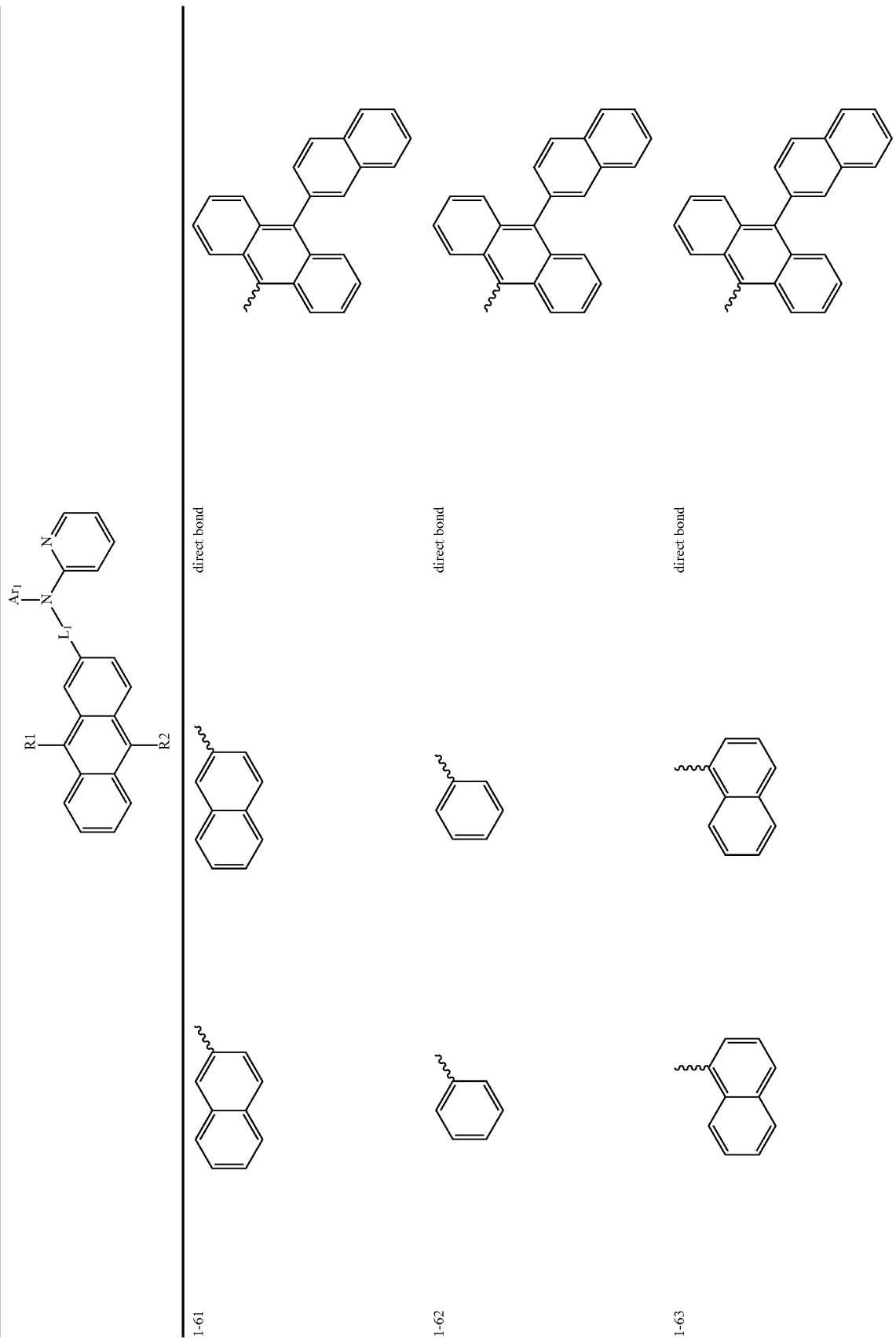

TABLE 1-continued
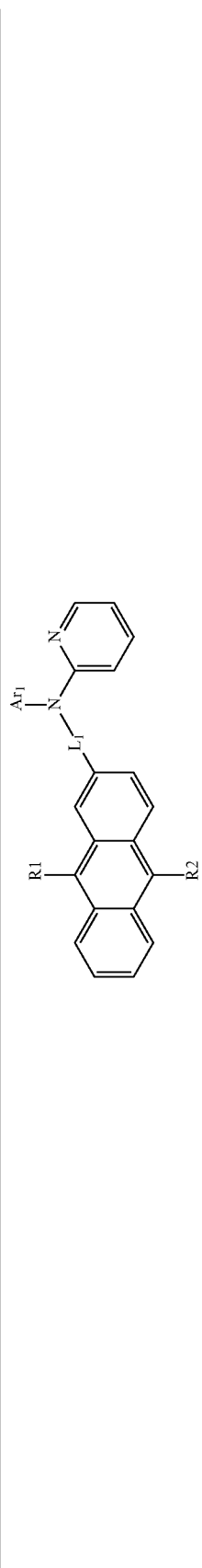
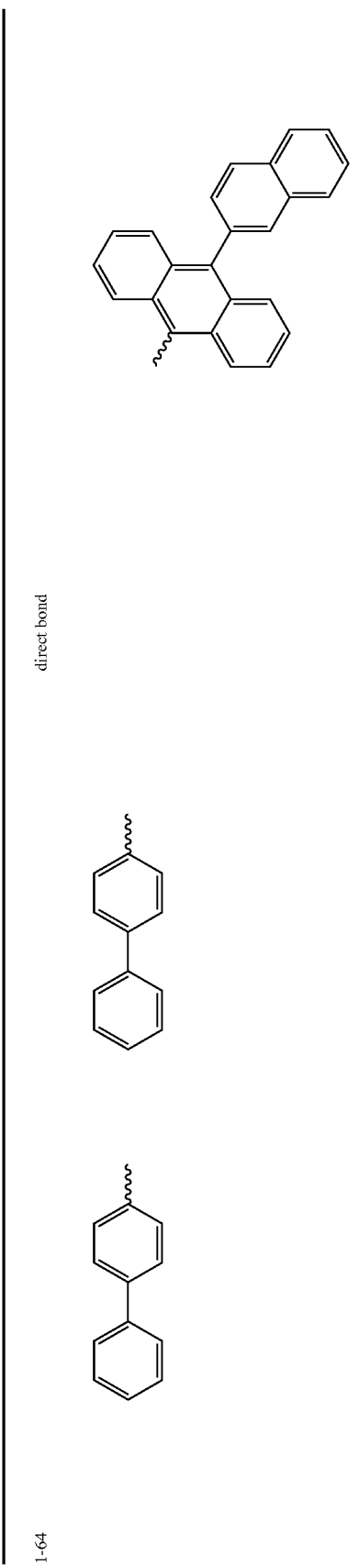
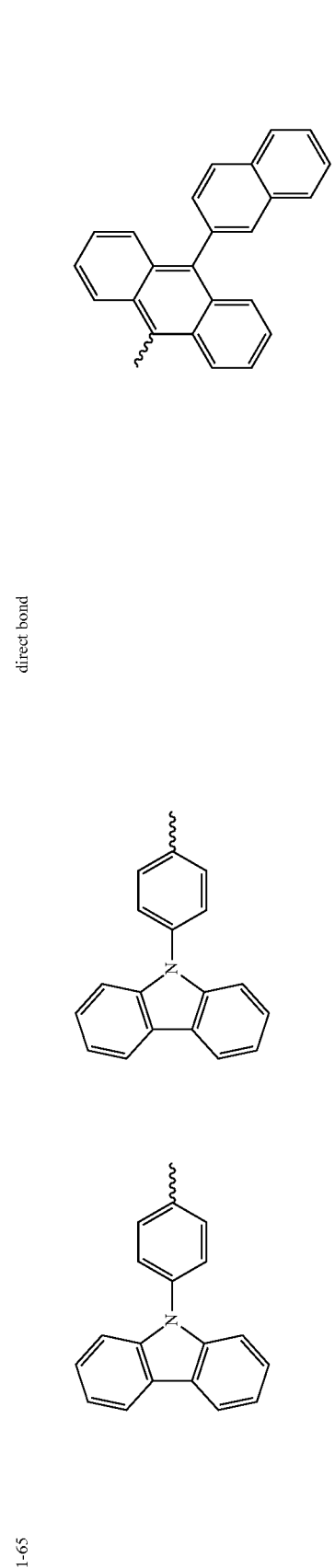
| | | | | |
|---|---|---|---|---|
| 1-64 | | | direct bond | |
| 1-65 | | | direct bond | |

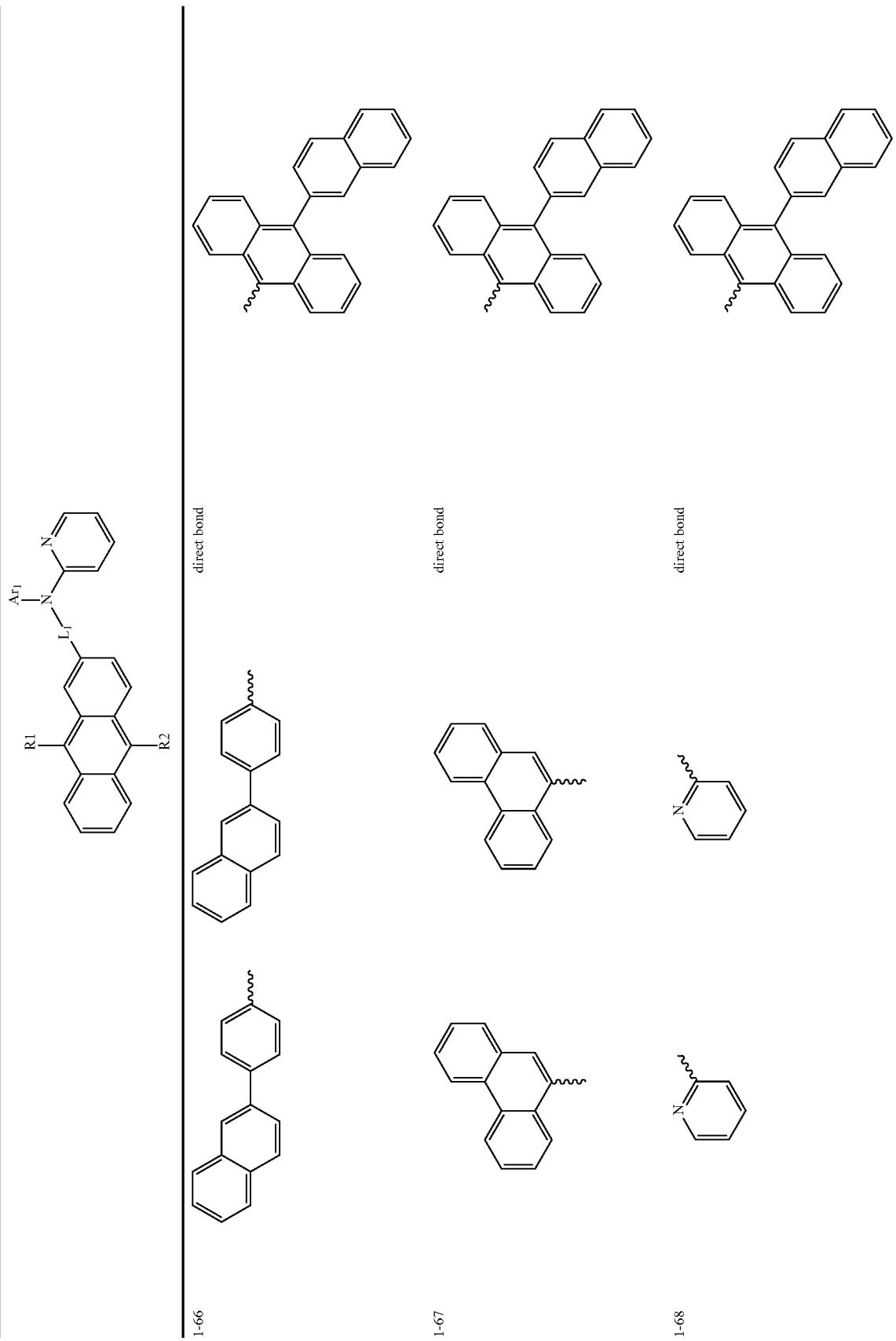

TABLE 1-continued
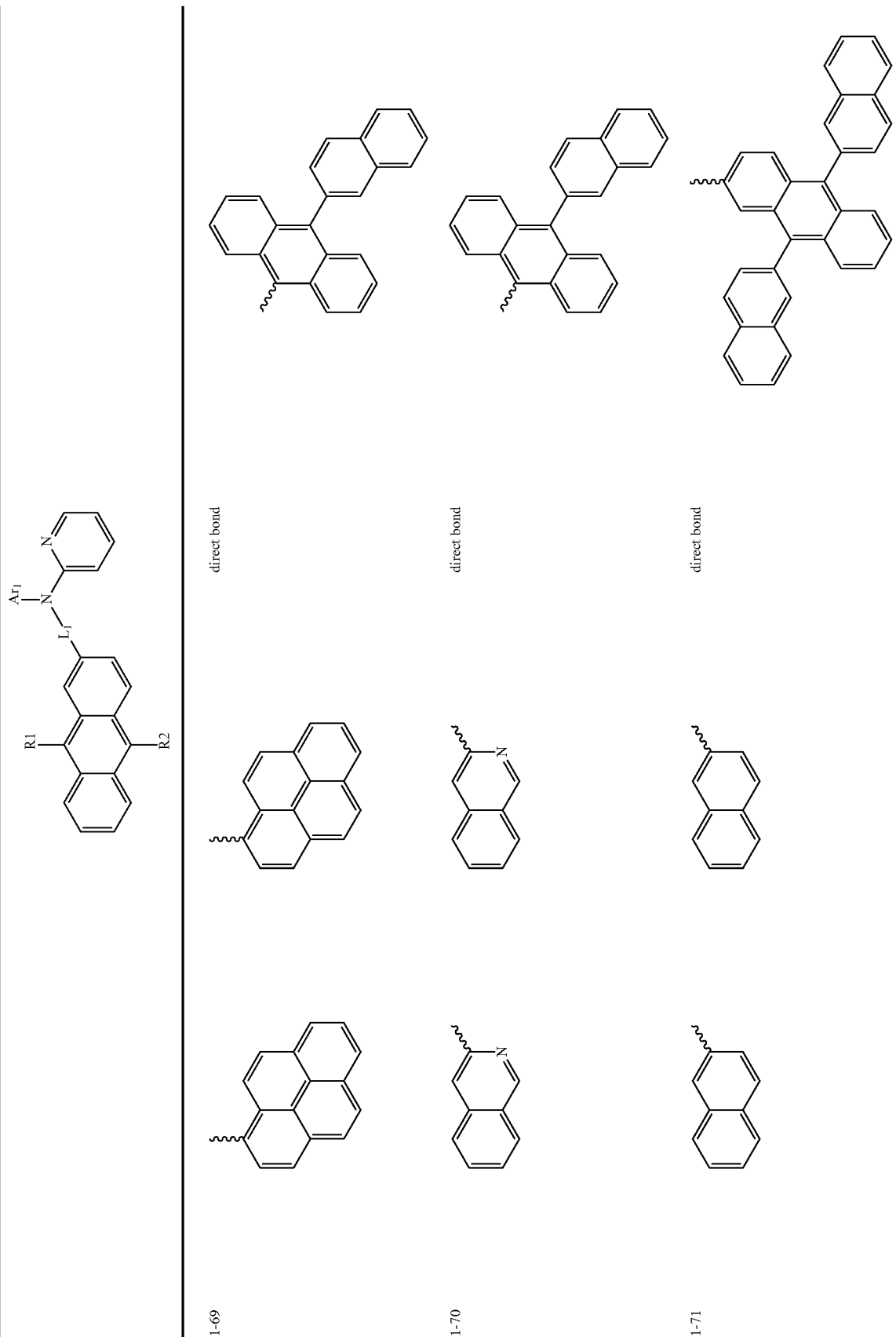

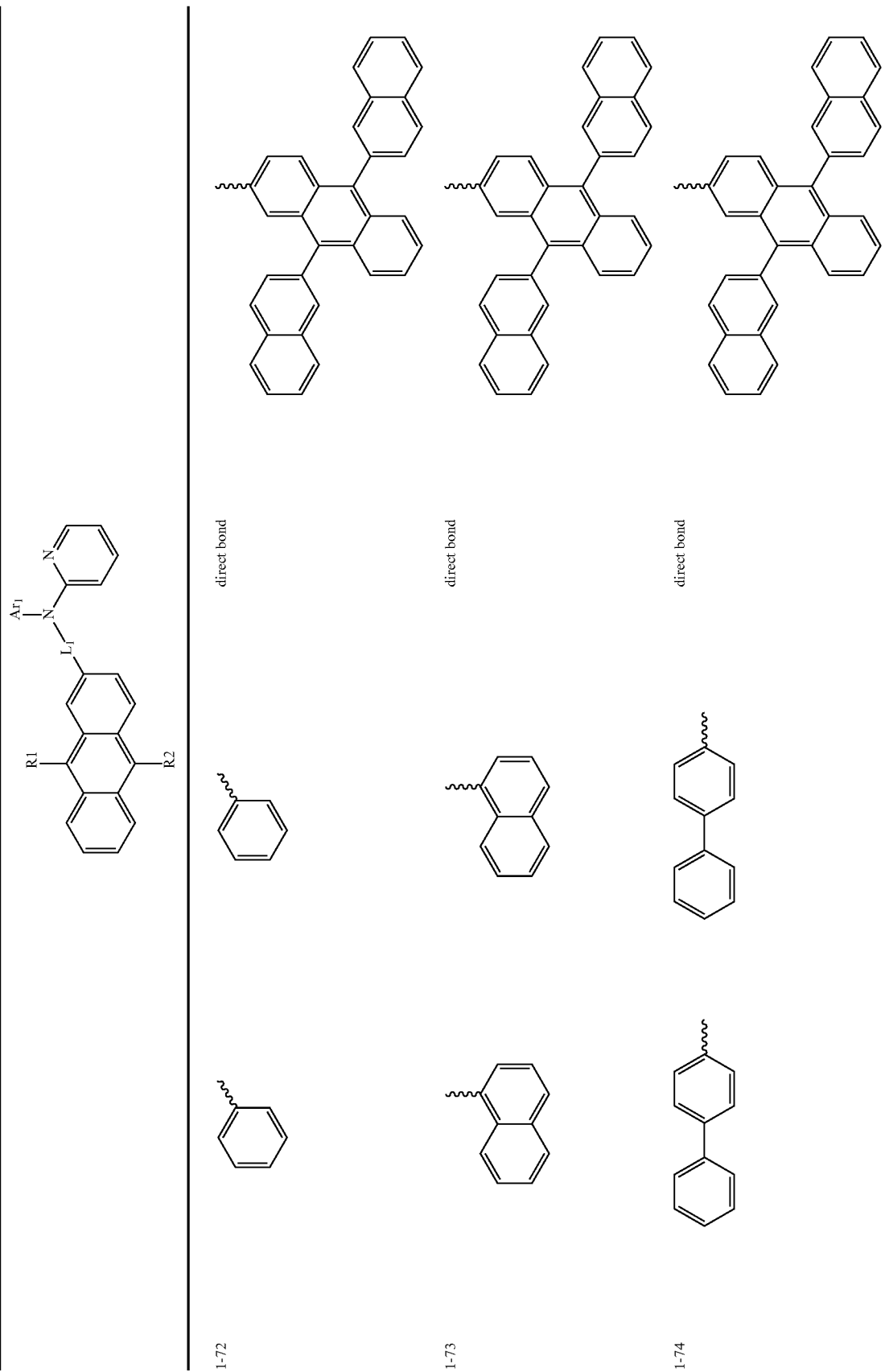

TABLE 1-continued
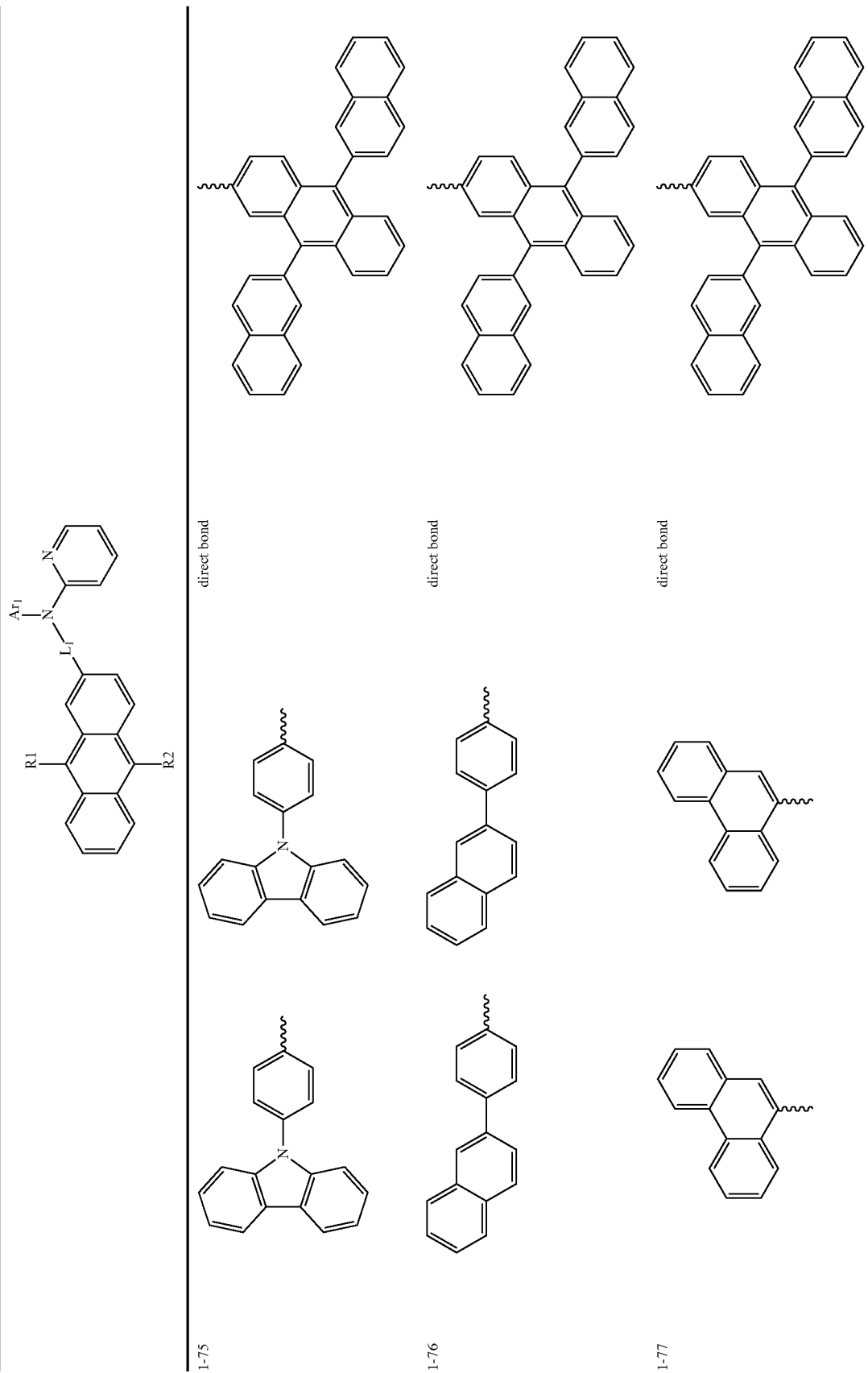

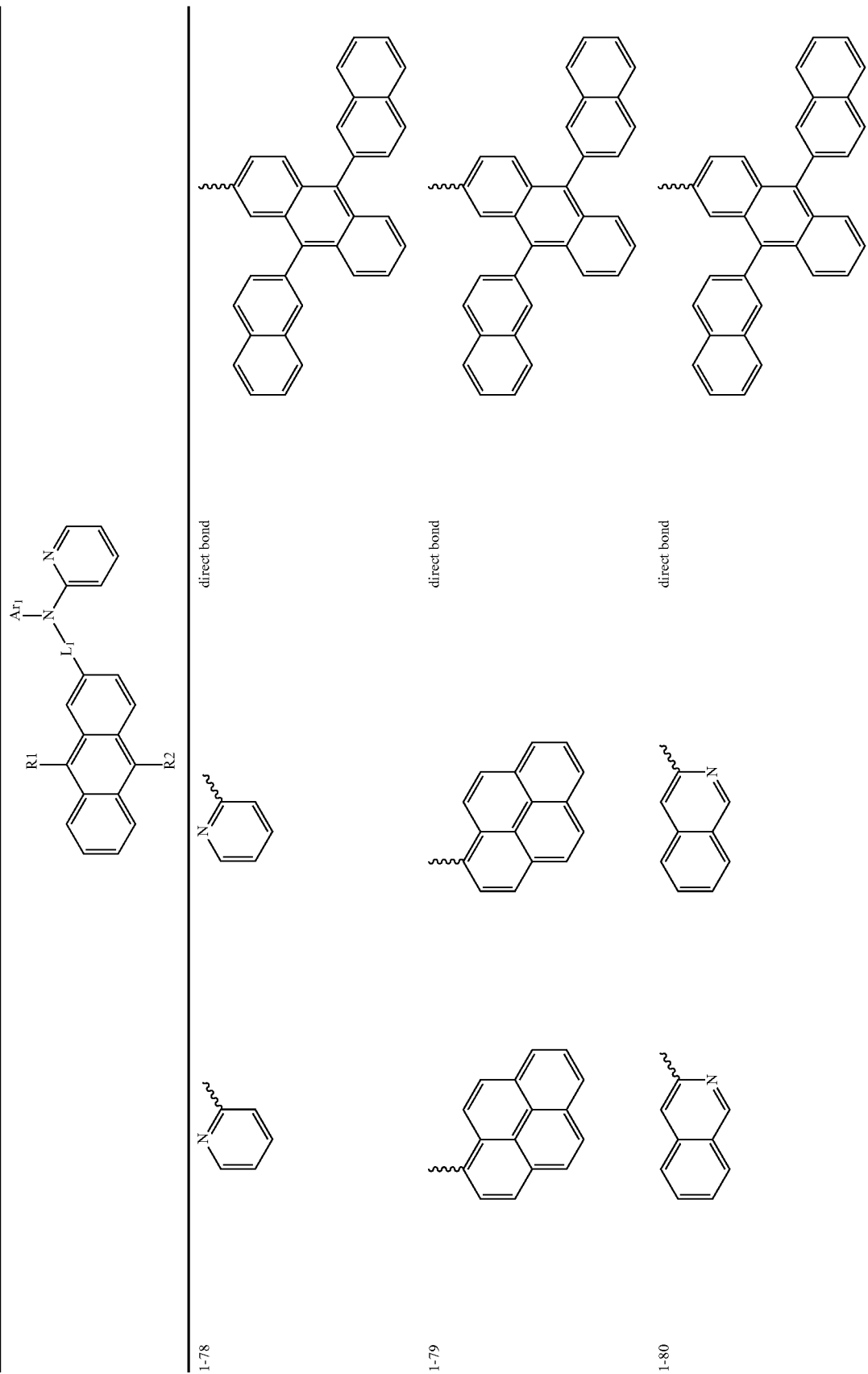

TABLE 1-continued
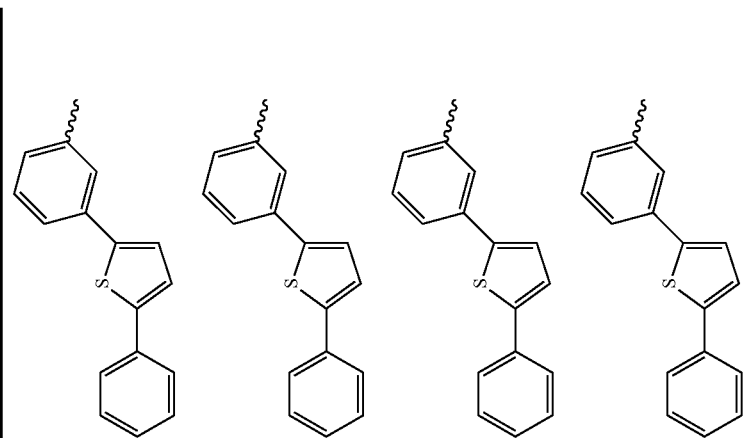
| | | | | |
|---|---|---|---|---|
| 1-81 | 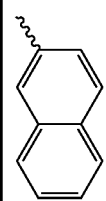 | 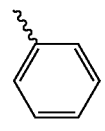 | direct bond | 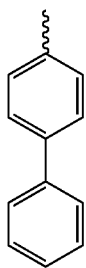 |
| 1-82 | phenyl | phenyl | direct bond | 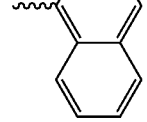 |
| 1-83 | naphthyl | naphthyl | direct bond | thiophene-phenyl |
| 1-84 | biphenyl | biphenyl | direct bond | thiophene-phenyl |

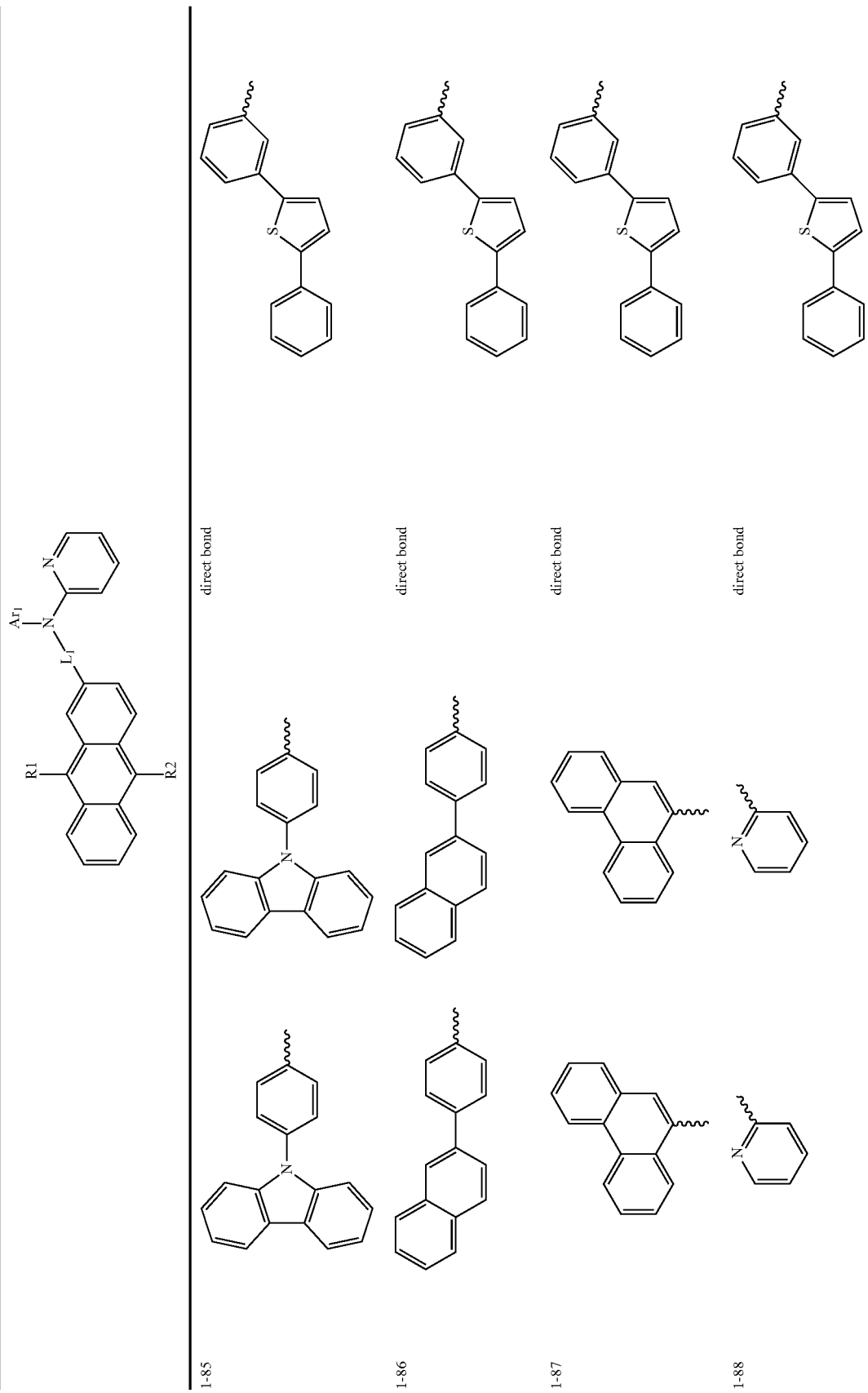

TABLE 1-continued
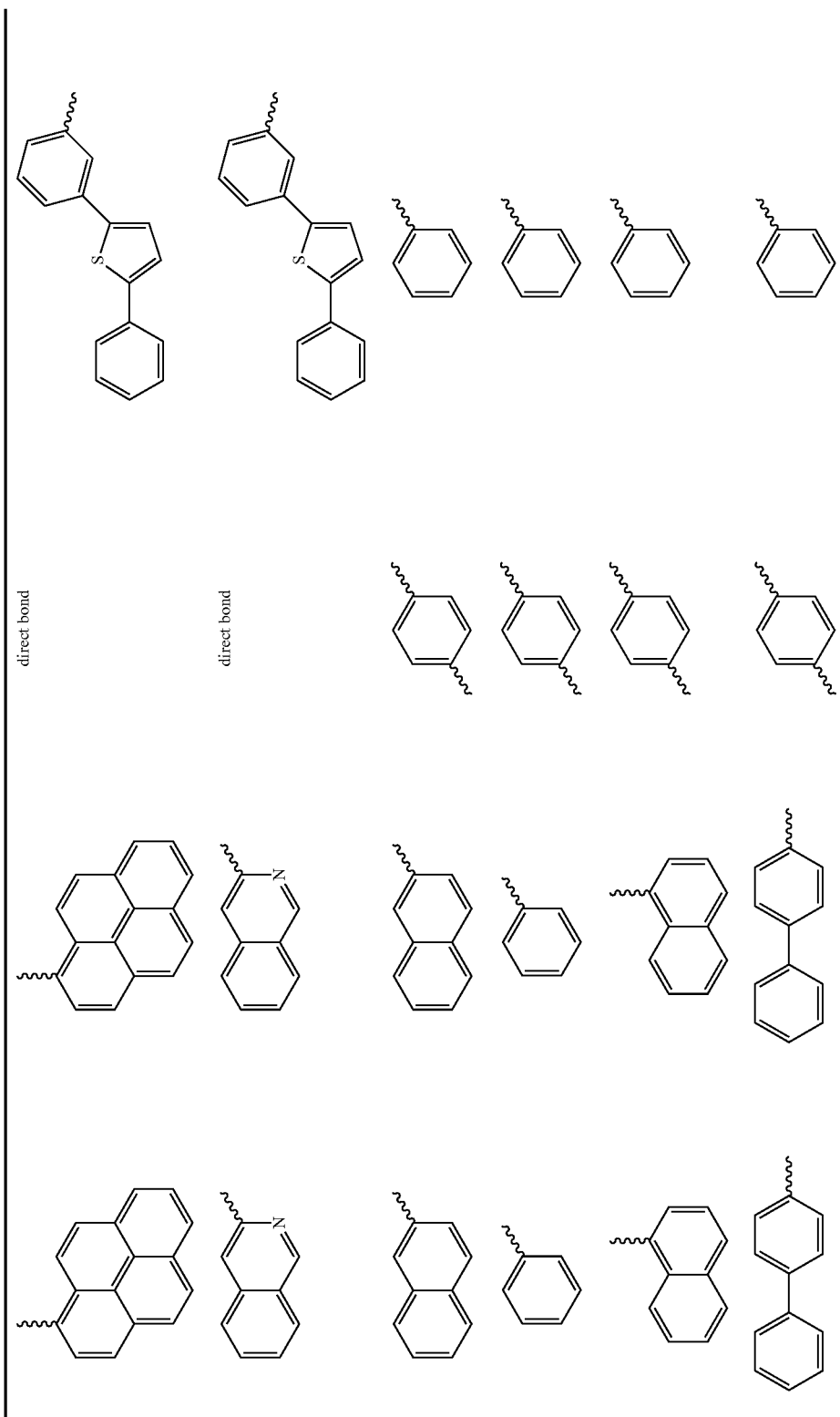

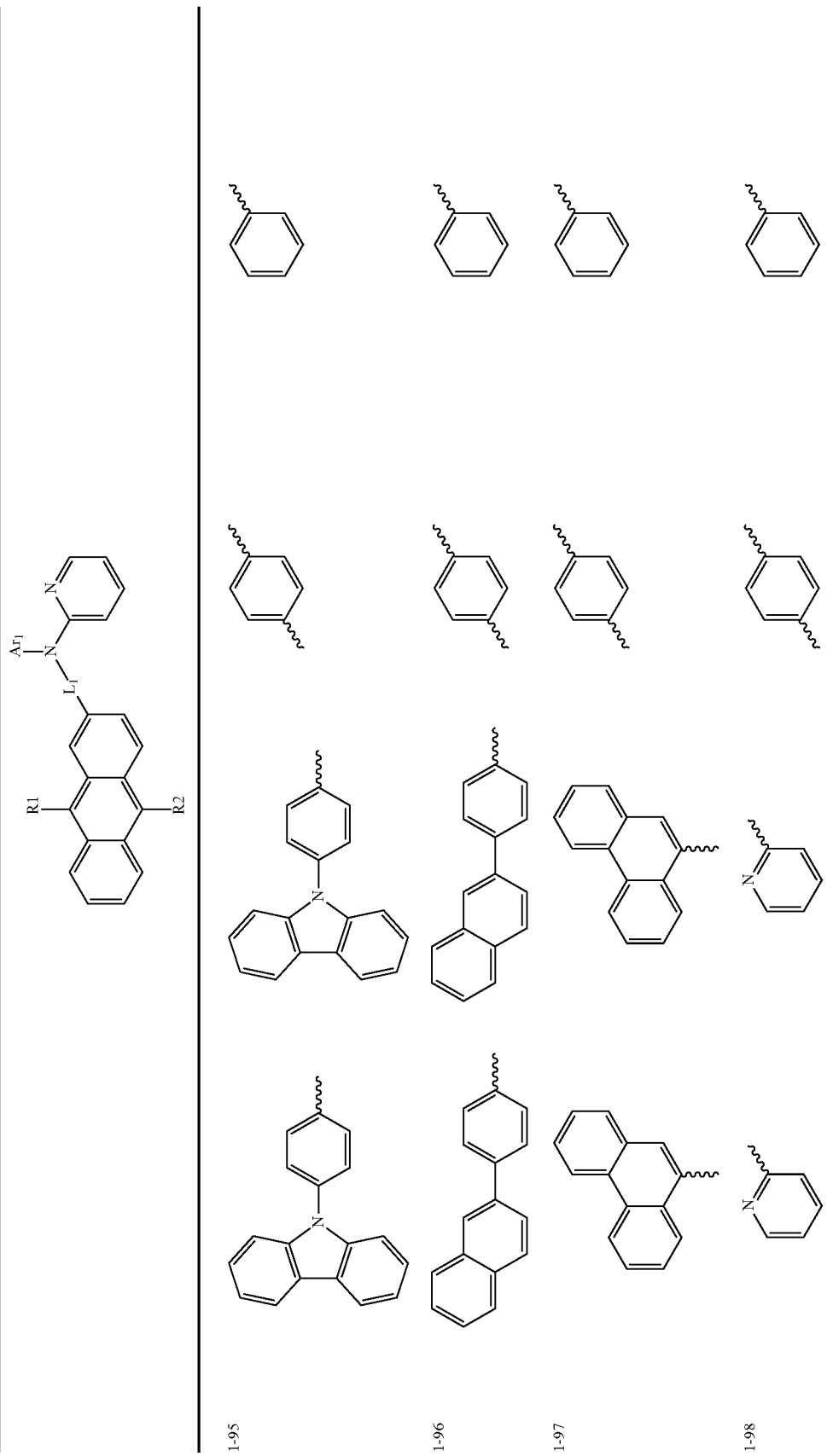

TABLE 1-continued

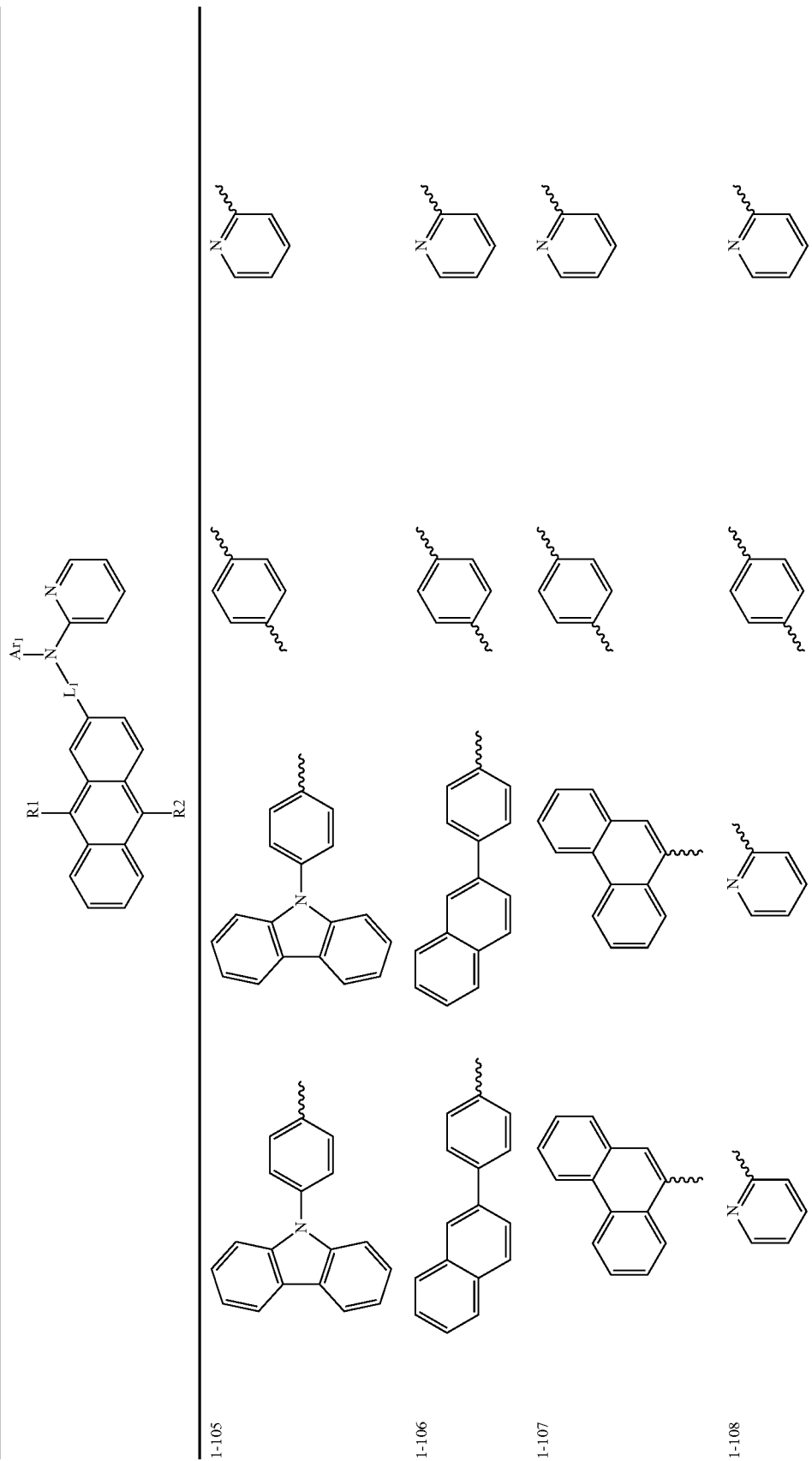

TABLE 1-continued

| | | | | |
|---|---|---|---|---|
| 1-109 | 1-110 | 1-111 | 1-112 | 1-113 |

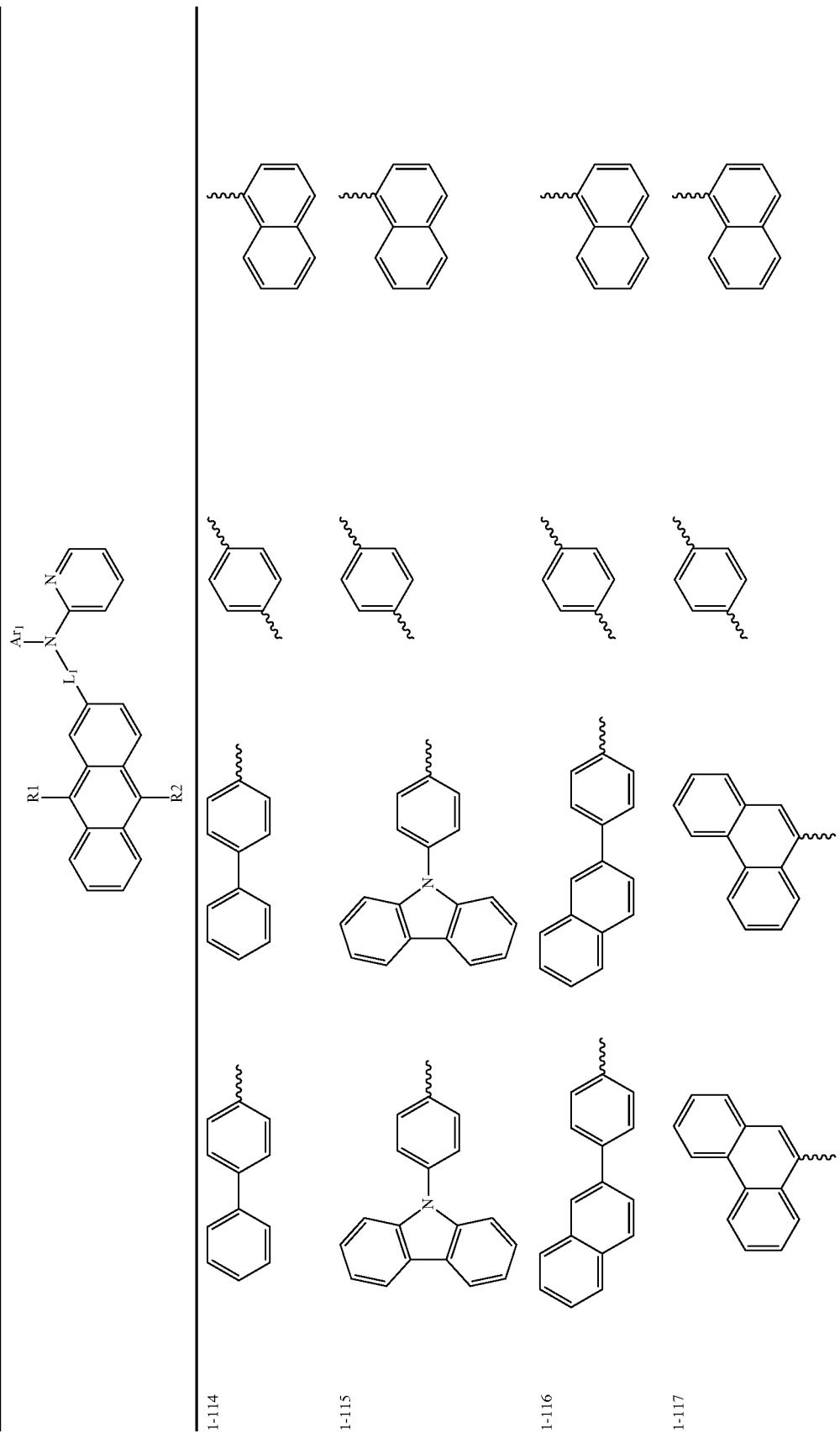

TABLE 1-continued

TABLE 1-continued
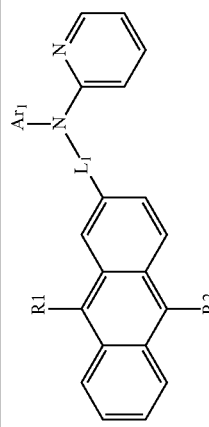
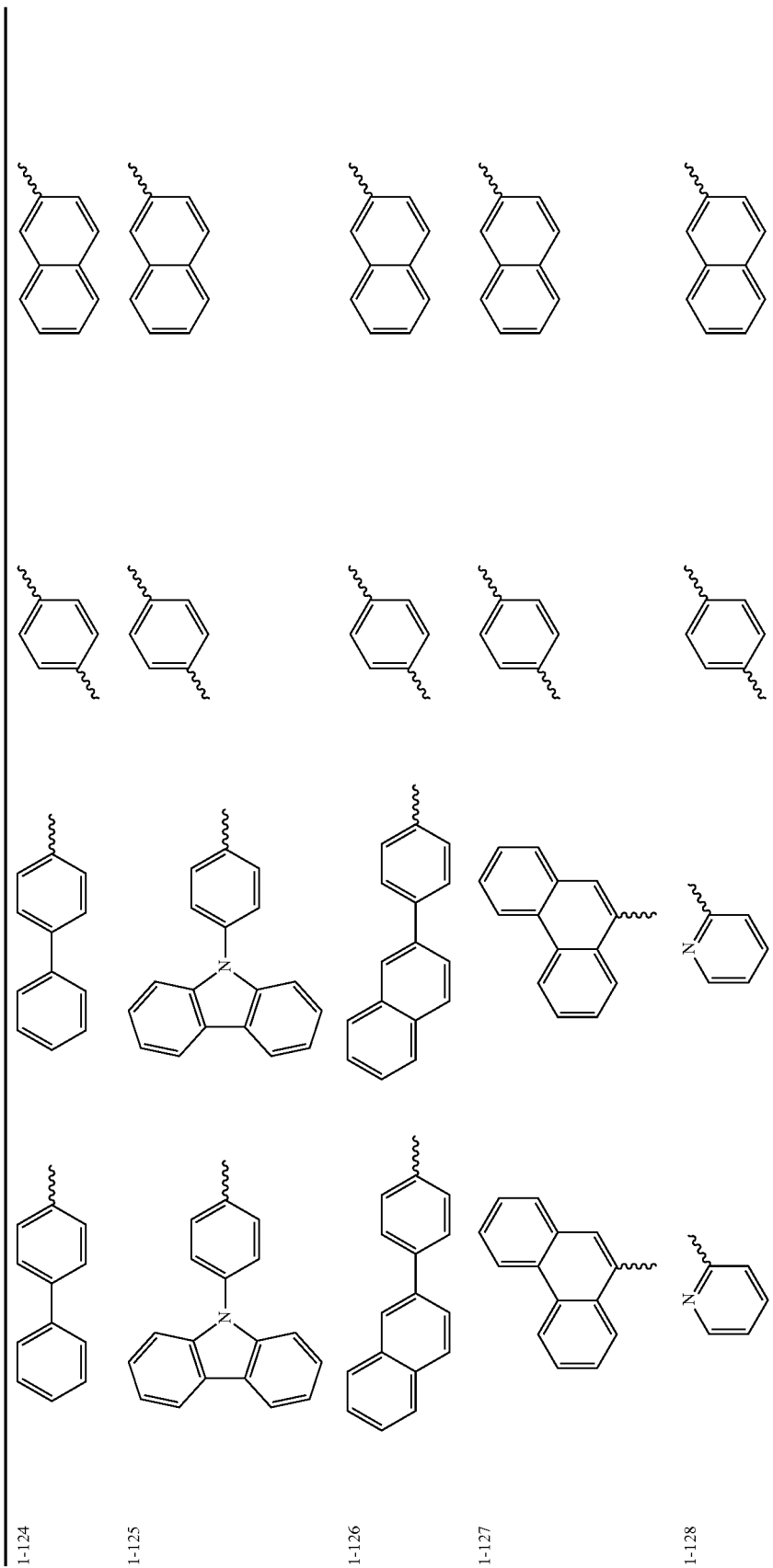
1-124
1-125
1-126
1-127
1-128

TABLE 1-continued
| | | | | |
|---|---|---|---|---|
| 1-129 | 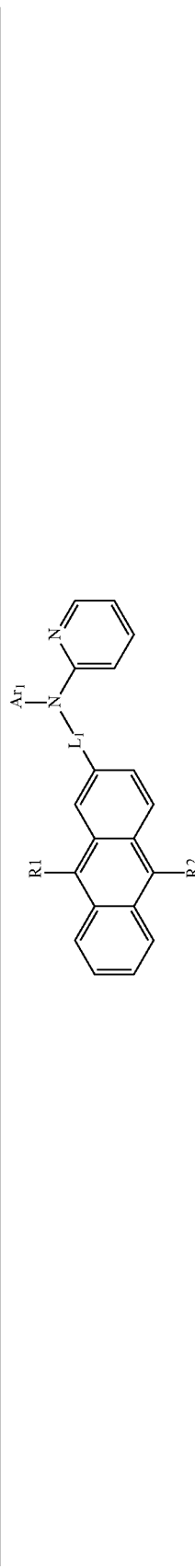 | 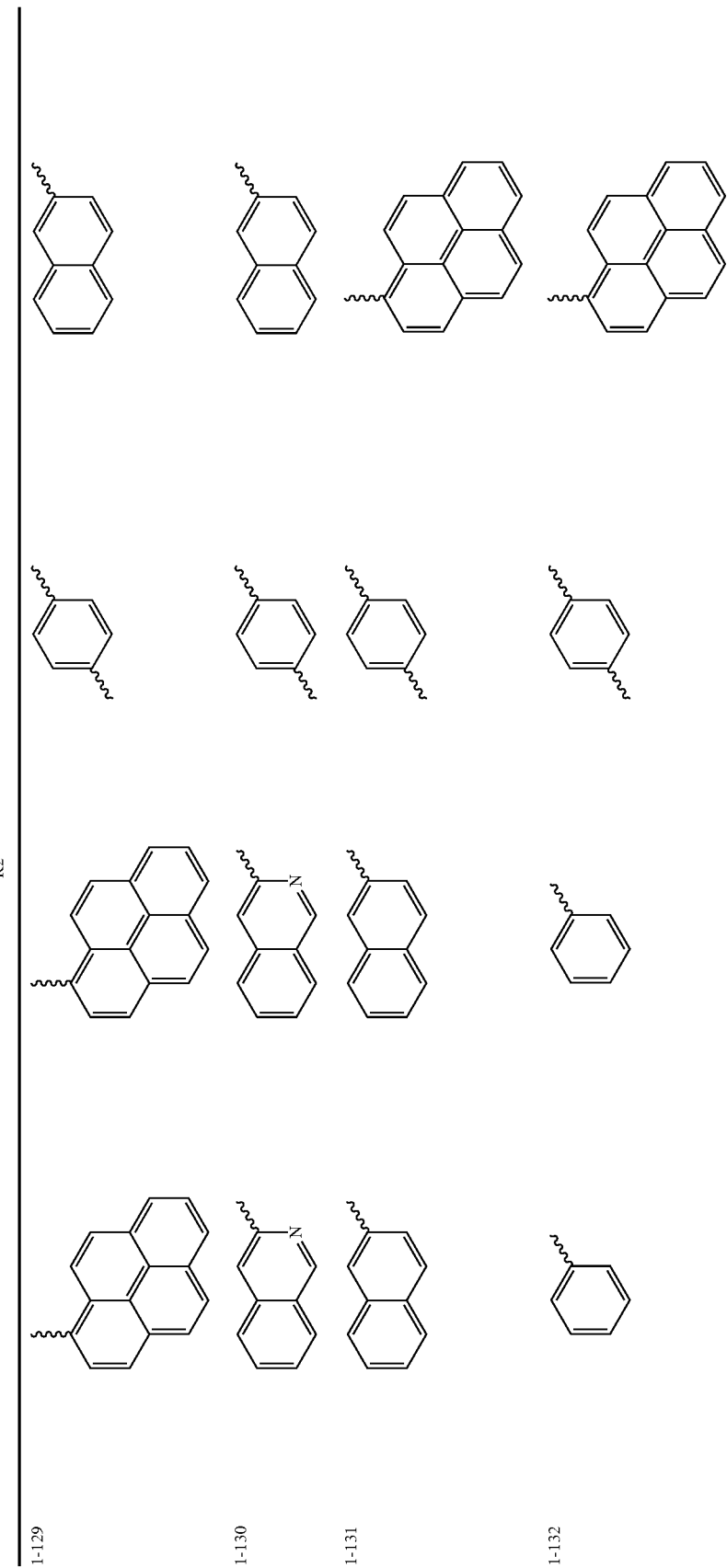 | 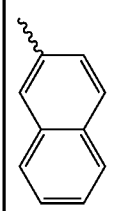 | 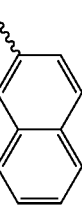 |
| 1-130 | | 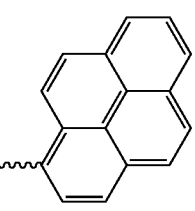 | 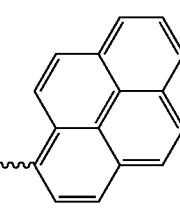 | 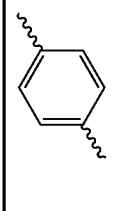 |
| 1-131 | | 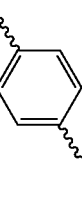 | 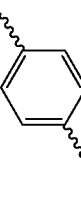 |  |
| 1-132 | | 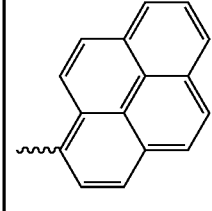 |  |  |

TABLE 1-continued
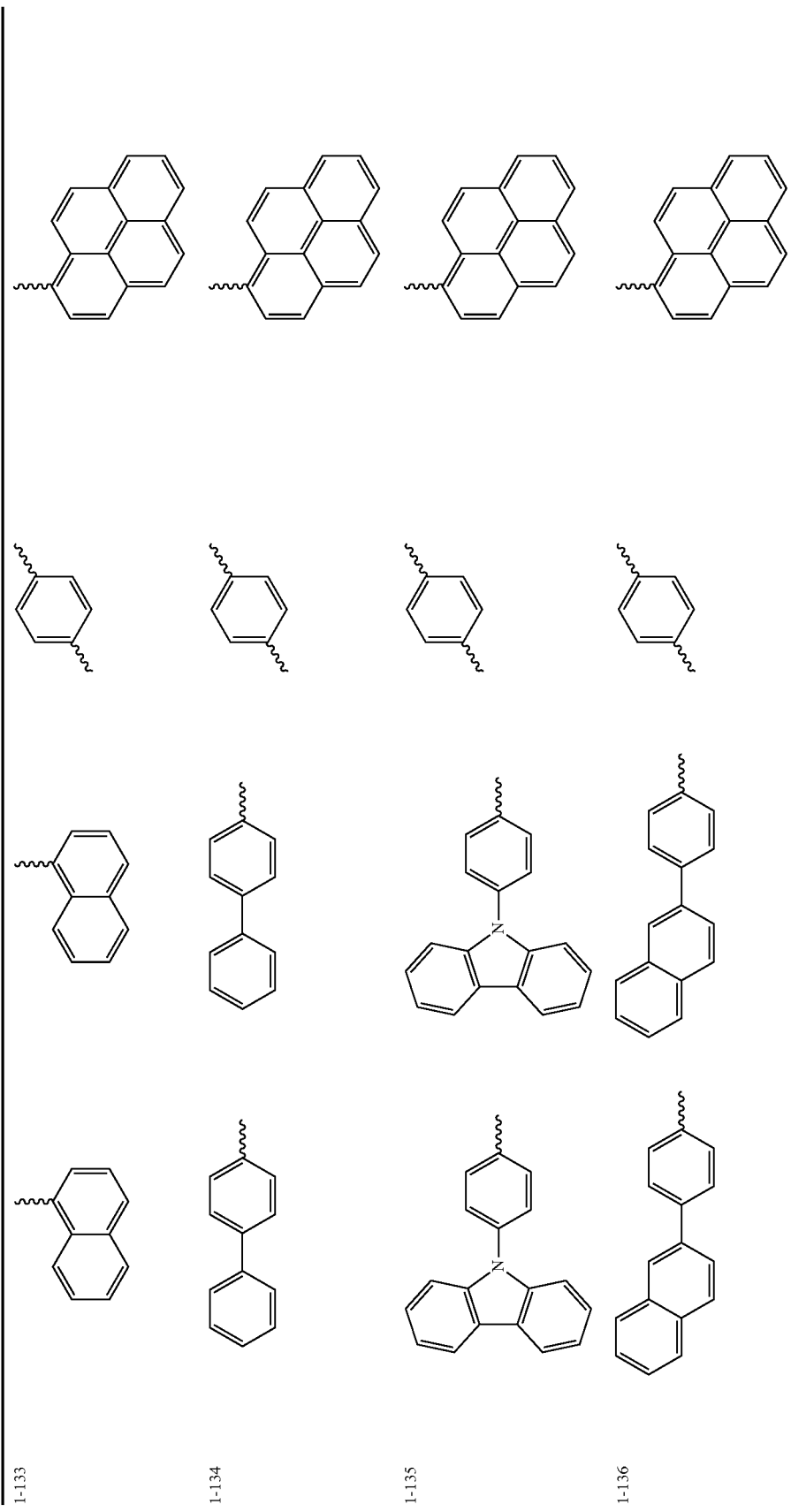

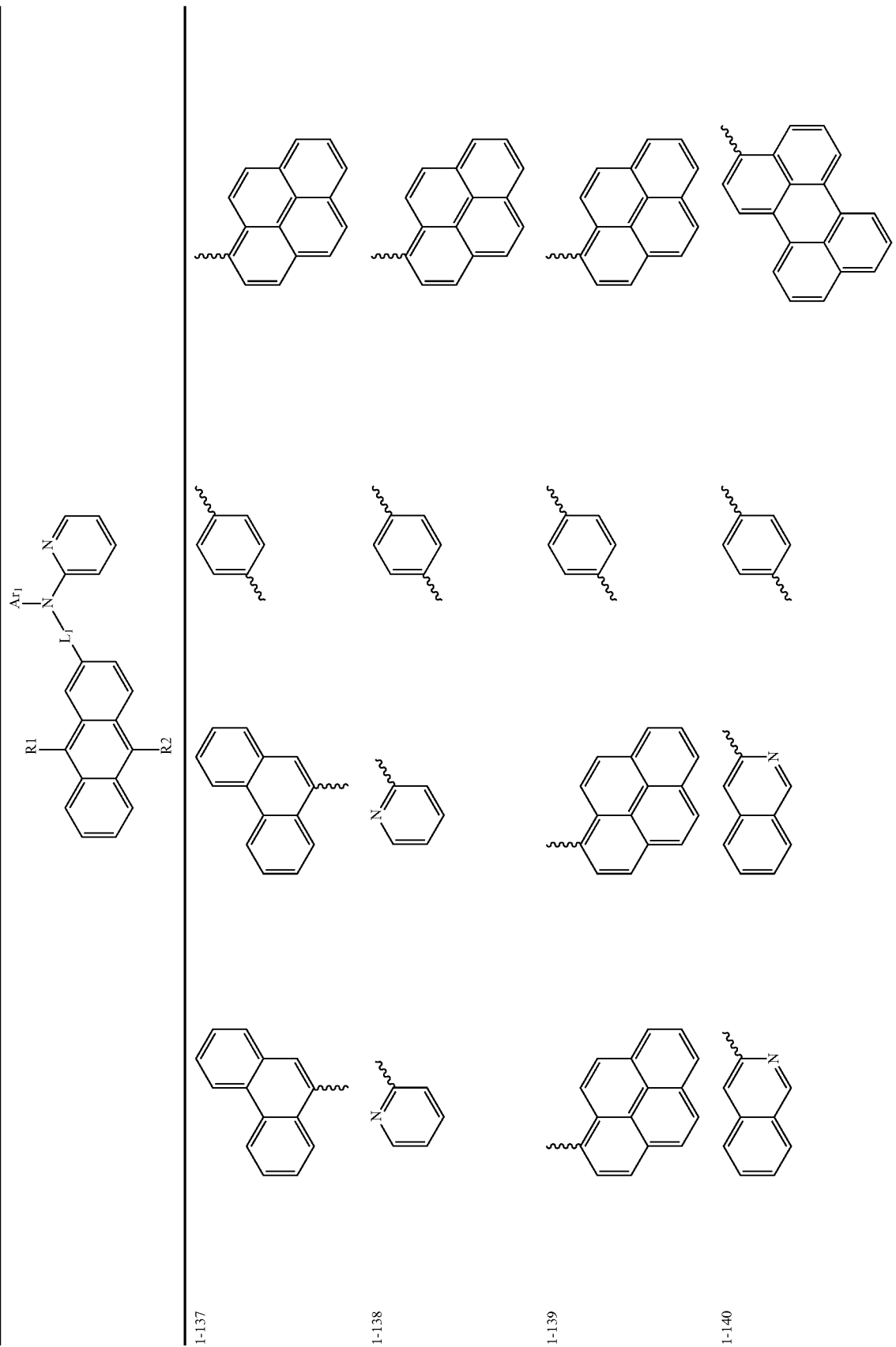

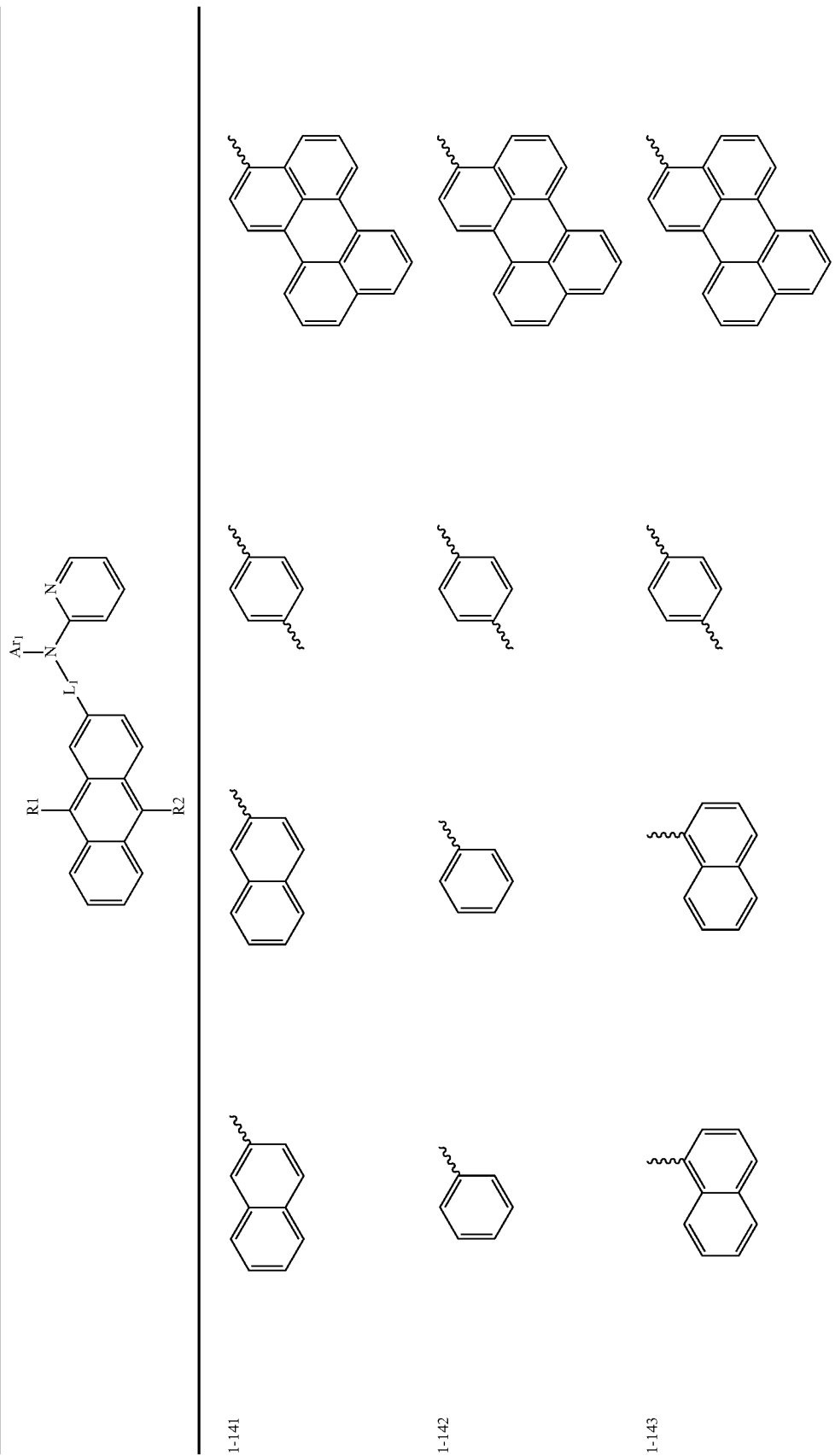

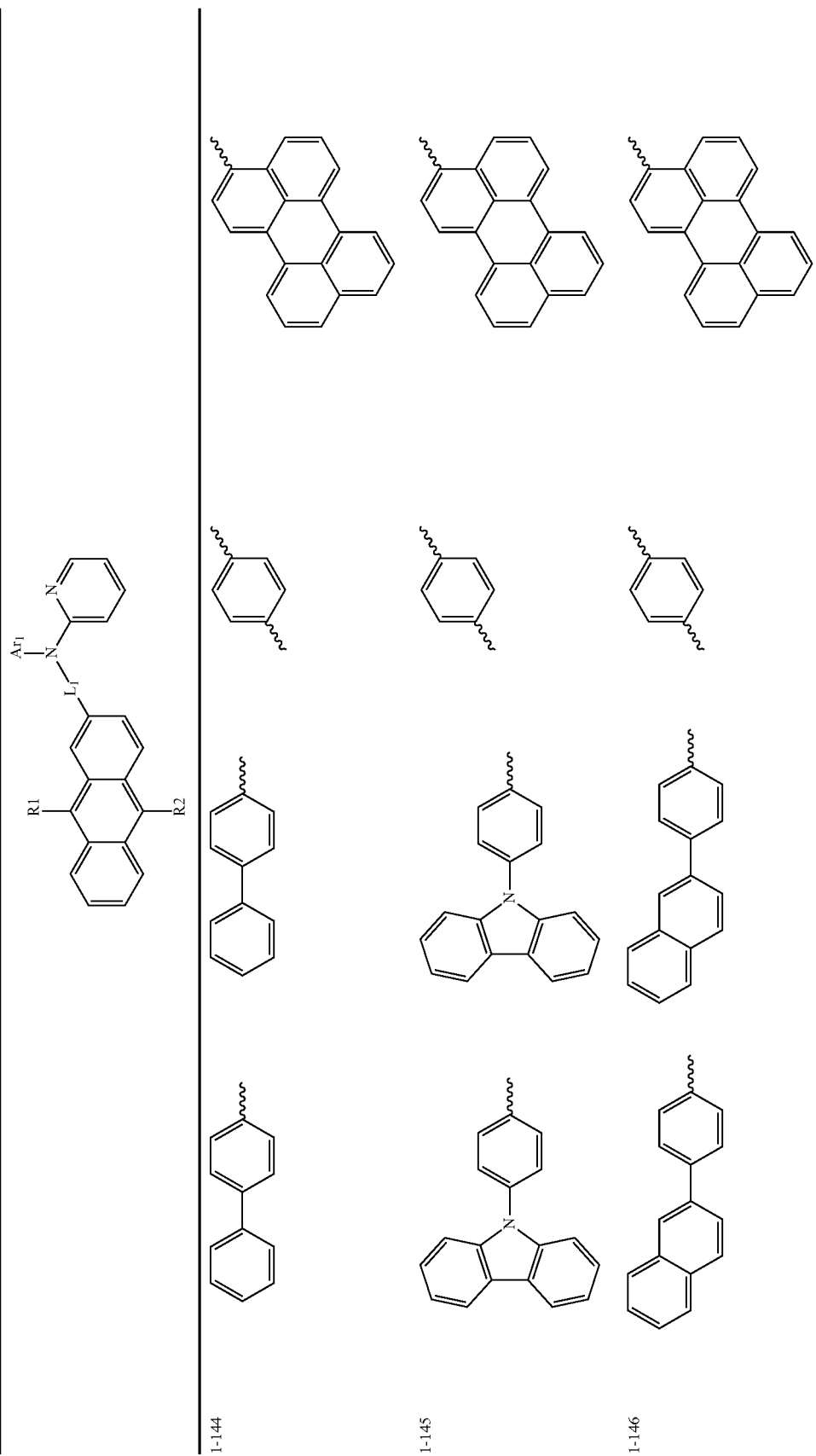

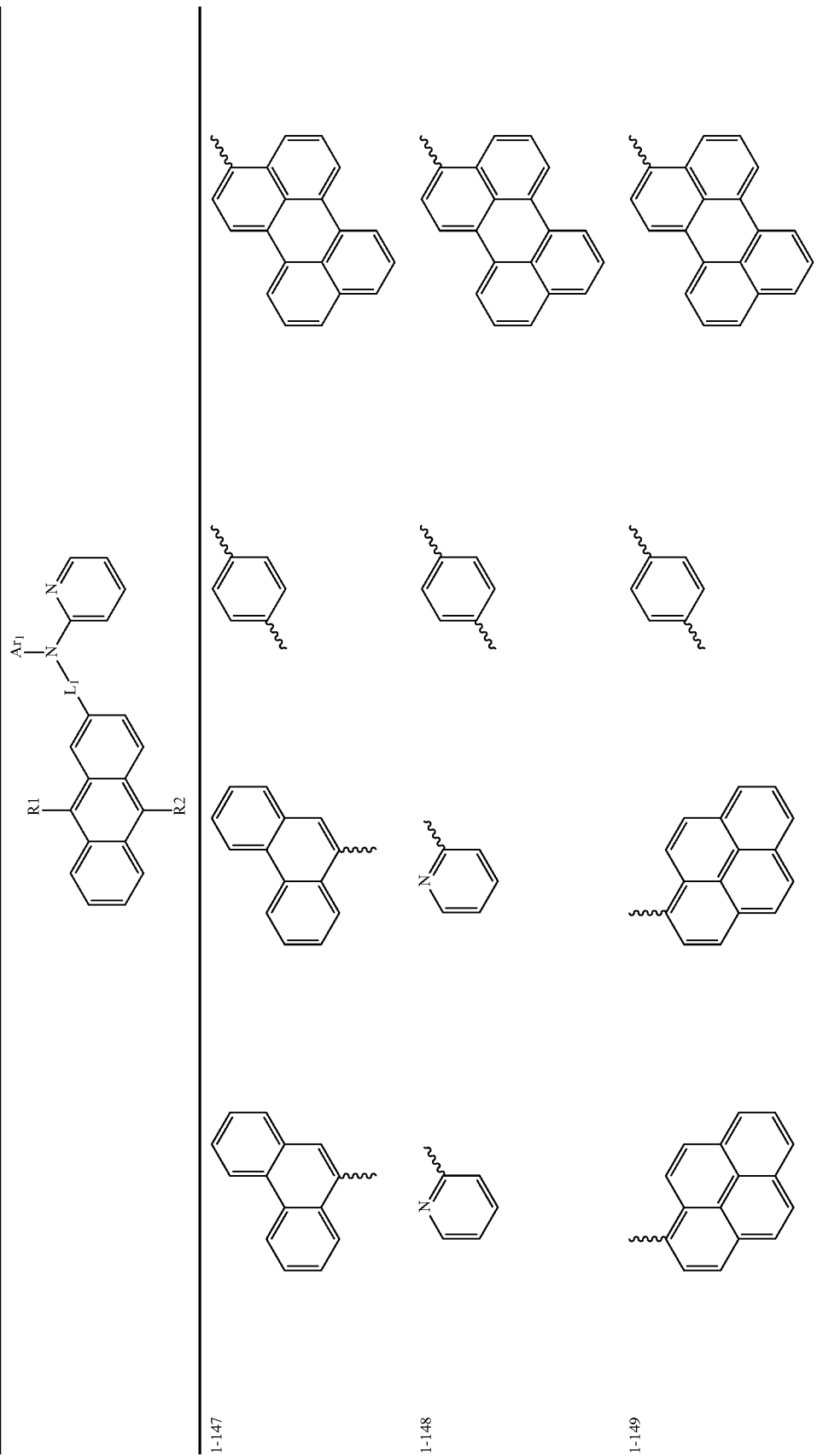

TABLE 1-continued
| | | | |
|---|---|---|---|
| 1-150 | 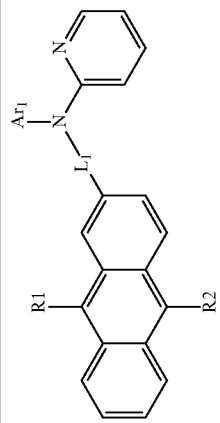 | 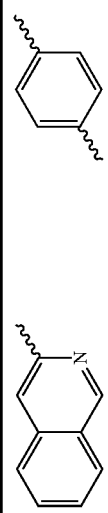 |  |
| 1-151 | | 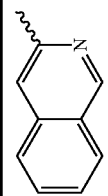 |  |
| 1-152 | | | 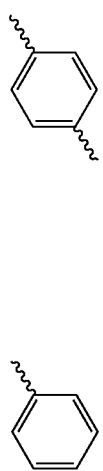 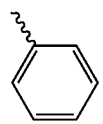 |

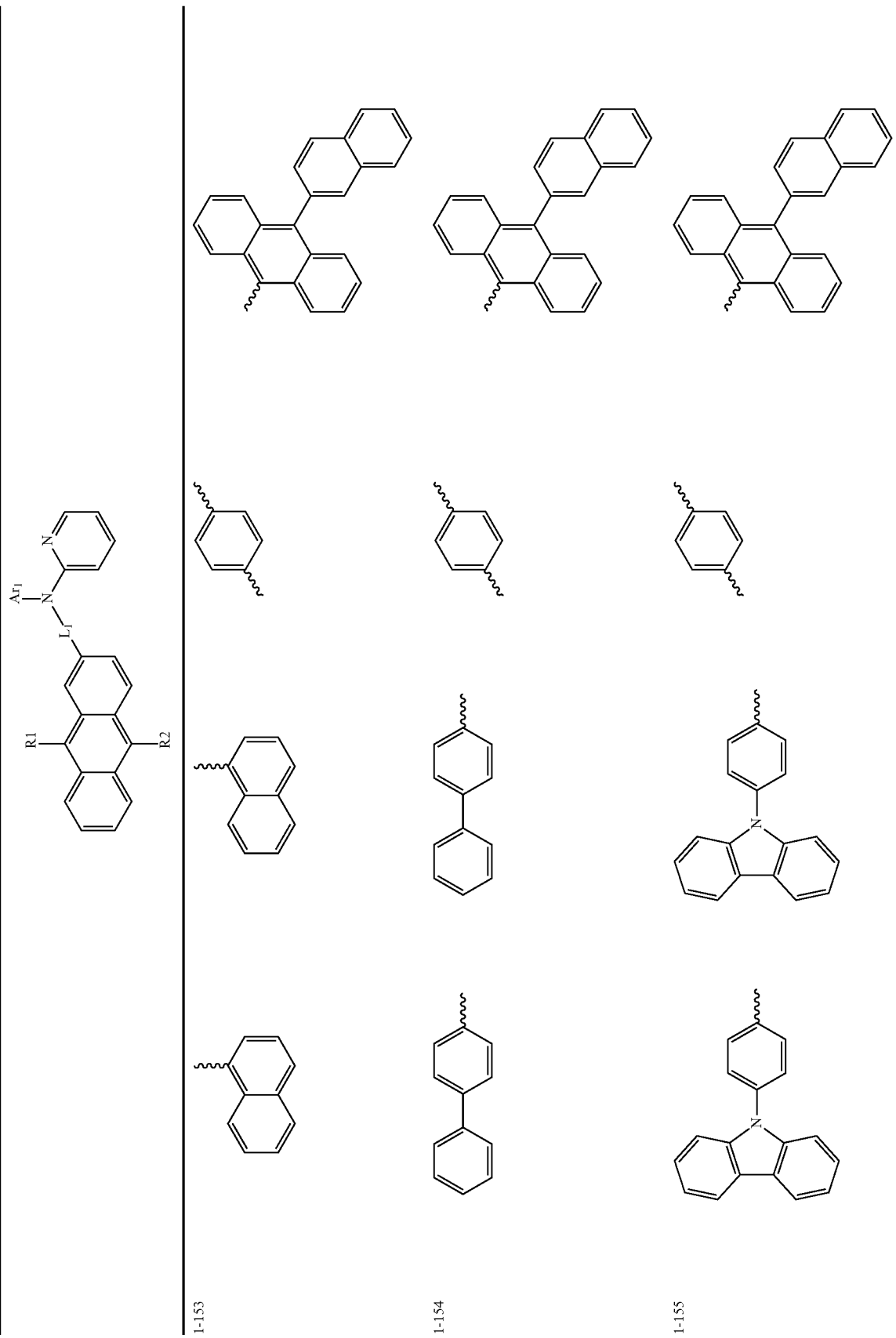

TABLE 1-continued
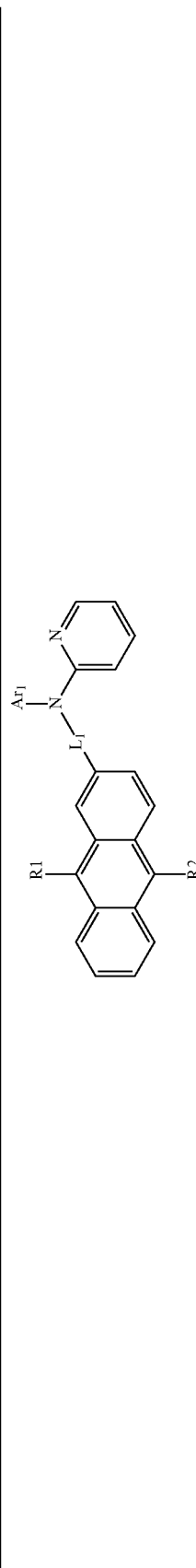
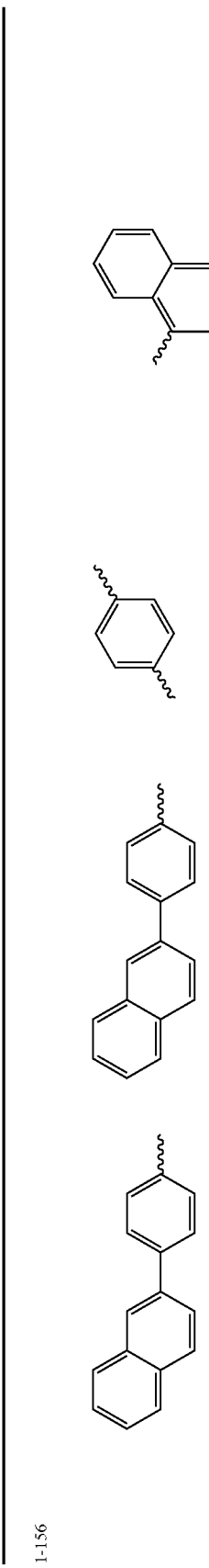
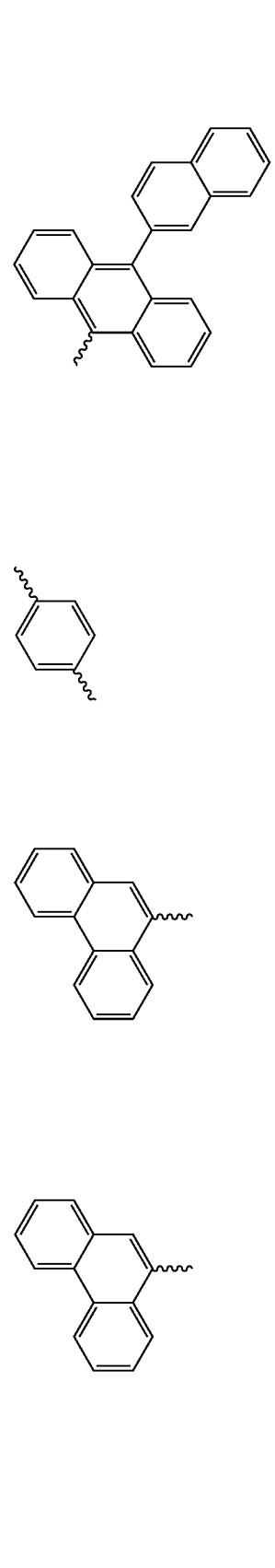
1-156
1-157

TABLE 1-continued
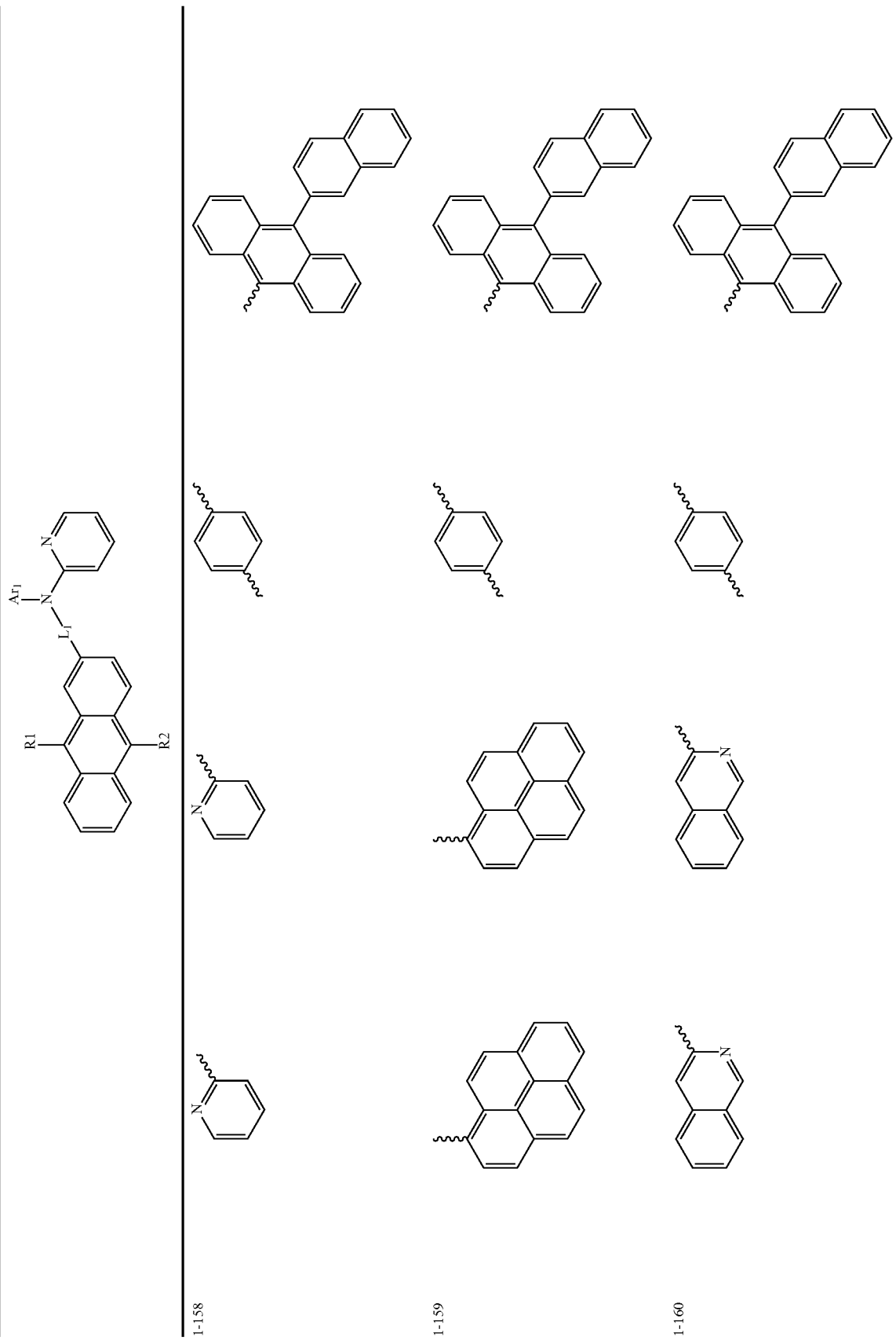

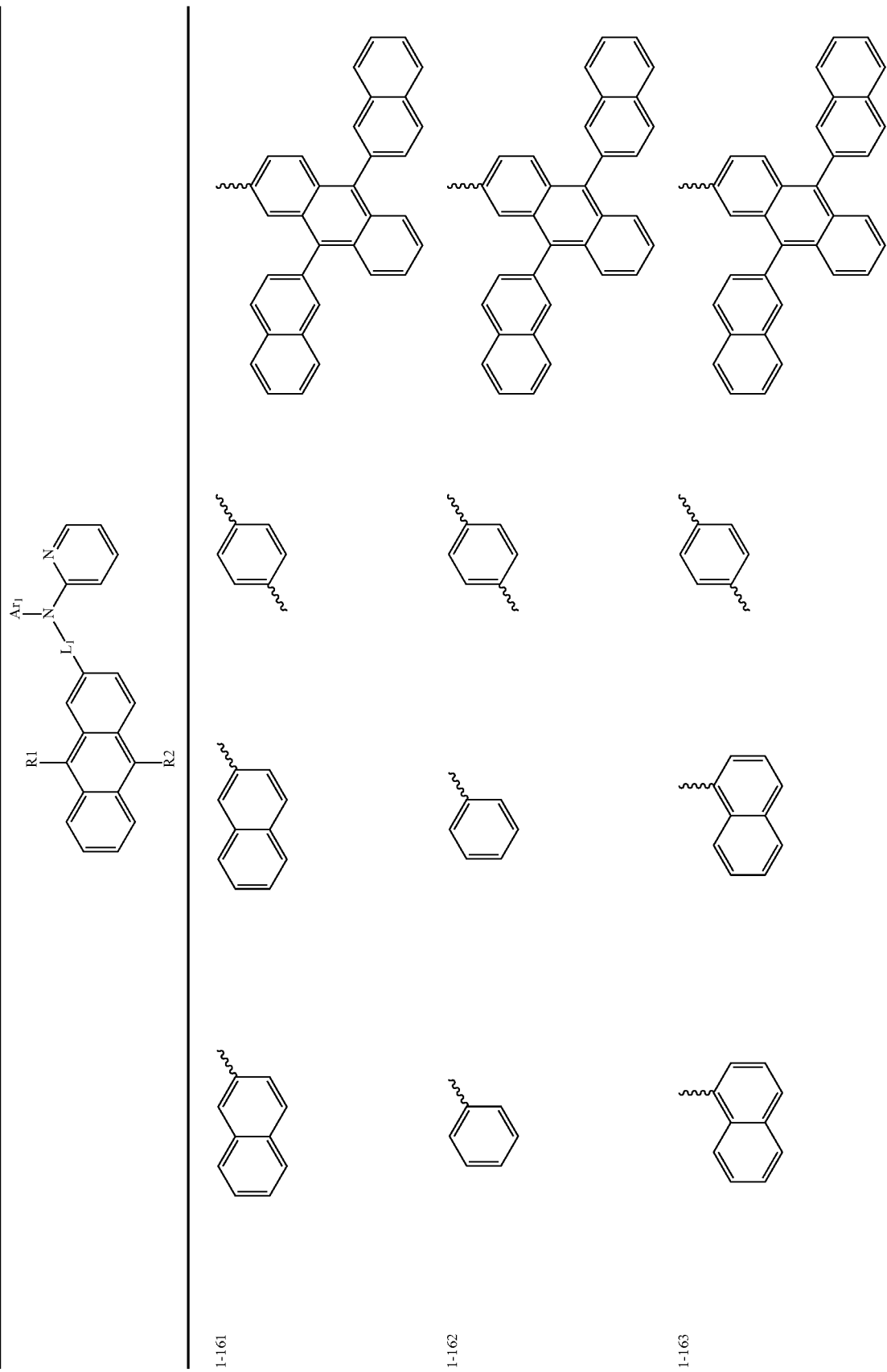

TABLE 1-continued
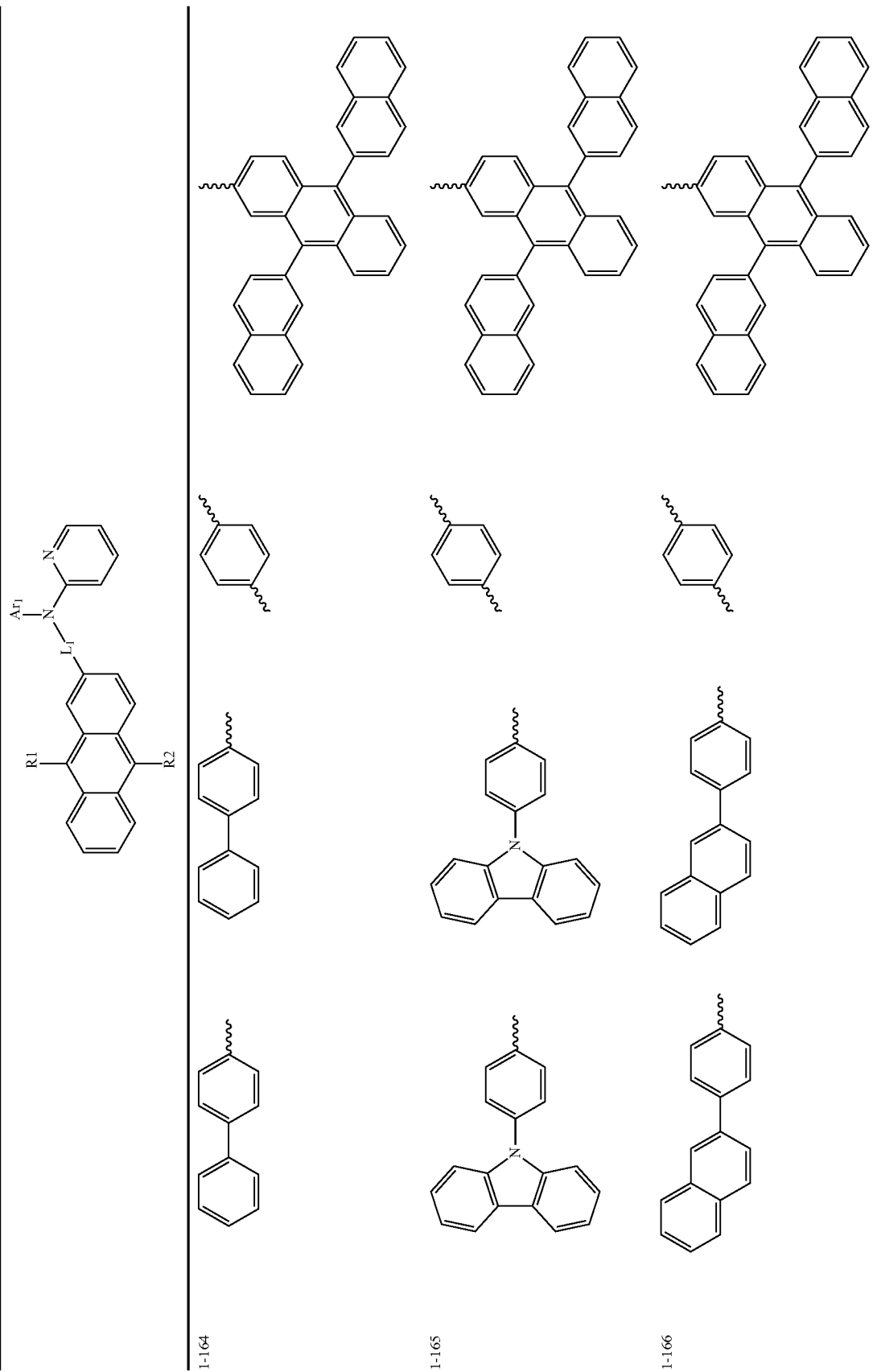

TABLE 1-continued
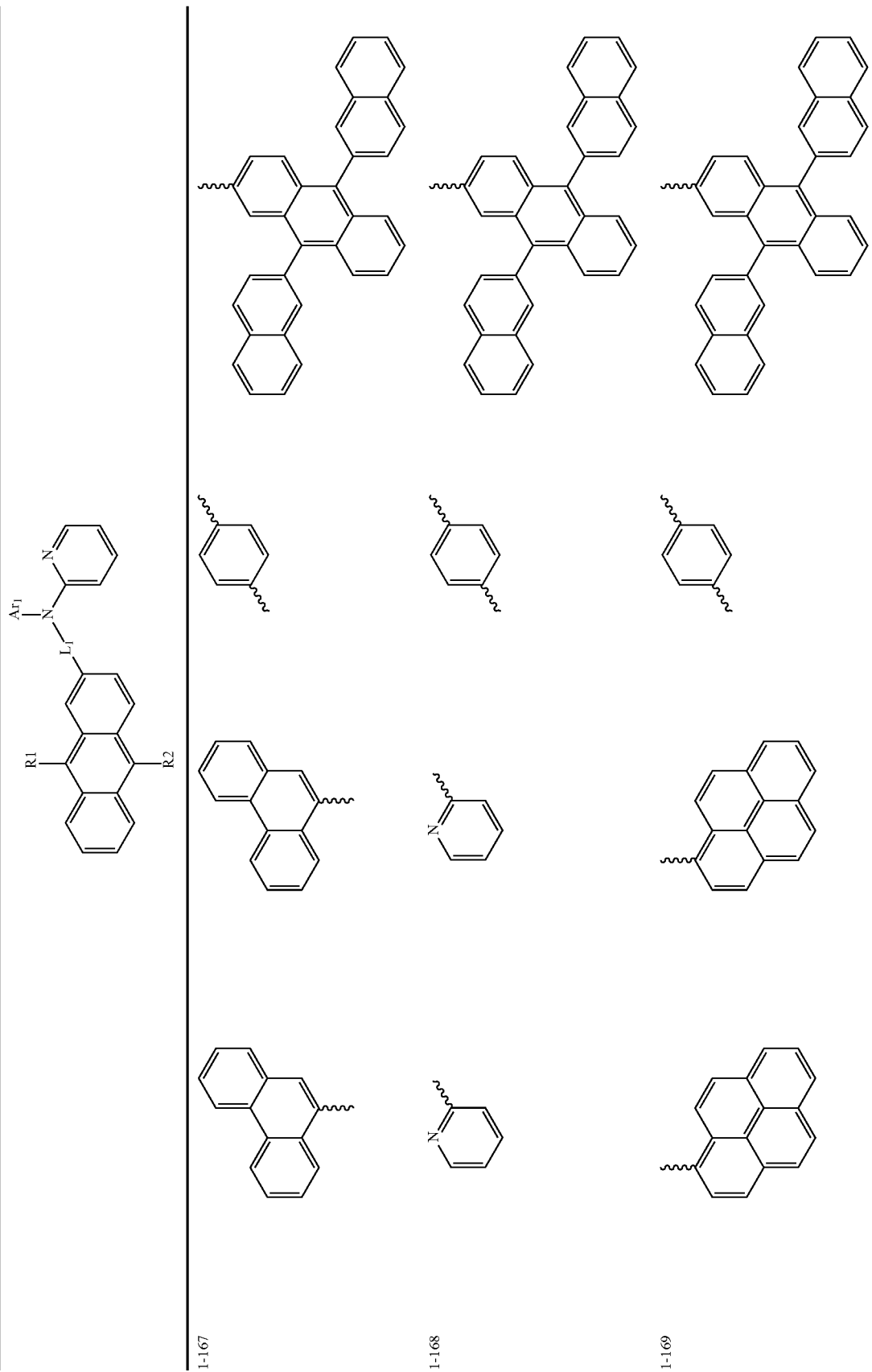

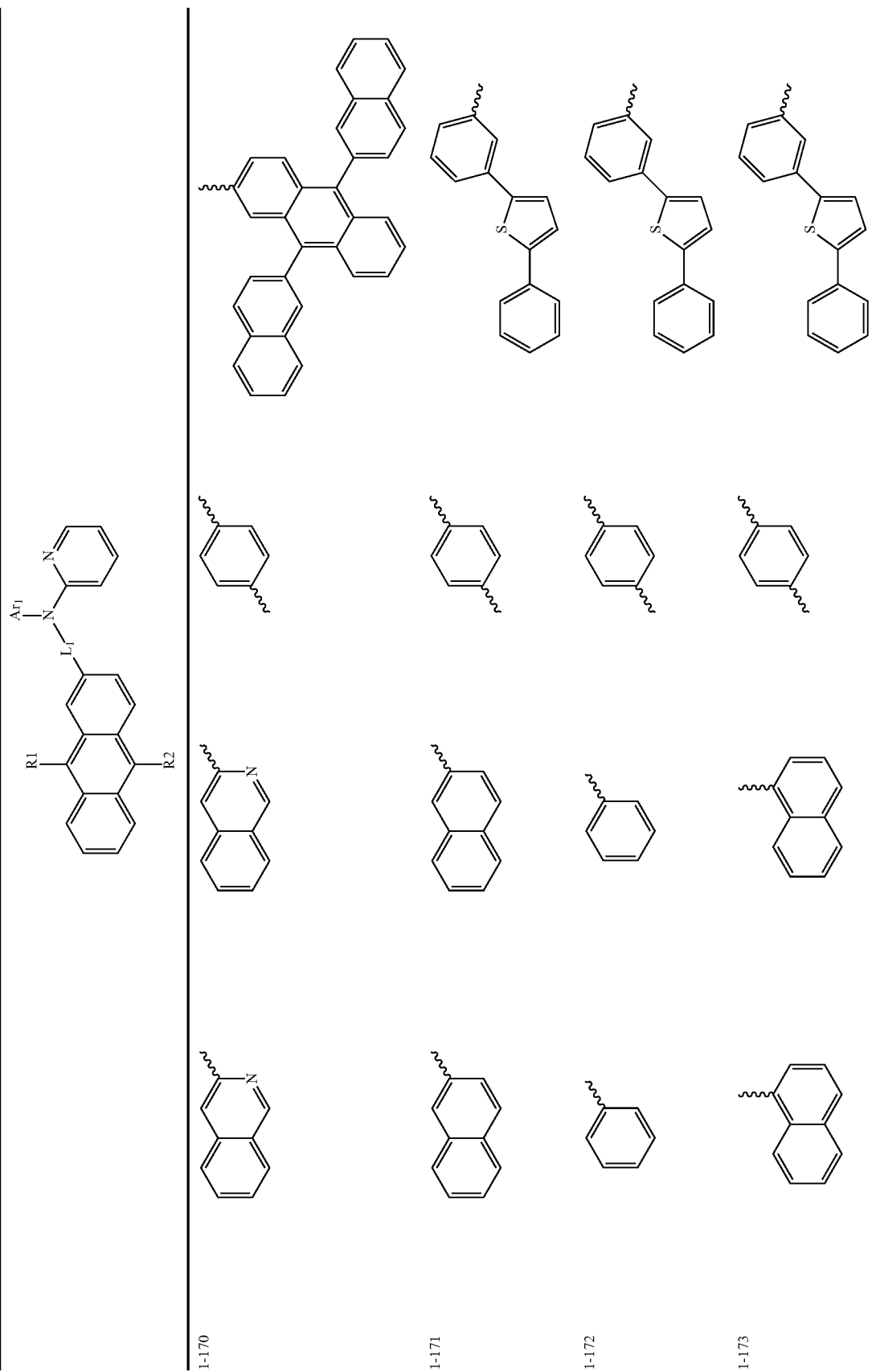

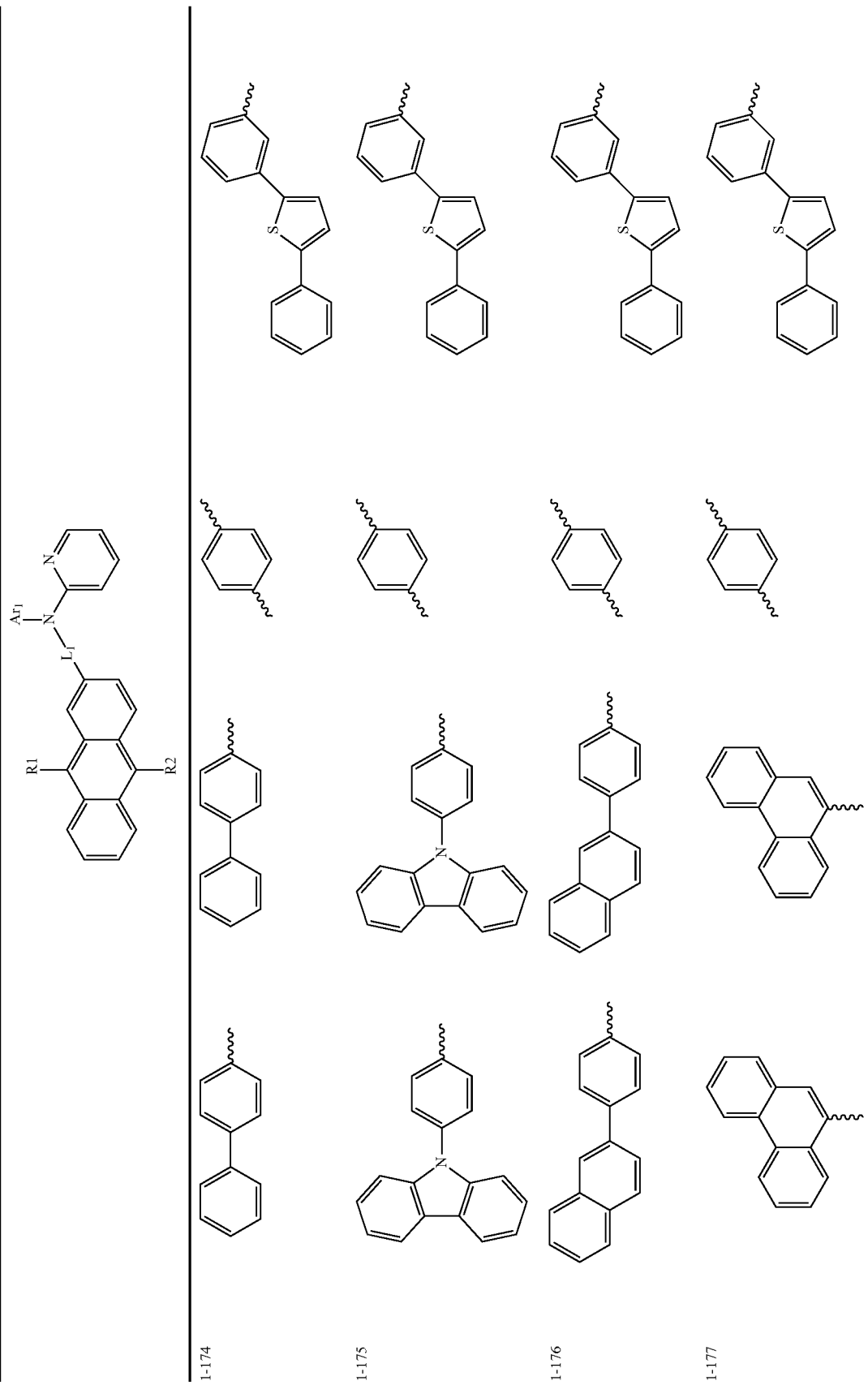

TABLE 1-continued

TABLE 1-continued

TABLE 1-continued

| | | | | |
|---|---|---|---|---|
| 1-188 | | | | |
| 1-189 | | | | |
| 1-190 | | | | |
| 1-191 | | | | |
| 1-192 | | | | |
| 1-193 | | | | |

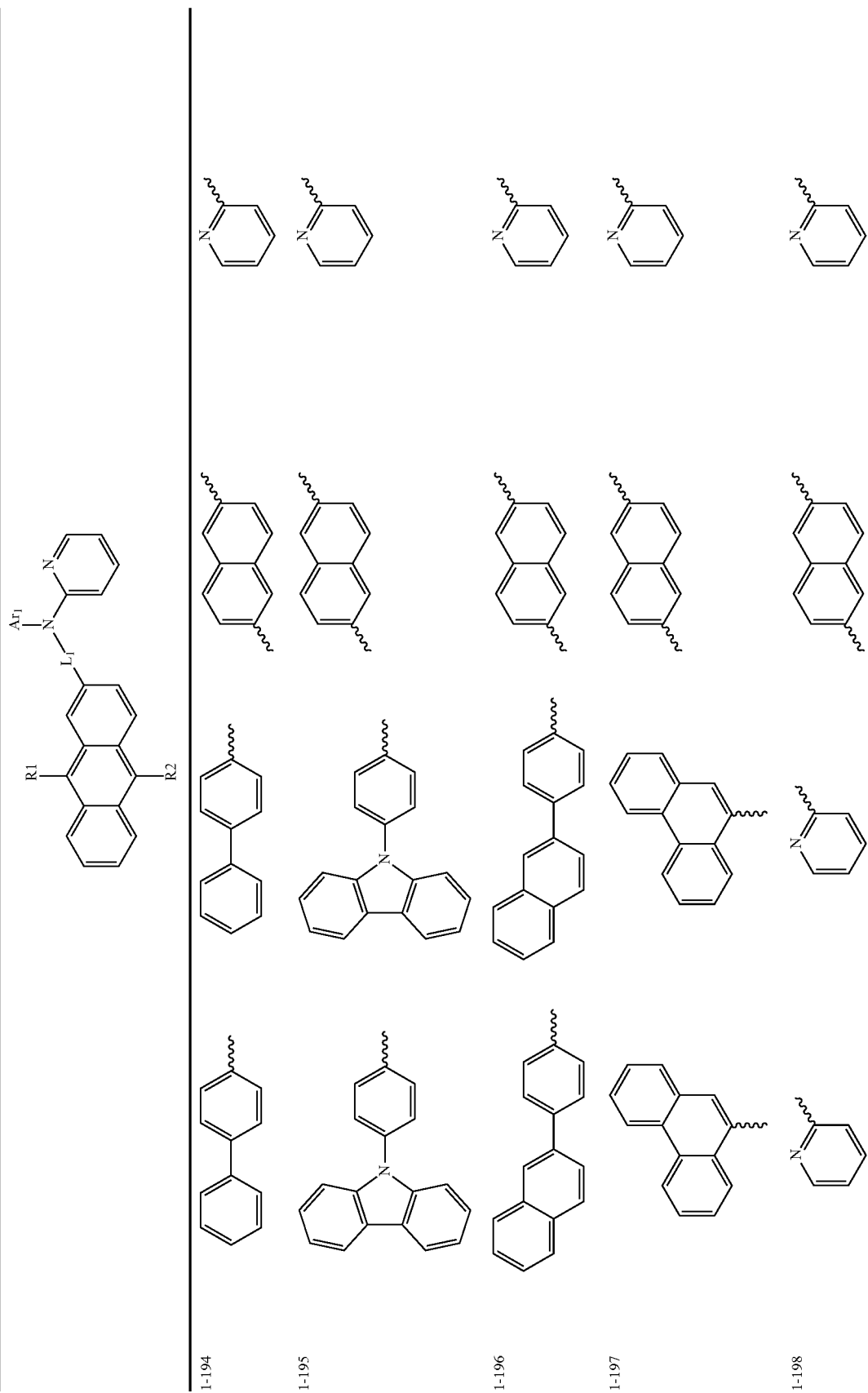

TABLE 1-continued
| | | | | |
|---|---|---|---|---|
| 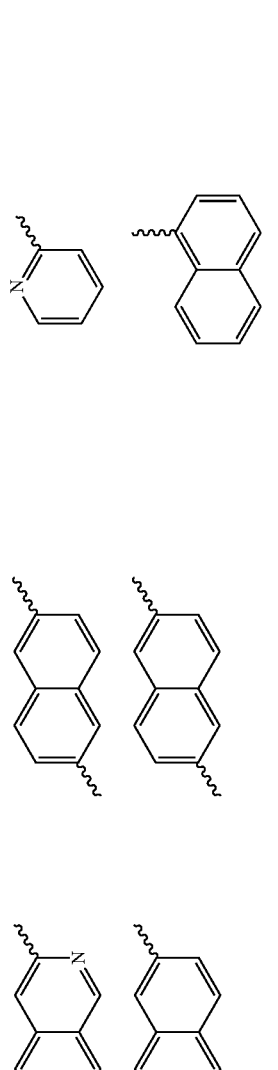 | | | | |
| 1-199 | 1-200 | 1-201 | 1-202 | 1-203 |

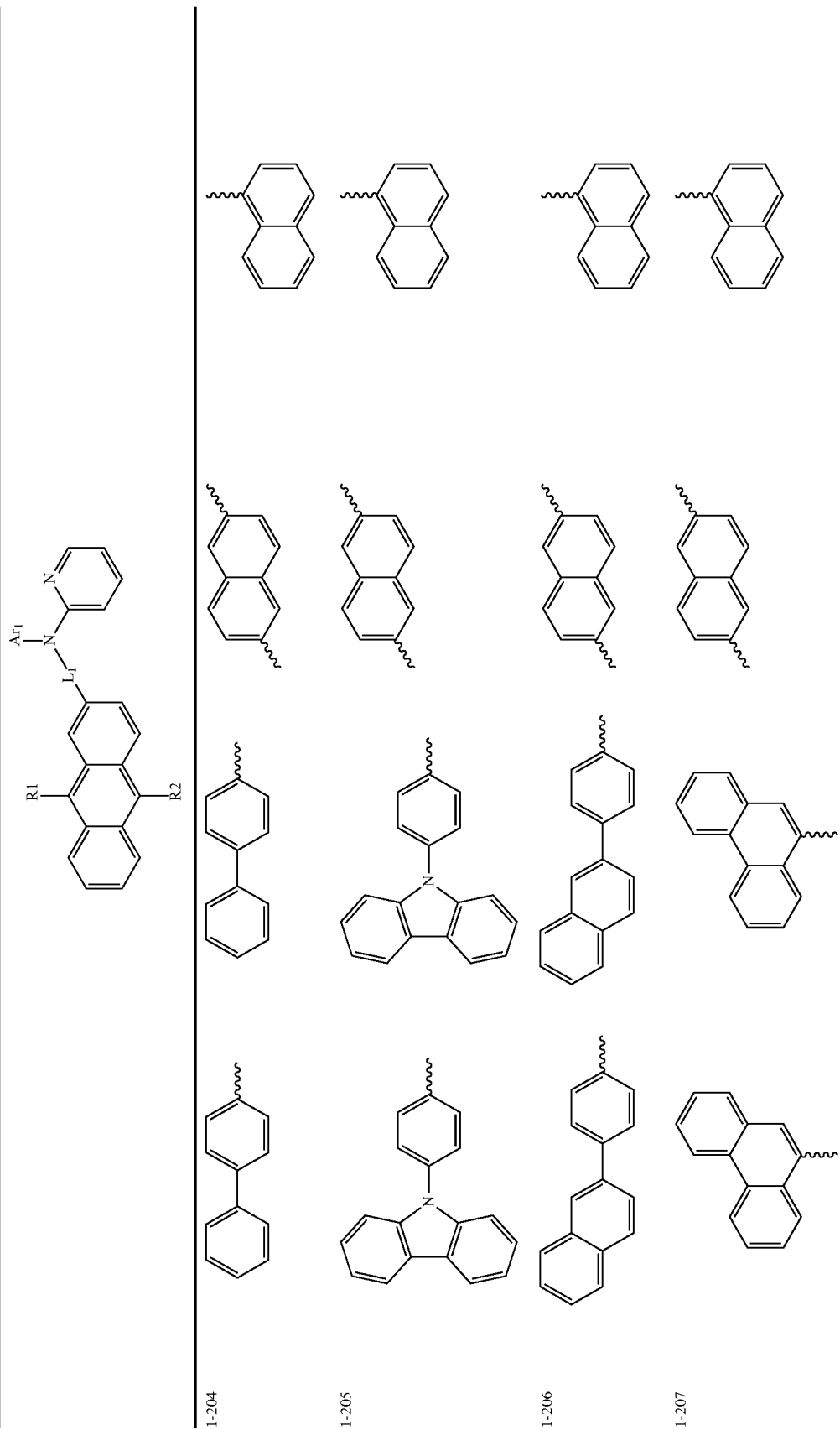

TABLE 1-continued
| | | | | |
|---|---|---|---|---|
| 1-208 | 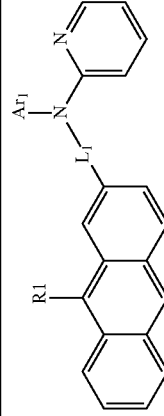 |  |  |  |
| 1-209 |  | 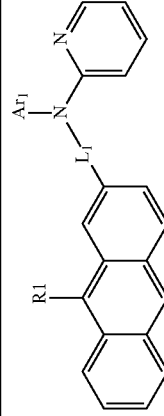 |  |  |
| 1-210 |  |  | 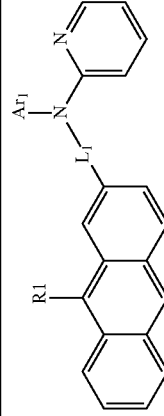 |  |
| 1-211 |  |  |  | 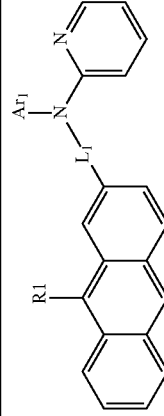 |
| 1-212 |  |  |  |  |

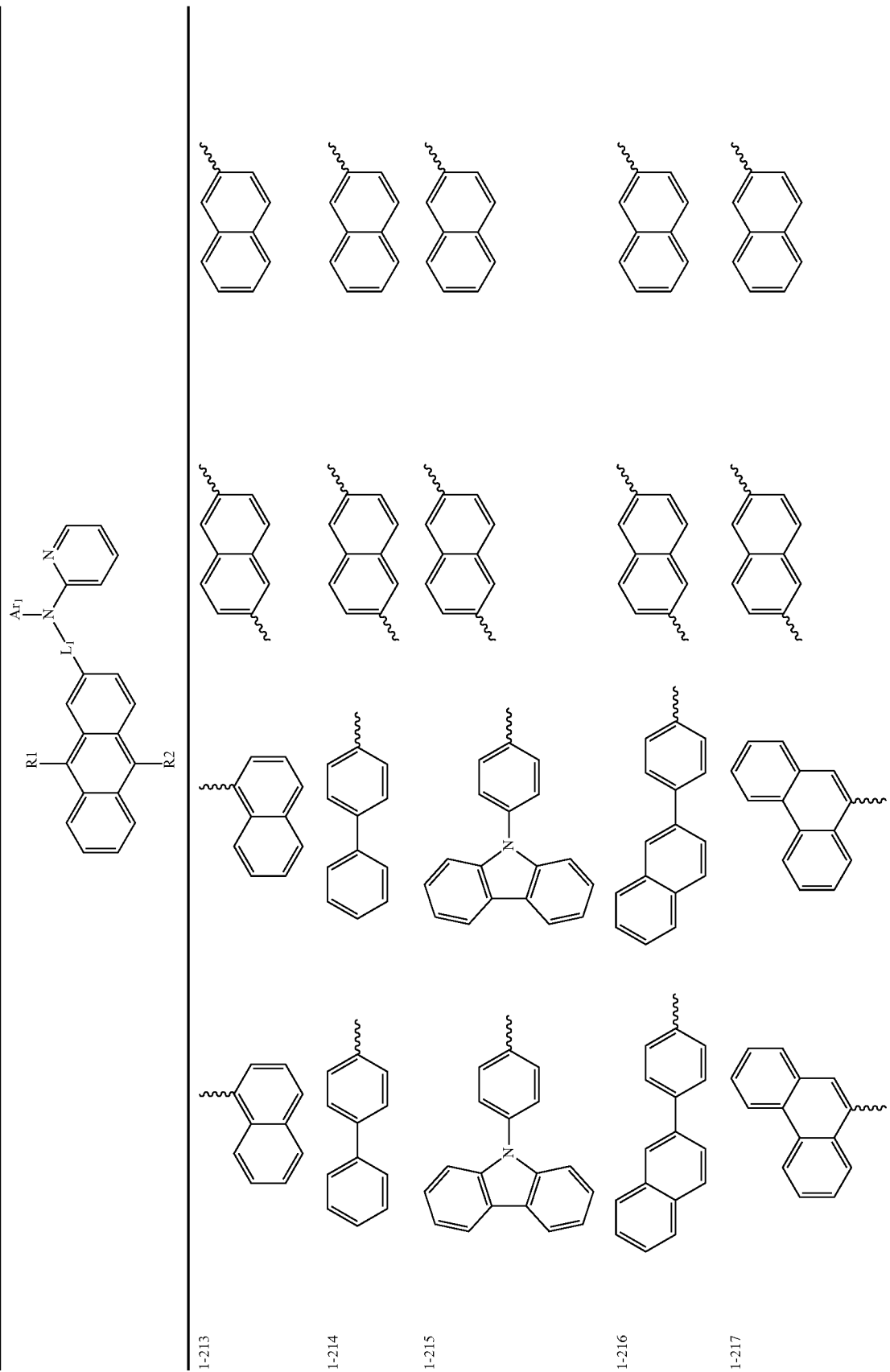

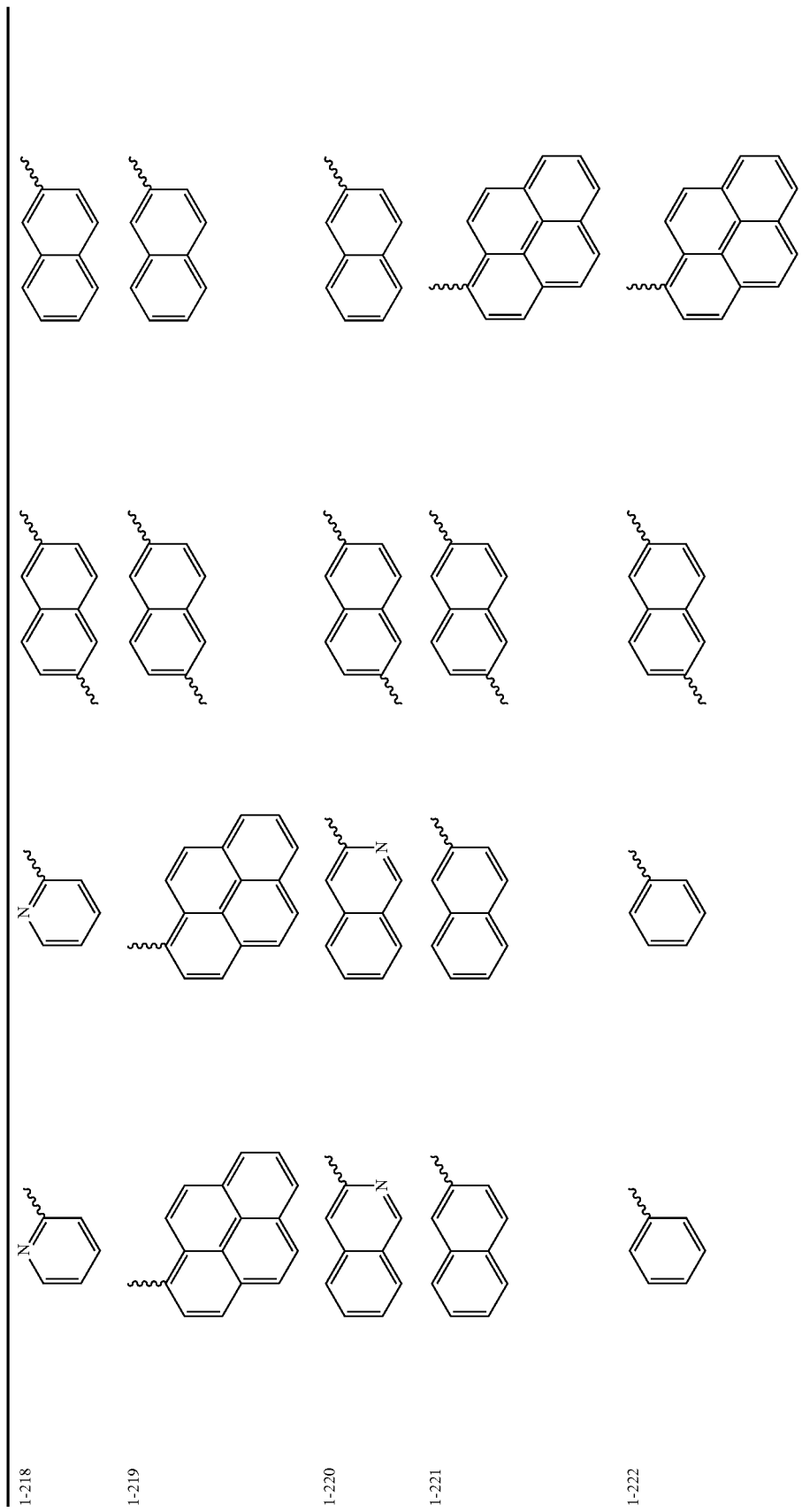

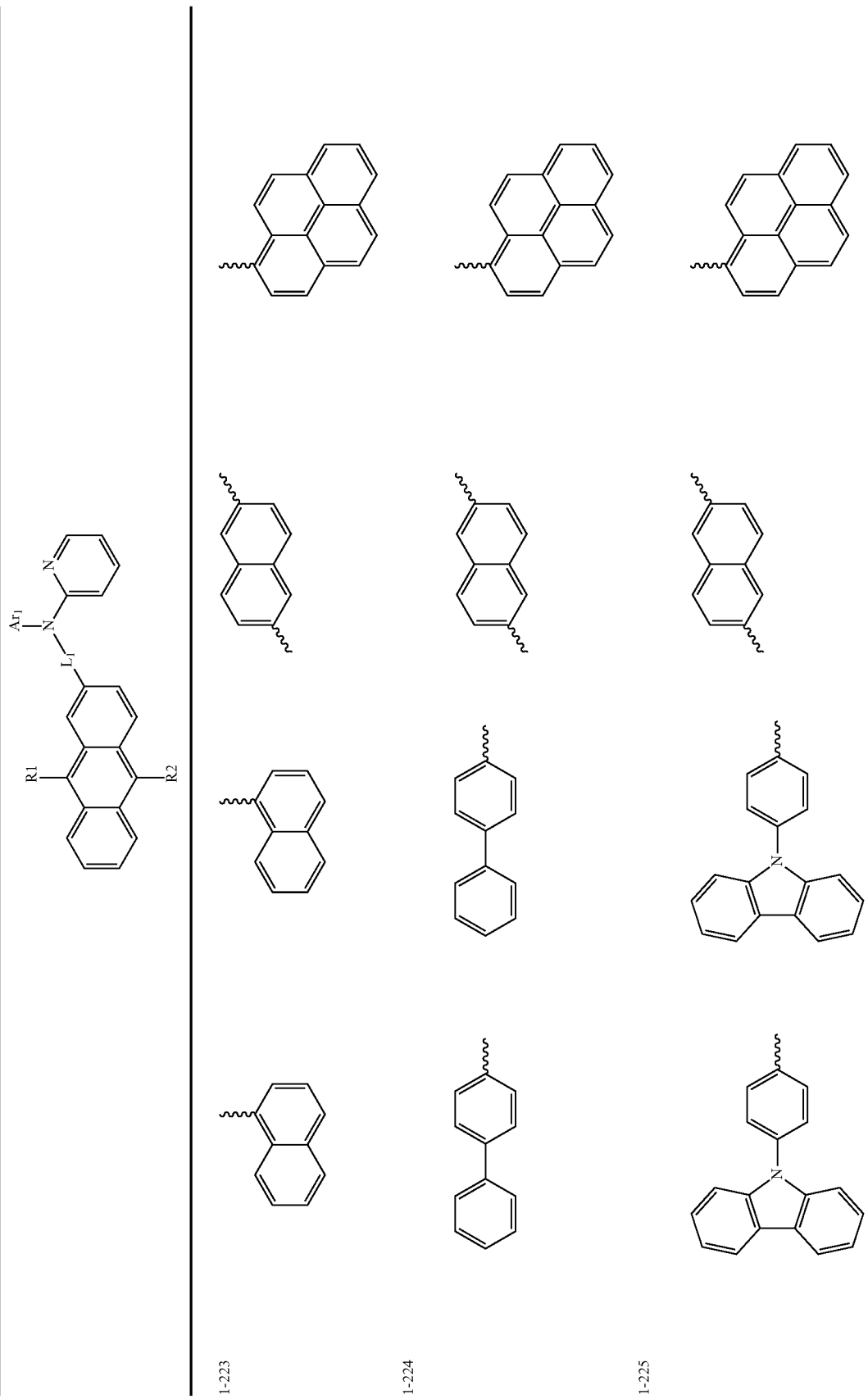

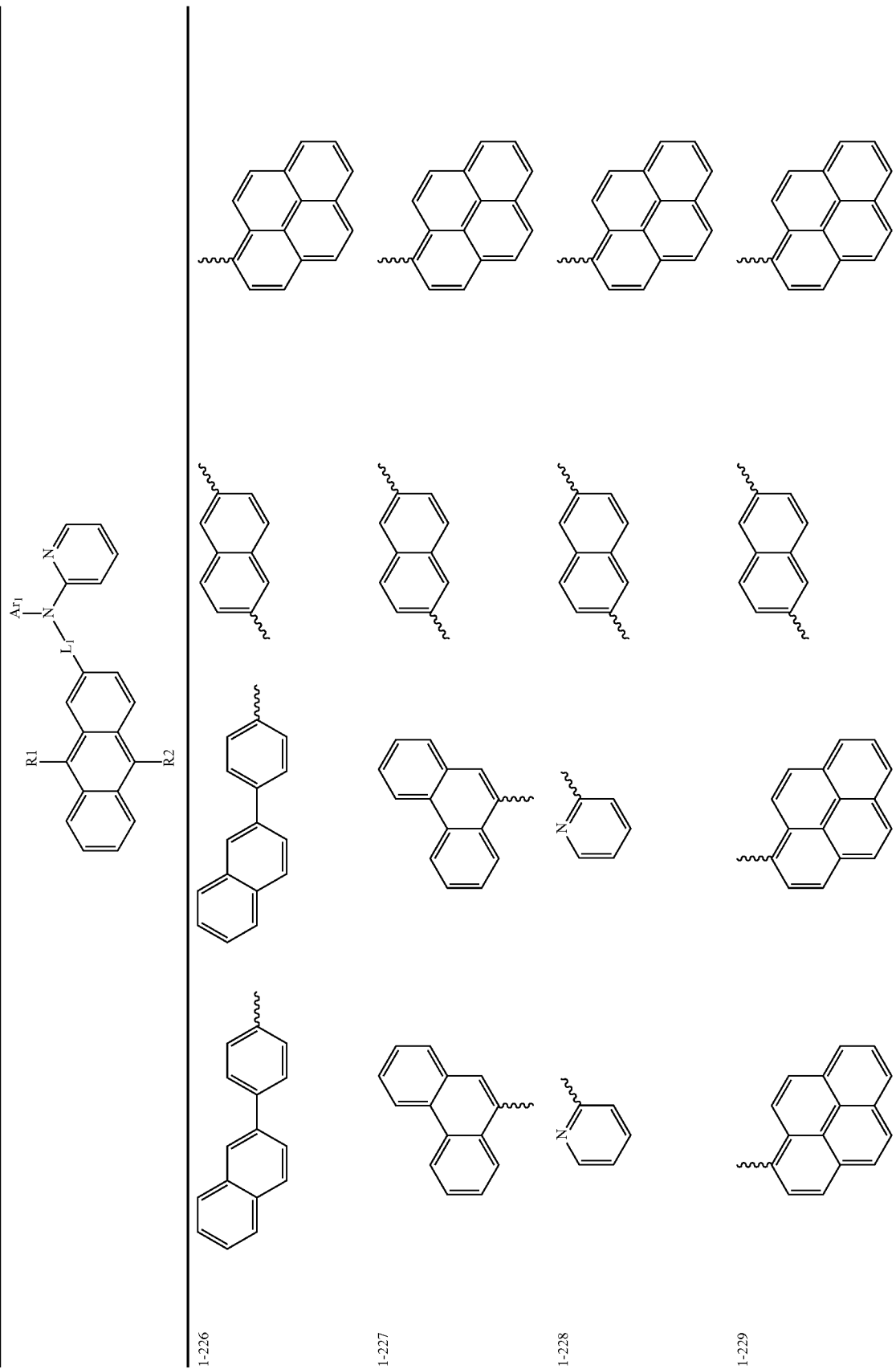

TABLE 1-continued
| | | | |
|---|---|---|---|
| 1-230 | 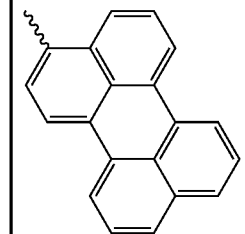  | 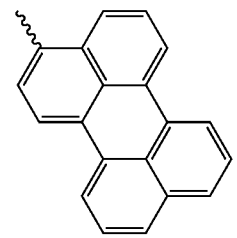  | 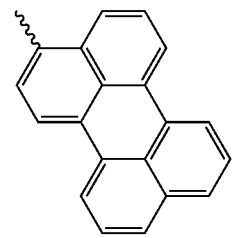 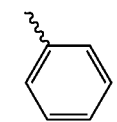 |
| 1-231 | | | |
| 1-232 | | | |

TABLE 1-continued
| | | | |
|---|---|---|---|
| 1-233 | 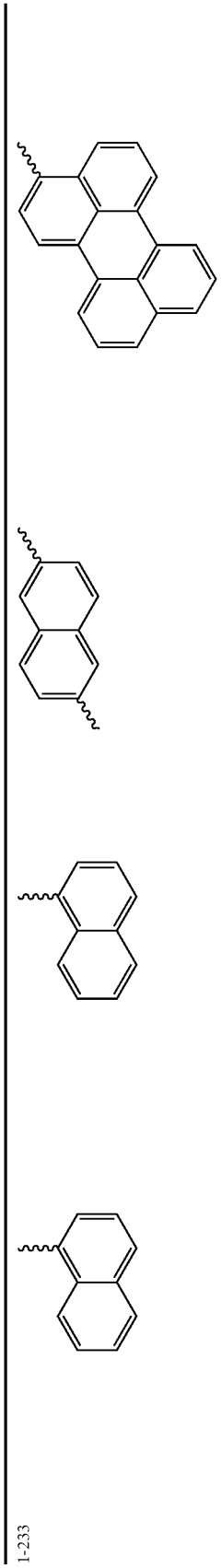 | | |
| 1-234 | | | |
| 1-235 | | | |
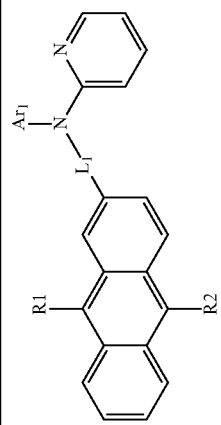
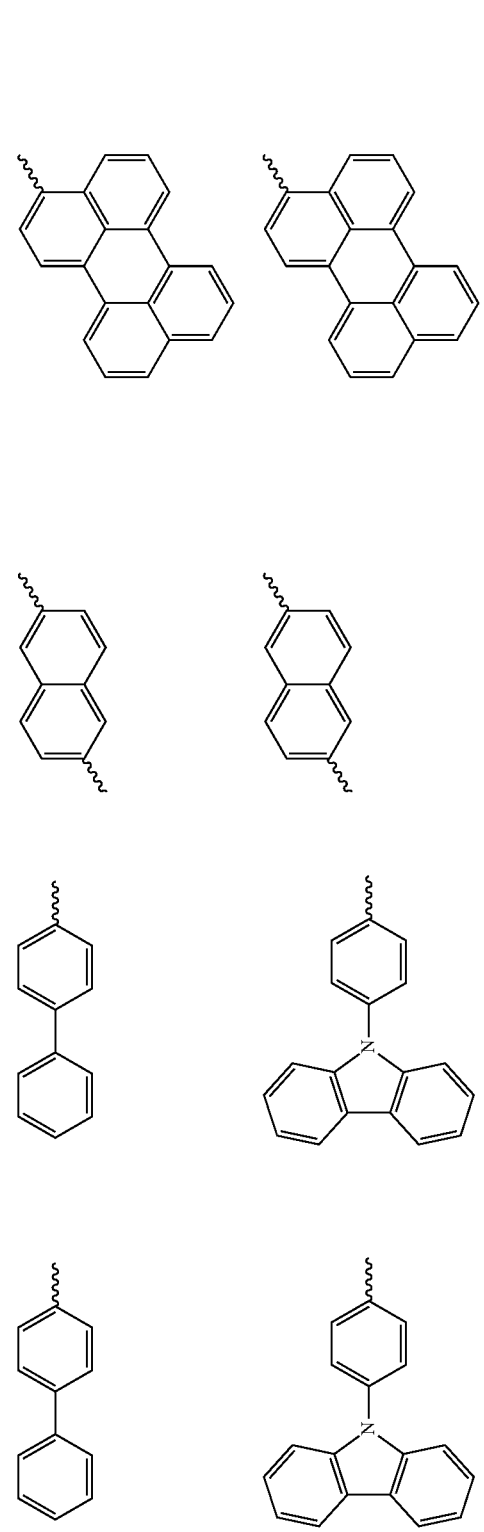

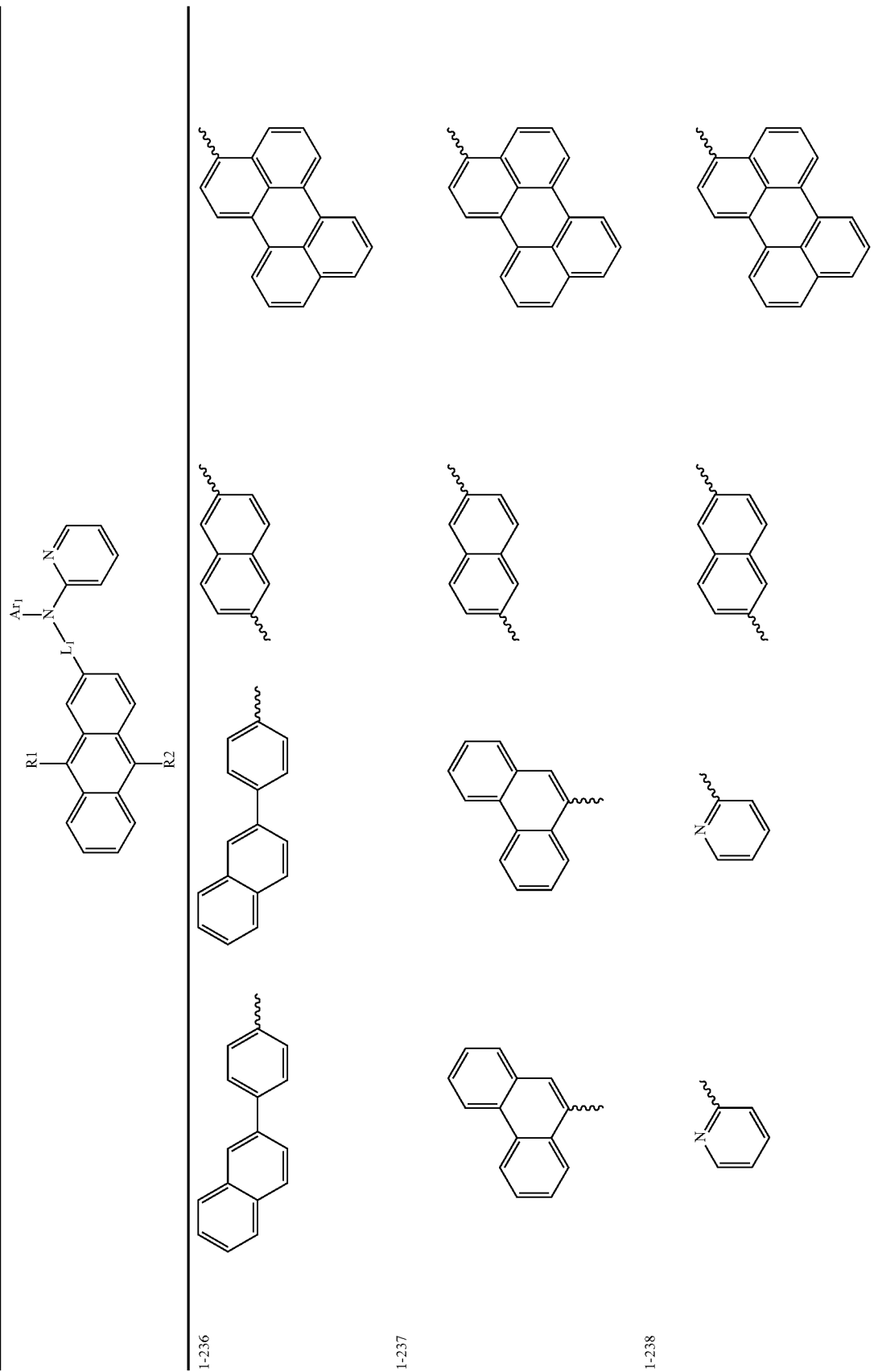

TABLE 1-continued
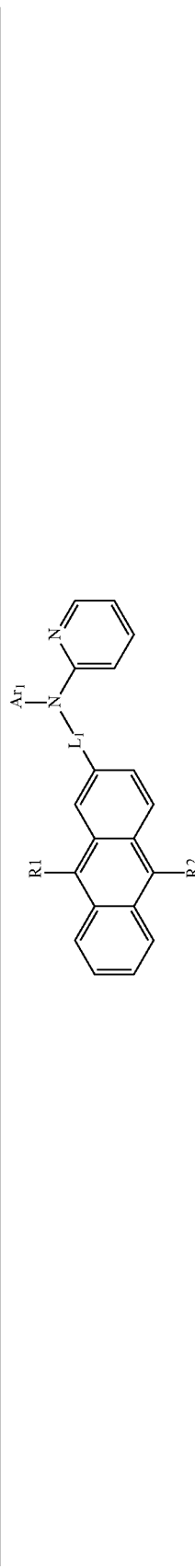
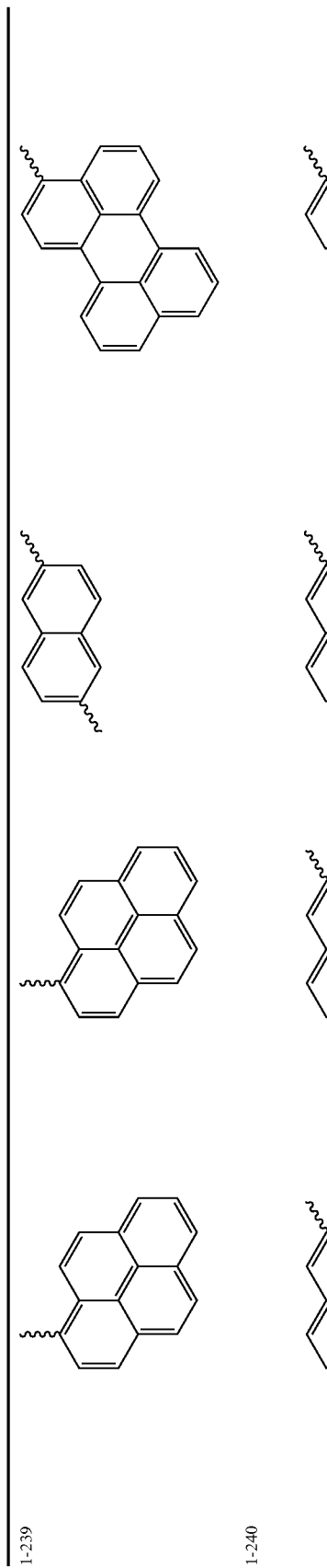
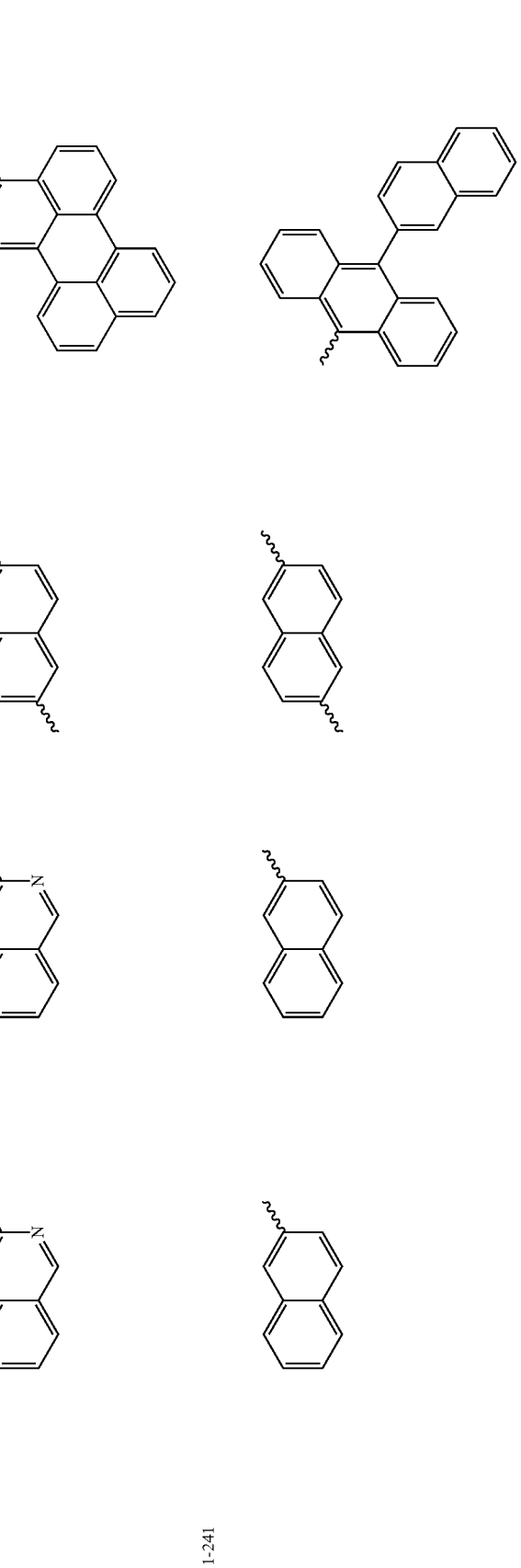

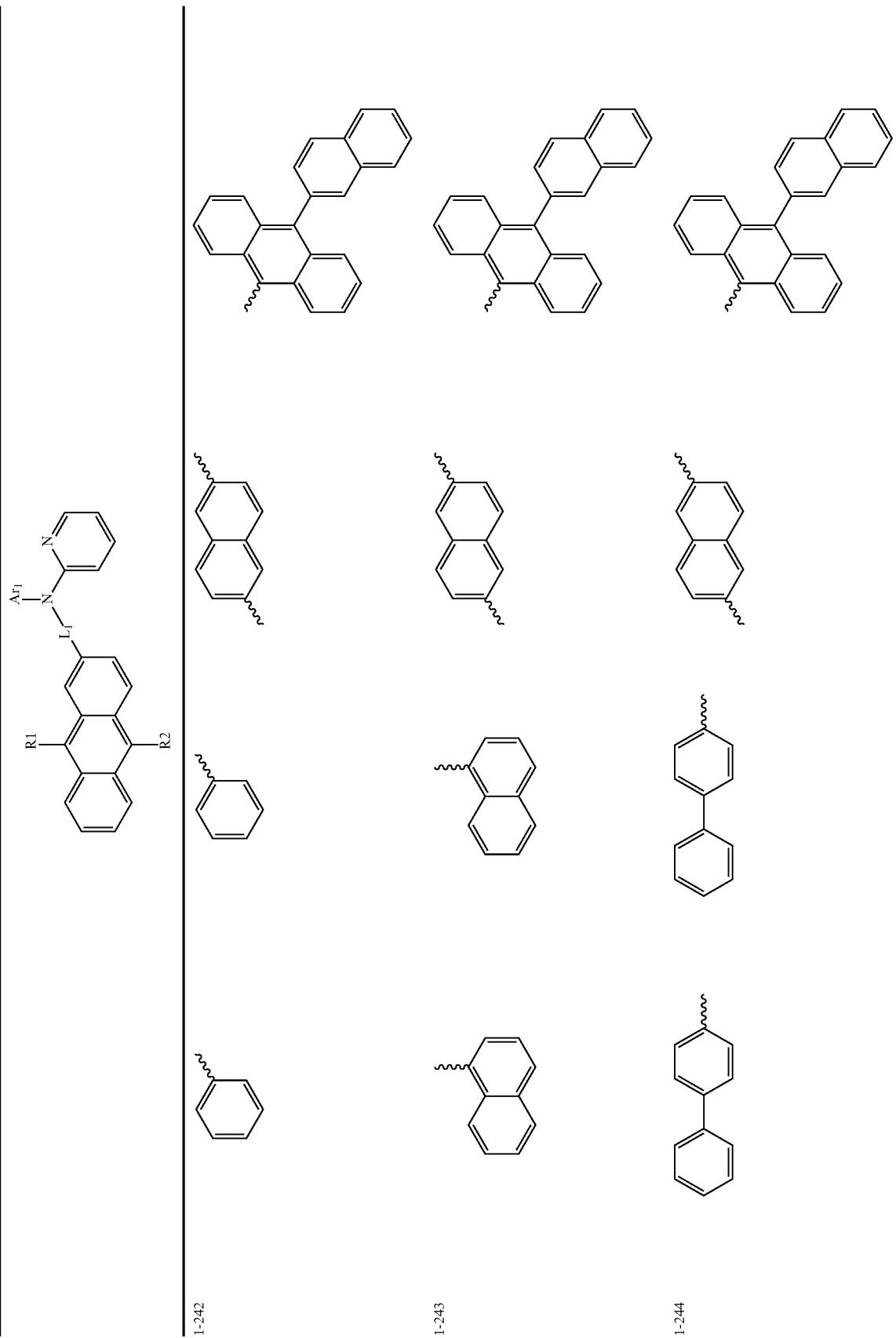

TABLE 1-continued
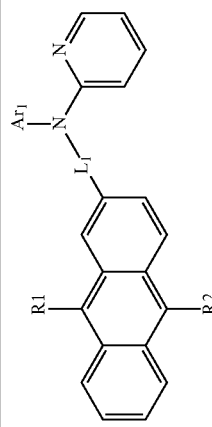
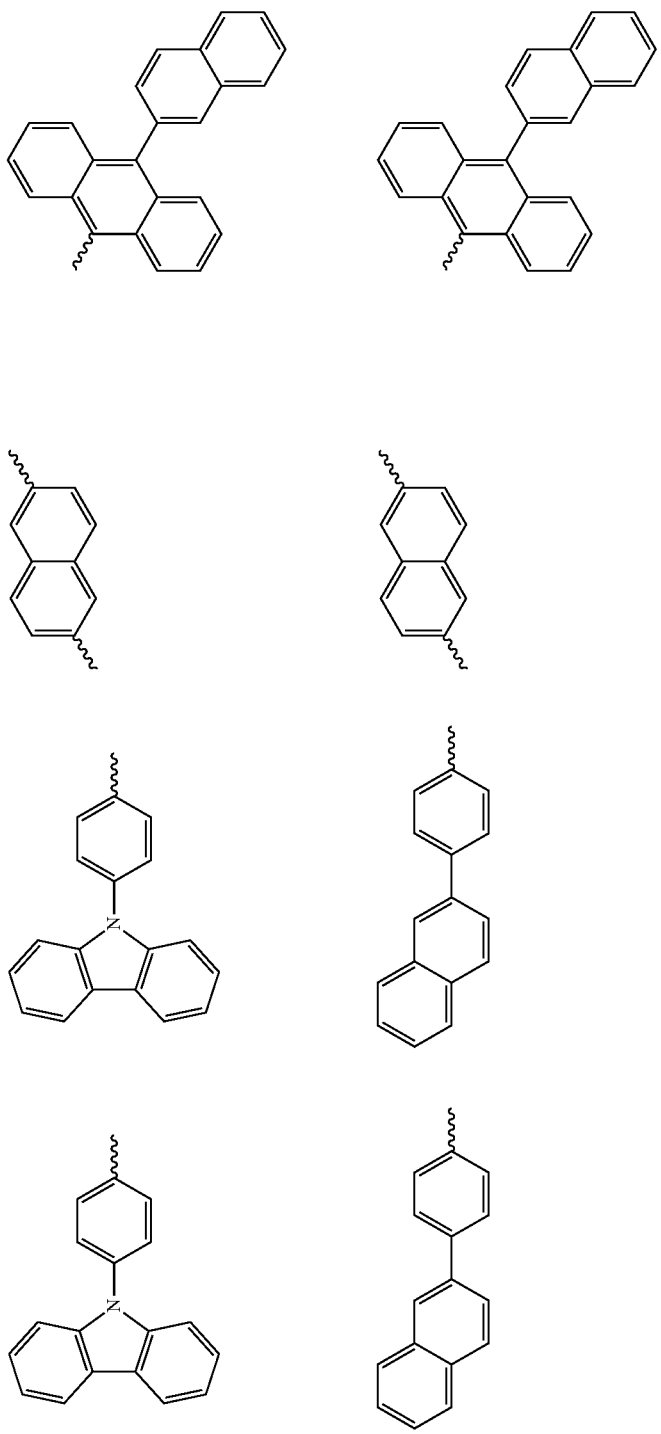
1-245
1-246

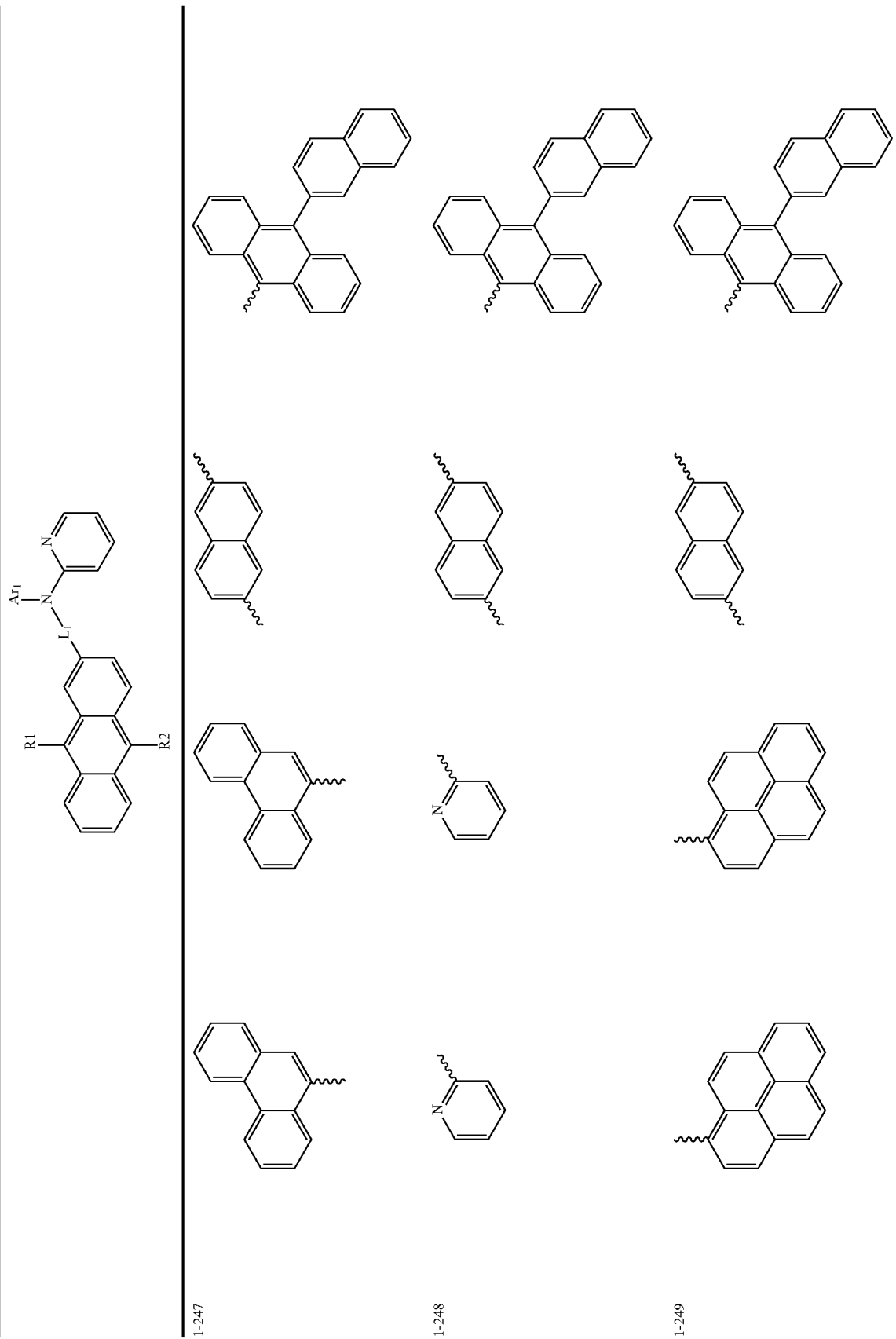

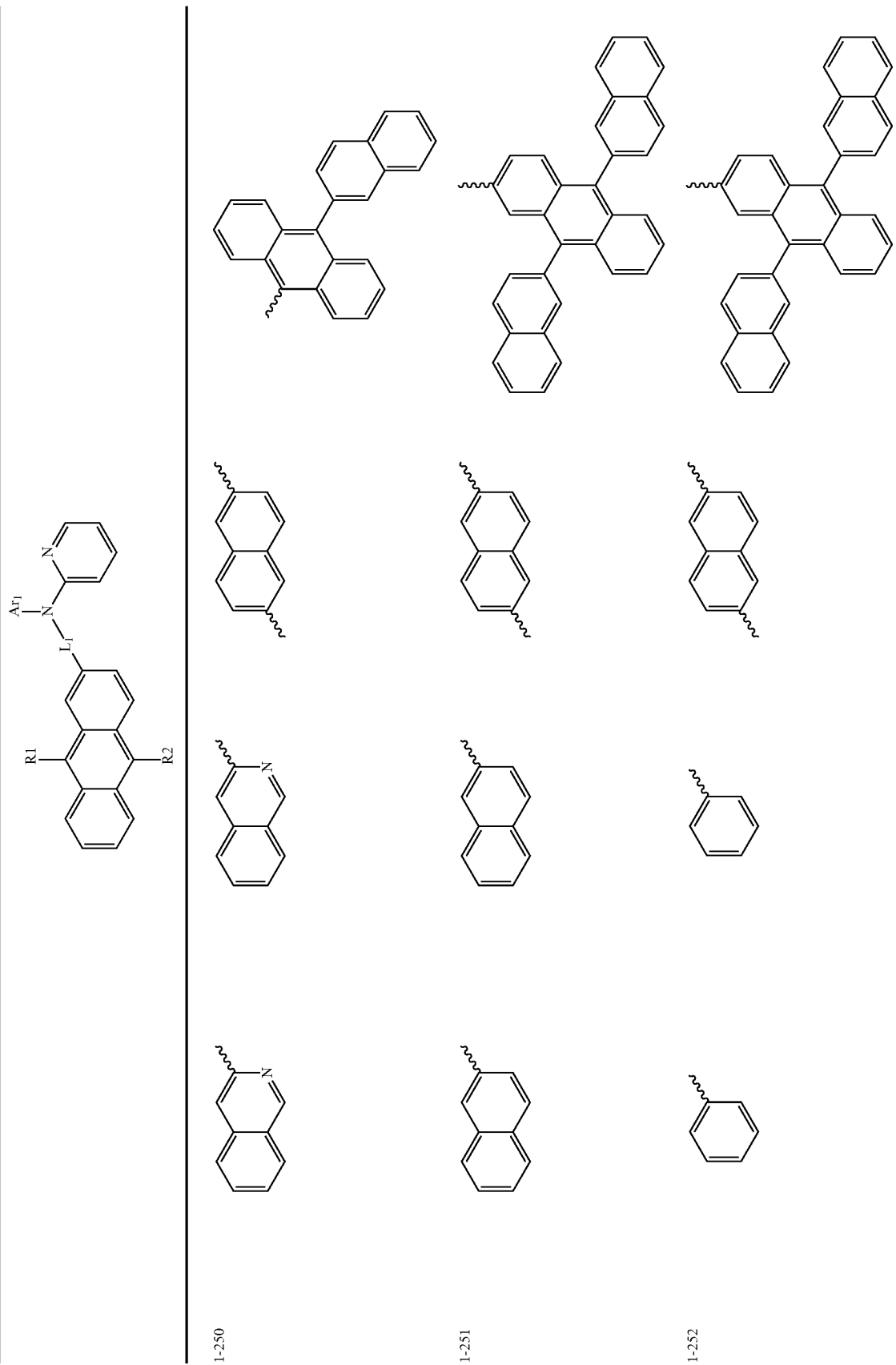

TABLE 1-continued
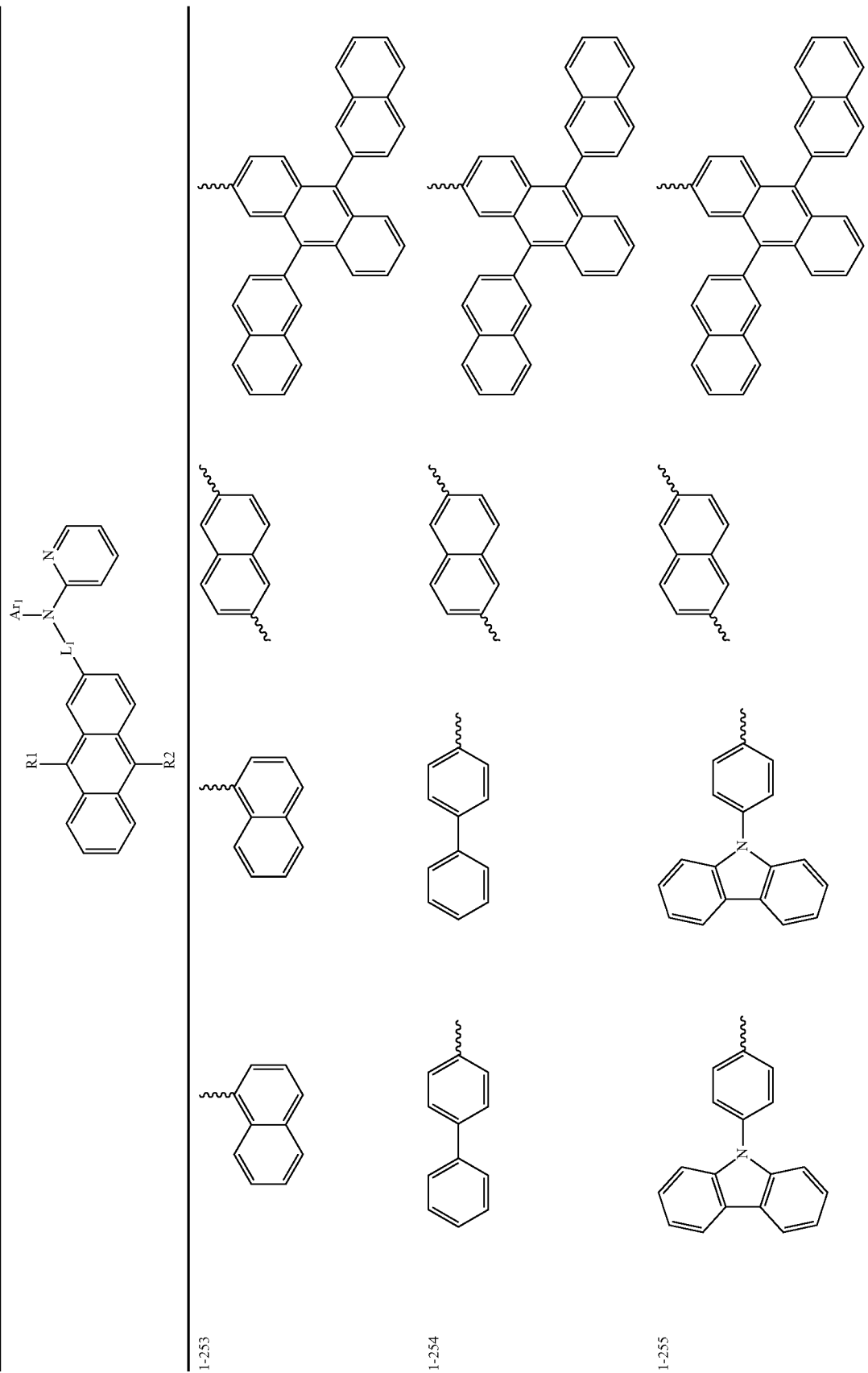

TABLE 1-continued
| | | | |
|---|---|---|---|
| 1-256 | 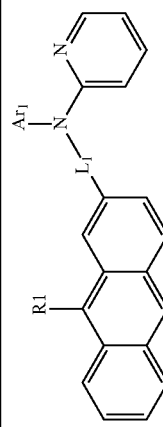 | 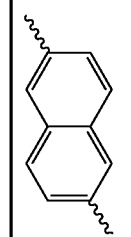 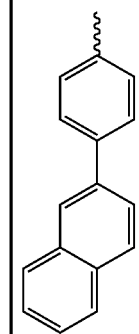 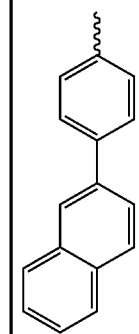 | 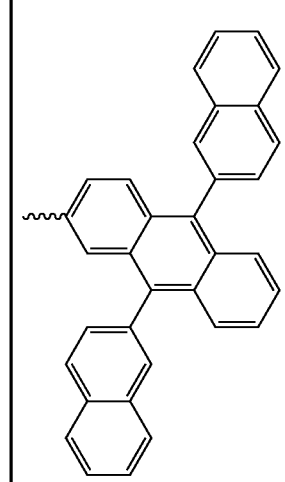 |
| 1-257 | |  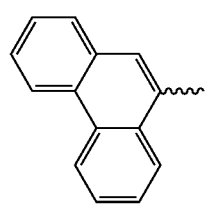 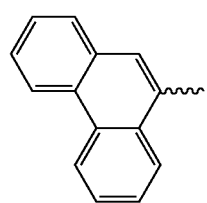 | 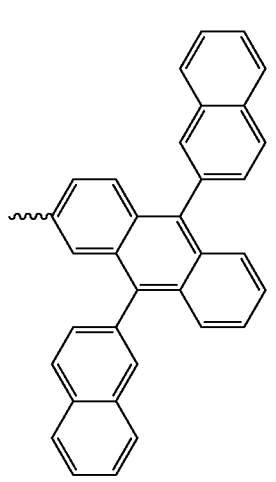 |
| 1-258 | |  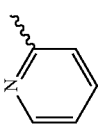 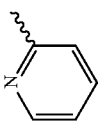 | 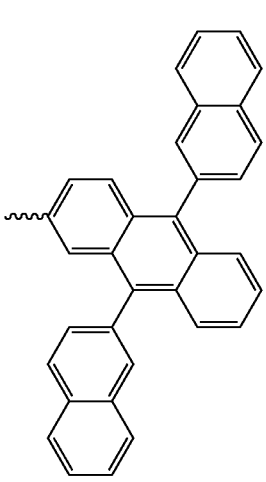 |

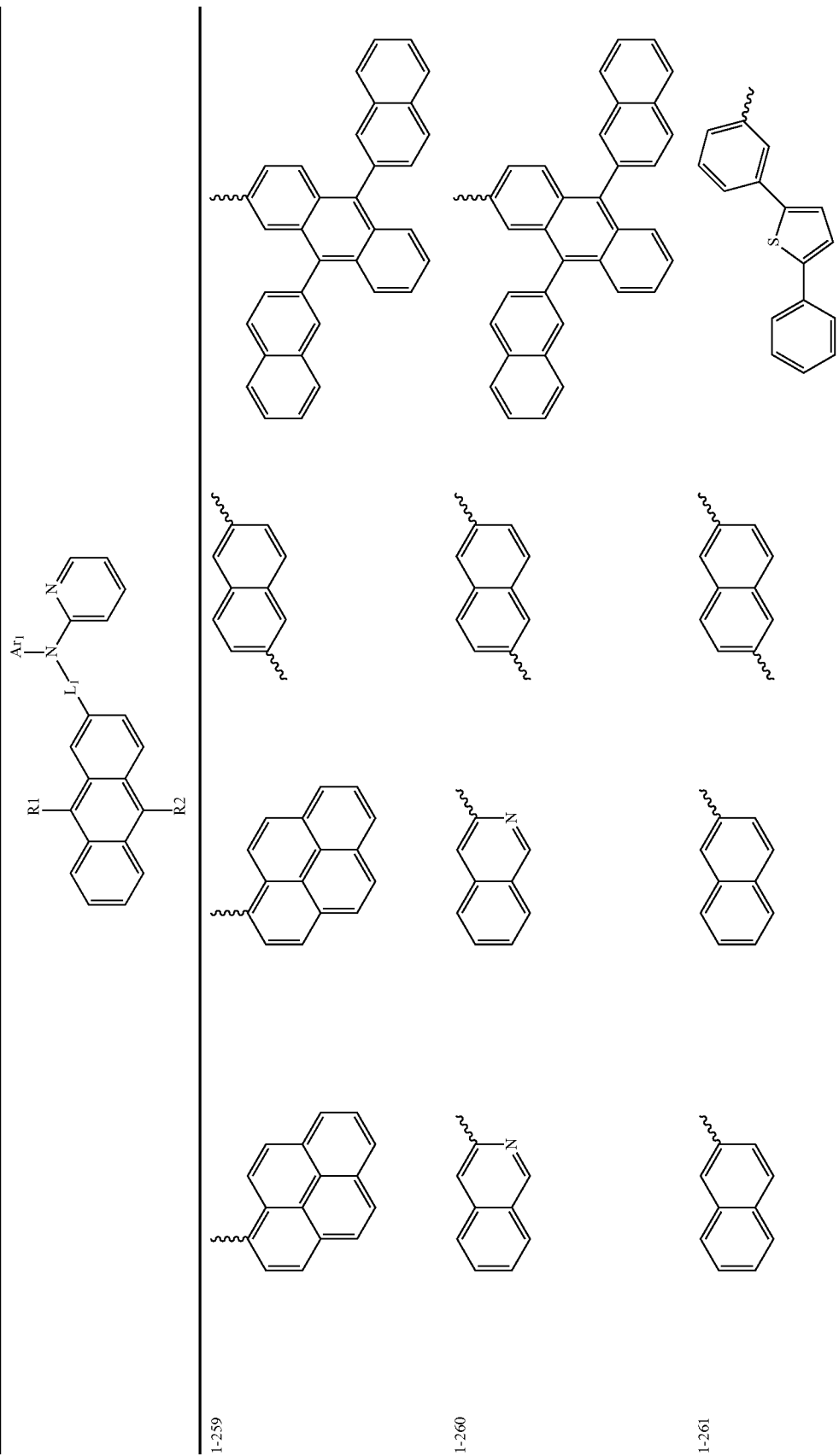

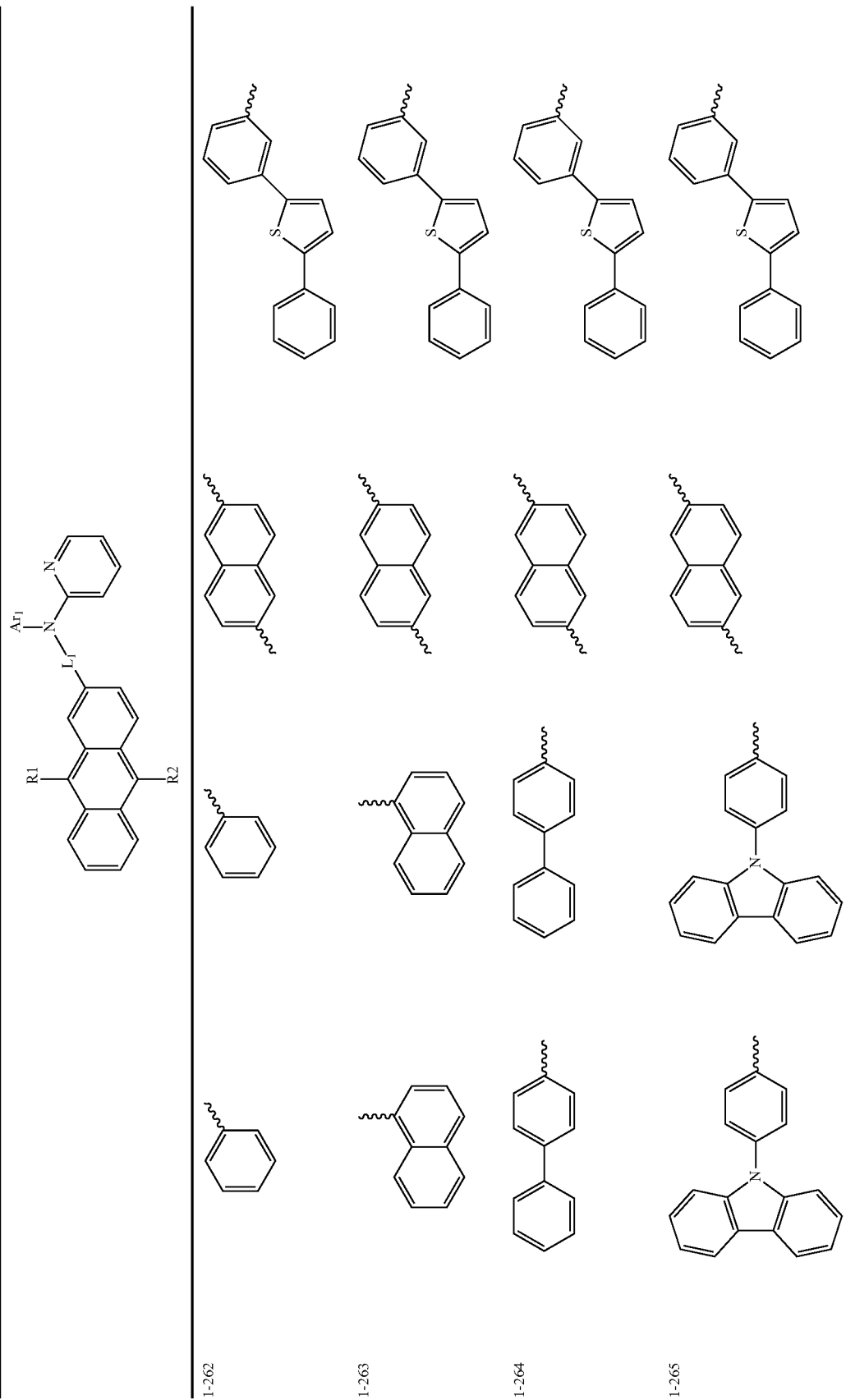

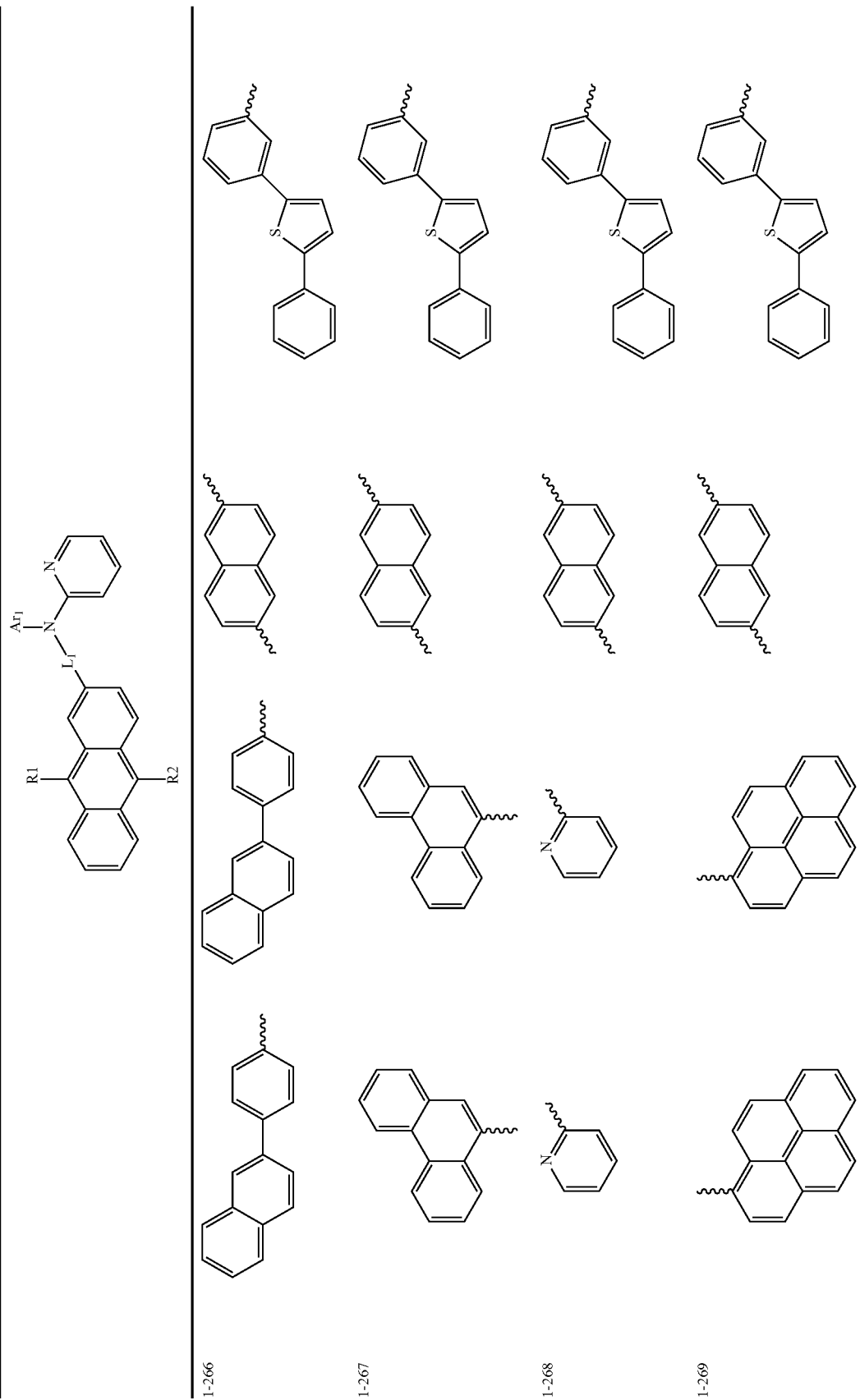

TABLE 1-continued

| | | | | |
|---|---|---|---|---|
| 1-270 | | | | |
| 1-271 | | | | |
| 1-272 | | | | |
| 1-273 | | | | |

TABLE 1-continued
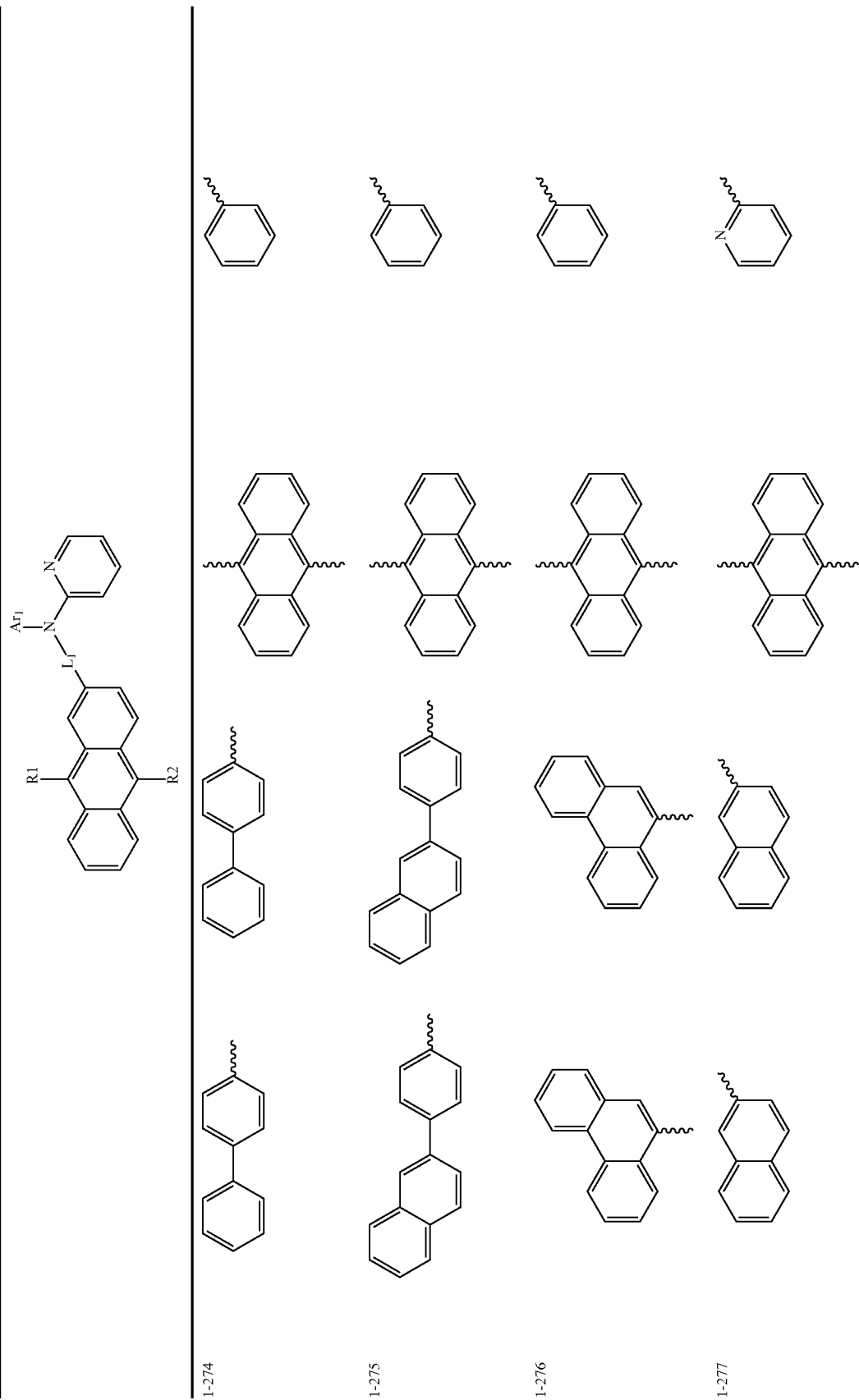

TABLE 1-continued

| | | | | |
|---|---|---|---|---|
| 1-278 | | | | |
| 1-279 | | | | |
| 1-280 | | | | |
| 1-281 | | | | |

TABLE 1-continued
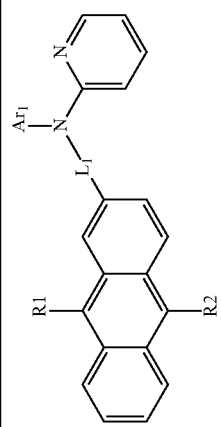
| | | | | |
|---|---|---|---|---|
| 1-282 | 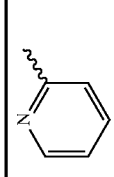 | 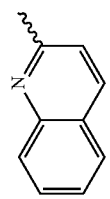 | 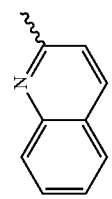 | 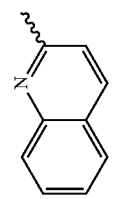 |
| | 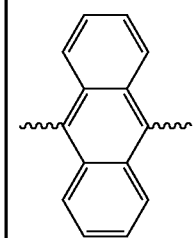 | 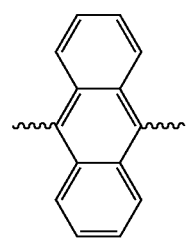 | 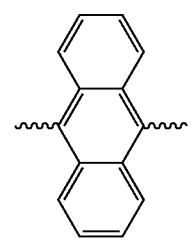 | 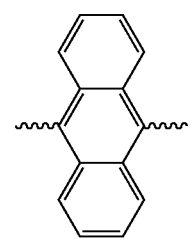 |
| 1-283 | | | |  |
| 1-284 | 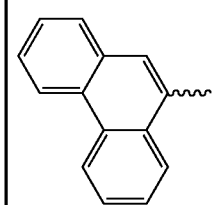 | 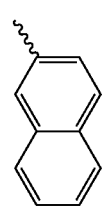 |  | 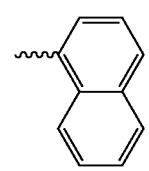 |
| 1-285 | | | | |

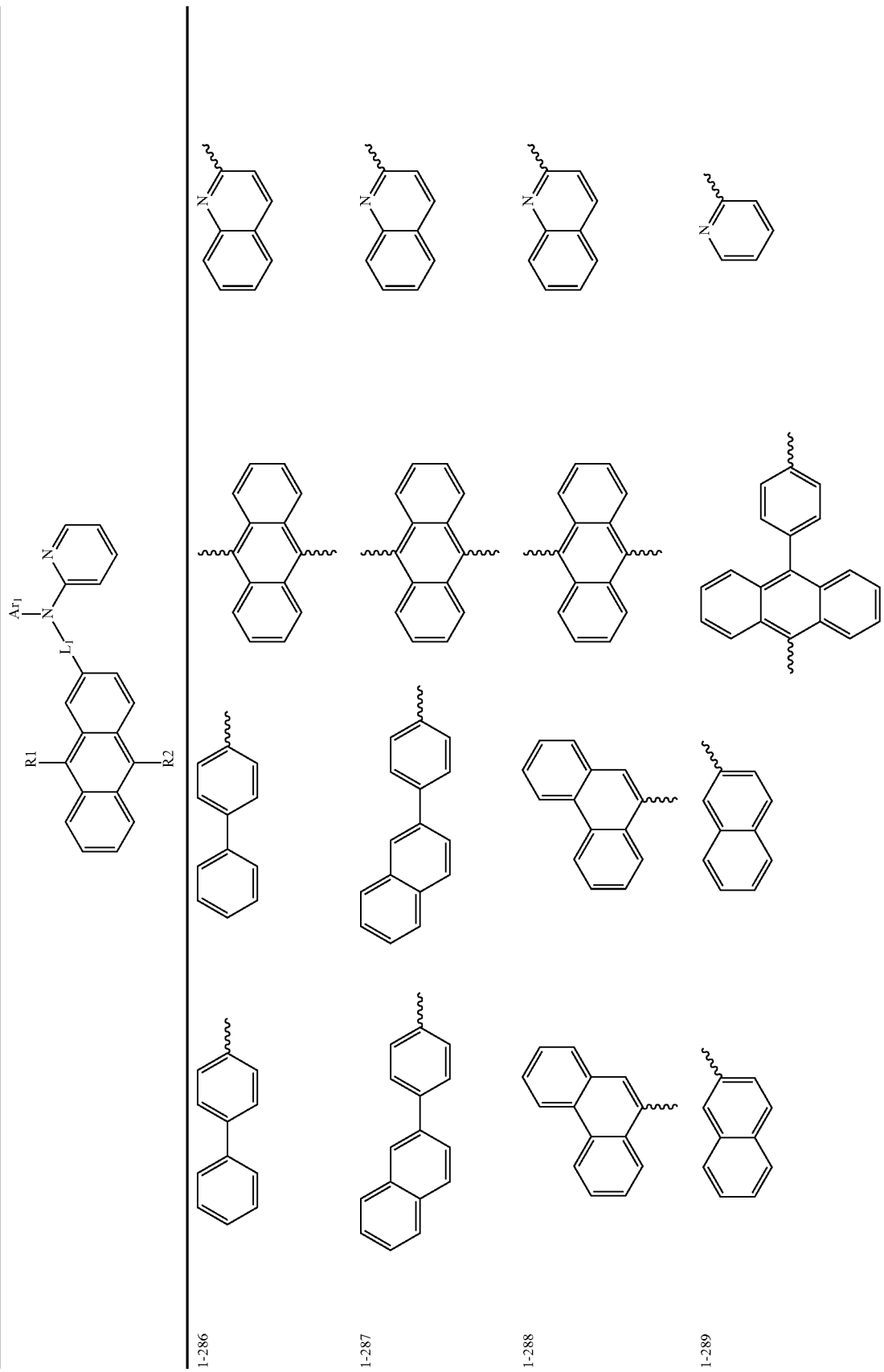

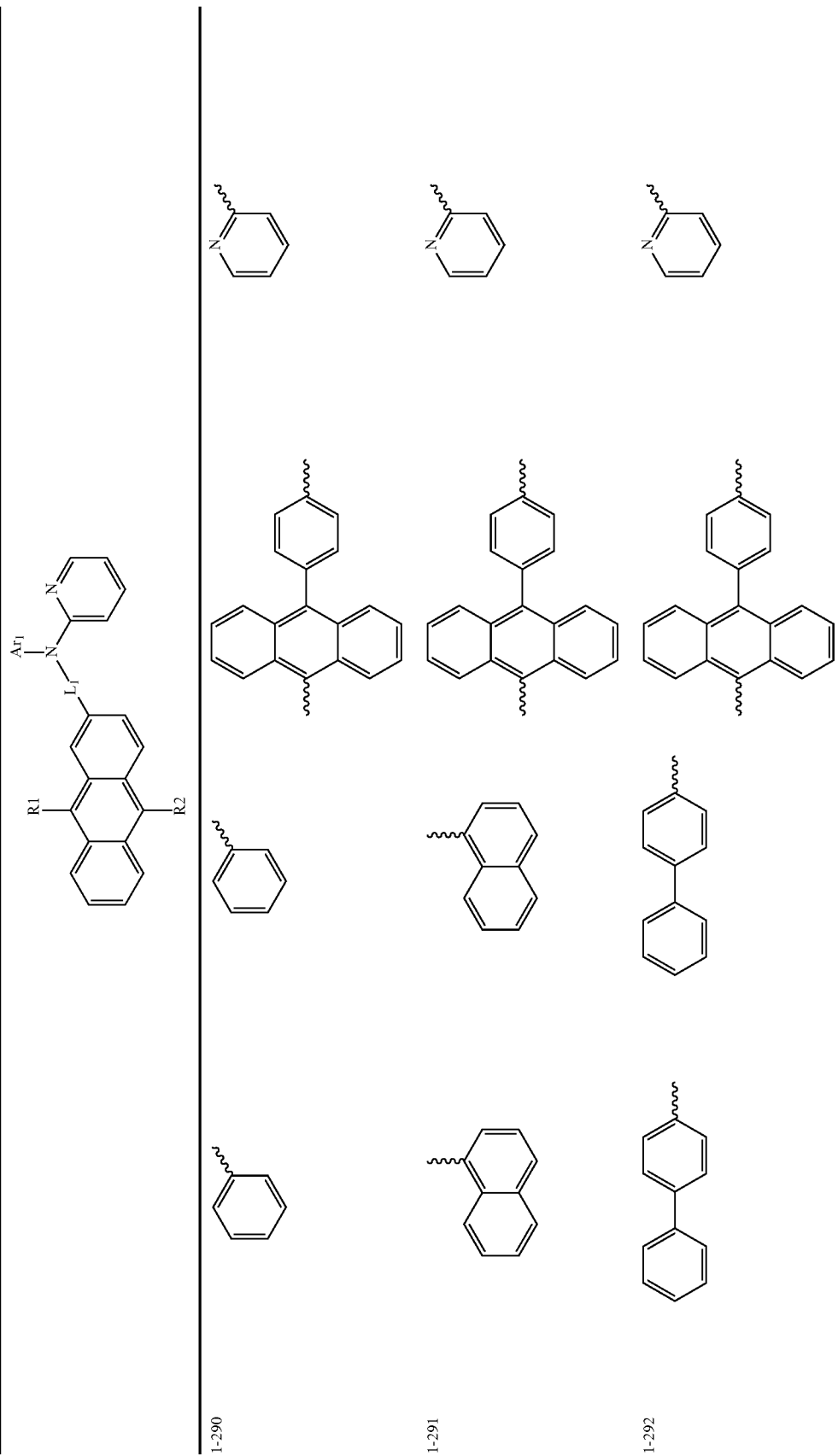

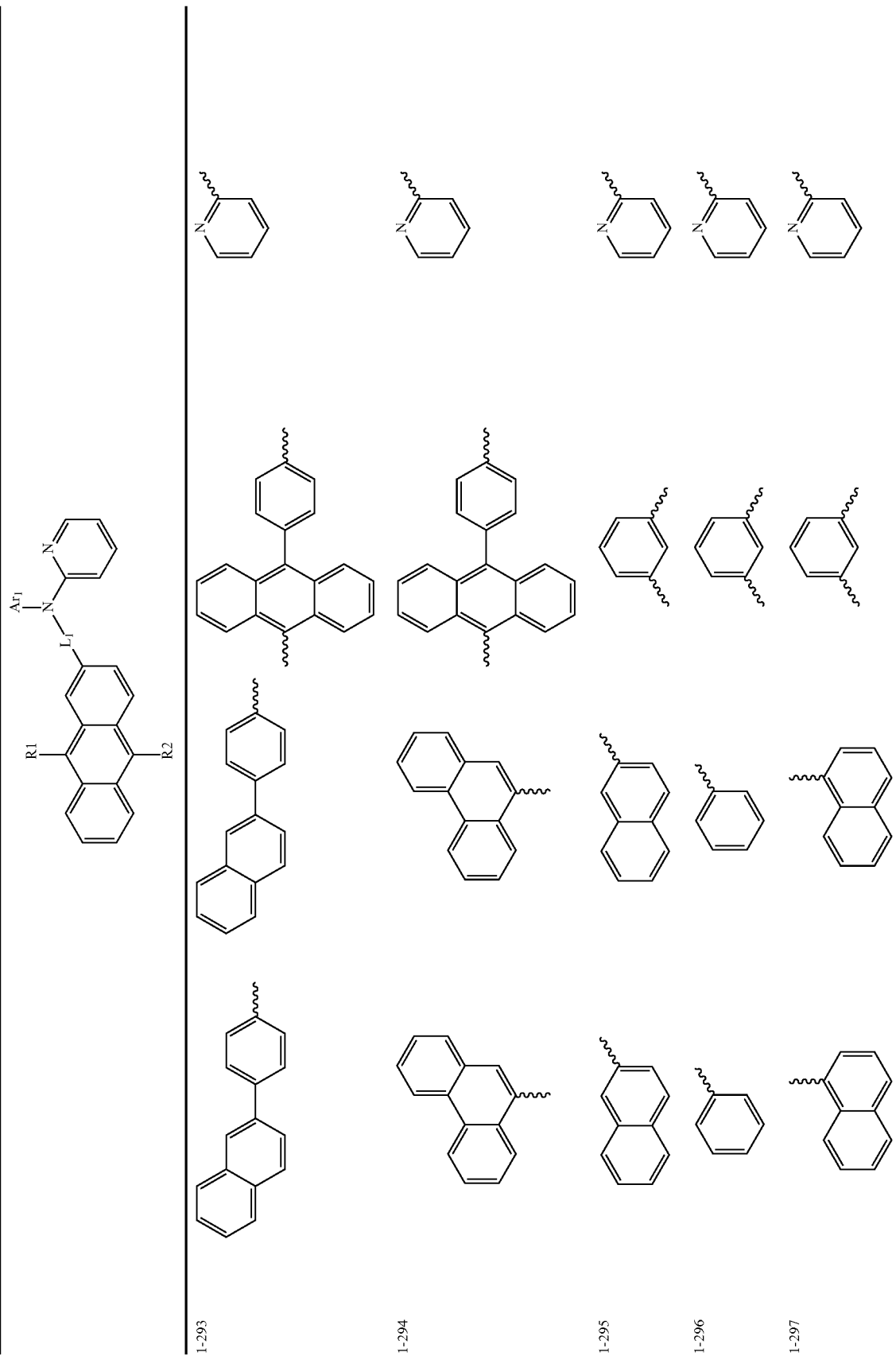

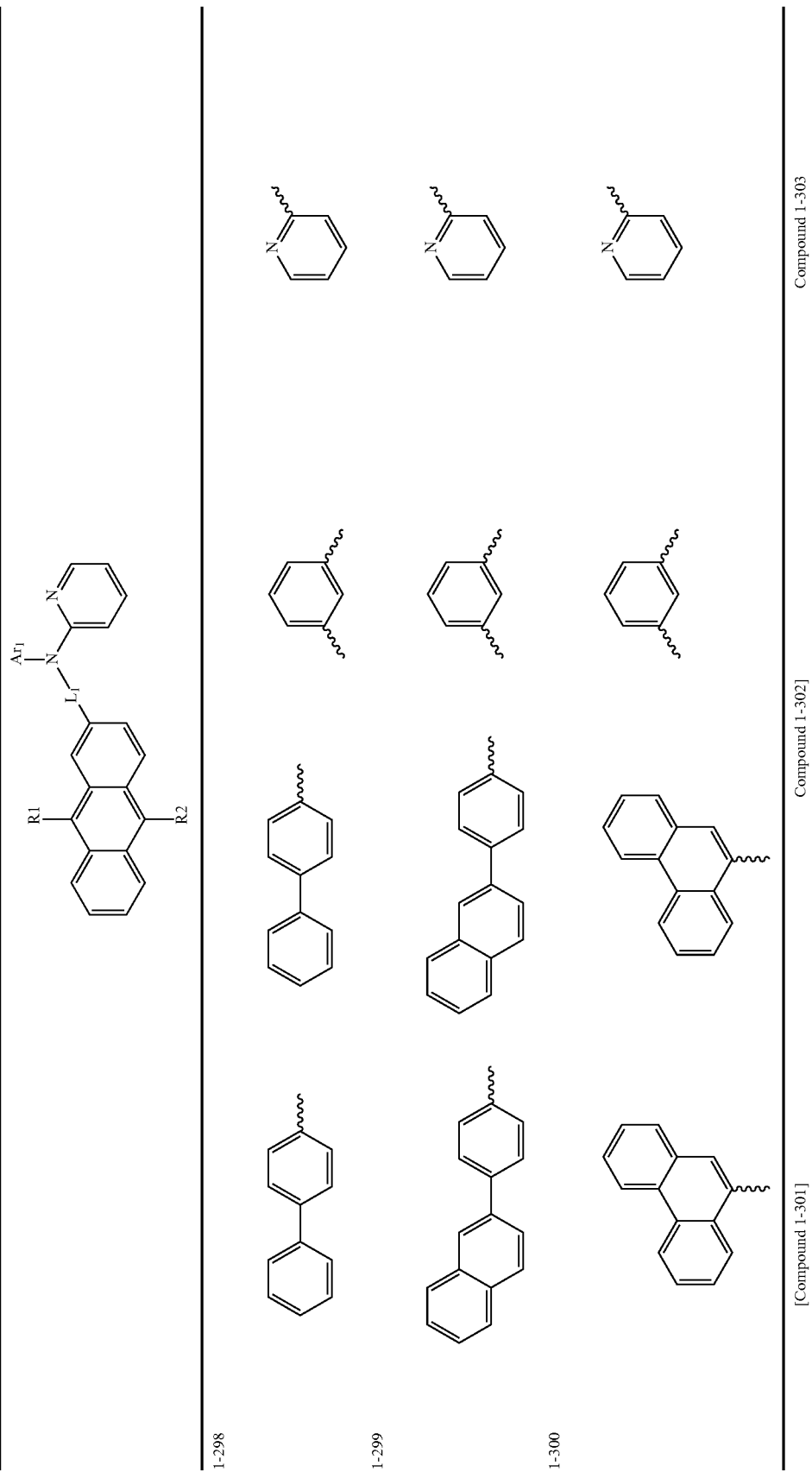

TABLE 1-continued
| | |
|---|---|
| 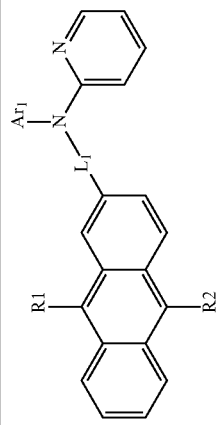 | 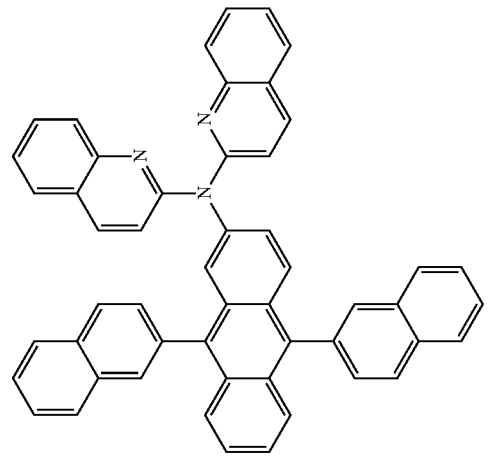
[Compound 1-306]
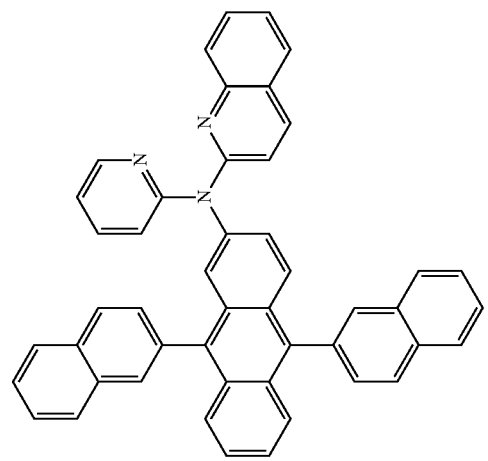
[Compound 1-305]
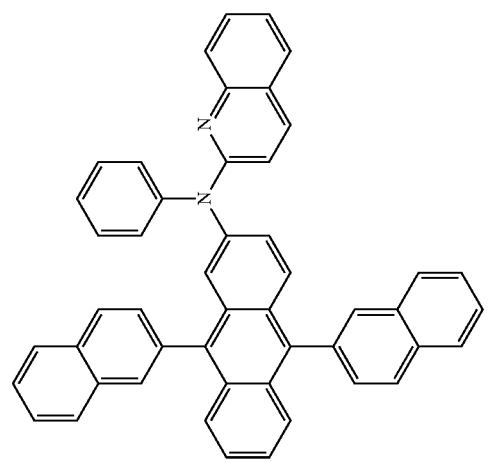
[Compound 1-304] |

TABLE 1-continued
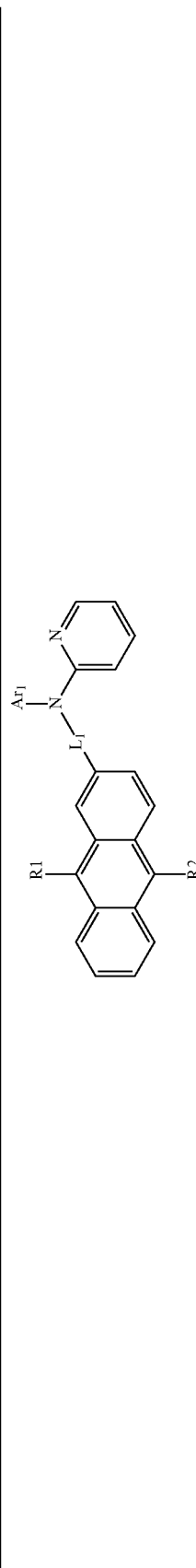
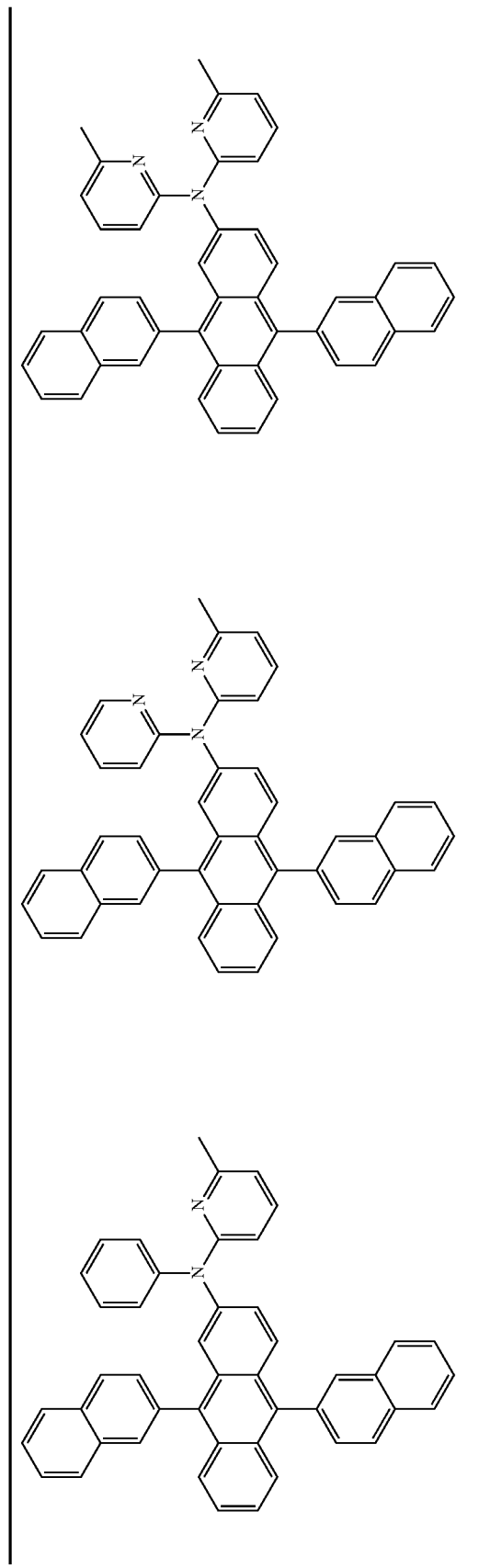
[Compound 1-307]
[Compound 1-308]
[Compound 1-309]

TABLE 1-continued
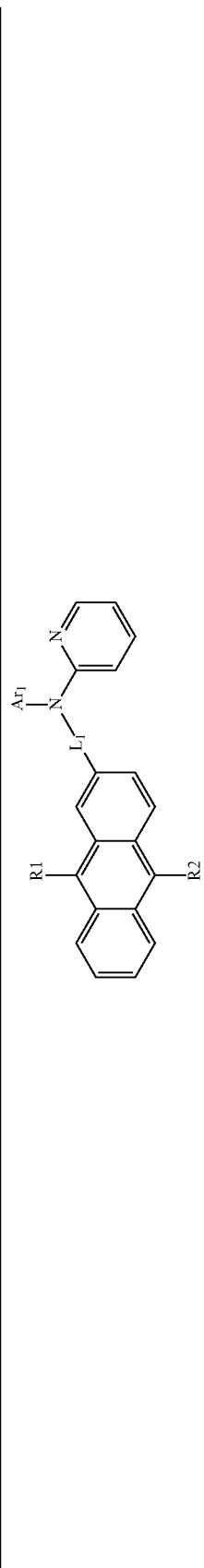
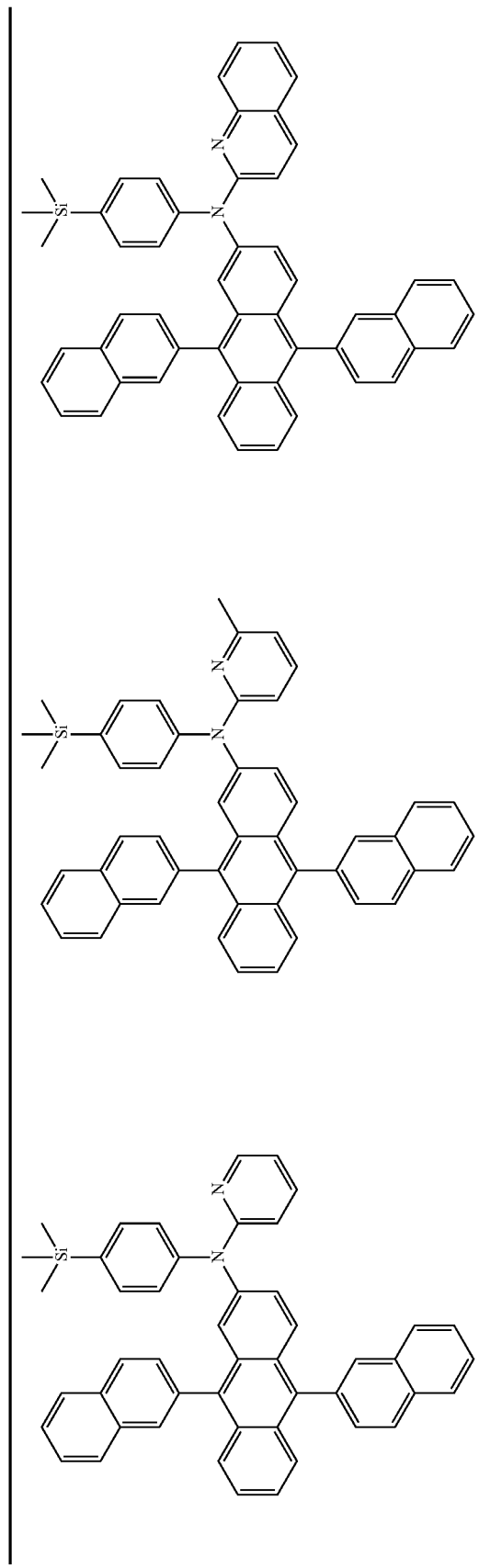
[Compound 1-310]
[Compound 1-311]
[Compound 1-312]

TABLE 1-continued
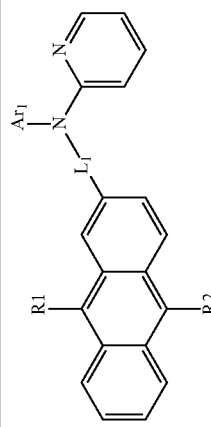
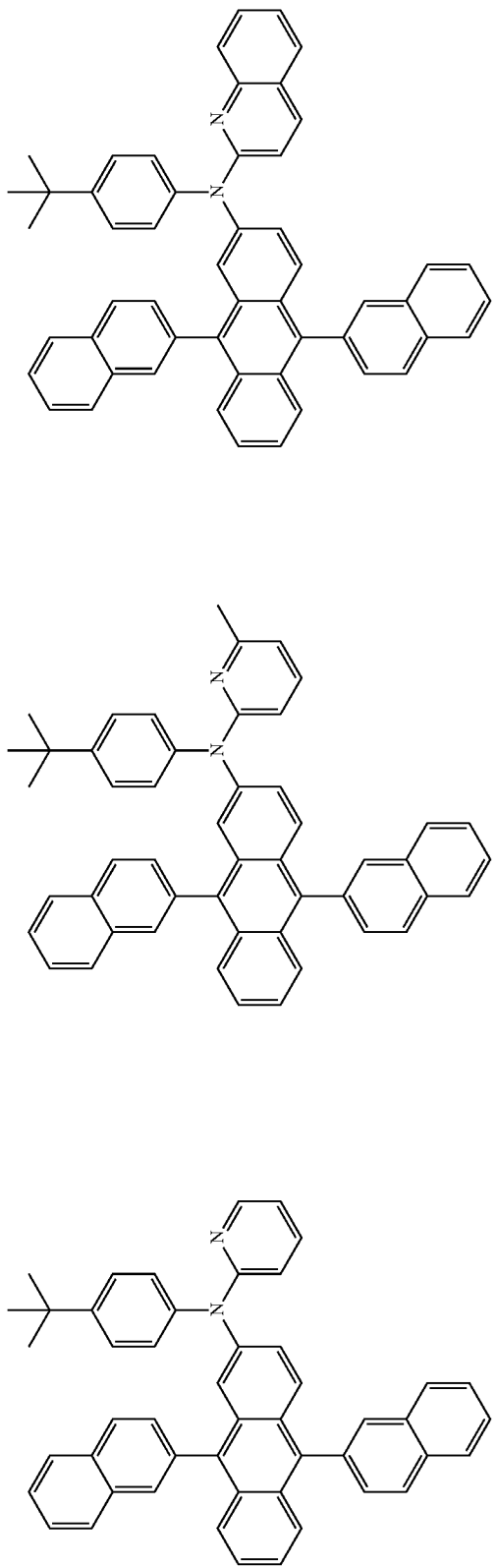
[Compound 1-315]
[Compound 1-314]
[Compound 1-313]

TABLE 1-continued
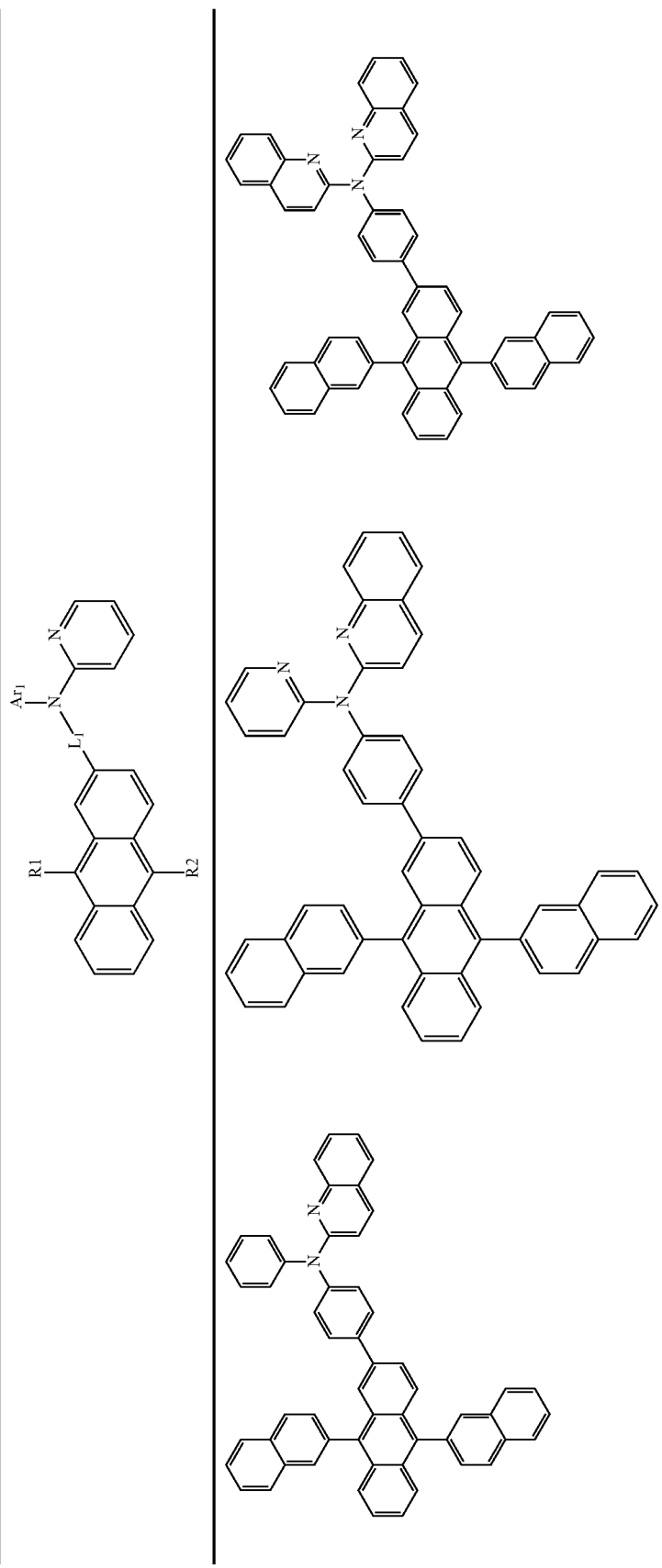
[Compound 1-316]
[Compound 1-317]
[Compound 1-318]

TABLE 1-continued
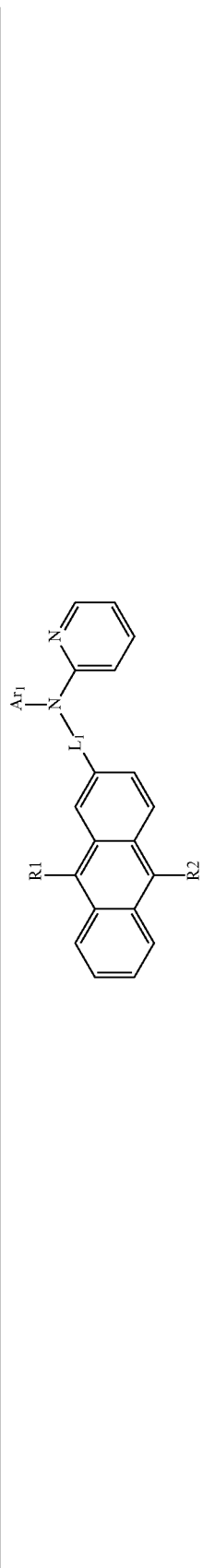
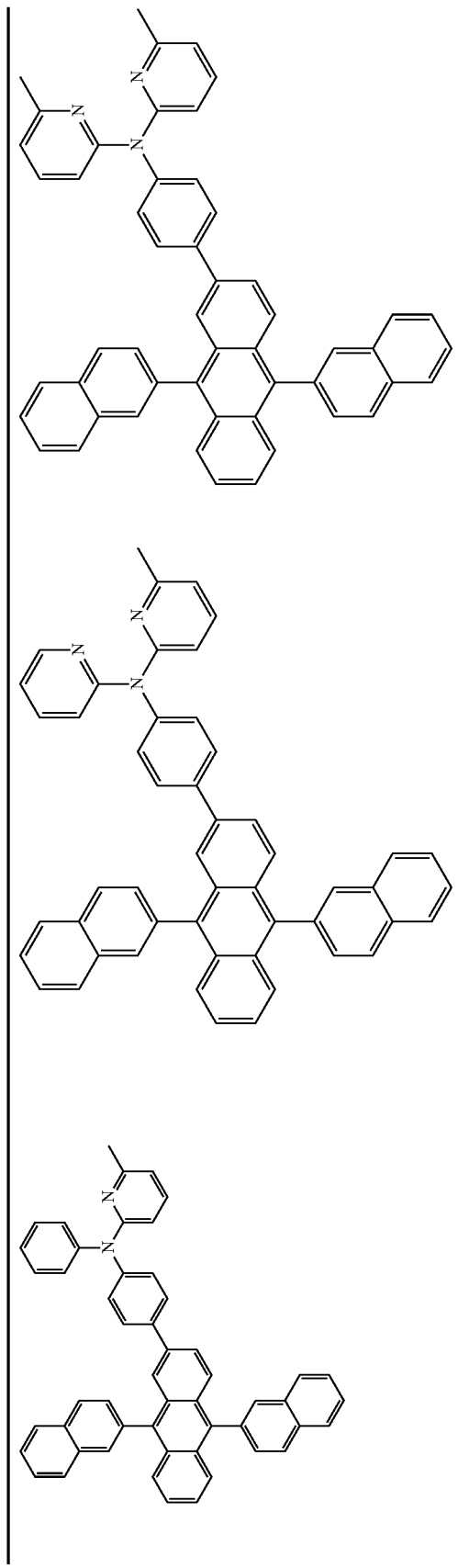
[Compound 1-321]
[Compound 1-320]
[Compound 1-319]

TABLE 1-continued
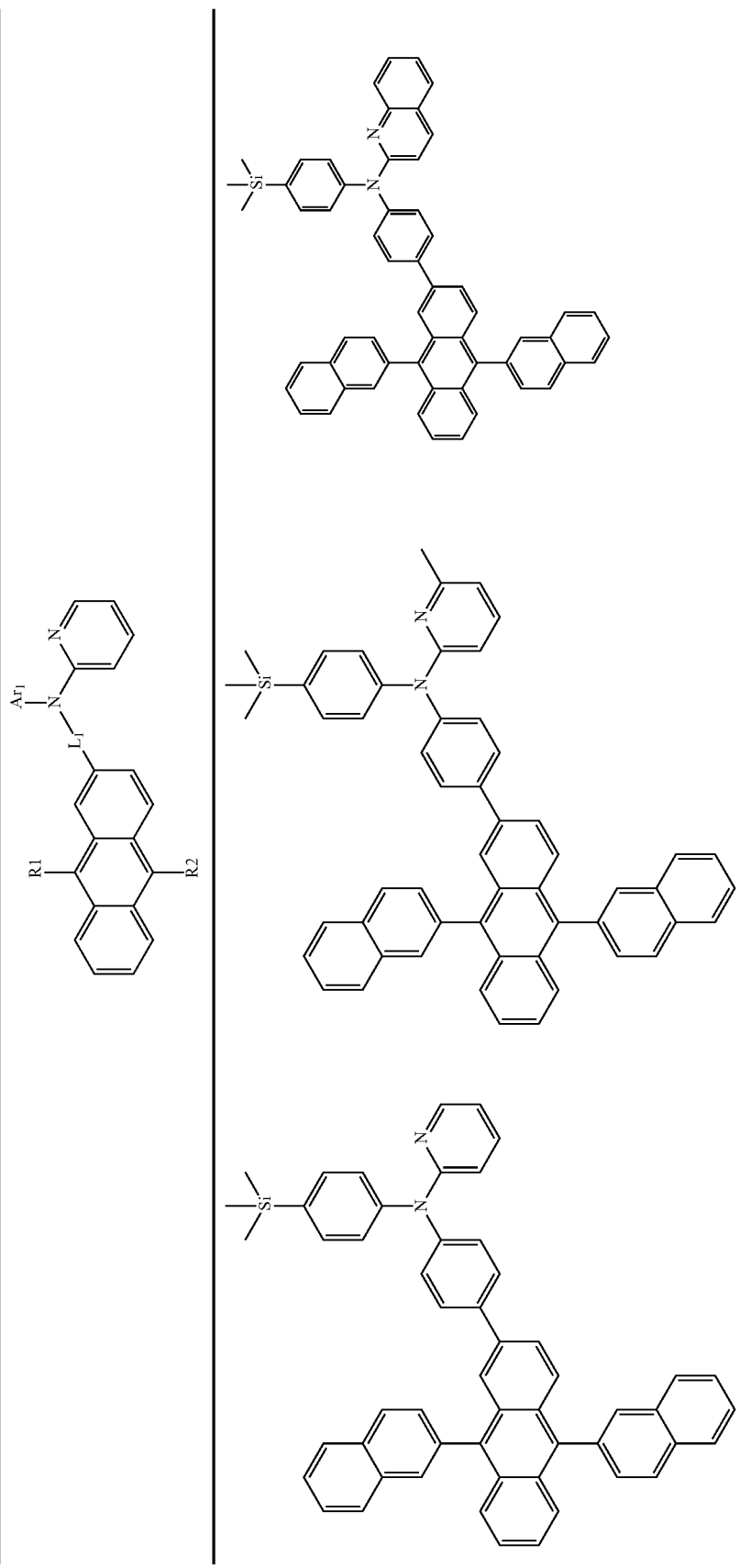

TABLE 1-continued
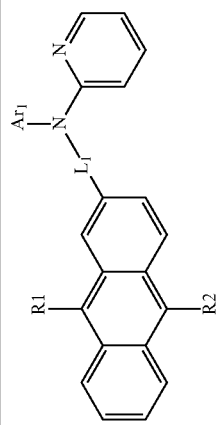
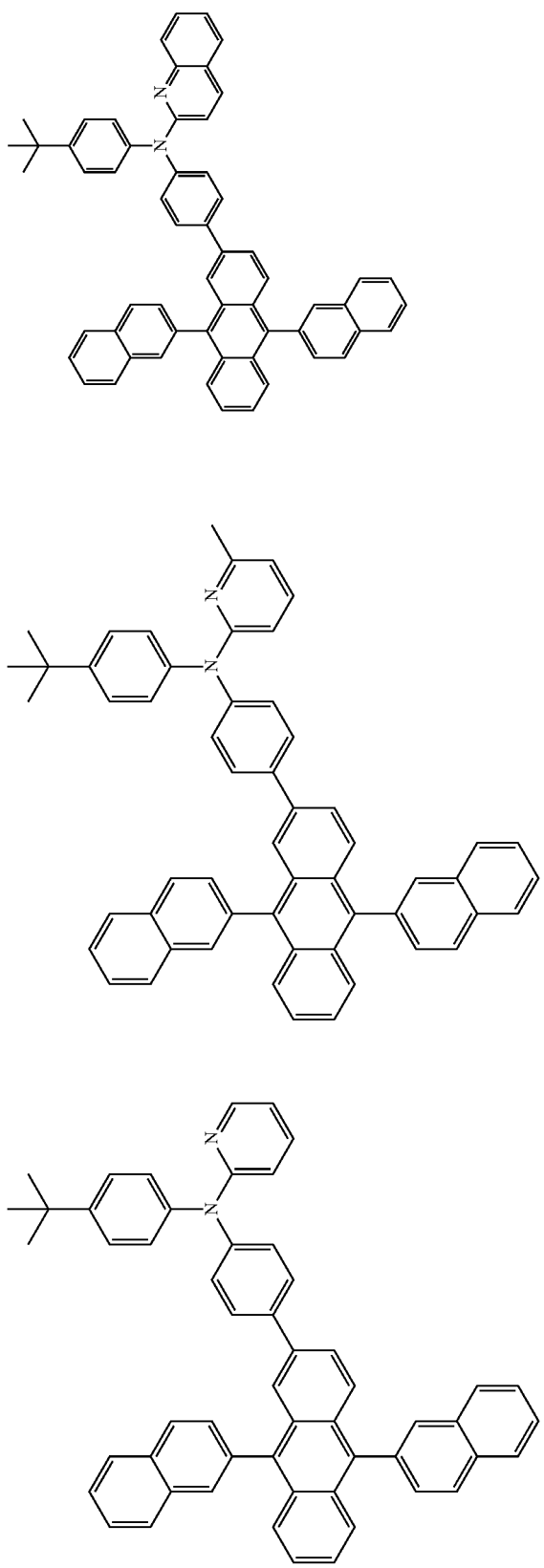

TABLE 2

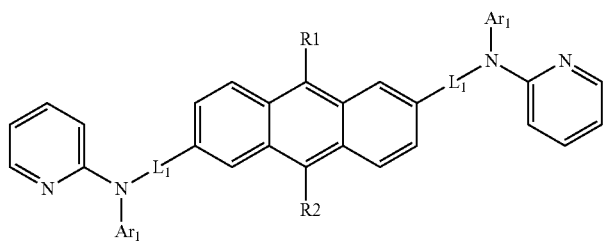

| Formula | R1 | R2 | L₁ | Ar₁ |
|---|---|---|---|---|
| 2-1 | 2-naphthyl | 2-naphthyl | direct bond | phenyl |
| 2-2 | phenyl | phenyl | direct bond | phenyl |
| 2-3 | 1-naphthyl | 1-naphthyl | direct bond | phenyl |
| 2-4 | biphenyl | biphenyl | direct bond | phenyl |
| 2-5 | 9-phenylcarbazol-4′-yl | 9-phenylcarbazol-4′-yl | direct bond | phenyl |
| 2-6 | 4-(2-naphthyl)phenyl | 4-(2-naphthyl)phenyl | direct bond | phenyl |
| 2-7 | phenanthren-9-yl | phenanthren-9-yl | direct bond | phenyl |
| 2-8 | pyridin-2-yl | pyridin-2-yl | direct bond | phenyl |

TABLE 2-continued

| Formula | R1 | R2 | L₁ | Ar₁ |
|---|---|---|---|---|
| 2-9 | pyrenyl | pyrenyl | direct bond | phenyl |
| 2-10 | isoquinolinyl | isoquinolinyl | direct bond | phenyl |
| 2-11 | naphthyl | naphthyl | direct bond | pyridyl |
| 2-12 | phenyl | phenyl | direct bond | pyridyl |
| 2-13 | 1-naphthyl | 1-naphthyl | direct bond | pyridyl |
| 2-14 | biphenyl | biphenyl | direct bond | pyridyl |
| 2-15 | 9-phenylcarbazolyl | 9-phenylcarbazolyl | direct bond | pyridyl |
| 2-16 | naphthylphenyl | naphthylphenyl | direct bond | pyridyl |

TABLE 2-continued
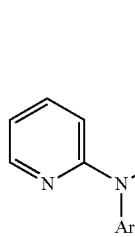
| Formula | R1 | R2 | L₁ | Ar₁ |
|---|---|---|---|---|
| 2-17 | 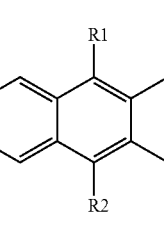 | 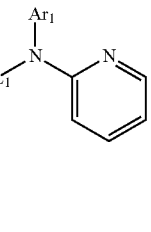 | direct bond |  |
| 2-18 | 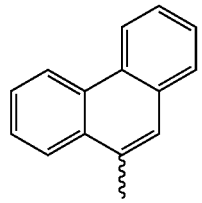 | 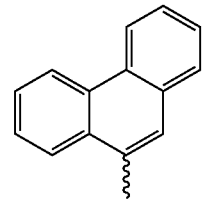 | direct bond | 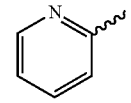 |
| 2-19 | 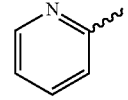 | 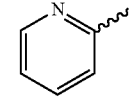 | direct bond | 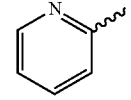 |
| 2-20 | 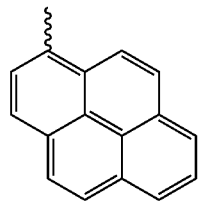 | 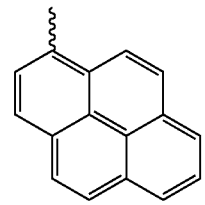 | direct bond | 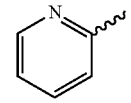 |
| 2-21 | 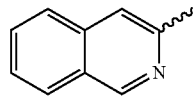 | 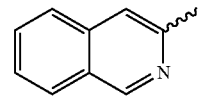 | direct bond | 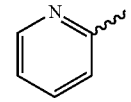 |
| 2-22 | 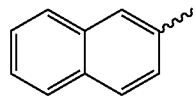 | 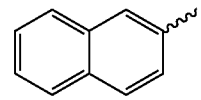 | direct bond | 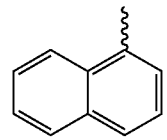 |
| 2-23 | 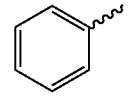 | 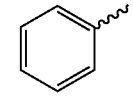 | direct bond | 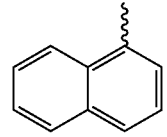 |
| 2-24 | 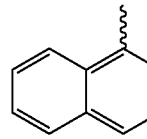 | 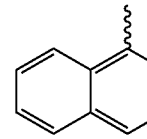 | direct bond | 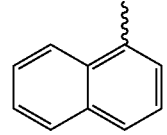 |

TABLE 2-continued

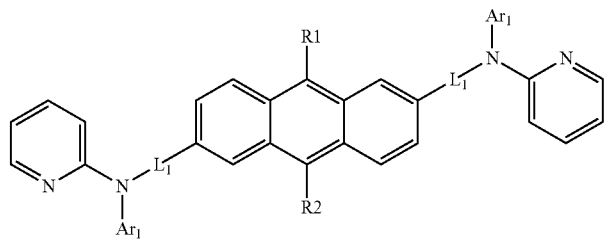

| Formula | R1 | R2 | L₁ | Ar₁ |
|---|---|---|---|---|
| 2-25 | 9-phenylcarbazol-4'-yl | 9-phenylcarbazol-4'-yl | direct bond | 1-naphthyl |
| 2-26 | 4-(2-naphthyl)phenyl | 4-(2-naphthyl)phenyl | direct bond | 1-naphthyl |
| 2-27 | phenanthren-9-yl | phenanthren-9-yl | direct bond | 1-naphthyl |
| 2-28 | pyridin-2-yl | pyridin-2-yl | direct bond | 1-naphthyl |
| 2-29 | pyren-1-yl | pyren-1-yl | direct bond | 1-naphthyl |
| 2-30 | isoquinolin-3-yl | isoquinolin-3-yl | direct bond | 1-naphthyl |
| 2-31 | 2-naphthyl | 2-naphthyl | direct bond | 2-naphthyl |
| 2-32 | phenyl | phenyl | direct bond | 2-naphthyl |

US 8,222,634 B2

TABLE 2-continued

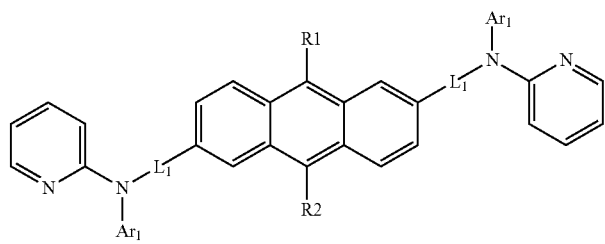

| Formula | R1 | R2 | L₁ | Ar₁ |
|---|---|---|---|---|
| 2-33 | 1-naphthyl | 1-naphthyl | direct bond | 2-naphthyl |
| 2-34 | 4-biphenyl | 4-biphenyl | direct bond | 2-naphthyl |
| 2-35 | 4-(9-carbazolyl)phenyl | 4-(9-carbazolyl)phenyl | direct bond | 2-naphthyl |
| 2-36 | 4-(2-naphthyl)phenyl | 4-(2-naphthyl)phenyl | direct bond | 2-naphthyl |
| 2-37 | phenanthren-9-yl | phenanthren-9-yl | direct bond | 2-naphthyl |
| 2-38 | 2-pyridyl | 2-pyridyl | direct bond | 2-naphthyl |
| 2-39 | 1-pyrenyl | 1-pyrenyl | direct bond | 2-naphthyl |
| 2-40 | isoquinolin-3-yl | isoquinolin-3-yl | direct bond | 2-naphthyl |

TABLE 2-continued
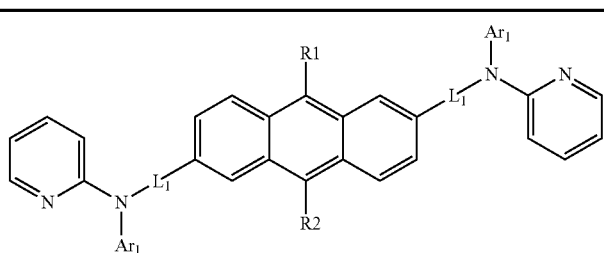
| Formula | R1 | R2 | L₁ | Ar₁ |
|---|---|---|---|---|
| 2-41 | 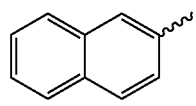 | 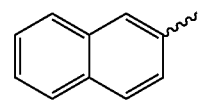 | direct bond | 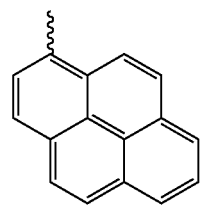 |
| 2-42 | 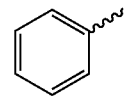 | 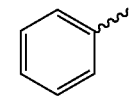 | direct bond | 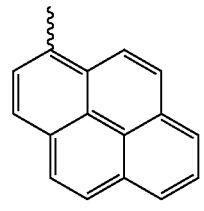 |
| 2-43 | 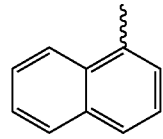 | 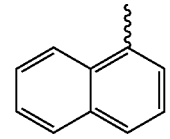 | direct bond | 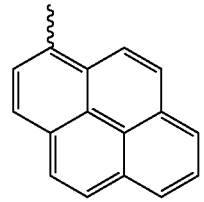 |
| 2-44 | 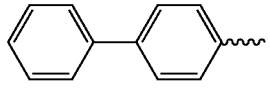 | 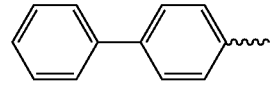 | direct bond | 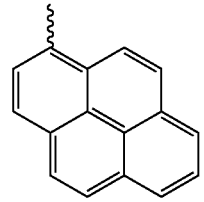 |
| 2-45 | 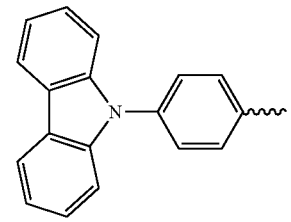 | 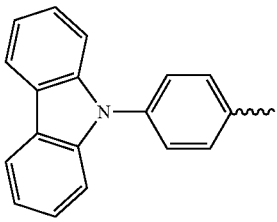 | direct bond | 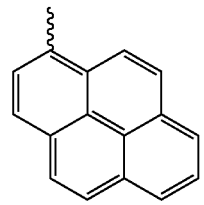 |
| 2-46 | 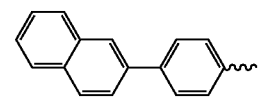 | 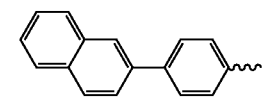 | direct bond | 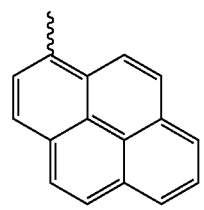 |

TABLE 2-continued
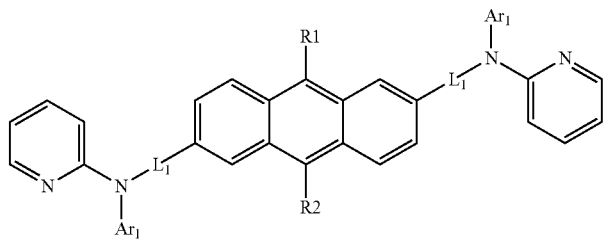
| Formula | R1 | R2 | L₁ | Ar₁ |
|---|---|---|---|---|
| 2-47 | 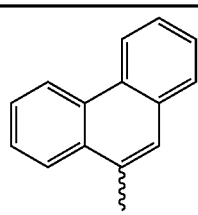 | 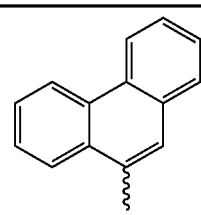 | direct bond | 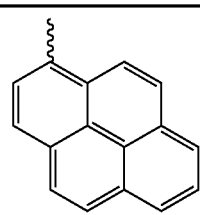 |
| 2-48 | 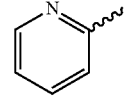 | 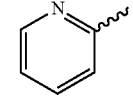 | direct bond | 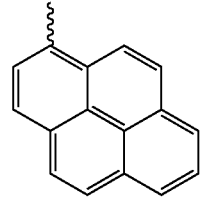 |
| 2-49 | 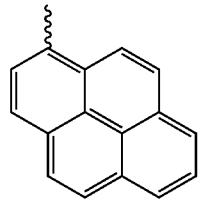 | 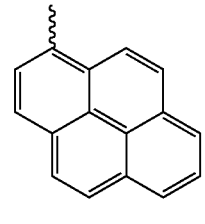 | direct bond | 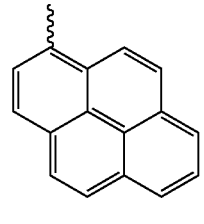 |
| 2-50 | 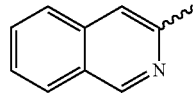 | 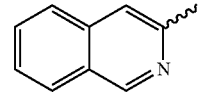 | direct bond | 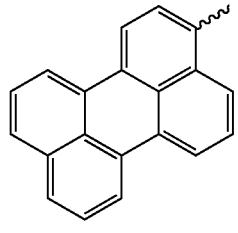 |
| 2-51 | 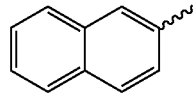 | 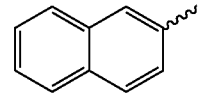 | direct bond | 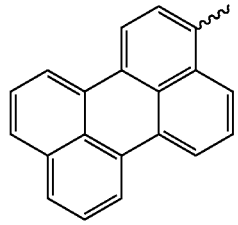 |
| 2-52 | 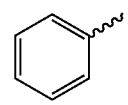 | 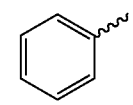 | direct bond | 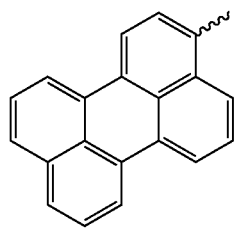 |

TABLE 2-continued
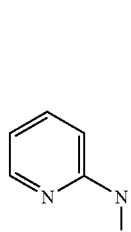
| Formula | R1 | R2 | L₁ | Ar₁ |
|---|---|---|---|---|
| 2-53 | 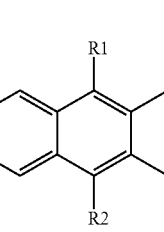 | 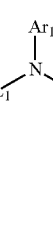 | direct bond | 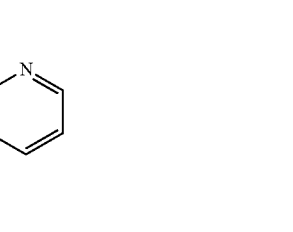 |
| 2-54 | 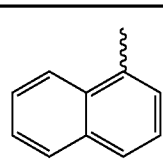 | 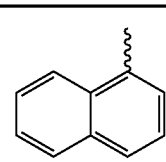 | direct bond | 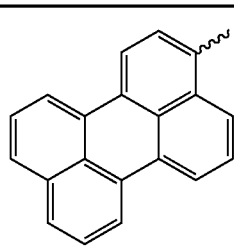 |
| 2-55 | 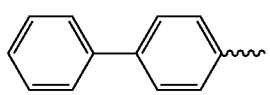 | 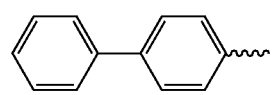 | direct bond | 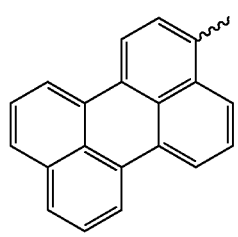 |
| 2-56 | 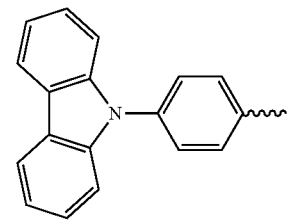 | 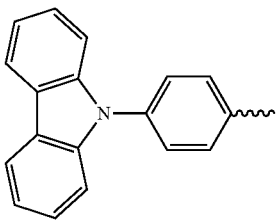 | direct bond | 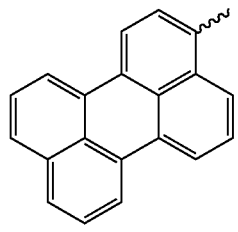 |
| 2-57 | 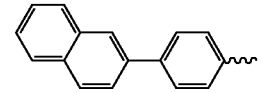 | 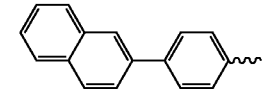 | direct bond | 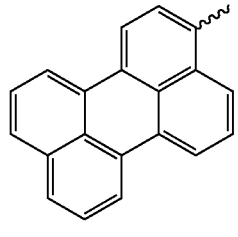 |

US 8,222,634 B2
197                                                                                                      198
TABLE 2-continued
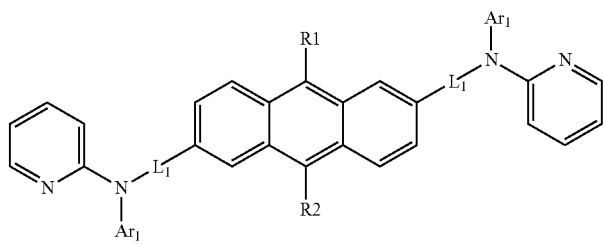
| Formula | R1 | R2 | L₁ | Ar₁ |
|---|---|---|---|---|
| 2-58 | 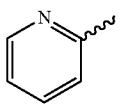 | 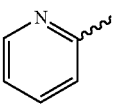 | direct bond | 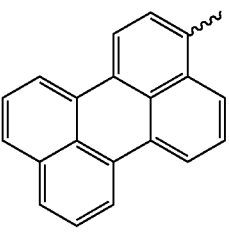 |
| 2-59 | 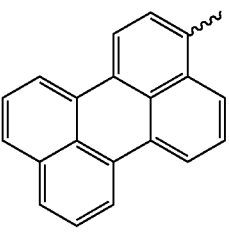 | 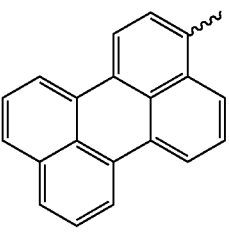 | direct bond | 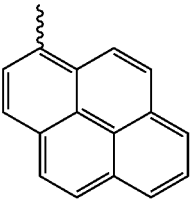 |
| 2-60 | 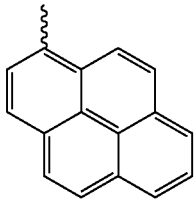 | 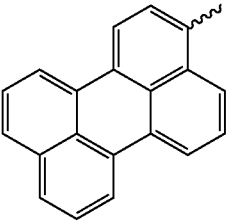 | direct bond | 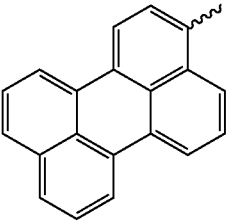 |
| 2-61 | 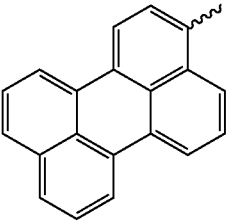 | 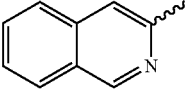 | direct bond | 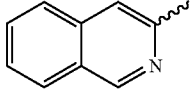 |
| 2-62 | 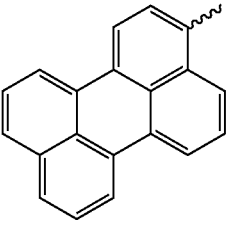 | 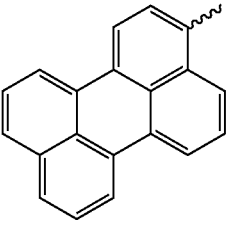 | direct bond | 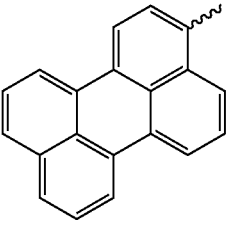 |
| 2-63 | 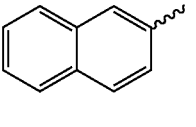 | 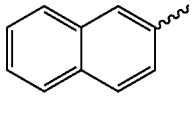 | direct bond | 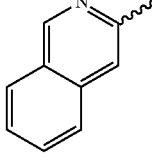 |

TABLE 2-continued
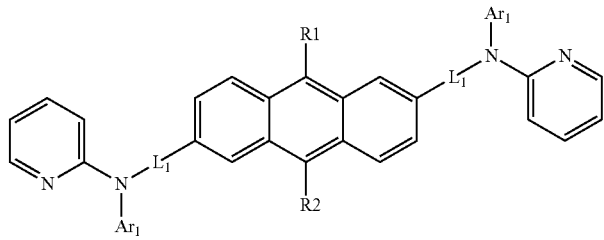
| Formula | R1 | R2 | L₁ | Ar₁ |
| --- | --- | --- | --- | --- |
| 2-64 | 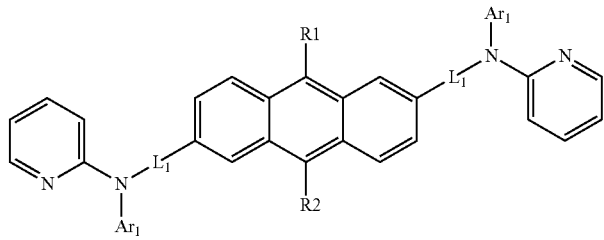 | 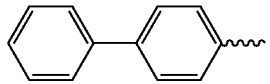 | direct bond | 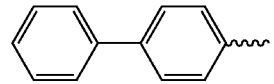 |
| 2-65 | 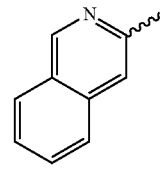 | 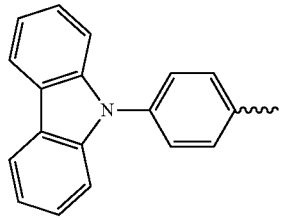 | direct bond | 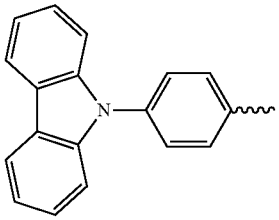 |
| 2-66 | 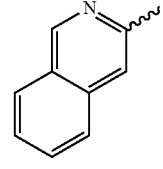 | 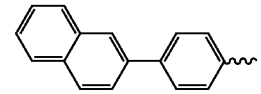 | direct bond | 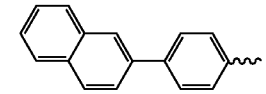 |
| 2-67 | 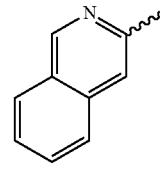 | 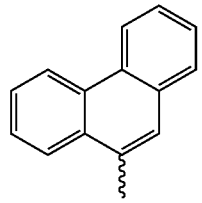 | direct bond | 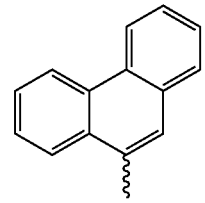 |
| 2-68 | 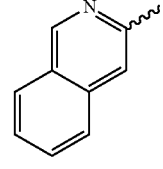 | 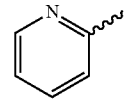 | direct bond | 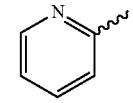 |
| 2-69 | 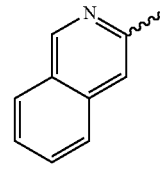 | 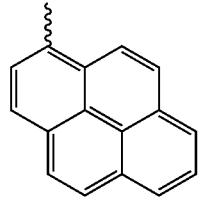 | direct bond | 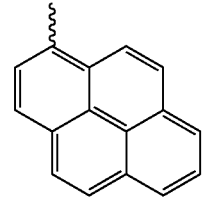 |

US 8,222,634 B2
TABLE 2-continued
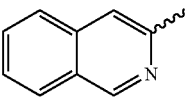
| Formula | R1 | R2 | L₁ | Ar₁ |
|---|---|---|---|---|
| 2-70 | 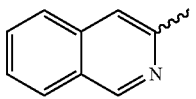 | 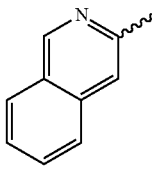 | direct bond | 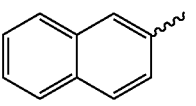 |
| 2-71 | 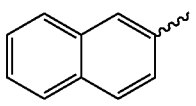 | 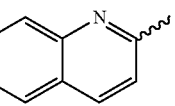 | direct bond | 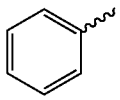 |
| 2-72 | 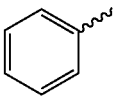 | 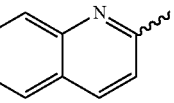 | direct bond | 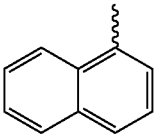 |
| 2-73 | 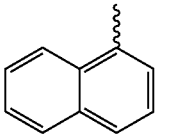 | 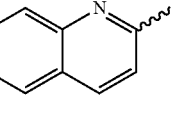 | direct bond | 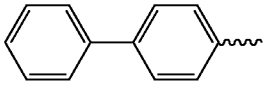 |
| 2-74 | 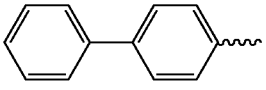 | 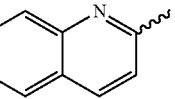 | direct bond | 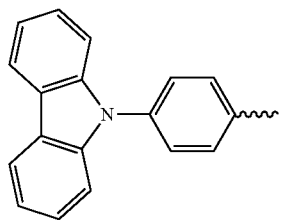 |
| 2-75 | 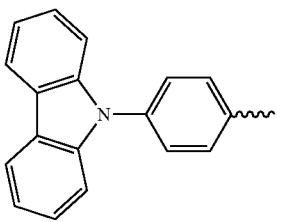 | 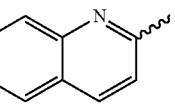 | direct bond | 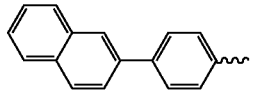 |
| 2-76 | 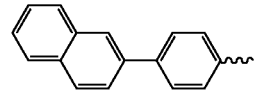 | 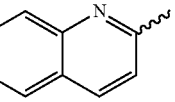 | direct bond | 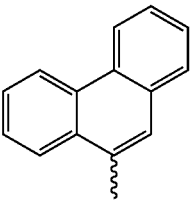 |
| 2-77 | 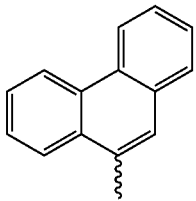 | 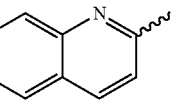 | direct bond | 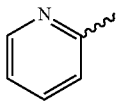 |
| 2-78 | 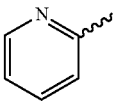 | 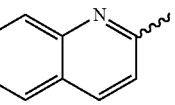 | direct bond |  |

TABLE 2-continued
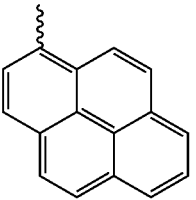
| Formula | R1 | R2 | L₁ | Ar₁ |
|---|---|---|---|---|
| 2-79 | 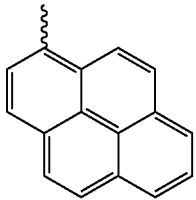 | 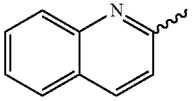 | direct bond | 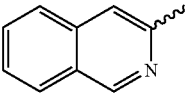 |
| 2-80 | 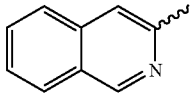 | 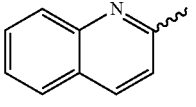 | direct bond | 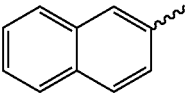 |
| 2-81 | 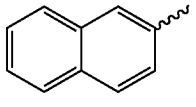 | 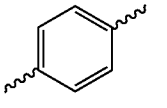 | 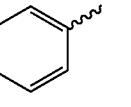 | 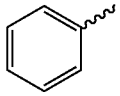 |
| 2-82 | 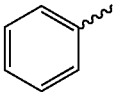 | 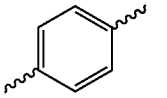 | 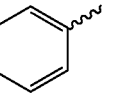 | 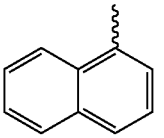 |
| 2-83 | 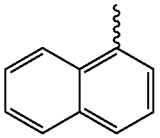 | 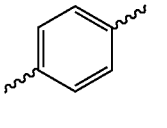 | 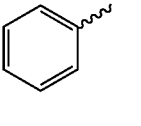 | 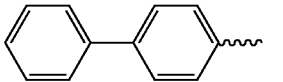 |
| 2-84 | 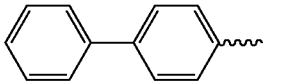 | 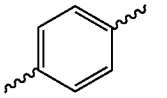 | 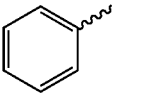 | 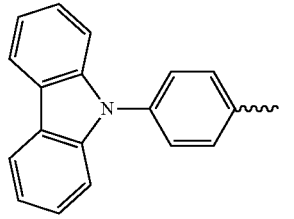 |
| 2-85 | 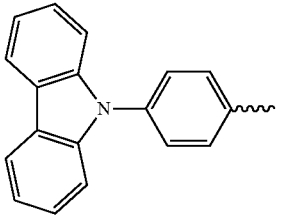 | 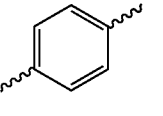 | 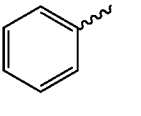 | 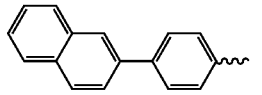 |
| 2-86 | 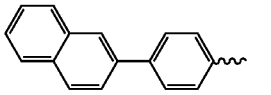 | 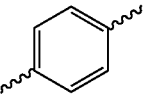 | 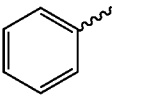 | |

TABLE 2-continued
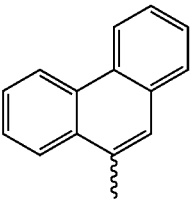
| Formula | R1 | R2 | L₁ | Ar₁ |
|---|---|---|---|---|
| 2-87 | 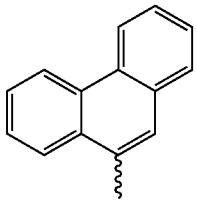 | 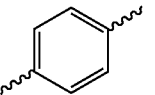 | 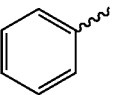 | 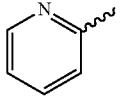 |
| 2-88 | 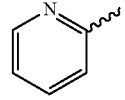 | 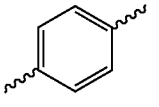 | 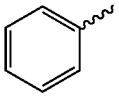 | 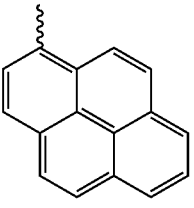 |
| 2-89 | 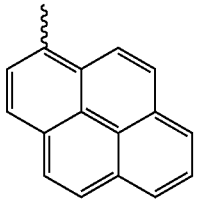 | 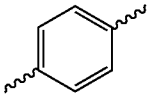 | 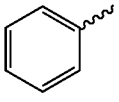 | 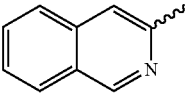 |
| 2-90 | 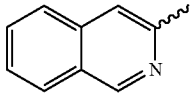 | 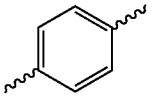 | 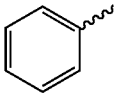 | 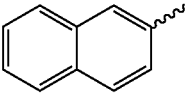 |
| 2-91 | 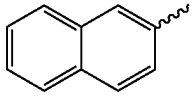 | 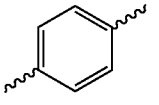 | 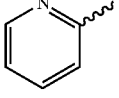 | 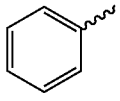 |
| 2-92 | 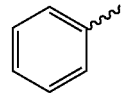 | 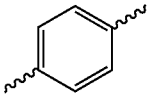 | 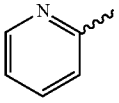 | 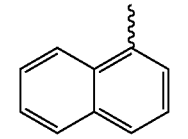 |
| 2-93 | 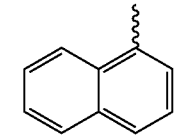 | 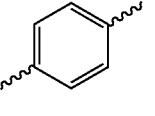 | 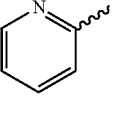 | 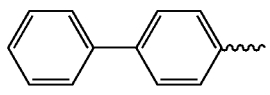 |
| 2-94 | 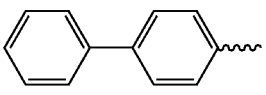 | 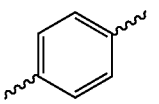 | 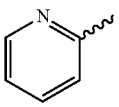 | |

TABLE 2-continued

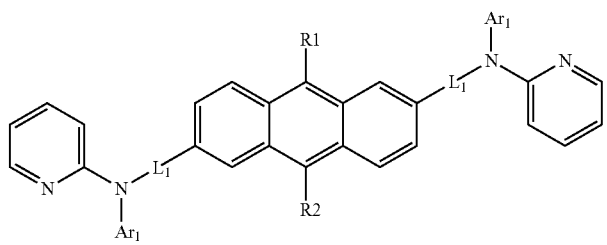

| Formula | R1 | R2 | L₁ | Ar₁ |
|---|---|---|---|---|
| 2-95 | N-phenyl-carbazol-phenyl | N-phenyl-carbazol-phenyl | phenylene | 2-pyridyl |
| 2-96 | 2-naphthyl-phenyl | 2-naphthyl-phenyl | phenylene | 2-pyridyl |
| 2-97 | phenanthren-9-yl | phenanthren-9-yl | phenylene | 2-pyridyl |
| 2-98 | 2-pyridyl | 2-pyridyl | phenylene | 2-pyridyl |
| 2-99 | pyren-1-yl | pyren-1-yl | phenylene | 2-pyridyl |
| 2-100 | isoquinolin-3-yl | isoquinolin-3-yl | phenylene | 2-pyridyl |
| 2-101 | 2-naphthyl | 2-naphthyl | phenylene | 1-naphthyl |
| 2-102 | phenyl | phenyl | phenylene | 1-naphthyl |

TABLE 2-continued

| Formula | R1 | R2 | L₁ | Ar₁ |
|---|---|---|---|---|
| 2-103 | naphthyl | naphthyl | phenylene | naphthyl |
| 2-104 | biphenyl | biphenyl | phenylene | naphthyl |
| 2-105 | N-phenylcarbazolyl | N-phenylcarbazolyl | phenylene | naphthyl |
| 2-106 | naphthylphenyl | naphthylphenyl | phenylene | naphthyl |
| 2-107 | phenanthrenyl | phenanthrenyl | phenylene | naphthyl |
| 2-108 | pyridyl | pyridyl | phenylene | naphthyl |
| 2-109 | pyrenyl | pyrenyl | phenylene | naphthyl |

TABLE 2-continued
| Formula | R1 | R2 | L₁ | Ar₁ |
|---|---|---|---|---|
| 2-110 | 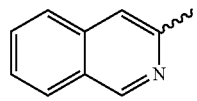 | 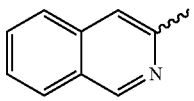 | 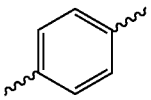 | 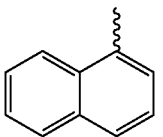 |
| 2-111 | 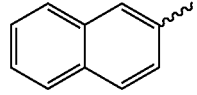 | 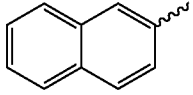 | 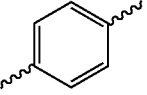 | 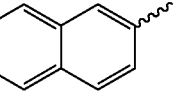 |
| 2-112 |  |  | 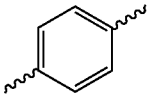 | 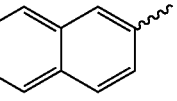 |
| 2-113 | 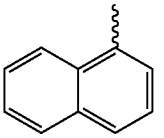 | 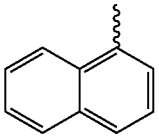 | 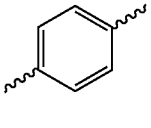 | 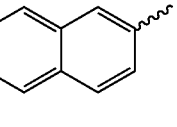 |
| 2-114 | 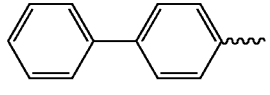 | 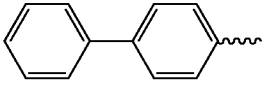 | 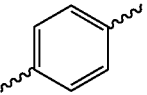 | 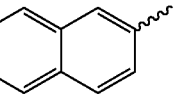 |
| 2-115 | 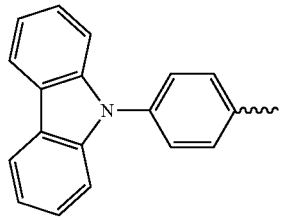 | 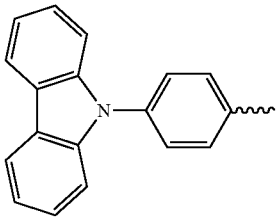 | 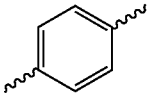 | 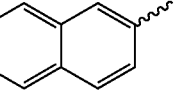 |
| 2-116 | 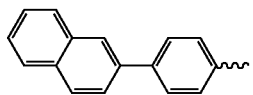 | 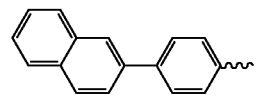 | 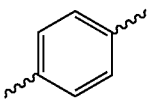 | 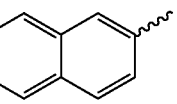 |
| 2-117 | 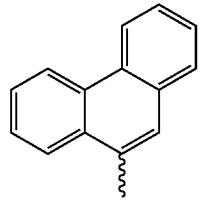 | 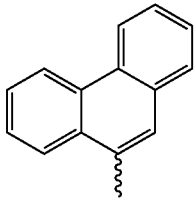 | 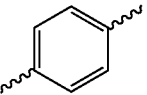 | 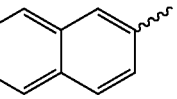 |
| 2-118 | 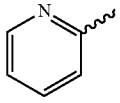 | 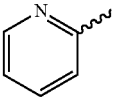 | 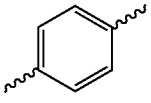 | 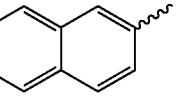 |
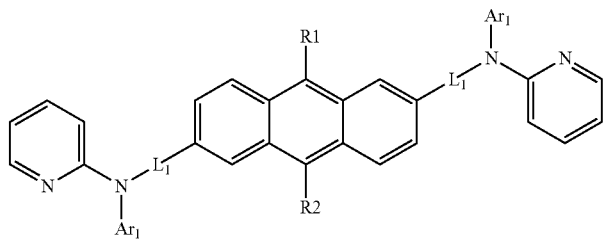

TABLE 2-continued

| Formula | R1 | R2 | L₁ | Ar₁ |
|---|---|---|---|---|
| 2-119 | pyrenyl | pyrenyl | phenylene | naphthyl |
| 2-120 | isoquinolinyl | isoquinolinyl | phenylene | naphthyl |
| 2-121 | naphthyl | naphthyl | phenylene | pyrenyl |
| 2-122 | phenyl | phenyl | phenylene | pyrenyl |
| 2-123 | naphthyl | naphthyl | phenylene | pyrenyl |
| 2-124 | biphenyl | biphenyl | phenylene | pyrenyl |

TABLE 2-continued
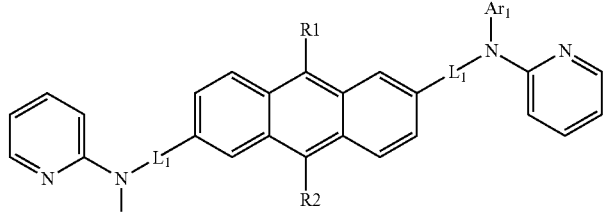
| Formula | R1 | R2 | L₁ | Ar₁ |
|---|---|---|---|---|
| 2-125 | 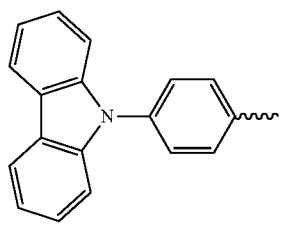 | 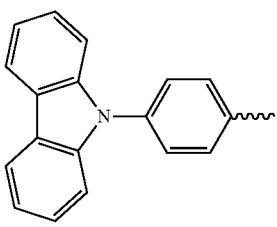 | 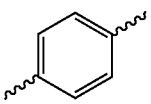 | 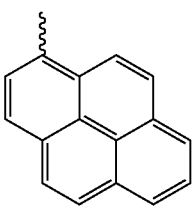 |
| 2-126 | 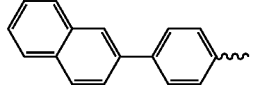 | 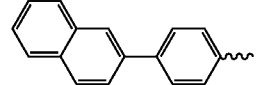 | 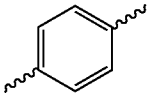 | 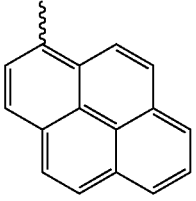 |
| 2-127 | 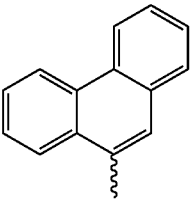 | 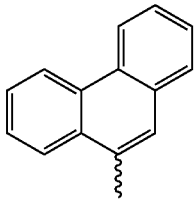 | 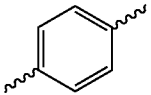 | 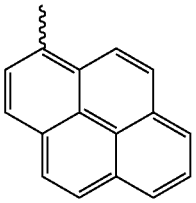 |
| 2-128 | 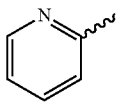 | 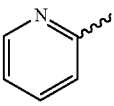 | 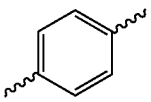 | 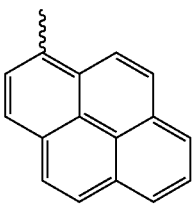 |
| 2-129 | 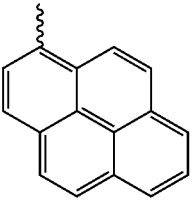 | 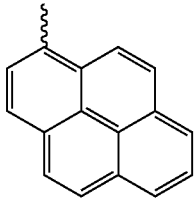 | 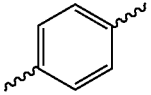 | 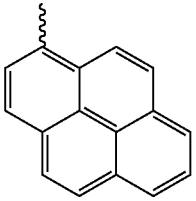 |
| 2-130 | 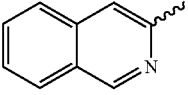 | 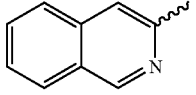 | 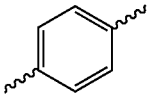 | 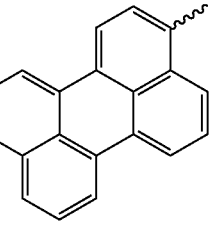 |

TABLE 2-continued

| Formula | R1 | R2 | L₁ | Ar₁ |
|---|---|---|---|---|
| 2-131 | 2-quinolinyl | 2-quinolinyl | 1,4-phenylene | perylenyl |
| 2-132 | phenyl | phenyl | 1,4-phenylene | perylenyl |
| 2-133 | 1-naphthyl | 1-naphthyl | 1,4-phenylene | perylenyl |
| 2-134 | biphenyl | biphenyl | 1,4-phenylene | perylenyl |
| 2-135 | 9-carbazolylphenyl | 9-carbazolylphenyl | 1,4-phenylene | perylenyl |

TABLE 2-continued
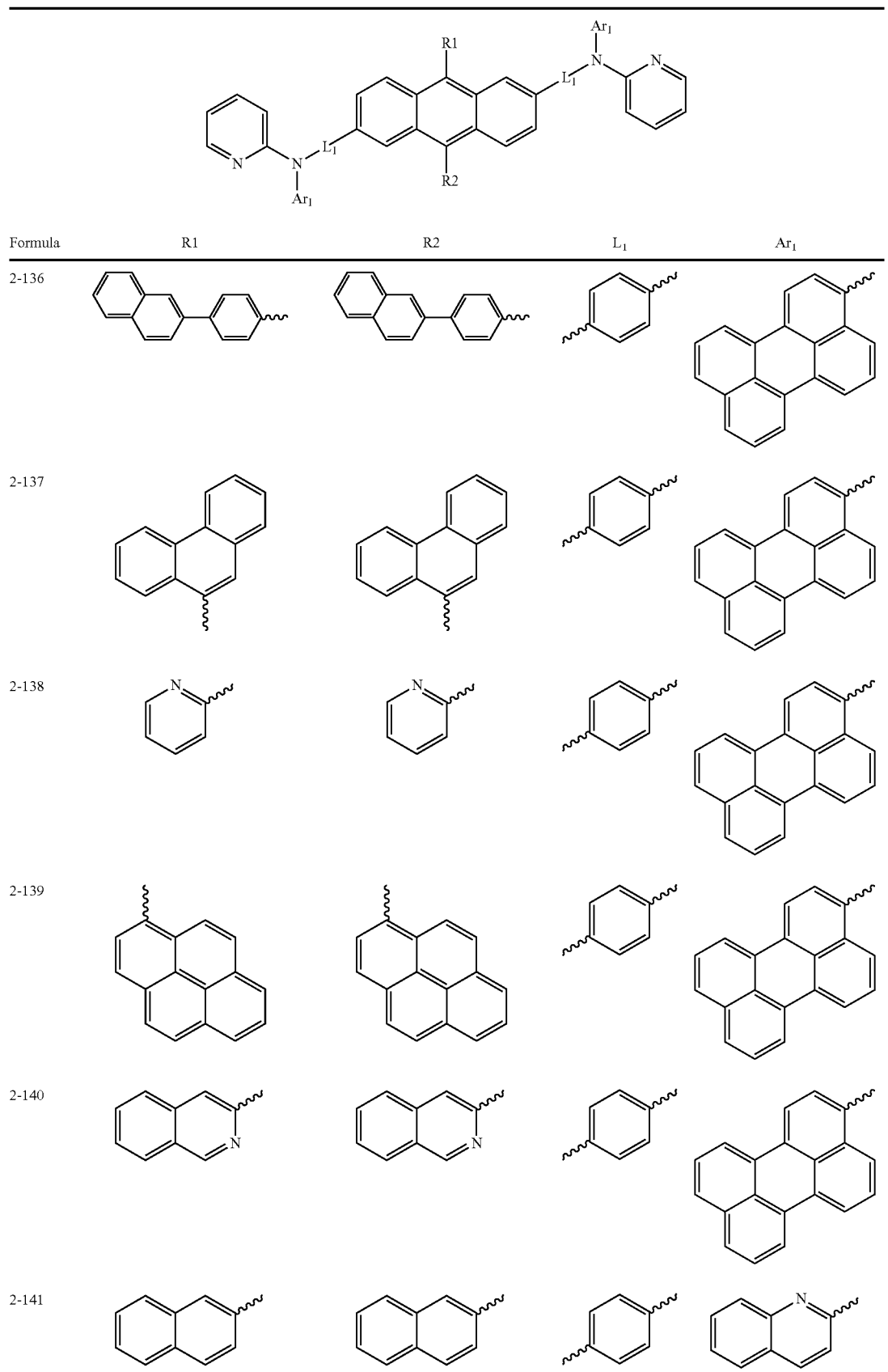

TABLE 2-continued
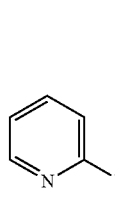
| Formula | R1 | R2 | L₁ | Ar₁ |
|---|---|---|---|---|
| 2-142 | 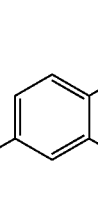 | 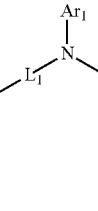 |  | 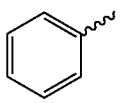 |
| 2-143 | 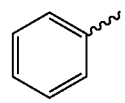 | 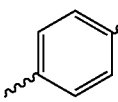 | 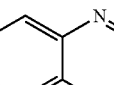 | 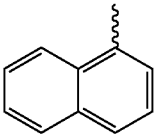 |
| 2-144 | 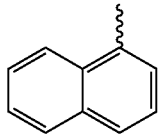 | 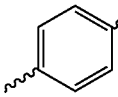 | 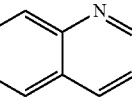 | 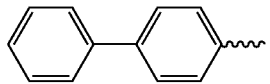 |
| 2-145 | 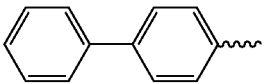 | 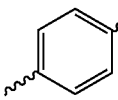 | 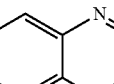 | 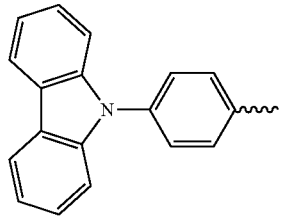 |
| 2-146 | 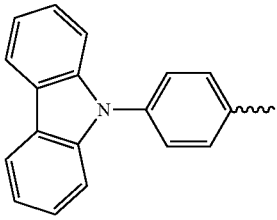 | 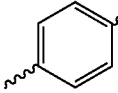 | 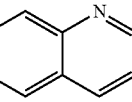 | 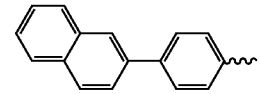 |
| 2-147 | 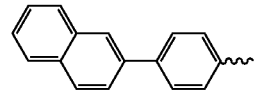 | 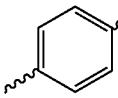 | 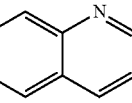 | 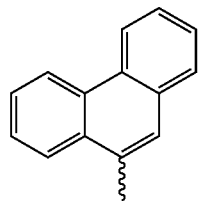 |
| 2-148 | 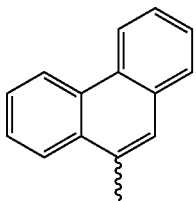 | 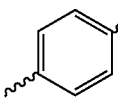 | 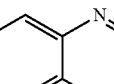 | 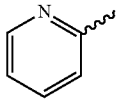 |
| 2-149 | 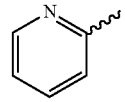 | 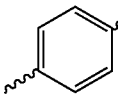 | 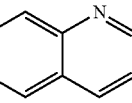 | 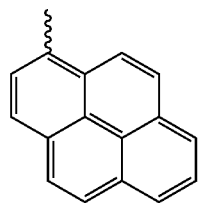 |

TABLE 2-continued
| Formula | R1 | R2 | L₁ | Ar₁ |
|---|---|---|---|---|
| 2-150 | 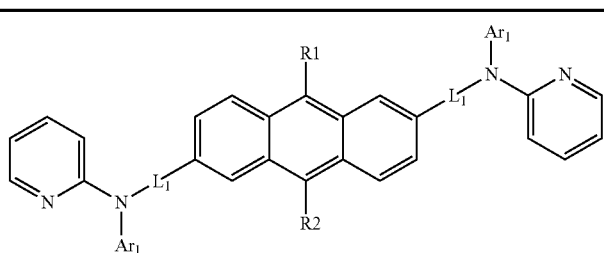 | 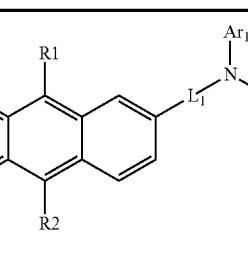 | 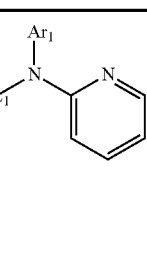 |  |
| 2-151 | 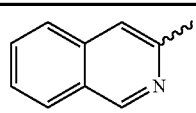 | 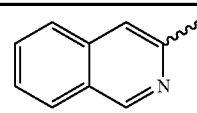 | 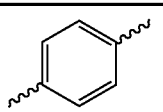 | 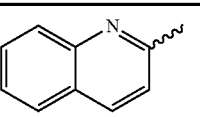 |
| 2-152 | 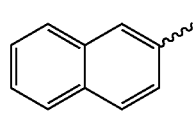 | 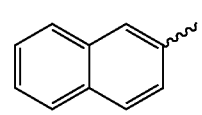 | 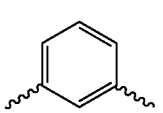 | 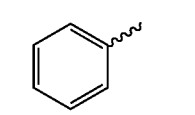 |
| 2-153 | 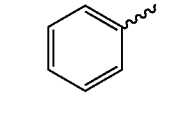 | 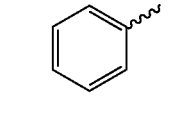 | 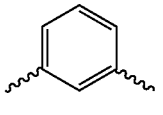 | 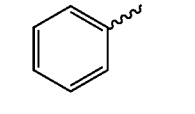 |
| 2-154 | 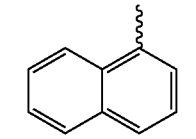 | 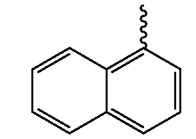 | 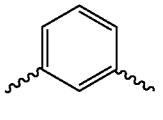 | 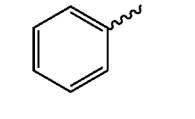 |
| 2-155 | 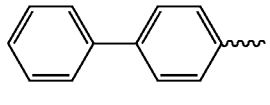 | 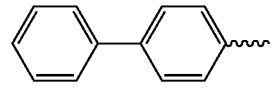 | 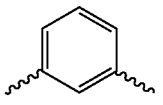 | 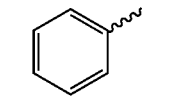 |
| 2-156 | 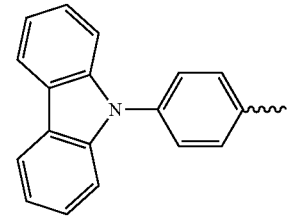 | 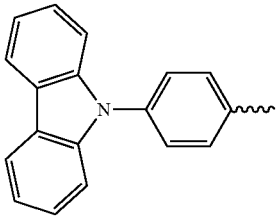 | 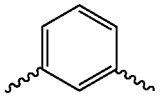 | 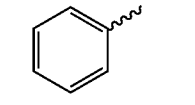 |
| 2-157 | 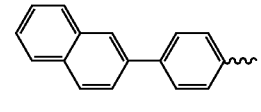 | 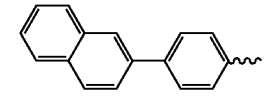 | 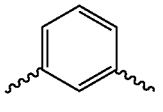 | 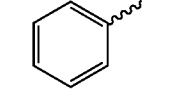 |
| 2-158 | 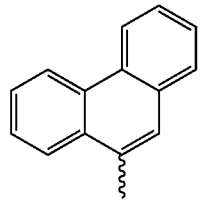 | 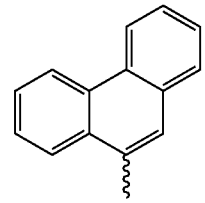 | 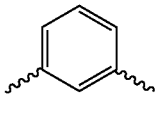 | 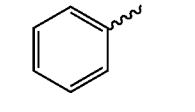 |

TABLE 2-continued

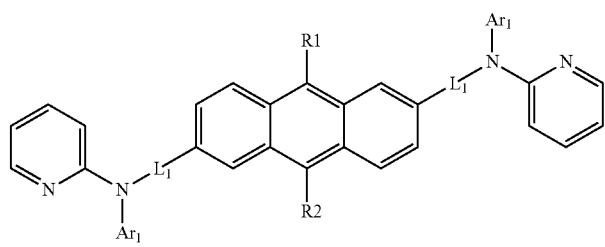

| Formula | R1 | R2 | L₁ | Ar₁ |
|---|---|---|---|---|
| 2-159 | 1-pyrenyl | 1-pyrenyl | m-phenylene | phenyl |
| 2-160 | isoquinolinyl | isoquinolinyl | m-phenylene | phenyl |
| 2-161 | 2-naphthyl | 2-naphthyl | m-phenylene | 2-pyridyl |
| 2-162 | phenyl | phenyl | m-phenylene | 2-pyridyl |
| 2-163 | 1-naphthyl | 1-naphthyl | m-phenylene | 2-pyridyl |
| 2-164 | 4-biphenylyl | 4-biphenylyl | m-phenylene | 2-pyridyl |
| 2-165 | 4-(9-carbazolyl)phenyl | 4-(9-carbazolyl)phenyl | m-phenylene | 2-pyridyl |
| 2-166 | 4-(2-naphthyl)phenyl | 4-(2-naphthyl)phenyl | m-phenylene | 2-pyridyl |

TABLE 2-continued
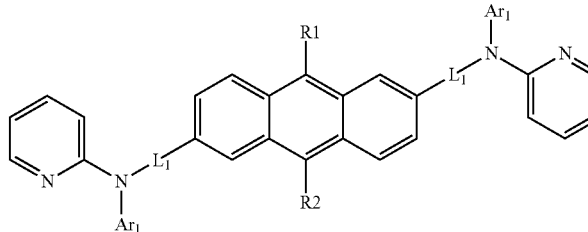
| Formula | R1 | R2 | L₁ | Ar₁ |
|---|---|---|---|---|
| 2-167 | 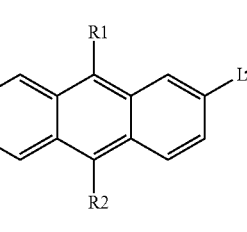 | 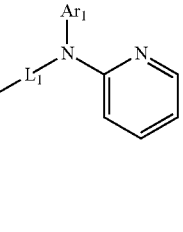 |  | 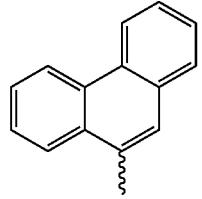 |
| 2-168 | 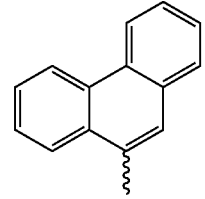 | 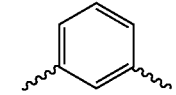 | 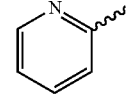 | 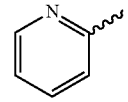 |
| 2-169 | 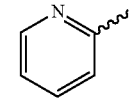 | 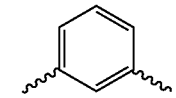 | 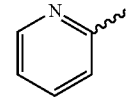 | 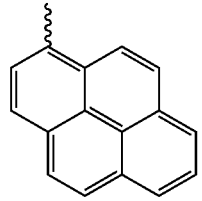 |
| 2-170 | 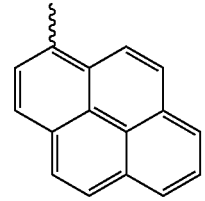 | 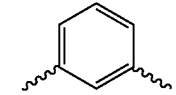 | 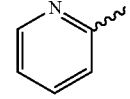 | 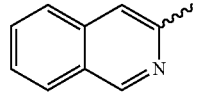 |
| 2-171 | 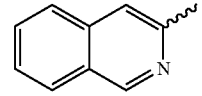 | 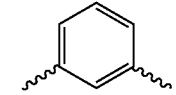 | 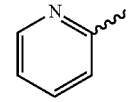 | 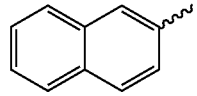 |
| 2-172 | 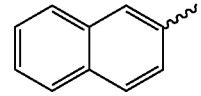 | 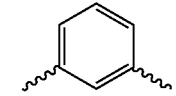 | 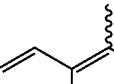 |  |
| 2-173 | 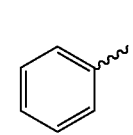 | 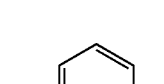 | 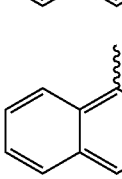 | 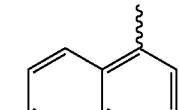 |
| 2-174 | 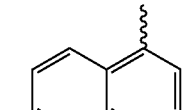 | 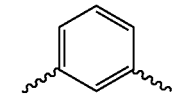 | 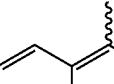 | 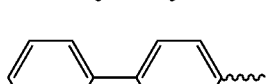 |

TABLE 2-continued
| Formula | R1 | R2 | L₁ | Ar₁ |
|---|---|---|---|---|
| 2-175 | 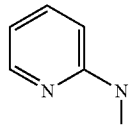 | 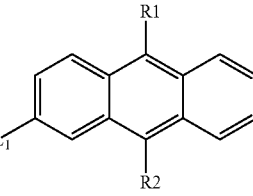 | 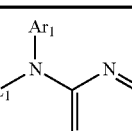 | 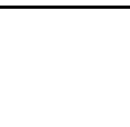 |
| 2-176 | 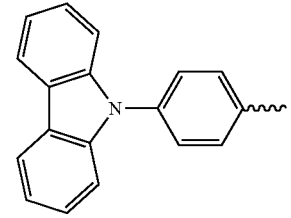 | 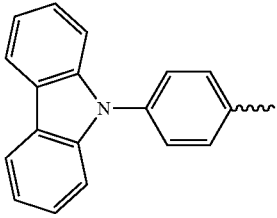 | 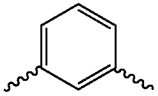 | 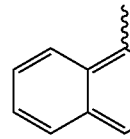 |
| 2-177 | 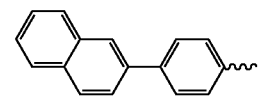 | 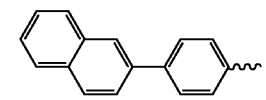 | 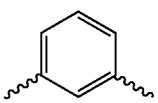 | 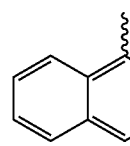 |
| 2-178 | 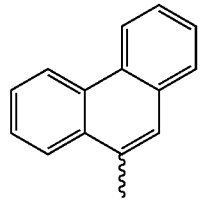 | 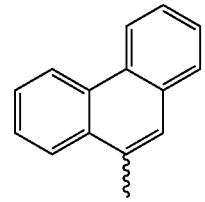 | 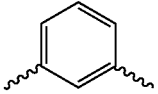 | 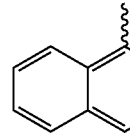 |
| 2-179 | 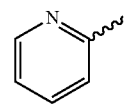 | 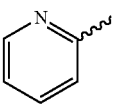 | 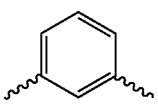 | 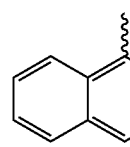 |
| 2-180 | 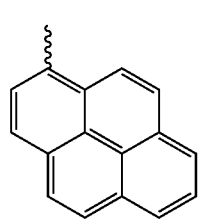 | 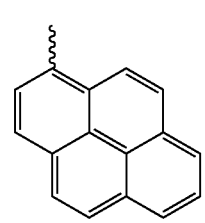 | 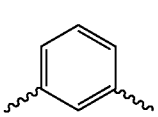 | 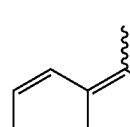 |
| 2-181 | 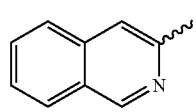 | 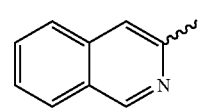 | 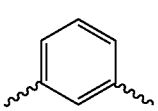 | 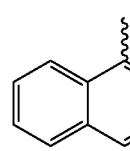 |
| 2-182 | 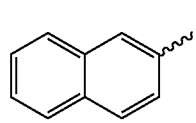 | 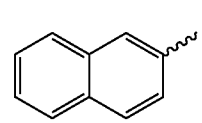 | 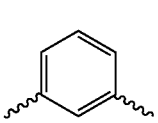 | 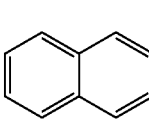 |

TABLE 2-continued

| Formula | R1 | R2 | L₁ | Ar₁ |
| --- | --- | --- | --- | --- |
| 2-183 | 1-naphthyl | 1-naphthyl | m-phenylene | 2-naphthyl |
| 2-184 | 4-biphenyl | 4-biphenyl | m-phenylene | 2-naphthyl |
| 2-185 | 4-(9-carbazolyl)phenyl | 4-(9-carbazolyl)phenyl | m-phenylene | 2-naphthyl |
| 2-186 | 4-(2-naphthyl)phenyl | 4-(2-naphthyl)phenyl | m-phenylene | 2-naphthyl |
| 2-187 | phenanthrenyl | phenanthrenyl | m-phenylene | 2-naphthyl |
| 2-188 | 2-pyridyl | 2-pyridyl | m-phenylene | 2-naphthyl |
| 2-189 | pyrenyl | pyrenyl | m-phenylene | 2-naphthyl |
| 2-190 | isoquinolinyl | isoquinolinyl | m-phenylene | 2-naphthyl |

US 8,222,634 B2
TABLE 2-continued
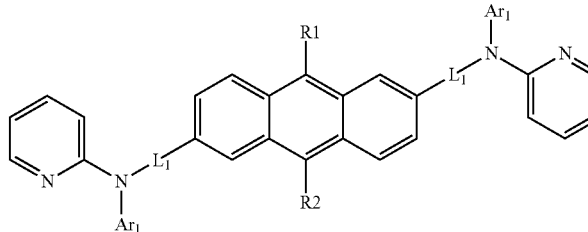
| Formula | R1 | R2 | L₁ | Ar₁ |
|---|---|---|---|---|
| 2-191 | 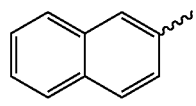 | 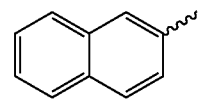 | 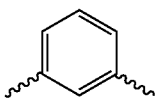 | 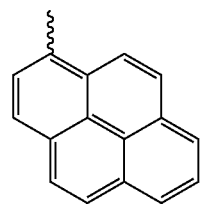 |
| 2-192 | 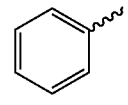 | 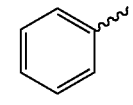 | 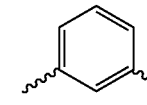 | 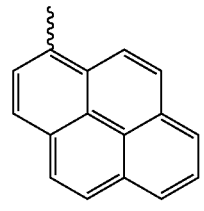 |
| 2-193 | 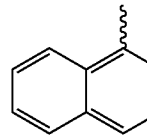 | 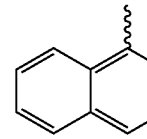 | 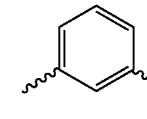 | 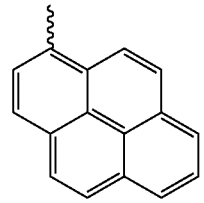 |
| 2-194 | 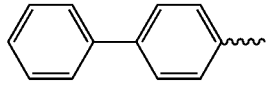 | 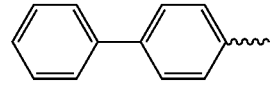 | 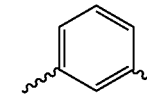 | 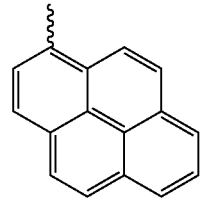 |
| 2-195 | 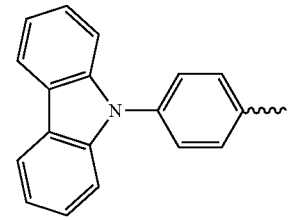 | 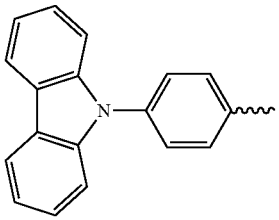 | 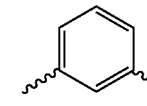 | 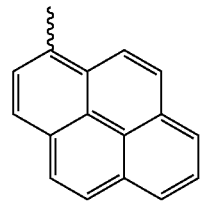 |
| 2-196 | 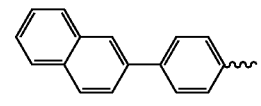 | 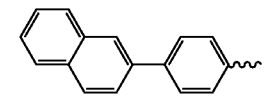 | 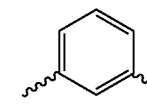 | 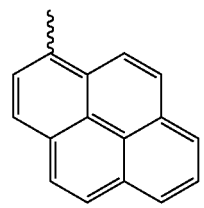 |

TABLE 2-continued
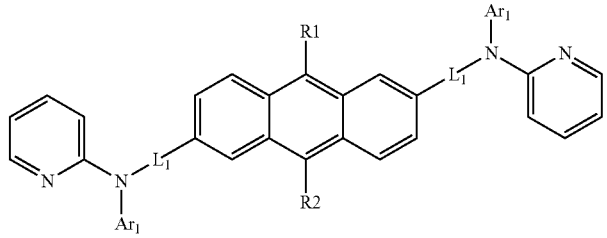
| Formula | R1 | R2 | L₁ | Ar₁ |
|---|---|---|---|---|
| 2-197 | 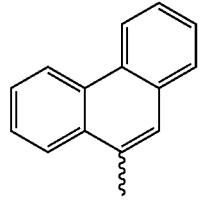 | 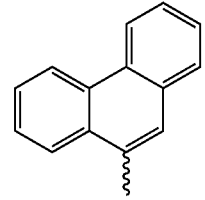 | 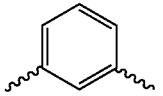 | 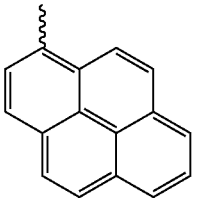 |
| 2-198 | 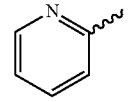 | 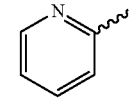 | 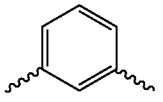 | 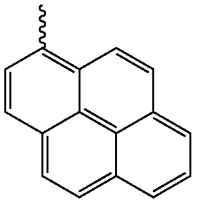 |
| 2-199 | 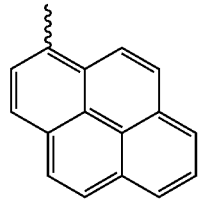 | 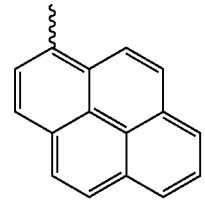 | 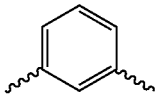 | 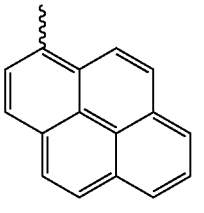 |
| 2-200 | 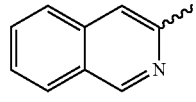 | 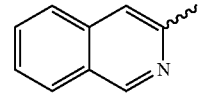 | 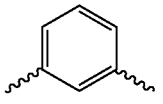 | 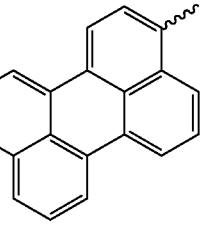 |
| 2-201 | 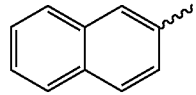 | 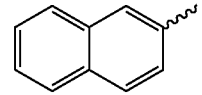 | 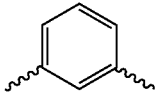 | 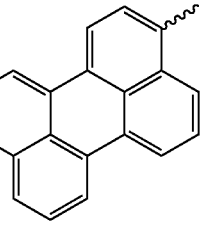 |
| 2-202 | 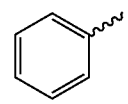 | 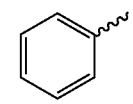 | 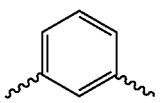 | 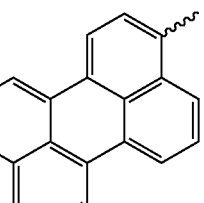 |

TABLE 2-continued

| Formula | R1 | R2 | L₁ | Ar₁ |
|---|---|---|---|---|
| 2-203 | | | | |
| 2-204 | | | | |
| 2-205 | | | | |
| 2-206 | | | | |
| 2-207 | | | | |

TABLE 2-continued
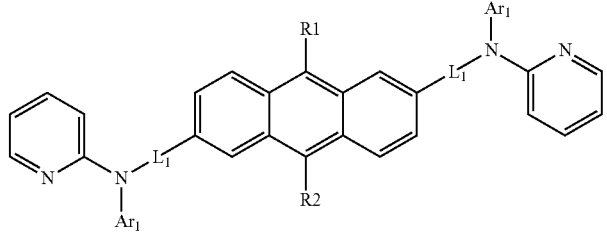
| Formula | R1 | R2 | L₁ | Ar₁ |
|---|---|---|---|---|
| 2-208 | 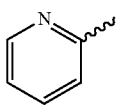 | 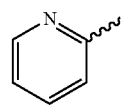 | 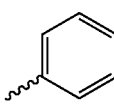 | 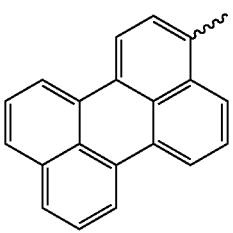 |
| 2-209 | 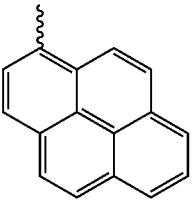 | 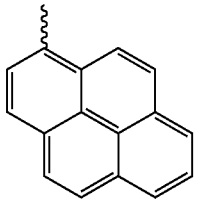 | 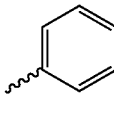 | 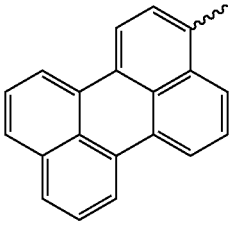 |
| 2-210 | 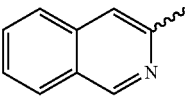 | 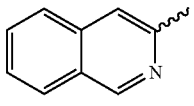 | 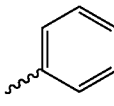 | 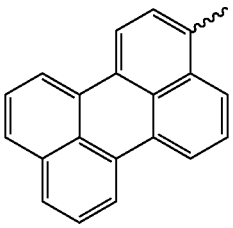 |
| 2-211 | 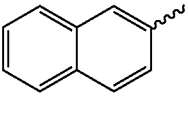 | 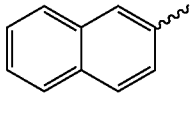 | 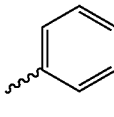 | 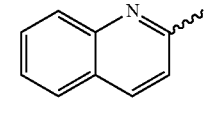 |
| 2-212 | 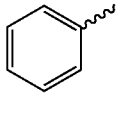 | 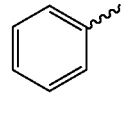 | 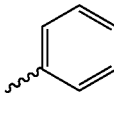 | 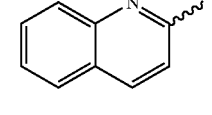 |
| 2-213 | 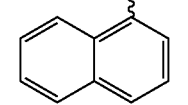 | 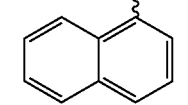 | 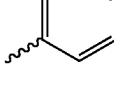 | 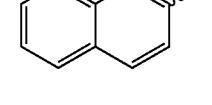 |
| 2-214 | 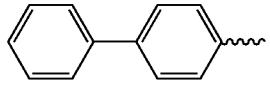 | 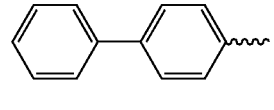 | 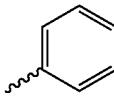 | 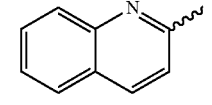 |

TABLE 2-continued
| Formula | R1 | R2 | L₁ | Ar₁ |
|---|---|---|---|---|
| 2-215 | 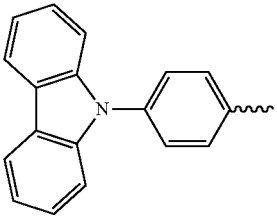 | 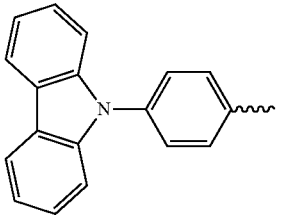 | 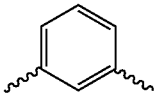 | 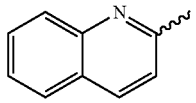 |
| 2-216 | 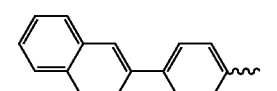 | 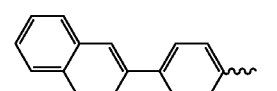 | 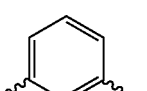 | 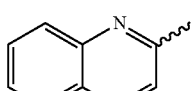 |
| 2-217 | 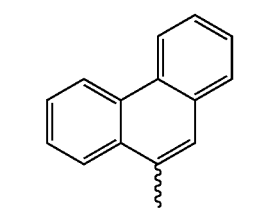 | 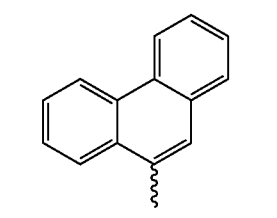 | 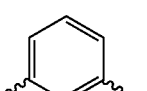 | 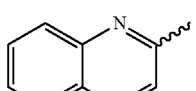 |
| 2-218 | 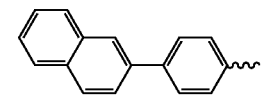 | 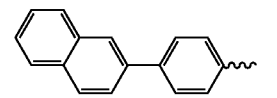 | 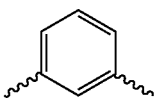 | 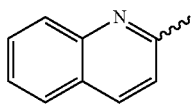 |
| 2-219 | 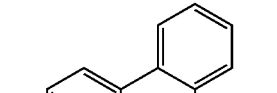 | 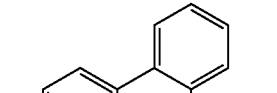 | 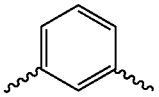 | 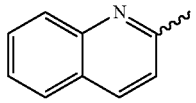 |
| 2-220 | 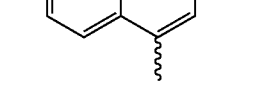 | 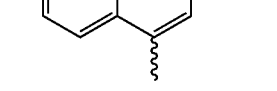 |  |  |
| 2-221 | 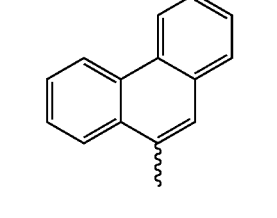 | 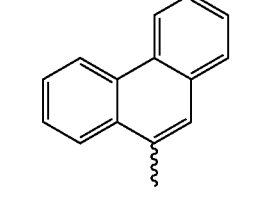 | 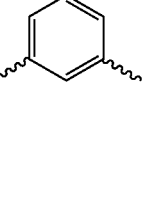 | 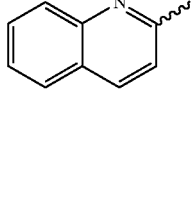 |
| 2-222 | 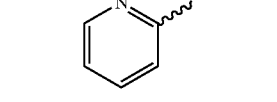 | 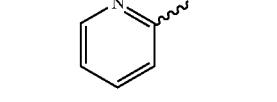 | 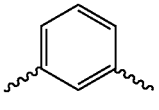 | 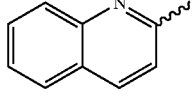 |

TABLE 2-continued
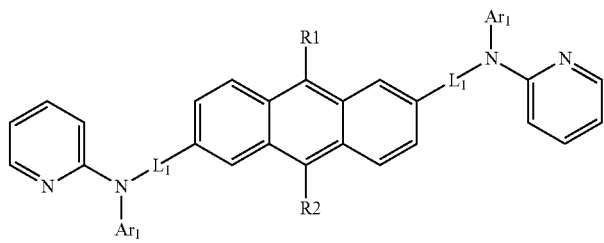
| Formula | R1 | R2 | L₁ | Ar₁ |
|---|---|---|---|---|
| 2-223 | 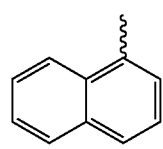 | 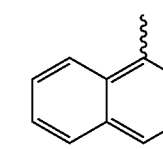 | 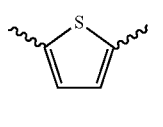 | 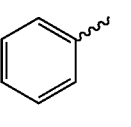 |
| 2-224 | 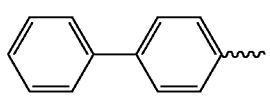 | 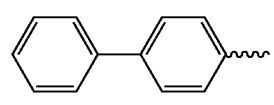 | 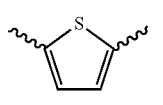 | 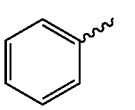 |
| 2-225 | 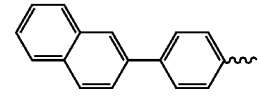 | 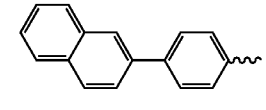 | 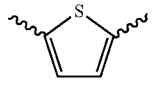 | 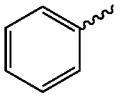 |
| 2-226 | 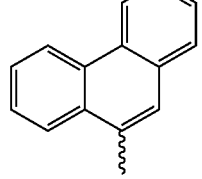 | 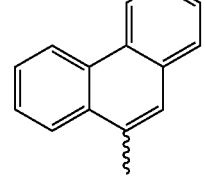 | 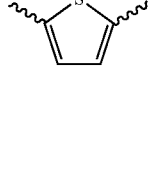 | 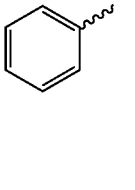 |
| 2-227 | 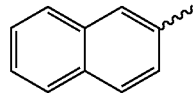 | 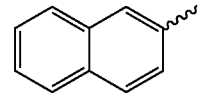 |  | 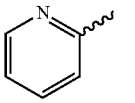 |
| 2-228 | 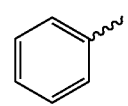 | 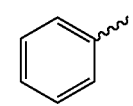 | 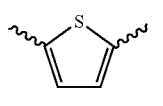 | 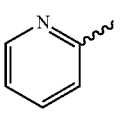 |
| 2-229 | 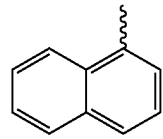 | 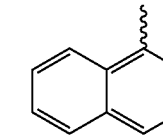 | 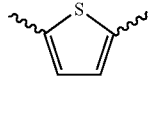 | 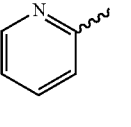 |
| 2-230 | 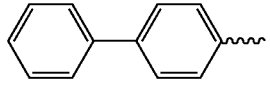 | 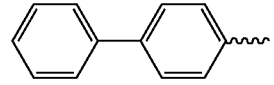 | 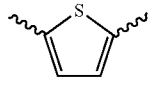 | 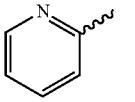 |
| 2-231 | 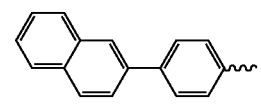 | 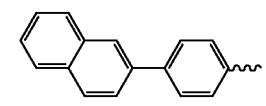 | 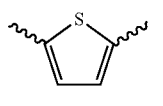 | 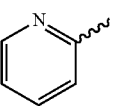 |

TABLE 2-continued

| Formula | R1 | R2 | L₁ | Ar₁ |
|---|---|---|---|---|
| 2-232 | phenanthren-9-yl | phenanthren-9-yl | thiophene-2,5-diyl | pyridin-2-yl |
| 2-233 | naphthalen-2-yl | naphthalen-2-yl | thiophene-2,5-diyl | quinolin-2-yl |
| 2-234 | phenyl | phenyl | thiophene-2,5-diyl | quinolin-2-yl |
| 2-235 | naphthalen-1-yl | naphthalen-1-yl | thiophene-2,5-diyl | quinolin-2-yl |
| 2-236 | biphenyl-4-yl | biphenyl-4-yl | thiophene-2,5-diyl | quinolin-2-yl |
| 2-237 | 4-(naphthalen-2-yl)phenyl | 4-(naphthalen-2-yl)phenyl | thiophene-2,5-diyl | quinolin-2-yl |
| 2-238 | phenanthren-9-yl | phenanthren-9-yl | thiophene-2,5-diyl | quinolin-2-yl |

Hereinbelow, a method for preparing an anthracene derivative that has a pyridyl group represented by formula 2 introduced to the compound of formula 1 will be described.

The compound of formula 1 can be prepared by introducing an aryl substituent to an anthracene derivative. Specifically, the compound of formula 1 can be prepared by subjecting a 2-anthracene boronic acid or 2-anthracene boronic ester derivative and an arylhalide derivative or heteroarylhalide derivative to a Suzuki coupling reaction in the presence of a Pd catalyst.

For the process used for preparation of the compound of formula 1, other general processes known in the art can be used, in addition to the Suzuki coupling reaction.

Specifically, the compound of formula 1 can be prepared by the method comprising the steps of:

1) subjecting a halogen-substituted anthraquinone derivative and a boronic acid or boronic ester compound having a R4 substituent to Suzuki coupling in the presence of a Pd catalyst to prepare a R4-substituted anthraquinone derivative, 2) preparing a dialcohol derivative from the anthraquinone derivative prepared in the step 1), and 3) reducing the dialcohol derivative prepared in the step 2) to prepared an anthracene derivative. This preparation method can be represented by each of Reaction scheme 1.

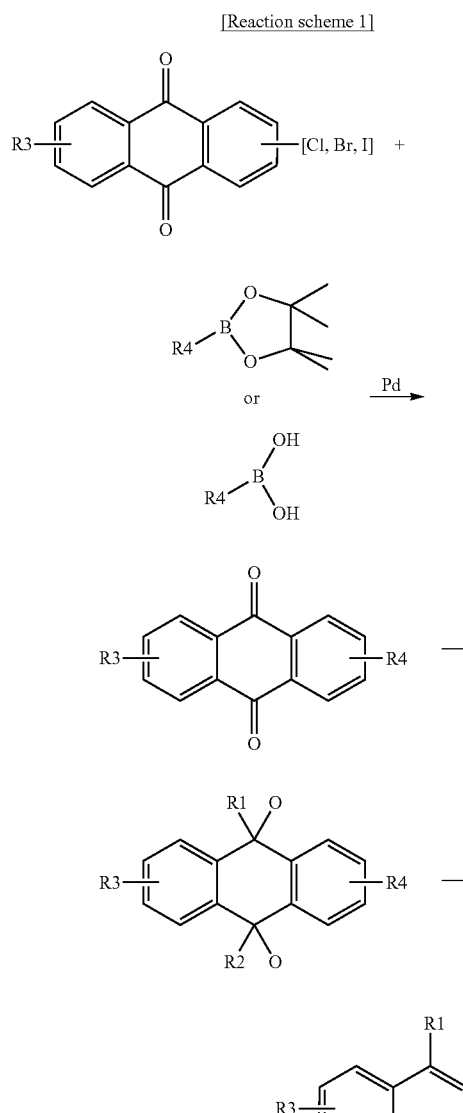

Further, the compound of formula 1 can be prepared by the method comprising the steps of:

1) preparing a dialcohol derivative from a halogen-substituted anthraquinone derivative, 2) reducing the dialcohol derivative prepared in the step 1) to prepared an anthracene derivative, 3) preparing an anthracene boronic ester derivative from an anthracene derivative prepared in the step 2), and 4) subject the anthracene boronic ester derivative prepared in the step 3) and a halide of R4 to Suzuki coupling in the presence of a Pd catalyst to prepare a R4-substituted compound of formula 1. This preparation method can be represented by each of Reaction scheme 2.

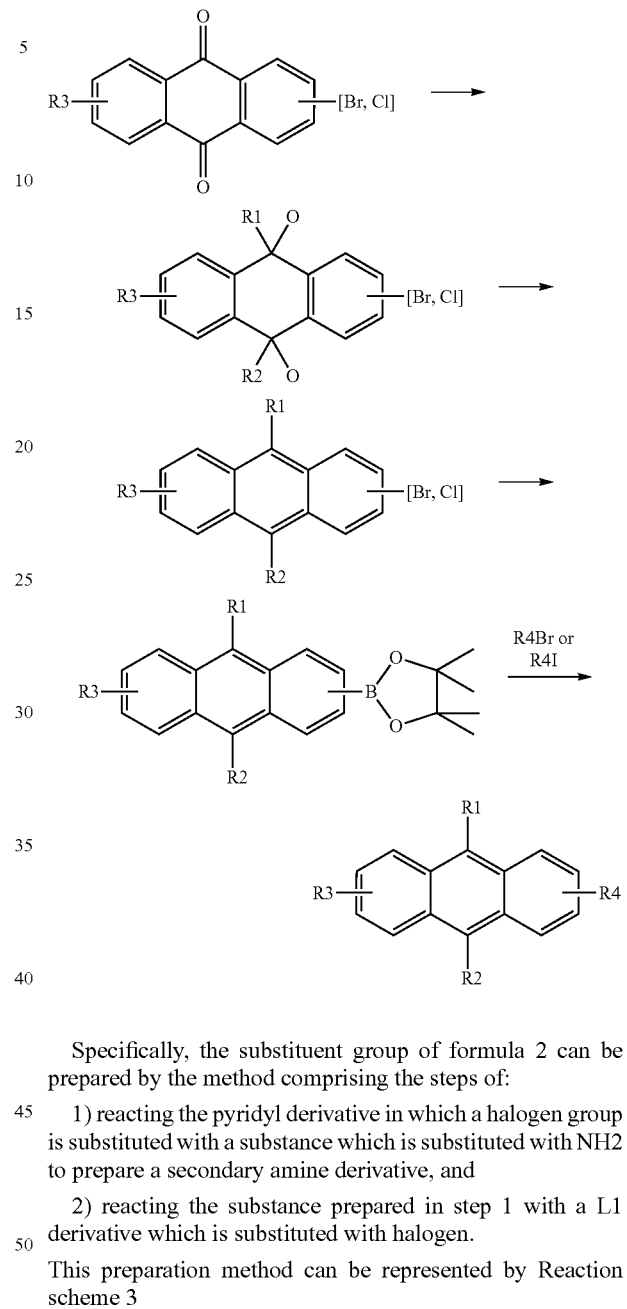

Specifically, the substituent group of formula 2 can be prepared by the method comprising the steps of:

1) reacting the pyridyl derivative in which a halogen group is substituted with a substance which is substituted with NH2 to prepare a secondary amine derivative, and 2) reacting the substance prepared in step 1 with a L1 derivative which is substituted with halogen.

This preparation method can be represented by Reaction scheme 3

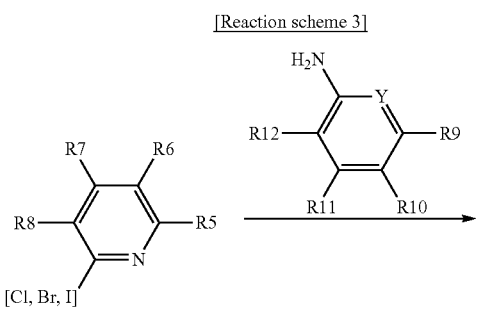

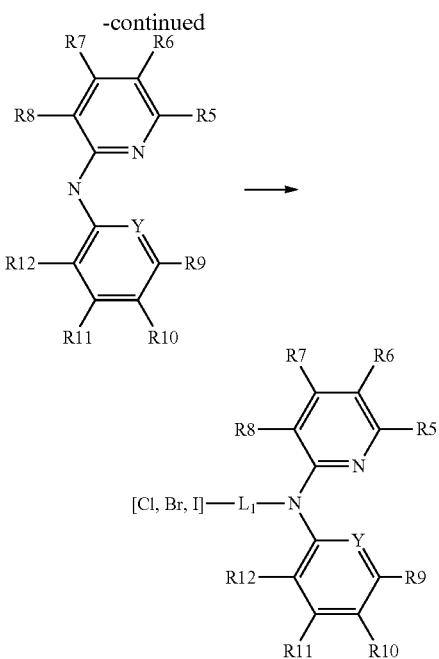

Further, the present invention provides an organic electronic device comprising a first electrode, a second electrode, and at least one organic material layer interposed between the first electrode and the second electrode, wherein at least one organic material layer comprises the compound of formula 1.

The organic electronic device of the present invention can be prepared by usual methods and materials for preparing an organic electronic device, except that the above-described anthracene derivative are used to form at least one organic material layer.

Hereinbelow, the organic light emitting device among organic electronic devices using the anthracene derivative according to the present invention will be exemplified.

In one embodiment of the present invention, the organic light emitting device can have a structure comprising a first electrode, a second electrode, and organic material layers interposed therebetween. The organic material layer in the organic light emitting device of the present invention may be a monolayer structure comprising a single layer, or a multilayer structure comprising two or more layers including a light emitting layer. If the organic material layer in the organic light emitting device of the present invention has a multilayer structure, it can has a structure in which a hole injecting layer, a hole transporting layer, a light emitting layer, an electron transporting layer, and the like are laminated. However, the structure of the organic light emitting device is not limited thereto, and it can further comprise a fewer number of organic materials layer. For example, the structure of the organic light emitting device of the present invention can be that as shown FIG. 1. In FIG. 1, the numeral reference 1 represents a substrate, 2 represents an anode, 3 represents a hole injecting layer, 4 represents a hole transporting layer, 5 represents an organic light emitting layer, 6 represents an electron transporting layer, and 7 represents a cathode. The organic light emitting device having the structure as shown in FIG. 1 is referred to as an organic light emitting device having a forward structure. The present invention is not limited thereto, and it also includes an organic light emitting device having a reverse structure. That is, the organic light emitting device of the present invention can have a structure in which a substrate, a cathode, an electron transporting layer, an organic light emitting layer, a hole transporting layer, a hole injecting layer and an anode are sequentially laminated.

If the organic light emitting device according to the present invention has a multilayer structure of the organic material layers, the compound of formula 1 can be contained in a light emitting layer, a hole transporting layer, a hole transporting and light emitting layer, a light emitting and electron transporting layer, an electron transporting layer, an electron transporting and/or injecting layer, and the like. In the present invention, the compound of formula 1 is particularly preferably contained in an electron injecting and/or transporting layer, or a light emitting layer.

The organic light emitting device of the present invention can be prepared by usual methods and materials for preparing an organic light emitting device, except that the anthracene derivative of formula 1 is used to form at least one of the organic material layers. For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer and an electron transporting layer on the anode; and depositing a material, which can be used as a cathode, thereon. Alternatively, an organic light emitting device can be prepared by sequentially depositing a cathode material, an organic material layer, and an anode material on a substrate, thus preparing the above-described organic light emitting device having a reverse structure.

Further, the organic material layer can be prepared to have a fewer number of layers, using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to the organic material layers. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide, such as $ZnO:Al$ and $SnO_2:Sb$; conductive polymers such as poly(3-methylthiophene), poly[3,4-(ethylene-1,2-dioxy)thiophene] (PEDT), polypyrrole and polyaniline, but are not limited thereto.

The cathode material is preferably a material having a small work function to facilitate electron injecting usually to an organic material layer. Specific examples of the cathode material include metals such as magnesium, calcium, sodium, potassium, titanium, indium, yttrium, lithium, gadolinium, aluminum, silver, tin and lead, and an alloy thereof; and multilayered materials such as LiF/Al and $LiO_2$/Al, but are not limited thereto.

The hole injecting material is a material facilitating hole injection from an anode at low voltage. The HOMO (highest occupied molecular orbital) of the hole injecting material is preferably located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is a material having high hole mobility, which can transfer holes from the anode or the hole injecting layer toward the light emitting layer. Specific examples thereof include organic materials of arylamine series, conductive polymers and block copolymers having both of the conjugated portions and the non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; spiro compounds; and polyfluorene and rubrene compounds, but are not limited thereto.

The electron transporting material is suitably a material having high electron mobility, which can easily receive electrons from the cathode and then transfer them to the light emitting layer. Specific examples thereof include an Al complex of an 8-hydroxyquinoline aluminum complex; complexes including $Alq_3$; organic radical compounds; and hydroxyflavone-metal complexes, but are not limited thereto.

The organic light emitting device according to the present invention may be of a front-sided, back-sided or double-sided light emission according to the materials used.

The compound according to the invention can also function in an organic electronic device including an organic solar cell, an organic photoconductor and an organic transistor, according to a principle similar to that applied to the organic light emitting device.

MODE FOR INVENTION

Hereinafter, preferable Examples are provided for the purpose of making the present invention more understandable. As such, Examples are provided for illustrating the Examples, but the scope of the invention is not limited thereto.

Preparative Example 1

1-1. Synthesis of Compound of the Following Formula 1-A

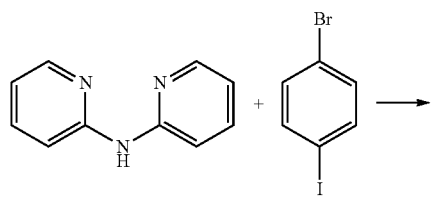

-continued

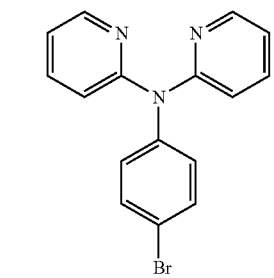

[Formula 1-A]

After 2,2'-dipyridylamine (5.0 g, 29 mmol) and 4-bromoiodobenzene (9.1 g, 32.1 mmol) were dissolved in 70 ml of dimethyl acetamide (DMAC), CuCl (0.4 g, 2.9 mmol), 2,2'-dipyridyl (0.45 g, 2.9 mmol), and $K_2CO_3$ (8 g, 58 mmol) were added, and the mixture was agitated at a room temperature for 10 min and agitated at 160° C. for 8 hours. If the reaction was finished, the cooling was performed to a normal temperature, the extraction was performed with water and THF (tetrahydrofurane), water was removed with $MgSO_4$, THF was removed under reduced pressure, silica gel short column was performed by using hexane and THF, and the precipitation was formed with water and ethanol (EtOH). The precipitate was filtered to prepare the compound of formula 1-A (5.2 g, yield 54%) that was the white solid. MS: $[M+H]^+=327$ 1-2. Synthesis of Compound of the Following Formula 1-B

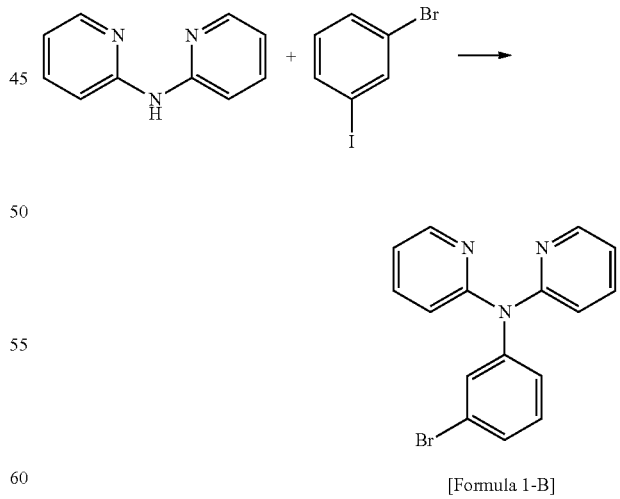

[Formula 1-B]

The compound of formula 1-B was prepared by using the same method as the synthesis method of the compound of formula 1-A, except that 3-bromoiodobenzene was used instead of 4-bromoiodobenzene in the course of synthesizing the compound of formula 1-A of Preparation Example 1-1. MS: [M+H]⁺=327

1-3. Synthesis of Compounds of the Following Formulas 1-C and 1-D

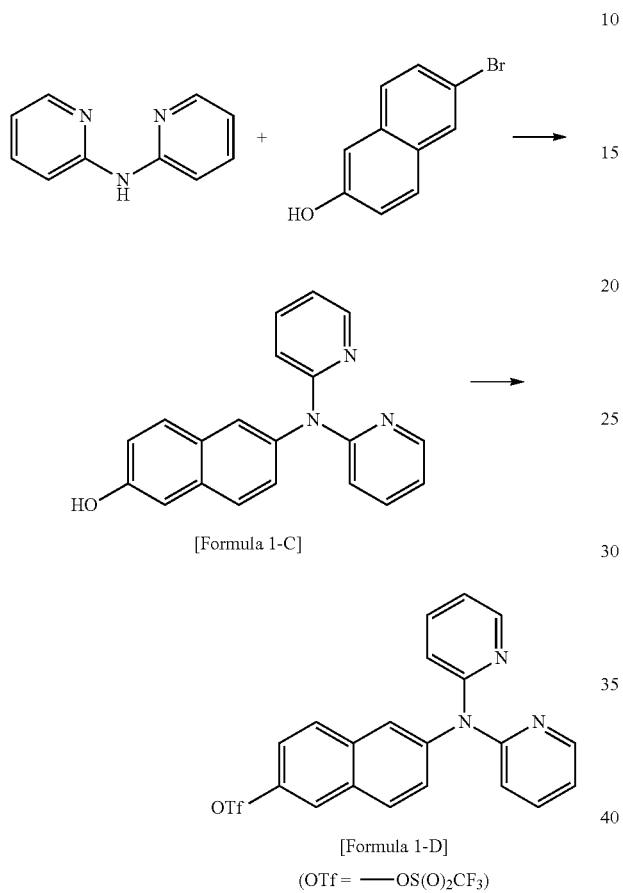

[Formula 1-C]

[Formula 1-D]

(OTf = —OS(O)$_2$CF$_3$)

After 2,2'-dipyridylamine (5.0 g, 29 mmol), 2-bromo-6-naphthol (5.4 g, 24.2 mmol), and NaOt-Bu (7 g, 72.6 mmol) were put into toluene (250 mL), the mixture was heated to 50° C. Pd(P(t-Bu)$_3$)$_2$ (61.5 mg, 0.12 mmol) was added and then heated and agitated for 3 hours. The temperature was cooled to normal temperature, celite was added, and the agitation was performed for 10 min. The suspension solution was filtered by using a filter in which silica gel was provided by 1.5 cm. The filtrate was distilled under reduced pressure and recrystallized with ethanol (200 mL) to obtain formula 1-C (3.8 g, yield 50%). MS: [M+H]⁺=314

After the compound of formula 1-C (8.4 g, 26.8 mmol) was dissolved in dichloromethane, triethylamine (7.47 mL, 53.6 mmol) was added thereto and then agitated for 10 min. After the temperature was cooled to 0° C., trifluoromethane sulfonic anhydride (4.4 mL, 40.2 mmol) was slowly added, the temperature was increased to normal temperature, and the agitation was performed for 1 hour. After the sodium hydrogen carbonate aqueous solution was added thereto, the water layer was removed and water was removed with anhydrous magnesium sulfate. After the filtration was performed, the concentration was performed under reduced pressure and the recrystallization was performed with hexane to prepare the compound of formula 1-D (10.8 g, yield 90%). MS: [M+H]⁺=446

1-4. Synthesis of Compound of the Following Formulas 1-E

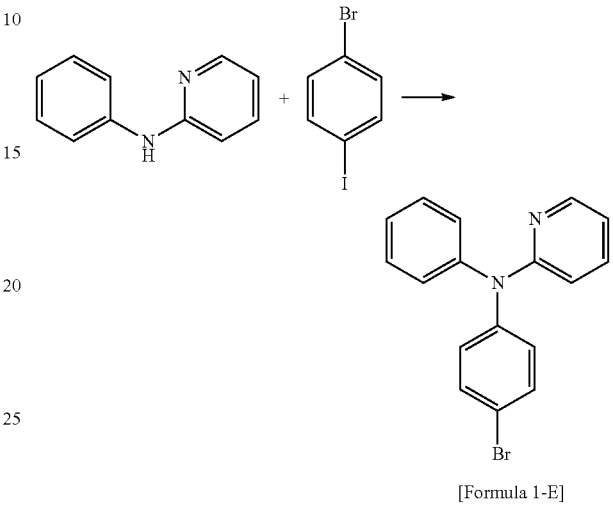

[Formula 1-E]

The compound of formula 1-E was prepared by using the same method as the synthesis method of the compound of formula 1-A, except that phenyl-pyridin-2-yl-amine was used instead of 2,2'-dipyridylamine in the course of synthesizing the compound of formula 1-A of Preparation Example 1-1. MS: [M+H]⁺=326

1-5. Synthesis of Compounds of the Following Formulas 1-F and 1-G

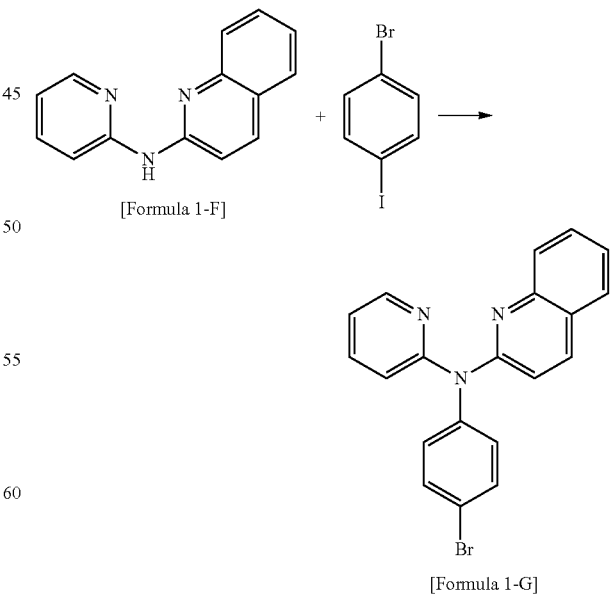

[Formula 1-F]

[Formula 1-G]

The compound of formula 1-G was prepared by using the same method as the synthesis method of the compound of formula 1-A, except that the compound of formula 1-F was used instead of 2,2'-dipyridylamine in the course of synthesizing the compound of formula 1-A of Preparation Example 1-1. MS: [M+H]$^+$=377

1-6. Synthesis of Compounds of the Following Formulas 1-H and 1-I

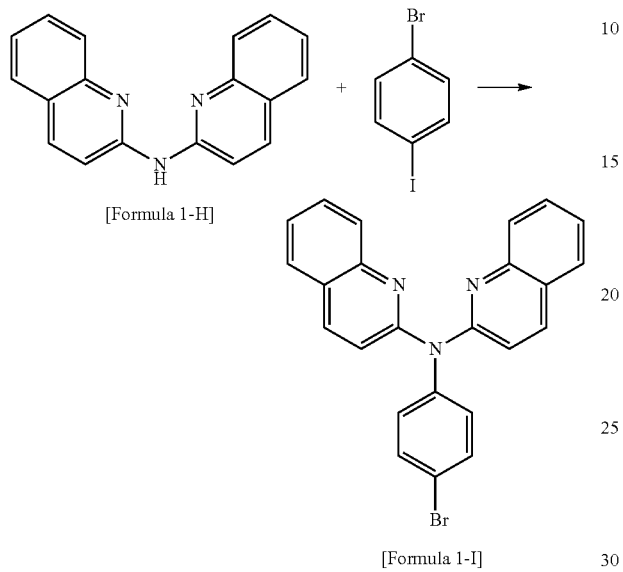

[Formula 1-H]

[Formula 1-I]

The compound of formula 1-I was prepared by using the same method as the synthesis method of the compound of formula 1-A, except that the compound of formula 1-H was used instead of 2,2'-dipyridylamine in the course of synthesizing the compound of formula 1-A of Preparation Example 1-1. MS: [M+H]$^+$=427

Preparative Example 2

2-1. Synthesis of Compound of the Following Formula 2-A

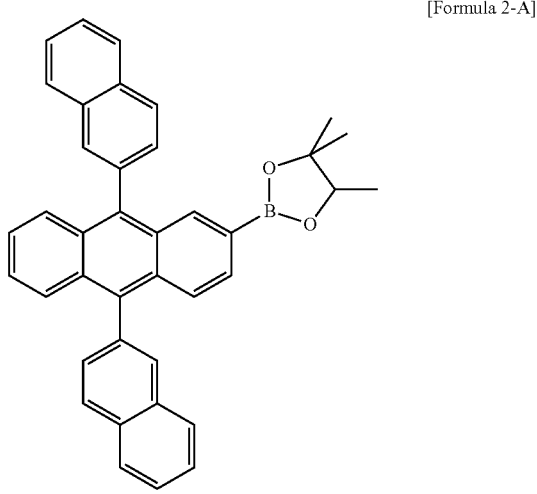

[Formula 2-A]

2-Bromo-9,10-dinaphthylanthracene (5.00 g, 9.81 mmol), bis(pinacolato)diboron (2.75 g, 10.8 mmol) and potassium acetate (2.89 g, 29.4 mmol) were suspended in dioxane (50 mL). To the suspension, was added palladium(diphenyl phosphinoferrocene)chloride (0.24 g, 0.3 mmol). The obtained mixture was stirred at 80° C. for about 6 hours, and then cooled to room temperature. The mixture was diluted with water (50 mL), and extracted from dichloromethane (3×50 mL). The organic extract was dried over magnesium sulfate, and concentrated in vacuo. The crude product washed with ethanol, and dried in vacuo to prepare a compound of formula 2-A (5.46 g, 92%), which is 9,10-dinaphthylanthracenyl-2-borate. MS: [M+H]$^+$=557

2-2. Synthesis of Compound of the Following Formula 2-B

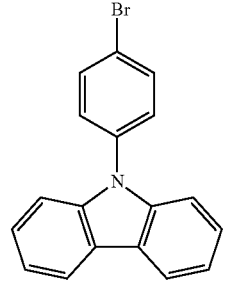

[Formula 2-B]

Carbazole (3.3 g, 20 mmol), 1-bromo-4-iodobenzene (3.0 mL, 24 mmol), potassium carbonate (K$_2$CO$_3$, 5.6 g, 41 mmol), copper iodide (CuI, 1.9 g, 1.0 mmol), and 50 mL of xylene were refluxed under nitrogen atmosphere. The resultant was cooled to normal temperature, and the product was extracted from ethyl acetate, the moisture was removed over anhydrous magnesium sulfate (MgSO$_4$), and the solvent was removed under reduced pressure. The resultant was passed through as silica gel using a hexane solvent to obtain a compound, and the solvent was removed under reduced pressure. The resultant was dried in vacuo to prepare a white solid compound of formula 2-B (1.6 g, 25% yield). MS: [M+H]$^+$=322

2-3. Synthesis of Compound of the Following Formula 2-C

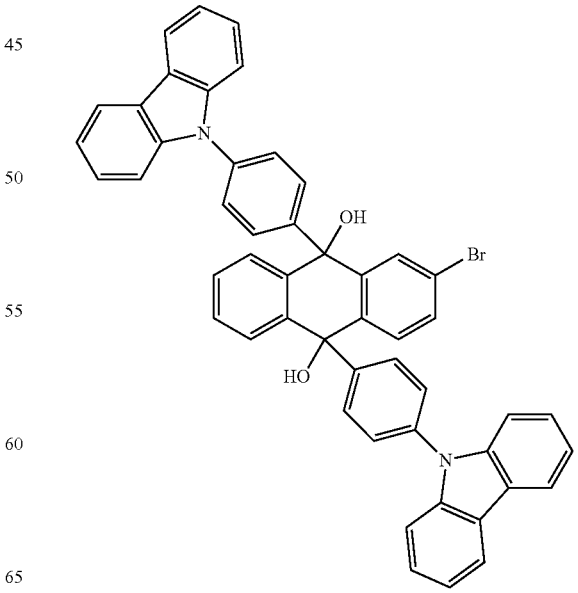

[Formula 2-C]

The compound of formula 2-B (4.38 g, 13.2 mmol) was dissolved in anhydrous tetrahydrofuran (80 mL) under a nitrogen atmosphere. The solution was cooled to −78° C., n-butyl lithium (6.6 mL, 2.5 M hexane solution) was slowly added over 10 minutes to the cooled solution, and the solution was stirred at −78° C. for about 40 minutes. 2-bromoanthraquinone compound (3.59 g, 5.5 mmol) was added to the reaction mixture, and the mixture was further stirred at −78° C. for about 3 hours. The mixture was stirred at room temperature for about 1 hour. To the mixture, an aqueous ammonium chloride solution (50 mL) was added. The organic layer was separated, and the aqueous layer was extracted from diethyl ether (60 mL). The combined organic extract was dried over magnesium sulfate, and concentrated under reduced pressure. The obtained solid was suspended in diethyl ether, stirred about 1 hour, filtered, and then dried to obtain a compound of formula 2-C (3.32 g, yield 73%), which is a dialcohol compound. MS [M+H]$^+$=773

2-4. Synthesis of Compound of the Following Formula 2-D

[Formula 2-D]

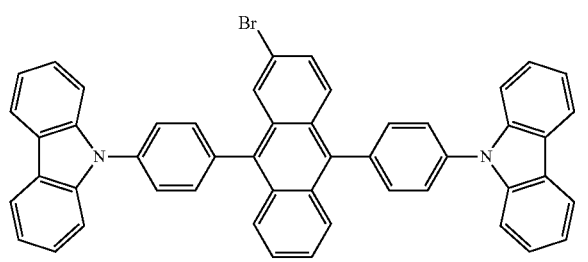

The compound of formula 2-C (2.82 g, 3.65 mmol) was added to a dispersion of acetic acid (60 mL), potassium iodide (3.32 g, 20 mmol) and hydrous sodium hypophosphite (3.52 g, 40 mmol) were added to the suspension. The mixture was continuously stirred under reflux for about 3 hours, and then cooled to room temperature. The mixture was filtered, washed with water, and then dried in vacuo to prepare a compound of formula 2-D (2.87 g, 90%). MS: [M+H]+=739

2-5. Synthesis of Compound of the Following Formula 2-E

[Formula 2-E]

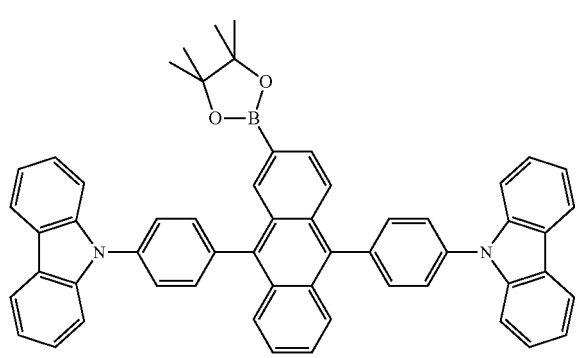

A compound of formula 2-E was prepared in the same manner as in the method for preparation of the compound of formula 2-A, except that a compound of formula 2-D was used instead of 2-bromo-9,10-dinaphthylanthracene and bis(pinacolato)diboron in the method for preparation of the compound of formula 2-A of Preparative Example 2-1. MS: [M+H]$^+$=787

2-6. Synthesis of Compound of the Following Formula 2-F

[Formula 2-F]

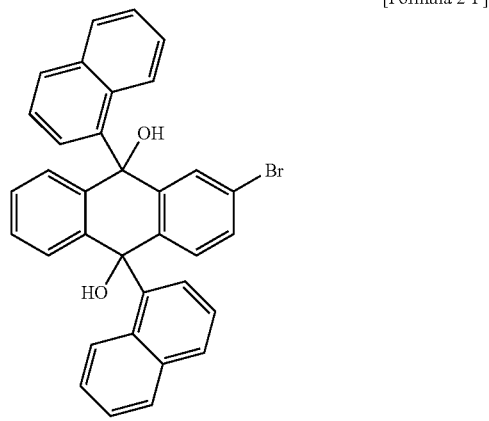

1-bromonaphthalene (34.8 g, 168.2 mmol) was dissolved in tetrahydrofuran (170 mL) and then cooled to −78° C., n-butyl lithium (67.3 mL, 168.2 mmol) was slowly added thereto, and the agitation was performed for 1 hour. 2-bromoanthraquinone (21 g, 73.1 mmol) was added thereto and then heated to normal temperature, and the agitation was performed for 3 hours. The saturated aqueous ammonium chloride solution was added thereto, the water layer was removed, the drying was performed with anhydrous magnesium sulfate, the filtration was performed, and the drying was performed under reduced pressure. The recrystallization was performed with ethyl ether and petroleum ether to prepare the compound of formula 2-F (32.3 g, 82%). MS [M+H]$^+$=544

2-7. Synthesis of Compound of the Following Formula 2-G

[Formula 2-G]

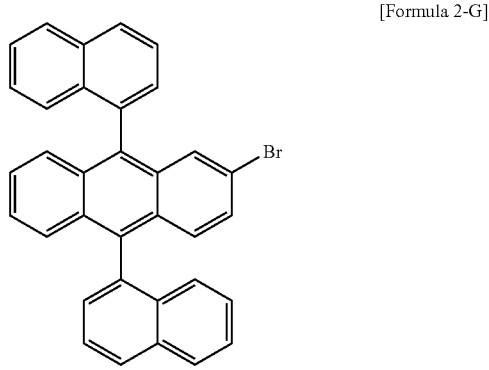

The compound of formula 2-F (32.3 g, 59.5 mmol), potassium iodide (29.6 g, 178.4 mmol), sodium hypophosphite (38 g, 256.8 mmol) were added to the acetic acid (40 ml), heated and agitated for 3 hours, and cooled to normal temperature, the precipitate was filtered, the recrystallization was performed with ethanol to prepare a compound of formula 2-G (25.5 g, 84%). MS: [M+H]$^+$=509

2-8. Synthesis of Compound of the Following Formula 2-H

[Formula 2-H]

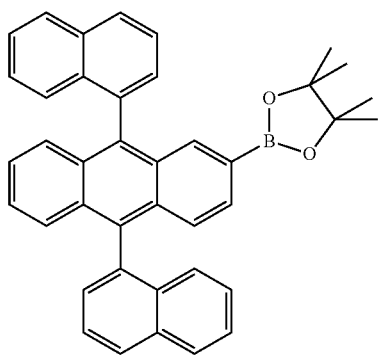

A compound of formula 2-H was prepared in the same manner as in the method for synthesis of the compound of formula 2-A, except that a compound of formula 2-G was used instead of 2-bromo-9,10-dinaphthylanthracene in the method for synthesis of the compound of formula 2-A of Preparative Example 2-1. MS: [M+H]$^+$=557

2-9. Synthesis of Compound of the Following Formula 2-I

[Formula 2-I]

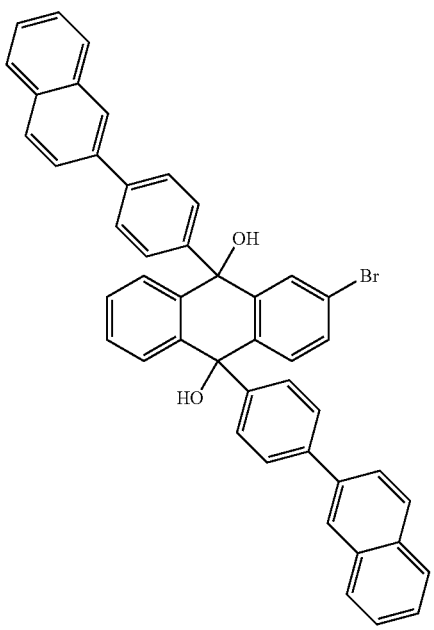

A compound of formula 2-I was prepared in the same manner as in the method for synthesis of the compound of formula 2-F, except that 1-bromo-4-(2-naphthyl)benzene was used instead of 1-bromonaphthalene in the method for synthesis of the compound of formula 2-F of Preparative Example 2-6. MS: [M+H]$^+$=696

2-10. Synthesis of Compound of the Following Formula 2-J

[Formula 2-J]

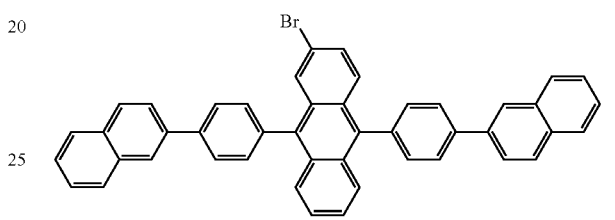

A compound of formula 2-J was prepared in the same manner as in the method for synthesis of the compound of formula 2-G, except that the compound of formula 2-I was used instead of the compound of formula 2-F in the method for synthesis of the compound of formula 2-G of Preparative Example 2-7. MS: [M+H]$^+$=661

2-11. Synthesis of Compound of the Following Formula 2-K

[Formula 2-K]

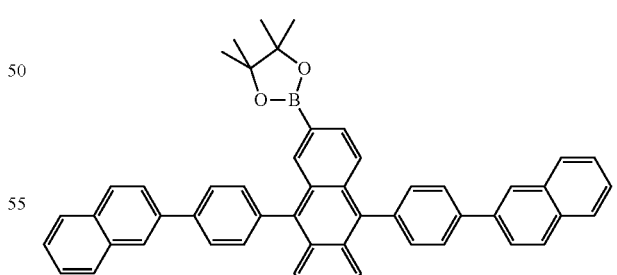

A compound of formula 2-K was prepared in the same manner as in the method for synthesis of the compound of formula 2-A, except that the compound of formula 2-J was used instead of 2-bromo-9,10-dinaphthylanthracene in the method for synthesis of the compound of formula 2-A of Preparative Example 2-1. MS: [M+H]$^+$=709

Preparative Example 3

3-1. Synthesis of Compound of the Following Formula 1-11

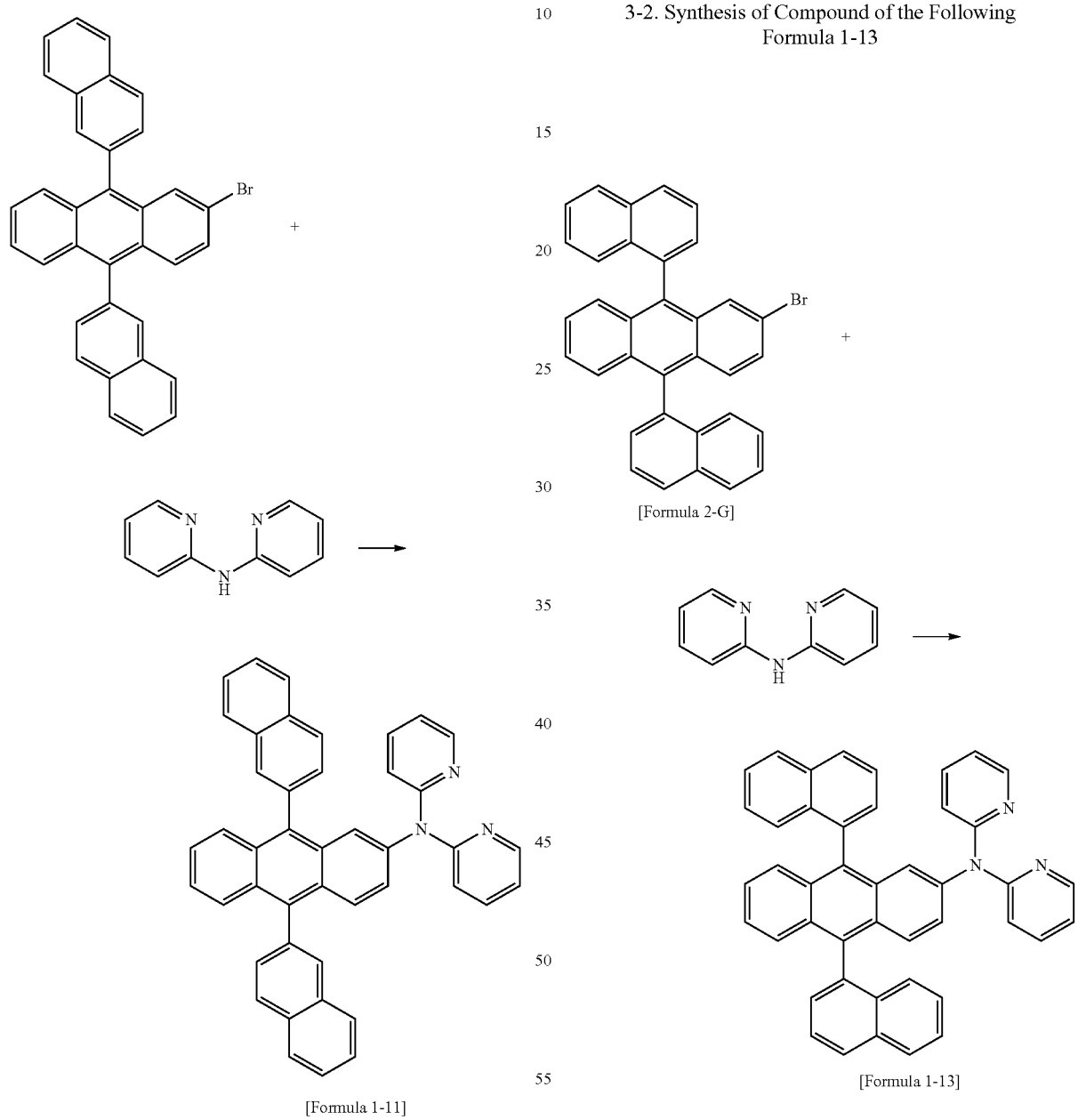

[Formula 1-11]

[Formula 2-G]

[Formula 1-13]

After 2,2'-dipyridylamine (5.0 g, 29 mmol), 2-bromo-9,10-dinaphthylanthracene (12.3 g, 24.2 mmol), and NaOt-Bu (7 g, 72.6 mmol) were put into toluene (250 mL), the mixture was heated to 50° C. Pd(P(t-Bu)$_3$)$_2$ (61.5 mg, 0.12 mmol) was added and then heated and agitated for 3 hours. The temperature was cooled to normal temperature, celite was added, and the agitation was performed for 10 min. The suspension solution was filtered by using a filter in which silica gel was provided by 1.5 cm. The filtrate was distilled under reduced pressure and recrystallized with ethanol (200 mL) to obtain a compound of formula 1-11 (10.1 g, yield 70%). MS: [M+H]$^+$=600

3-2. Synthesis of Compound of the Following Formula 1-13

A compound of formula 1-13 was prepared in the same manner as in the method for synthesis of the compound of formula 1-11, except that the compound of formula 2-G was used instead of 2-bromo-9,10-dinaphthylanthracene in the method for synthesis of the compound of formula 1-11 of Preparative Example 3-1. MS: [M+H]$^+$=600

3-3. Synthesis of Compound of the Following Formula 1-21

3-4. Synthesis of Compound of the Following Formula 1-75

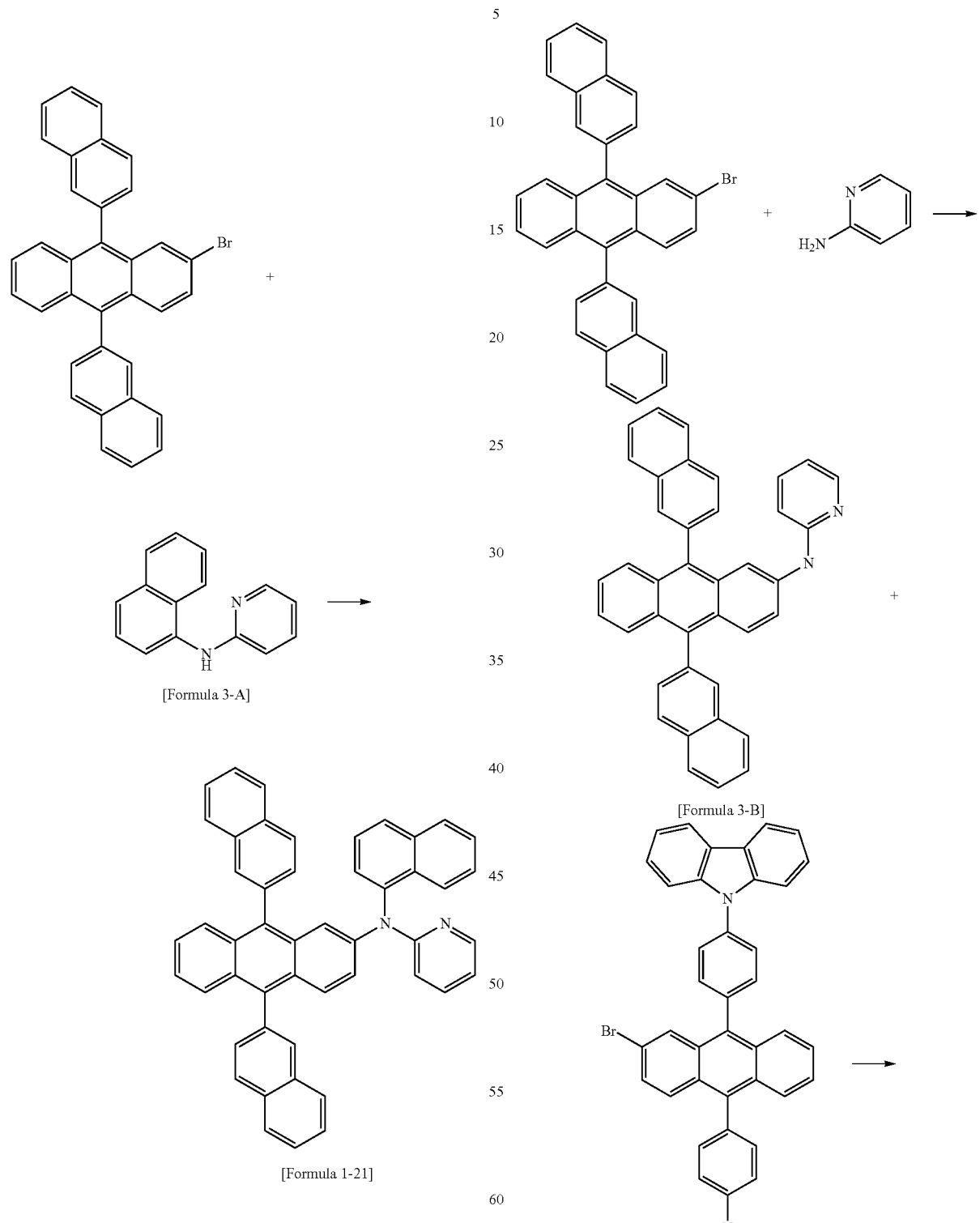

A compound of formula 1-21 was prepared in the same mariner as in the method for synthesis of the compound of formula 1-11, except that the compound of formula 3-A was used instead of 2,2'-dipyridylamine in the method for synthesis of the compound of formula 1-11 of Preparative Example 3-1. MS: [M+H]$^+$=649

3-5. Synthesis of Compound of the Following Formula 1-91

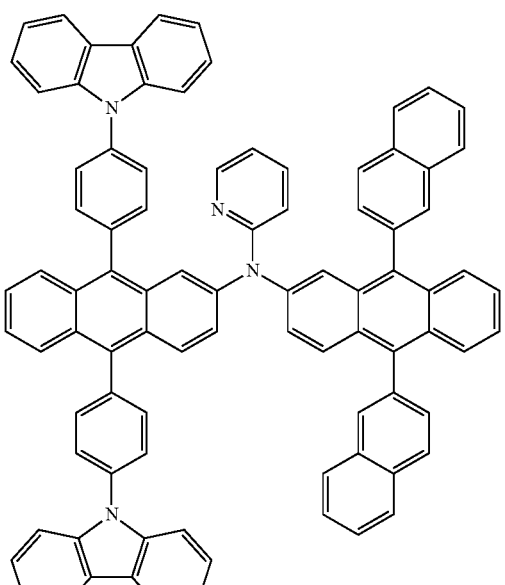

[Formula 1-75]

After 2-aminopyridine (2.7 g, 29 mmol), 2-bromo-9,10-dinaphthylanthracene (12.3 g, 24.2 mmol), NaOt-Bu (7 g, 72.6 mmol) were put into toluene (250 mL), the mixture was heated to 50° C. Pd(P(t-Bu)$_3$)$_2$ (61.5 mg, 0.12 mmol) was added and then heated and agitated for 3 hours. The temperature was cooled to normal temperature, celite was added, and the agitation was performed for 10 min. The suspension solution was filtered by using a filter in which silica gel was provided by 1.5 cm. The filtrate was distilled under reduced pressure and recrystallized with ethanol (200 mL) to obtain the compound of formula 3-B (7.6 g, yield 60%). MS: [M+H]$^+$=523

After the compound of formula 3-B (15.1 g, 29 mmol), the compound of formula 2-D (17.9 g, 24.2 mmol), and NaOt-Bu (7 g, 72.6 mmol) were put into toluene (250 mL), the mixture was heated to 50° C. Pd(P(t-Bu)$_3$)$_2$ (61.5 mg, 0.12 mmol) was added and then heated and agitated for 3 hours. The temperature was cooled to normal temperature, celite was added, and the agitation was performed for 10 min. The suspension solution was filtered by using a filter in which silica gel was provided by 1.5 cm. The filtrate was distilled under reduced pressure and recrystallized with ethanol (200 mL) to obtain the compound of formula 1-75 (14.5 g, yield 50%). MS: [M+H]$^+$=1198

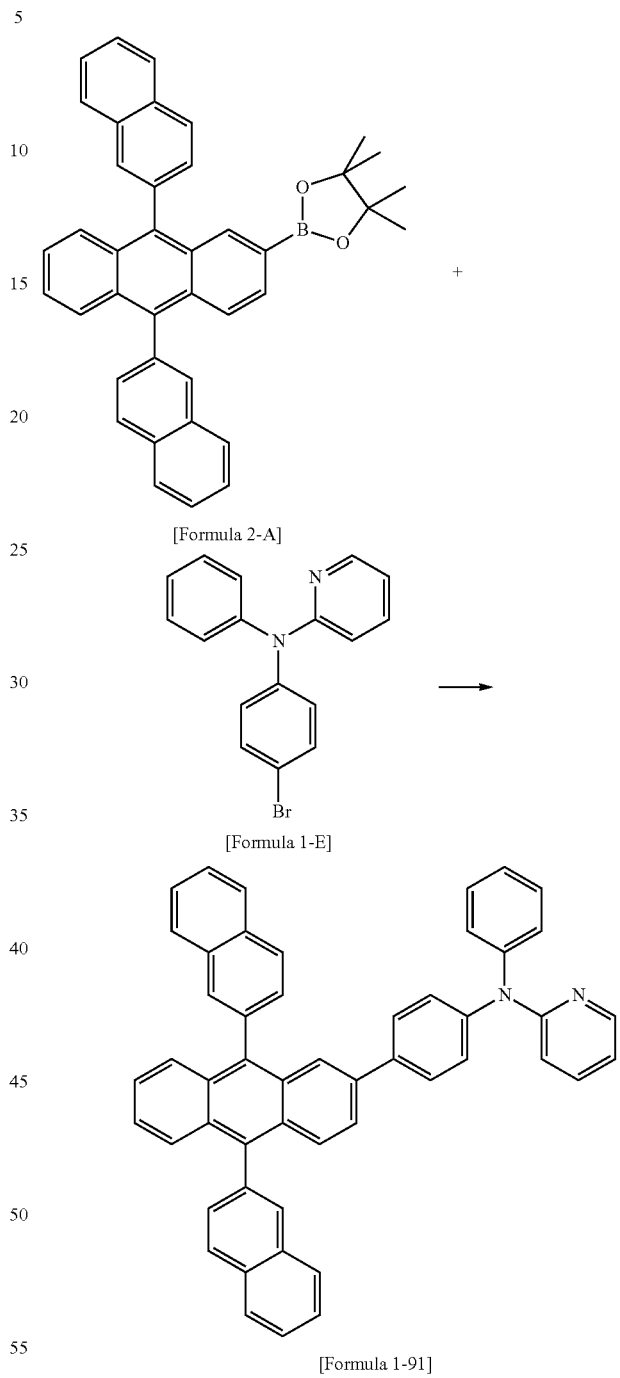

After the compound of formula 2-A (3.5 g, 6.3 mmol) and the compound (2.2 g, 6.9 mmol) of formula 1-E were completely dissolved in tetrahydrofurnae (100 ml), 2M potassium carbonate aqueous solution was added thereto, tetrakistriphenylphosphinopalladium (155 mg, 0.013 mmol) was added thereto, and the heating and the agitation were performed for 5 hours. The temperature was cooled to a normal temperature, the water layer was removed, the drying was performed with anhydrous magnesium sulfate, the concentration was performed under reduced pressure, the column was performed so that the ratio of tetrahydrofurane:hexane was in the range of 1:6 to prepare the compound of formula 1-91 (2.8 g, 66%). MS: [M+H]⁺=675

3-6. Synthesis of Compound of the Following Formula 1-101

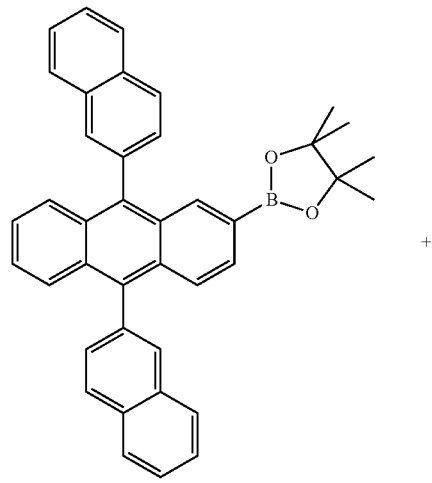

[Formula 2-A]

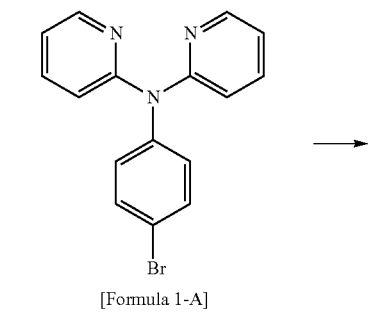

[Formula 1-A]

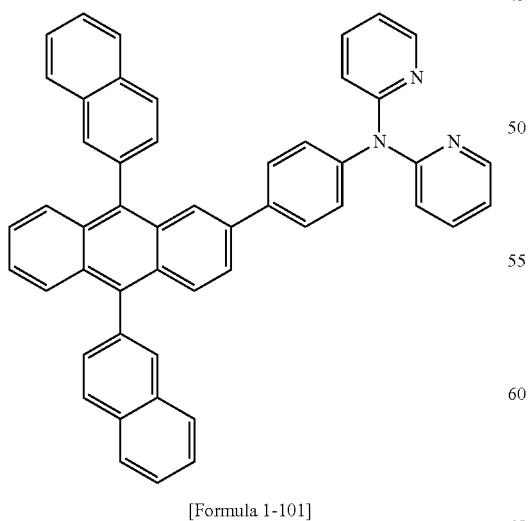

[Formula 1-101]

A compound of formula 1-101 was prepared in the same manner as in the method for synthesis of the compound of formula 1-91, except that the compound of formula 1-A was used instead of the compound of formula 1-E in the method for synthesis of the compound of formula 1-91 of Preparative Example 3-5. MS: [M+H]⁺=676

3-7. Synthesis of Compound of the Following Formula 1-103

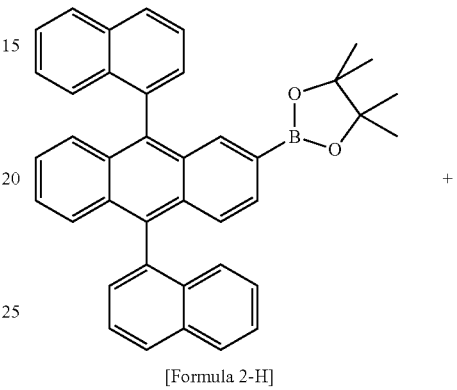

[Formula 2-H]

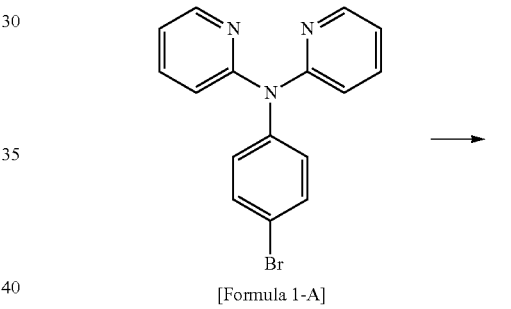

[Formula 1-A]

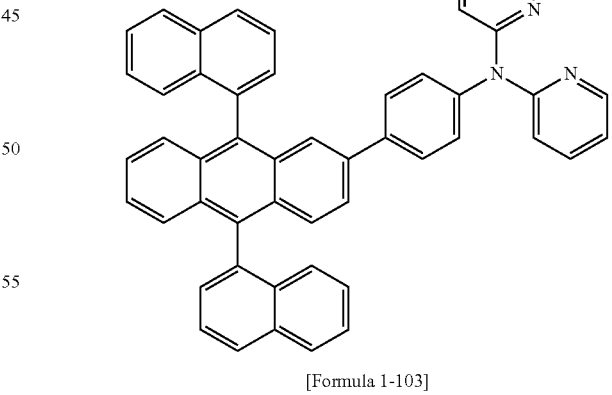

[Formula 1-103]

A compound of formula 1-103 was prepared in the same manner as in the method for synthesis of the compound of formula 1-101, except that the compound of formula 2-H was used instead of the compound of formula 2-A in the method for synthesis of the compound of formula 1-101 of Preparative Example 3-6. MS: [M+H]⁺=676

3-8. Synthesis of Compound of the Following Formula 1-106

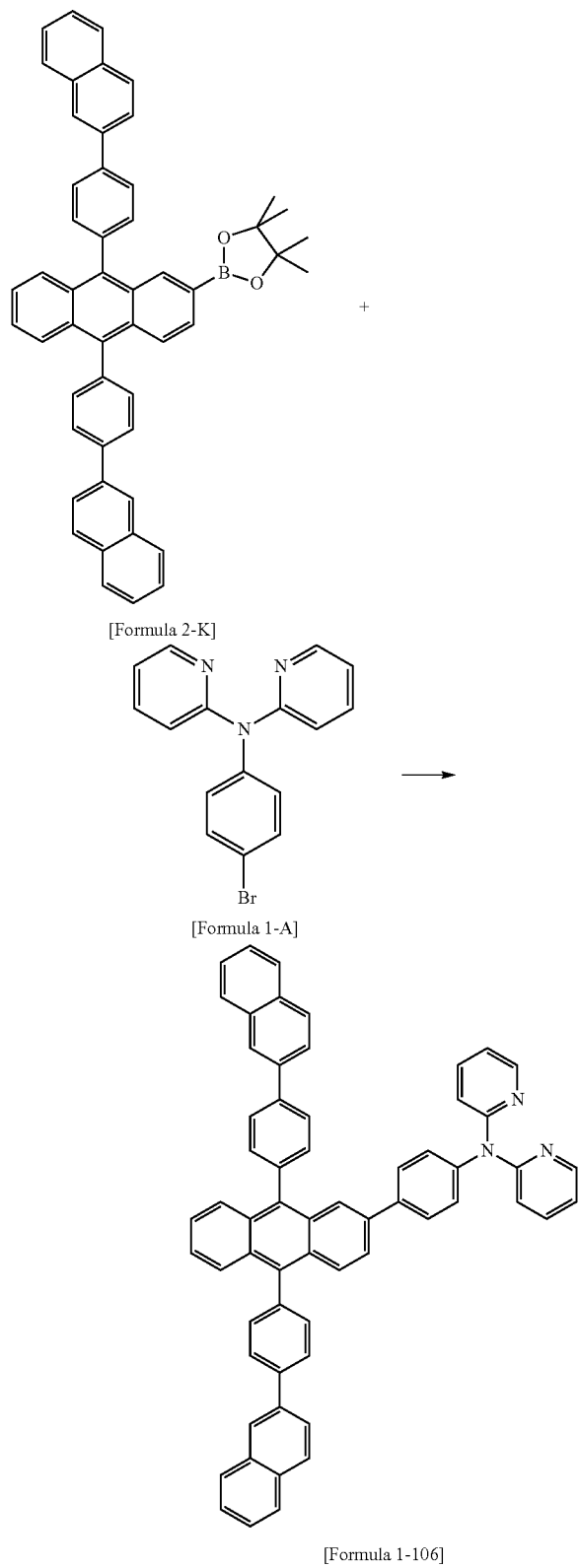

A compound of formula 1-106 was prepared in the same manner as in the method for synthesis of the compound of formula 1-101, except that the compound of formula 2-K was used instead of the compound of formula 2-A in the method for synthesis of the compound of formula 1-101 of Preparative Example 3-6. MS: [M+H]$^+$=829

3-9. Synthesis of Compound of the Following Formula 1-171

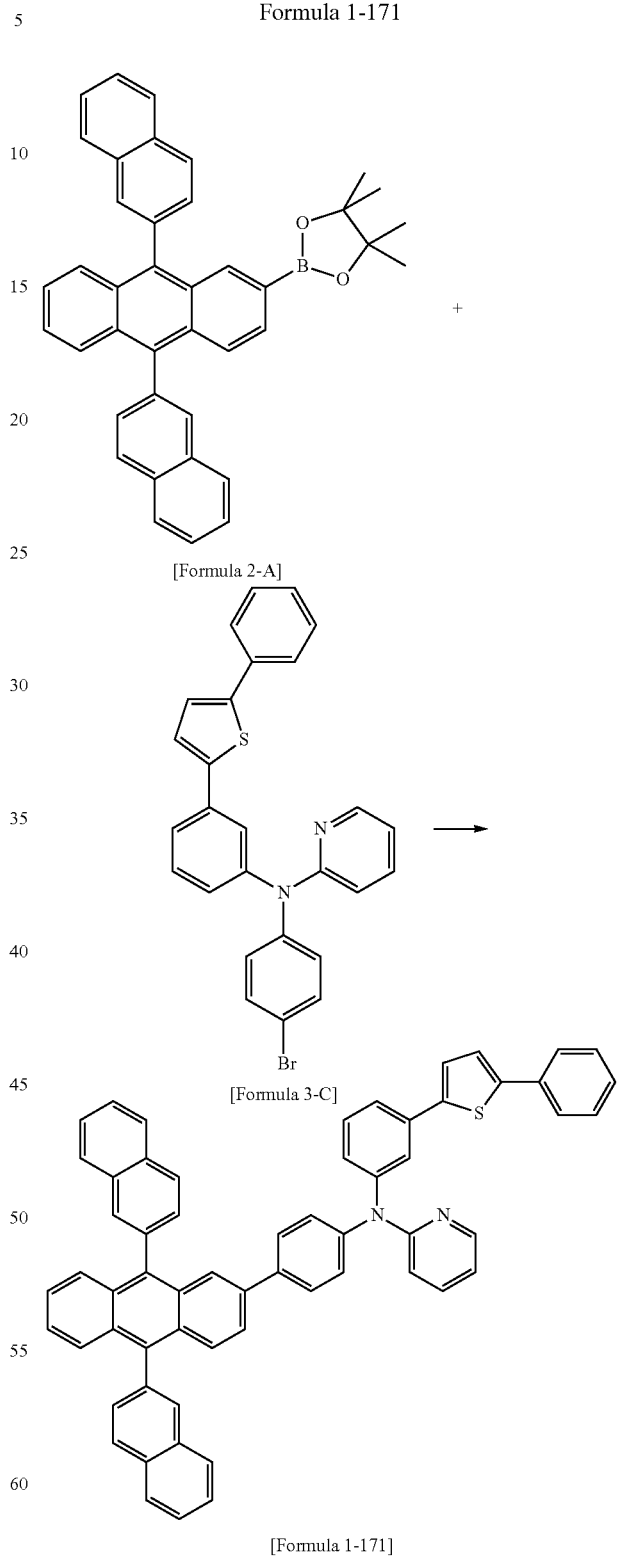

A compound of formula 1-171 was prepared in the same manner as in the method for synthesis of the compound of formula 1-101, except that the compound of formula 3-C was used instead of the compound of formula 1-A in the method for synthesis of the compound of formula 1-101 of Preparative Example 3-6. MS: [M+H]⁺=834

3-10. Synthesis of Compound of the Following Formula 1-191

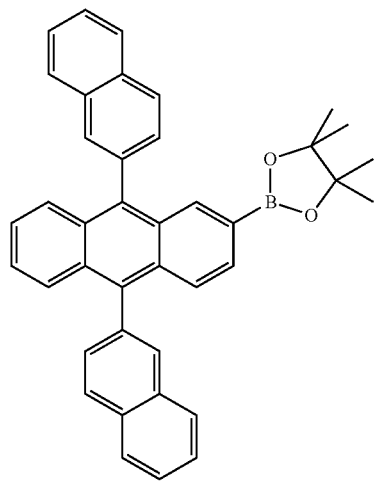
[Formula 2-A]

+

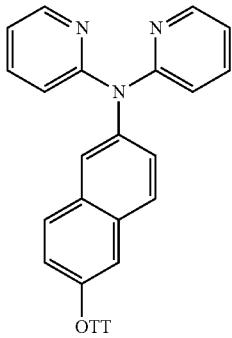
[Formula 1-D]

→

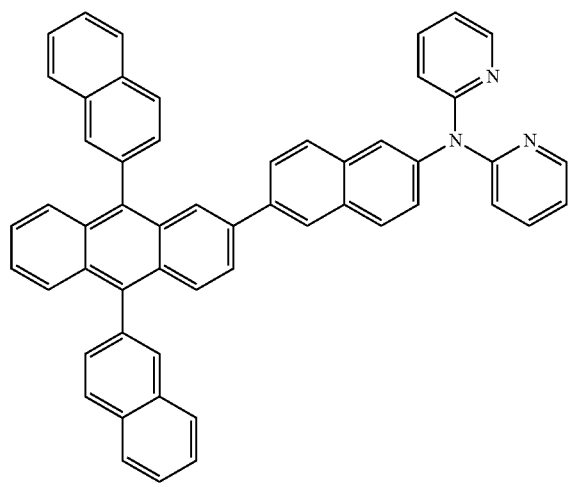
[Formula 1-191]

A compound of formula 1-191 was prepared in the same manner as in the method for synthesis of the compound of formula 1-101, except that the compound of formula 1-D was used instead of the compound of formula 1-A in the method for synthesis of the compound of formula 1-101 of Preparative Example 3-6. MS: [M+H]⁺=726

3-11. Synthesis of Compound of the Following Formula 1-193

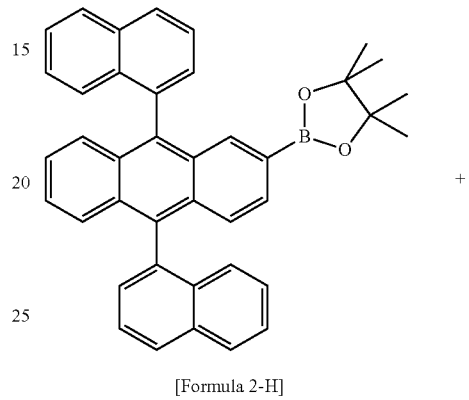
[Formula 2-H]

+

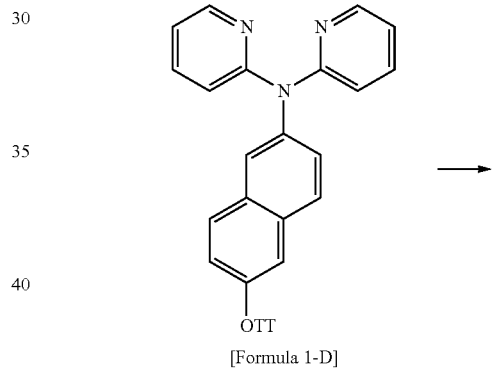
[Formula 1-D]

→

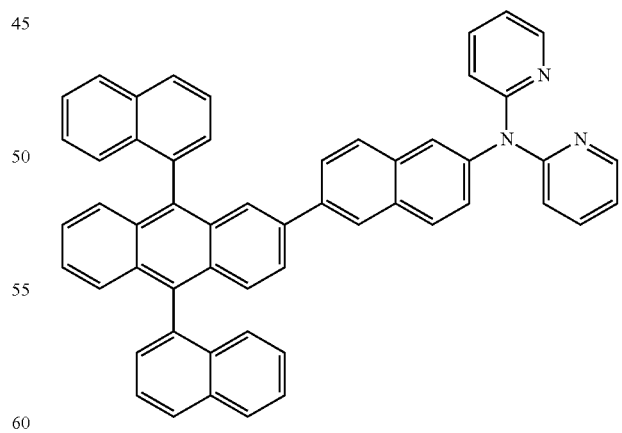
[Formula 1-193]

A compound of formula 1-193 was prepared in the same manner as in the method for synthesis of the compound of formula 1-191, except that the compound of formula 2-H was used instead of the compound of formula 2-A in the method for synthesis of the compound of formula 1-191 of Preparative Example 3-10. MS: [M+]+=726

3-12. Synthesis of Compound of the Following Formula 1-302 used instead of 2,2'-dipyridylamine in the method for synthesis of the compound of formula 1-11 of Preparative Example 3-1. MS: [M+H]+=650

3-13. Synthesis of Compound of the Following Formula 1-303

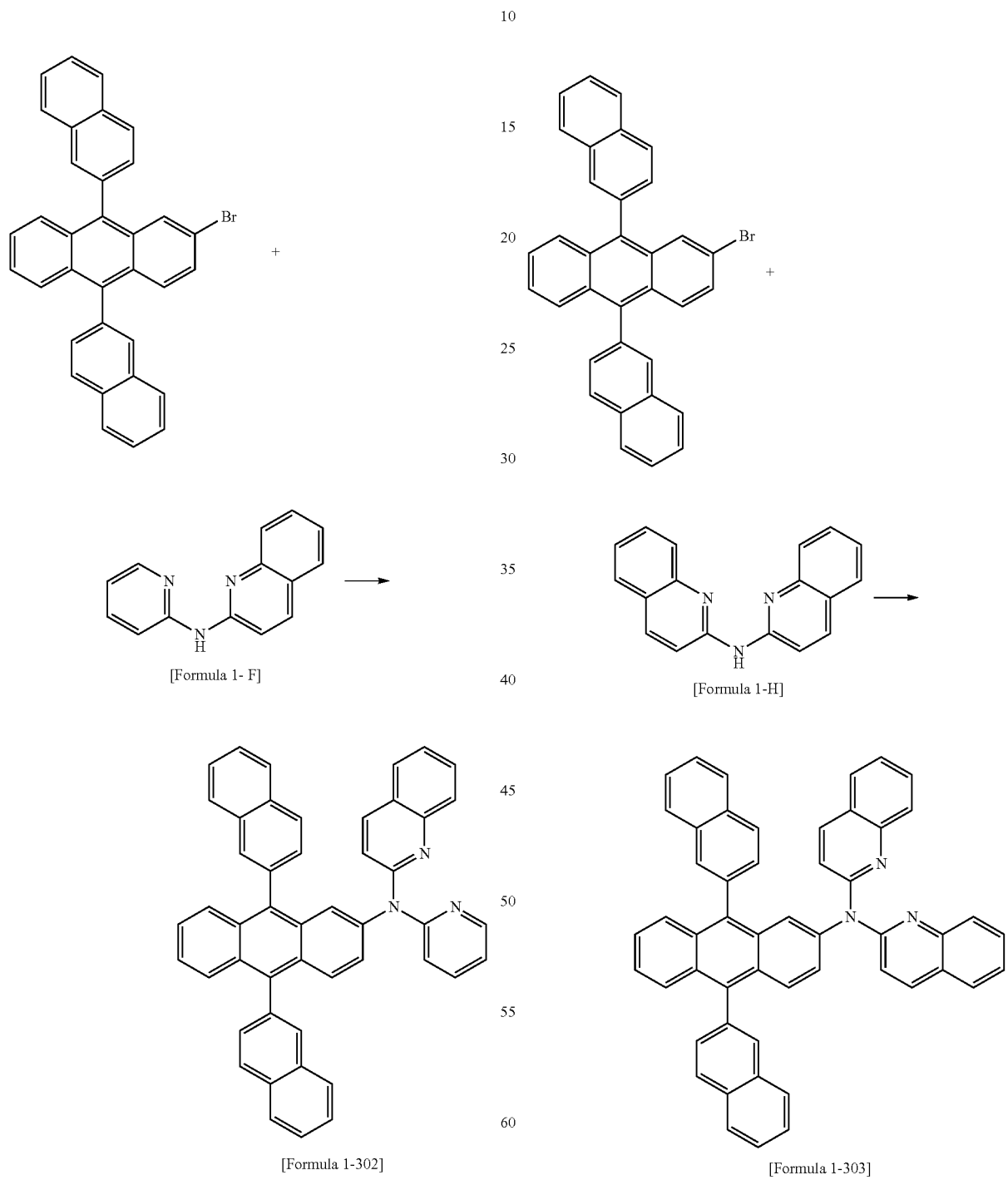

A compound of formula 1-302 was prepared in the same manner as in the method for synthesis of the compound of formula 1-11, except that the compound of formula 1-F was A compound of formula 1-303 was prepared in the same manner as in the method for synthesis of the compound of formula 1-11, except that the compound of formula 1-H was used instead of 2,2'-dipyridylamine in the method for synthesis of the compound of formula 1-11 of Preparative Example 3-1. MS: [M+H]⁺=700

3-14. Synthesis of Compound of the Following Formula 1-314

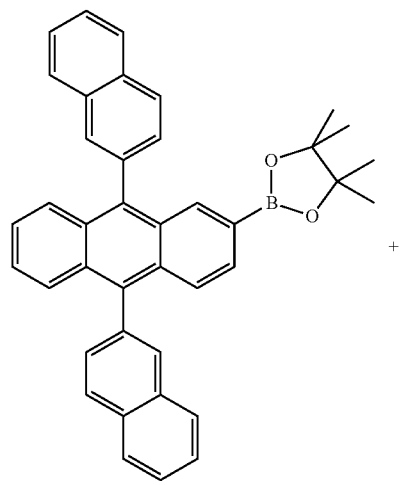

[Formula 2-A]

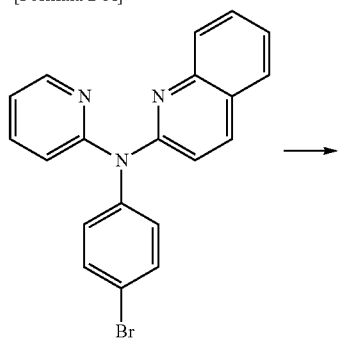

[Formula 1-G]

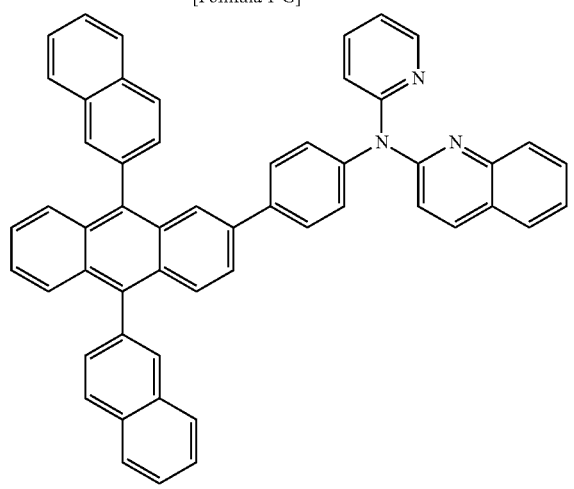

[Formula 1-314]

A compound of formula 1-314 was prepared in the same manner as in the method for synthesis of the compound of formula 1-91, except that the compound of formula 1-G was used instead of the compound of formula 1-E in the method for synthesis of the compound of formula 1-91 of Preparative Example 3-5. MS: [M+H]⁺=726

3-15. Synthesis of Compound of the Following Formula 1-315

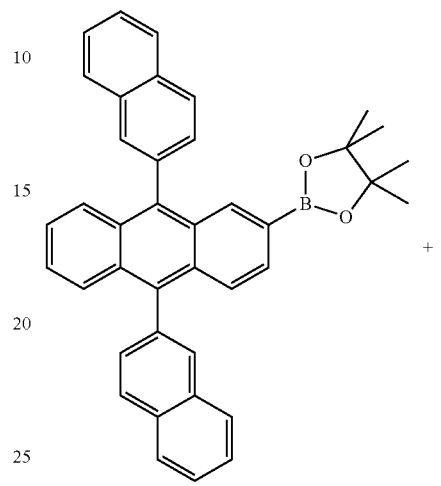

[Formula 2-A]

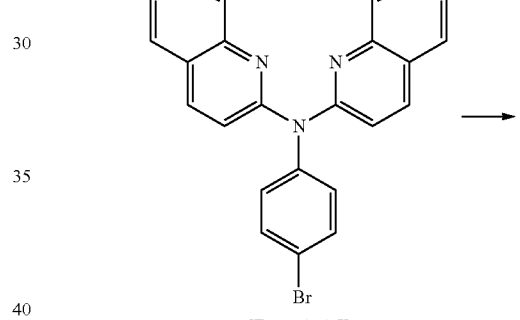

[Formula 1-I]

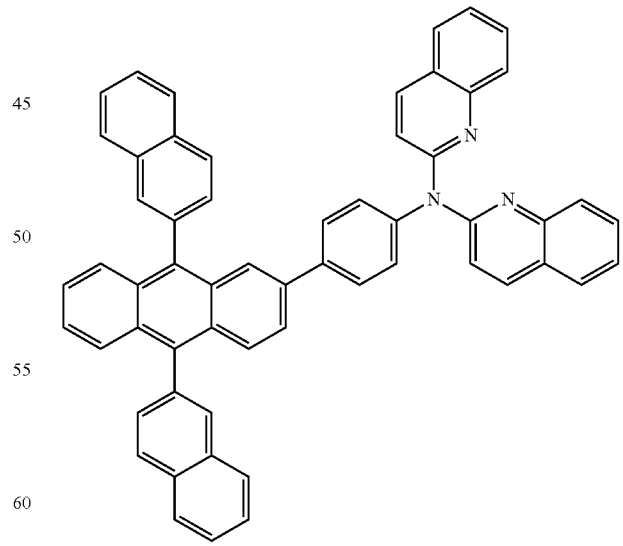

[Formula 1-315]

A compound of formula 1-315 was prepared in the same manner as in the method for synthesis of the compound of formula 1-91, except that the compound of formula 1-I was used instead of the compound of formula 1-E in the method for synthesis of the compound of formula 1-91 of Preparative Example 3-5. MS: [M+H]⁺=776

3-16. Synthesis of Compound of the Following Formula 1-319

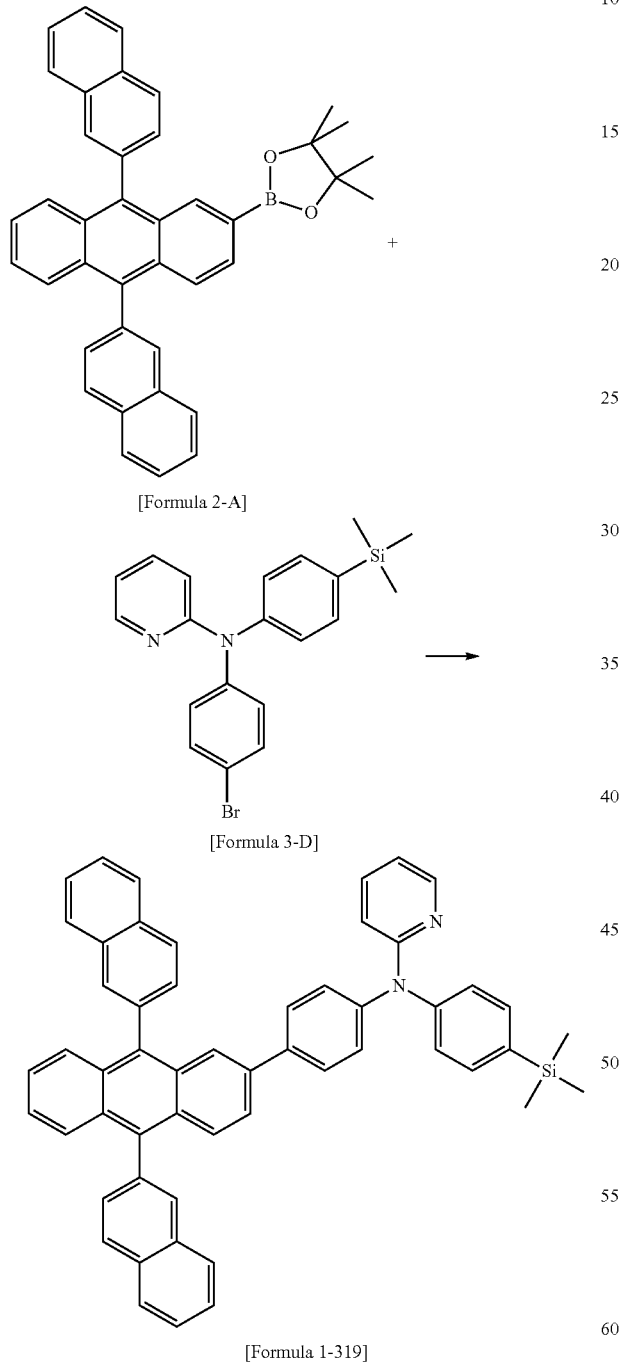

[Formula 2-A]

[Formula 3-D]

[Formula 1-319]

A compound of formula 1-319 was prepared in the same manner as in the method for synthesis of the compound of formula 1-91, except that the compound of formula 3-D was used instead of the compound of formula 1-E in the method for synthesis of the compound of formula 1-91 of Preparative Example 3-5. MS: [M+H]⁺=747

Preparative Example 4

4-1. Synthesis of Compound of the Following Formula 2-11

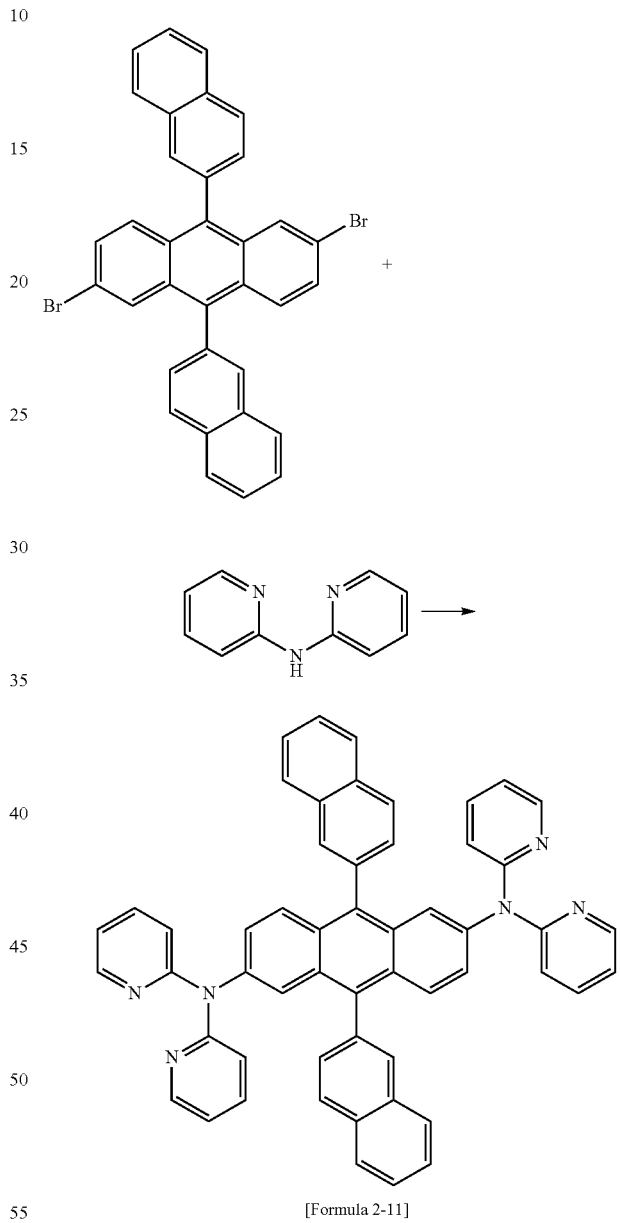

[Formula 2-11]

After 2,2'-dipyridylamine (17.7 g, 103.7 mmol), 2,6-di-bromo-9,10-bis(2-naphthyl)anthracene (25.4 g, 43.2 mmol), and NaOt-Bu (12.5 g, 129.6 mmol) were put into toluene (346 mL), the mixture was heated to 50° C. Pd(P(t-Bu)$_3$)$_2$ (220.5 mg, 0.43 mmol) was added and then heated and agitated for 3 hours. The temperature was cooled to normal temperature, celite was added, and the agitation was performed for 10 min. The suspension solution was filtered by using a filter in which silica gel was provided by 1.5 cm. The filtrate was distilled under reduced pressure and recrystallized with ethanol (200 mL) to obtain a compound of formula 2-11 (10 g, yield 30%). MS: [M+H]$^+$=769

4-2. Synthesis of Compound of the Following Formula 2-13

4-3. Synthesis of Compound of the Following Formula 2-21

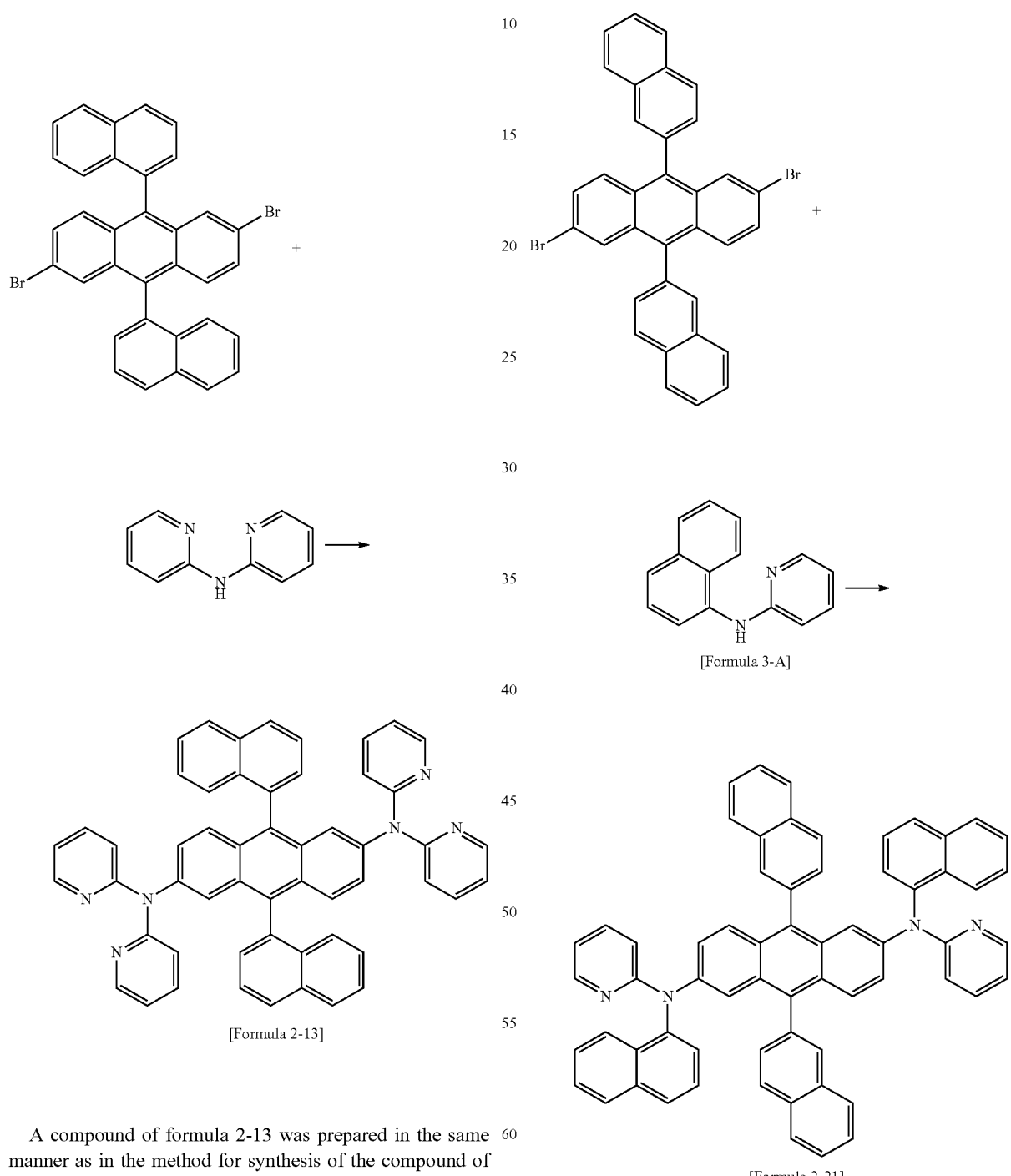

[Formula 2-13]

[Formula 3-A]

[Formula 2-21]

A compound of formula 2-13 was prepared in the same manner as in the method for synthesis of the compound of formula 2-11, except that 2,6-dibromo-9,10-bis(1-naphthyl)anthracene was used instead of 2,6-dibromo-9,10-bis(2-naphthyl)anthracene in the method for synthesis of the compound of formula 2-11 of Preparative Example 4-1. MS: [M+H]$^+$=769

A compound of formula 2-21 was prepared in the same manner as in the method for synthesis of the compound of formula 2-11, except that the compound of formula 3-A was used instead of 2,2'-dipyridylamine in the method for synthesis of the compound of formula 2-11 of Preparative Example 4-1. MS: [M+H]⁺=867

4-4. Synthesis of Compound of the Following Formula 2-71

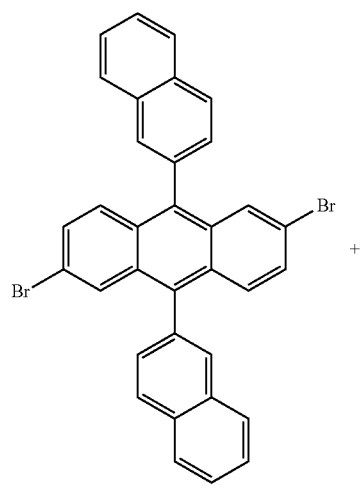

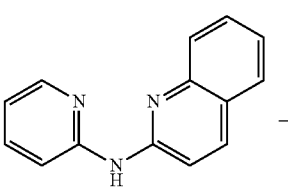

[Formula 1-F]

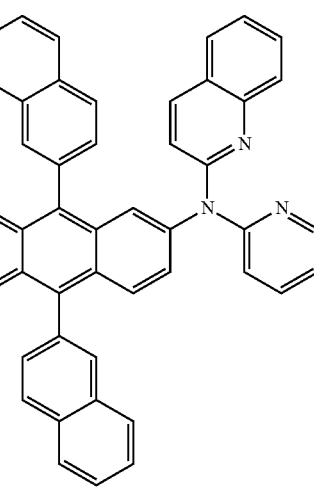

[Formula 2-71]

A compound of formula 2-71 was prepared in the same manner as in the method for synthesis of the compound of formula 2-11, except that the compound of formula 1-F was used instead of 2,2'-dipyridylamine in the method for synthesis of the compound of formula 2-11 of Preparative Example 4-1. MS: [M+H]⁺=869

4-5. Synthesis of Compound of the Following Formula 2-81

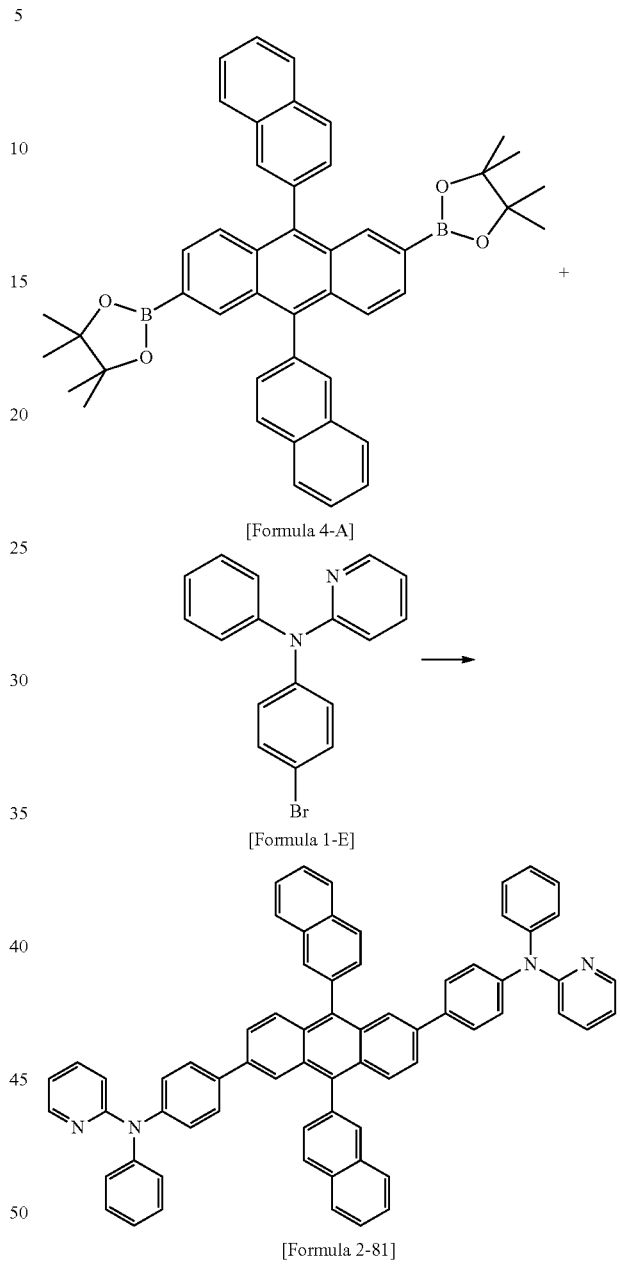

After the compound of formula 4-A (2.2 g, 3.2 mmol) and the compound (2.2 g, 6.9 mmol) of formula 1-E were completely dissolved in tetrahydrofurnae (100 ml), 2M potassium carbonate aqueous solution was added thereto, tetrakistriphenylphosphinopalladium (155 mg, 0.013 mmol) was added thereto, and the heating and the agitation were performed for 5 hours. The temperature was cooled to a normal temperature, the water layer was removed, the drying was performed with anhydrous magnesium sulfate, the concentration was performed under reduced pressure, the column was performed so that the ratio of tetrahydrofurane:hexane was in the range of 1:6 to prepare the compound of formula 2-81 (1.3 g, 45%). MS: [M+H]⁺=919

4-6. Synthesis of Compound of the Following Formula 2-91

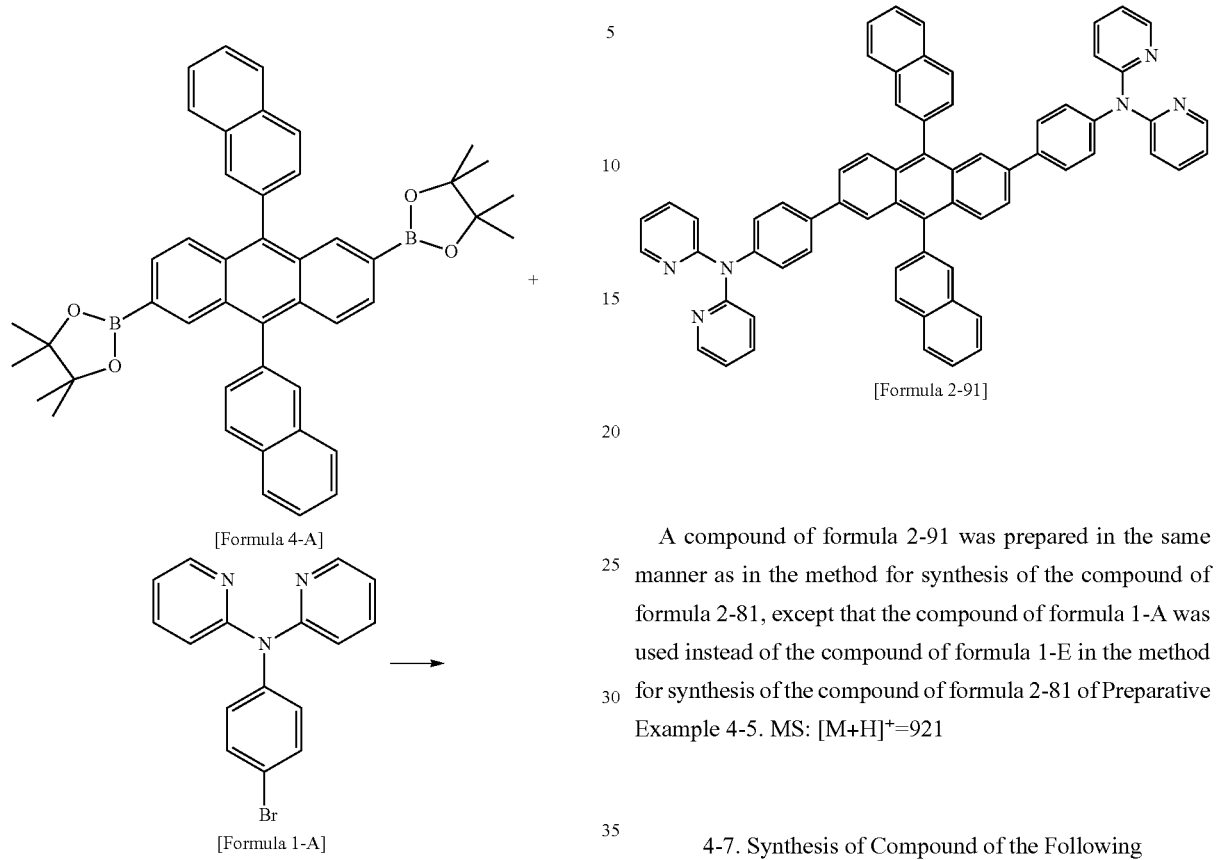

A compound of formula 2-91 was prepared in the same manner as in the method for synthesis of the compound of formula 2-81, except that the compound of formula 1-A was used instead of the compound of formula 1-E in the method for synthesis of the compound of formula 2-81 of Preparative Example 4-5. MS: $[M+H]^+=921$

4-7. Synthesis of Compound of the Following Formula 2-141

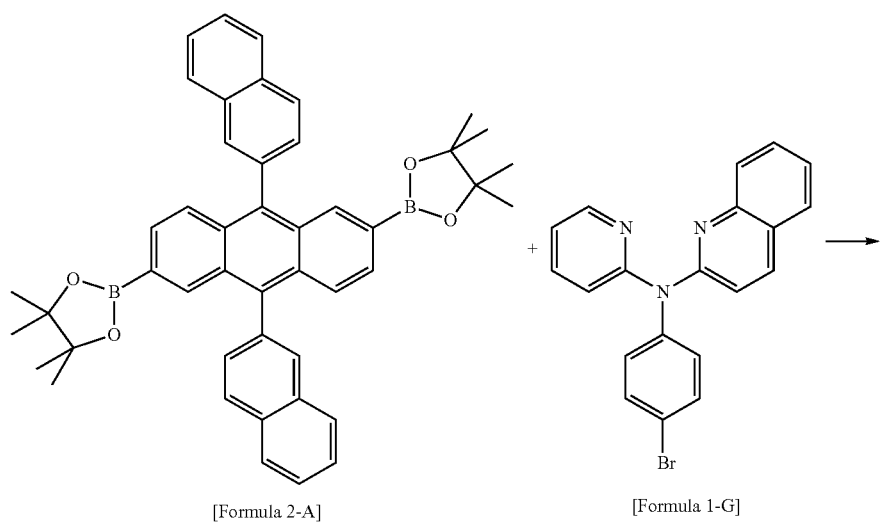

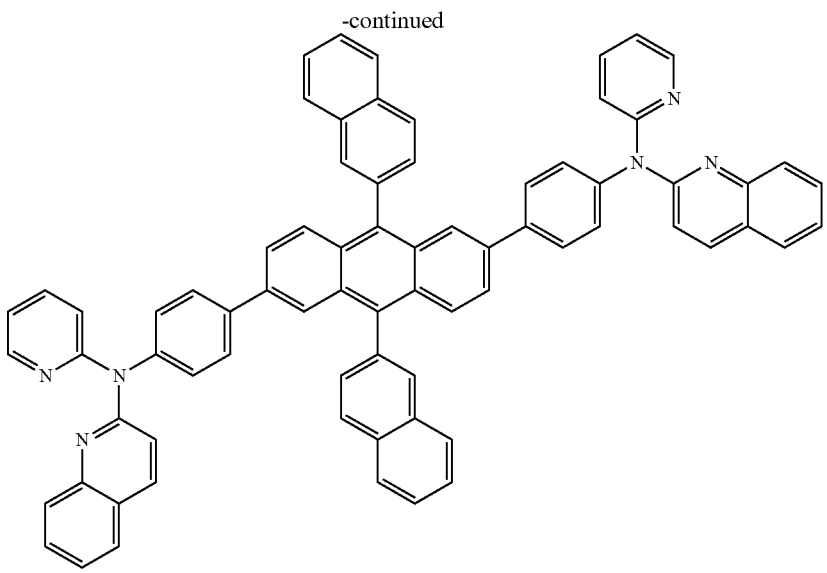

[Formula 2-141]

A compound of formula 2-141 was prepared in the same manner as in the method for synthesis of the compound of formula 2-81, except that the compound of formula 1-G was used instead of the compound of formula 1-E in the method for synthesis of the compound of formula 2-81 of Preparative Example 4-5. MS: $[M+H]^+=1021$ Experimental Example 1

A glass substrate on which a thin film of ITO (indium tin oxide) was coated to a thickness of 1500 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried, and then transported to a plasma washing machine. Using an oxygen plasma, the substrate was washed for 5 minutes and then transported to a vacuum depositing machine.

On the ITO transparent electrode thus prepared, hexanitrile hexaazatriphenylene (HAT) of the following formula was coated to thicknesses of 500 Å by thermal vacuum deposition to form a hole injecting layer.

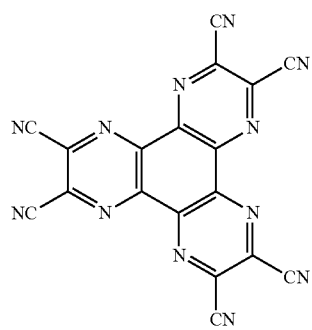

[HAT]

4,4'-Bis[N-(1-naphthyl)-N-phenylamino]biphenyl (NPB) (400 Å) of the following formula, which is a hole transporting material, was coated on the hole injecting layer by vacuum deposition, to form a hole transporting layer.

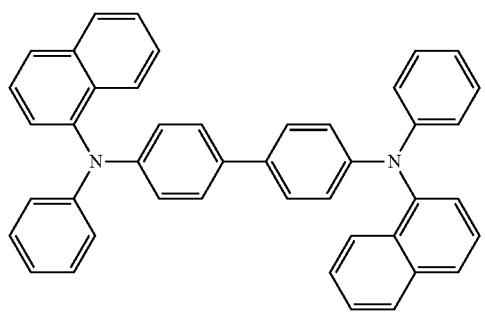

[NPB]

Then, Alq₃ (aluminum tris(8-hydroxyquinoline)) of the following formula was coated to a thickness of 300 Å on the hole transporting layer by vacuum deposition to form a light emitting layer.

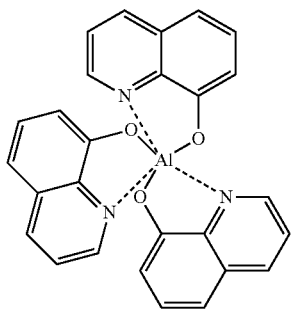

[Alq₃]

The compound of formula 1-21 as prepared in Preparative Example 3 was coated to a thickness of 200 Å on the light emitting layer by vacuum deposition to form an electron injecting and transporting layer.

Lithium fluoride (LiF) and aluminum were sequentially deposited on the electron injecting and transporting layer to thicknesses of 12 Å and 2000 Å respectively, to form a cathode.

In the above process, the deposition rate of the organic material was maintained at 0.4 to 0.7 Å/sec and the deposition rate of lithium fluoride was maintained at 0.3 Å/sec and the deposition rate of aluminum was maintained at 2 Å/sec, respectively. The degree of vacuum upon deposition was maintained at $2\times10^{-7}$ to $5\times10^{-8}$ torr.

When a forward electric field of 5.6 V was applied to the organic light emitting device as prepared above, green light emission was observed with x=0.32 and y=0.55 based on the 1931 CIE color coordinate at a current density of 50 mA/cm$^2$. When a forward electric field of 6.4 V was applied, green light emission of 2.6 cd/A was observed at a current density of 100 mA/cm$^2$.

Experimental Example 2

On the ITO electrode as prepared as in Example 1, hexanitrile hexaazatriphenylene (500 Å), 4,4'-bis[N-(1-naphthyl)-N-phenylamino]biphenyl (NPB) (400 Å), Alq$_3$ (300 Å), and the compound 1-101 (200 Å) were sequentially coated by thermal vacuum deposition, to form a hole injecting layer, a hole transporting layer, a light emitting layer, and an electron transporting layer in this order.

Lithium fluoride (LiF) and aluminum were sequentially deposited on the electron transporting layer to thicknesses of 12 Å and 2000 Å respectively, to form a cathode, thereby preparing an organic light emitting device.

In the above process, the deposition rate of the organic material was maintained at 0.4 to 0.7 Å/sec and the deposition rate of lithium fluoride was maintained at 0.3 Å/sec and the deposition rate of aluminum was maintained at 2 Å/sec, respectively. The degree of vacuum upon deposition was maintained at $2\times10^{-7}$ to $5\times10^{-8}$ torr.

When a forward electric field of 4.1 V was applied to the organic light emitting device as prepared above, green light emission was observed with x=0.33 and y=0.56 based on the 1931 CIE color coordinate at a current density of 50 mA/cm$^2$. When a forward electric field of 5.0 V was applied, green light emission of 2.0 cd/A was observed at a current density of 100 mA/cm$^2$.

Experimental Example 3

On the ITO electrode as prepared as in Example 1, hexanitrile hexaazatriphenylene (500 Å), 4,4'-bis[N-(1-naphthyl)-N-phenylamino]biphenyl (NPB) (400 Å), and the compound I-191 (400 Å) were sequentially coated by thermal vacuum deposition, to form a hole injecting layer, a hole transporting layer, and a light emitting and electron transporting layer in this order.

Lithium fluoride (LiF) and aluminum were sequentially deposited on the light emitting and electron transporting layer to thicknesses of 12 Å and 2000 Å respectively, to form a cathode, thereby preparing an organic light emitting device.

In the above process, the deposition rate of the organic material was maintained at 0.4 to 0.7 Å/sec and the deposition rate of lithium fluoride was maintained at 0.3 Å/sec and the deposition rate of aluminum was maintained at 2 Å/sec, respectively. The degree of vacuum upon deposition was maintained at $2\times10^{-7}$ to $5\times10^{-8}$ torr.

When a forward electric field of 4.3 V was applied to the organic light emitting device as prepared above, green light emission was observed with x=0.33 and y=0.58 based on the 1931 CIE color coordinate at a current density of 50 mA/cm$^2$. When a forward electric field of 5.2 V was applied, green light emission of 2.1 cd/A was observed at a current density of 100 mA/cm$^2$.

Experimental Example 4

On the ITO electrode as prepared as in Example 1, hexanitrile hexaazatriphenylene (500 Å), 4,4'-bis[N-(1-naphthyl)-N-phenylamino]biphenyl (NPB) (400 Å), Alq$_3$ (300 Å), the compound of formula 1-315 (200 Å), lithium fluoride (LiF) (12 Å) were sequentially coated by thermal vacuum deposition, to form a hole injecting layer, a hole transporting layer, a light emitting layer, an electron transporting layer and an electron injecting layer in this order. Aluminum was deposited thereon to a thickness of 2000 Å to form a cathode, thereby preparing an organic light emitting device.

When a forward electric field of 4.2 V was applied to the organic light emitting device as prepared above, green light emission was observed with x=0.32 and y=0.56 based on the 1931 CIE color coordinate at a current density of 50 mA/cm$^2$. When a forward electric field of 5.1 V was applied, green light emission of 2.1 cd/A was observed at a current density of 100 mA/cd.

Experimental Example 5

On the ITO electrode as prepared as in Example 1, hexanitrile hexaazatriphenylene (500 Å), 4,4'-bis[N-(1-naphthyl)-N-phenylamino]biphenyl (NPB) (400 Å), Alq$_3$ (300 Å), the compound of formula 2-91 (200 Å), and lithium fluoride (LiF) (12 Å) were sequentially coated by thermal vacuum deposition, to form a hole injecting layer, a hole transporting layer, a light emitting layer, an electron transporting layer and an electron injecting layer in this order. Aluminum was deposited thereon to a thickness of 2000 Å to form a cathode, thereby preparing an organic light emitting device.

When a forward electric field of 4.3 V was applied to the organic light emitting device as prepared above, green light emission was observed with x=0.33 and y=0.58 based on the 1931 CIE color coordinate at a current density of 50 mA/cm$^2$. When a forward electric field of 5.1 V was applied, green light emission of 2.0 cd/A was observed at a current density of 100 mA/cm$^2$.

Comparative Example 1

On the ITO electrode as prepared as in Example 1, hexanitrile hexaazatriphenylene (500 Å), 4,4'-bis[N-(1-naphthyl)-N-phenylamino]biphenyl (NPB) (400 Å), Alq$_3$ (300 Å), the electron transporting substance represented by the following formula (200 Å), and lithium fluoride (LiF) (12 Å) were sequentially coated by thermal vacuum deposition, to form a hole injecting layer, a hole transporting layer, a light emitting layer, an electron transporting layer and an electron injecting layer in this order. Aluminum was deposited thereon to a thickness of 2000 Å to form a cathode, thereby preparing an organic light emitting device.

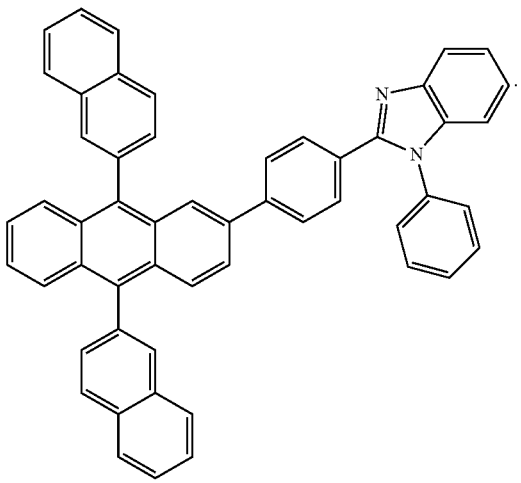

[Electron transporting material]

When a forward electric field of 4.3 V was applied to the organic light emitting device as prepared above, green light emission was observed with x=0.33 and y=0.56 based on the 1931 CIE color coordinate at a current density of 50 mA/cm². When a forward electric field of 6.8 V was applied, green light emission of 2.4 cd/A was observed at a current density of 100 mA/cd.

Comparative Example 2

On the ITO electrode as prepared as in Example 1, hexanitrile hexaazatriphenylene (500 Å), 4,4'-bis[N-(1-naphthyl)-N-phenylamino]biphenyl (NPB) (400 Å), Alq₃ (300 Å), the electron transporting substance-1 represented by the following formula (200 Å), and lithium fluoride (LiF) (12 Å) were sequentially coated by thermal vacuum deposition, to form a hole injecting layer, a hole transporting layer, a light emitting layer, an electron transporting layer and an electron injecting layer in this order. Aluminum was deposited thereon to a thickness of 2000 Å to form a cathode, thereby preparing an organic light emitting device.

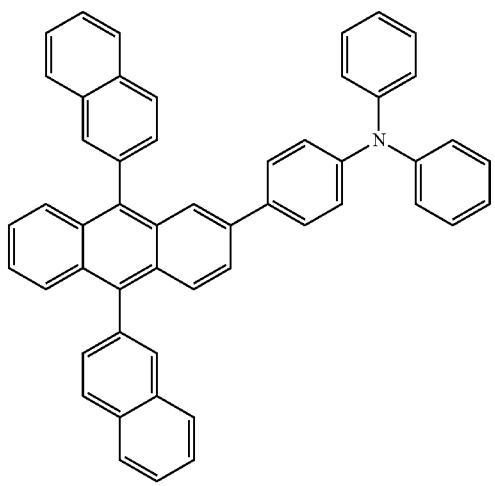

[Electron transporting material-1]

When a forward electric field of 4.3 V was applied to the organic light emitting device as prepared above, green light emission was observed with x=0.34 and y=0.58 based on the 1931 CIE color coordinate at a current density of 50 mA/cm². When a forward electric field of 7.8 V was applied, green light emission of 1.4 cd/A was observed at a current density of 100 mA/cm².

The invention claimed is:
1. An anthracene derivative that is represented by the following formula 1:

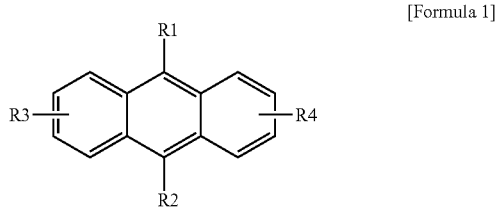

[Formula 1]

wherein R1 and R2 may be the same as or different from each other, and are independently selected from the following formulae:

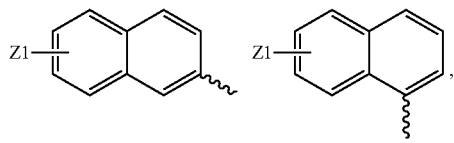

wherein Z1 is hydrogen,
at least one of R3 and R4 is represented by the following formula 2:

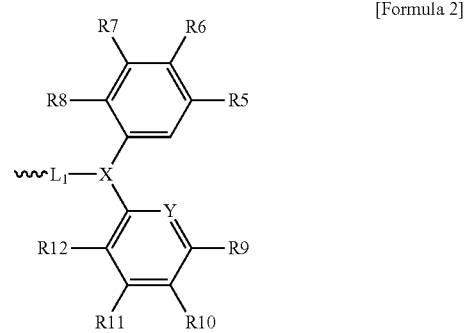

[Formula 2]

wherein X is,
Y is selected from the group consisting of C—H and N,
L₁ is a direct bond; or is selected from the group consisting of a phenylene group and a naphthalenylene group,
R5, R6, R9, R10, R11, and R12 may be the same as or different from each other, and are selected from the group consisting of hydrogen; Si(CH₃)₃; and a phenyl group which is substituted with a C₄ heteroaryl group; or are bonded with an adjacent group to form an aromatic condensed ring,
R7 and R8 may be the same as or different from each other, and are selected from the group consisting of hydrogen; Si(CH₃)₃; and a phenyl group which is substituted with a C₄ heteroaryl group, and
when any one of R3 and R4 is represented by formula 2, the other is selected from the group consisting of hydrogen; a $C_6$ to $C_o$ aryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, a $C_3$ to $C_{40}$ heteroaryl group and an arylamine group; a $C_3$ to $C_{40}$ heteroaryl group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group; and a $C_6$ to $C_{40}$ amino group which is unsubstituted or substituted with at least one selected from the group consisting of halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group and a $C_3$ to $C_{40}$ heteroaryl group.

2. The anthracene derivative as set forth in claim 1, wherein the alkyl group is selected from the group consisting of a methyl group, an ethyl group, a propyl group, an isopropyl group, a butyl group, a t-butyl group, a pentyl group, a hexyl group and a heptyl group; the cycloalkyl group is a cyclopentyl group or a cyclohexyl group; the alkenyl group is an alkenyl group in which an aryl group of a stilbenzyl group or a styrenyl group is substituted; the alkoxy group is an alkoxy group having 1 to 40 carbon atoms; the aryl group is selected from the group consisting of a phenyl group, a naphthyl group, an anthracenyl group, a biphenyl group, a pyrenyl group, a perylenyl group, and a derivative thereof; the aryl amine group is selected from the group consisting of a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a ditolylamine group, a phenyltolylamine group, a carbazole group and a triphenylamine group; the heterocyclic group is selected from the group consisting of a pyridyl group, a bipyridyl group, a triazine group, an acridyl group, a thiophene group, a puran group, an imidazole group, an oxazole group, a thiazole group, a triazole group, a quinolinyl group, and an isoquinoline group; and the halogen group is selected from the group consisting of fluorine, chlorine, bromine, and iodine.

3. An organic electronic device comprising a first electrode, a second electrode, and at least one organic material layer interposed between the first electrode and the second electrode, wherein at least one of the organic material layers comprises the anthracene derivative of formula 1 according to claim 1.

4. The organic electronic device as set forth in claim 3, wherein the organic electronic device is selected from the group consisting of an organic light emitting device, an organic solar cell, an organic photoconductor (OPC) drum and an organic transistor.

5. The organic electronic device as set forth in claim 3, wherein the organic electronic device is an organic light emitting device.

6. The organic electronic device as set forth in claim 5, wherein the organic light emitting device has a forward structure in which an anode, at least one organic material layer, and a cathode are sequentially laminated on a substrate.

7. The organic electronic device as set forth in claim 5, wherein the organic light emitting device has a reverse structure in which a cathode, at least one organic material layer, and an anode are sequentially laminated on a substrate.

8. The organic electronic device as set forth in claim 5, wherein the organic light emitting device comprises the anthracene derivative of formula 1 which is included in the organic material layer comprising one or more selected from a hole injecting layer, a hole transporting layer, a light emitting layer, an electron injecting and an electron transporting layer.

9. The organic electronic device as set forth in claim 3, wherein the organic material layer comprises a light emitting layer, and the light emitting layer comprises the anthracene derivative of formula 1.

10. The organic electronic device as set forth in claim 3, wherein the organic material layer comprises an electron transporting layer or electron injecting layer, and the electron transporting layer or the electron injecting layer comprises the anthracene derivative of formula 1.

* * * * *